(12) United States Patent
Bajji et al.

(10) Patent No.: US 7,547,804 B2
(45) Date of Patent: Jun. 16, 2009

(54) COMPOUNDS, COMPOSITIONS, AND METHODS EMPLOYING SAME

(75) Inventors: Ashok C. Bajji, Salt Lake City, UT (US); Esther Arranz, Salt Lake City, UT (US); Jayasree M. Srinivasan, Bloomington, IN (US); Eric Delmar, Salt Lake City, UT (US); Rachel Slade, Salt Lake City, UT (US); Jon Adam Willardsen, Sandy, UT (US)

(73) Assignee: Myriad Genetics, Inc., Salt Lake City, UT (US)

( * ) Notice: Subject to any disclaimer, the term of this patent is extended or adjusted under 35 U.S.C. 154(b) by 182 days.

(21) Appl. No.: 11/039,275

(22) Filed: Jan. 18, 2005

(65) Prior Publication Data

US 2005/0187300 A1 Aug. 25, 2005

Related U.S. Application Data

(63) Continuation-in-part of application No. PCT/US03/022183, filed on Jul. 15, 2003.

(60) Provisional application No. 60/396,773, filed on Jul. 16, 2002, provisional application No. 60/396,266, filed on Jul. 15, 2002.

(51) Int. Cl.
  *C07C 233/65* (2006.01)
  *A01K 31/16* (2006.01)
(52) U.S. Cl. ........................ 564/176; 564/177; 514/617
(58) Field of Classification Search ................. 564/176, 564/177; 514/617
  See application file for complete search history.

(56) References Cited

U.S. PATENT DOCUMENTS

| | | | |
|---|---|---|---|
| 3,142,703 A | 7/1964 | Stecker | |
| 3,577,550 A | 5/1971 | Moyle | |
| 3,674,850 A | 7/1972 | Osborne | |
| 3,706,799 A | 12/1972 | Osborne et al. | |
| 3,715,395 A | 2/1973 | Mrozik et al. | |
| 3,798,258 A | 3/1974 | Patchett et al. | |
| 3,914,418 A | 10/1975 | Patchett et al. | |
| 5,094,938 A | 3/1992 | Tsukahara et al. | |
| 5,532,412 A | 7/1996 | Matsuki et al. | |
| 5,552,426 A | 9/1996 | Lunn et al. | |
| 5,755,999 A | 5/1998 | Shi et al. | |
| 6,001,879 A | 12/1999 | Seitz et al. | |
| 6,025,379 A | 2/2000 | Iyengar et al. | |
| 6,030,992 A | 2/2000 | Gitter et al. | |
| 6,054,457 A | 4/2000 | Setoi et al. | |
| 6,203,979 B1 | 3/2001 | Bandman et al. | |
| 6,319,940 B1 | 11/2001 | Elbe et al. | |
| 6,407,288 B1 | 6/2002 | Coburn et al. | |
| 6,534,532 B1 | 3/2003 | Elbe et al. | |
| 6,548,549 B1 | 4/2003 | Seitz et al. | |
| 6,590,118 B1 | 7/2003 | Kristiansen et al. | |
| 6,653,309 B1 * | 11/2003 | Saunders et al. | ............ 514/242 |
| 6,716,881 B2 | 4/2004 | Elbe et al. | |
| 6,930,106 B2 | 8/2005 | Finzel et al. | |
| 2003/0186944 A1 | 10/2003 | Kristiansen et al. | |
| 2004/0087650 A1 | 5/2004 | Saunders et al. | |
| 2004/0122244 A1 | 6/2004 | Suzuki et al. | |
| 2004/0142993 A1 | 7/2004 | Battistini et al. | |

FOREIGN PATENT DOCUMENTS

| | | |
|---|---|---|
| CA | 2148053 | 10/1995 |
| DE | 2126149 | 12/1972 |
| DE | 106030 | 5/1974 |
| DE | 112255 | 4/1975 |
| DE | 220902 A1 | 4/1985 |
| DE | 19629828 A1 | 1/1998 |
| EP | 0423764 A2 | 4/1991 |
| EP | 643039 A1 | 3/1995 |
| EP | 832061 B1 | 9/2001 |
| EP | 1314712 A1 | 5/2003 |
| EP | 1510207 A1 | 3/2005 |
| EP | 1510210 A1 | 3/2005 |
| EP | 1512396 A1 | 3/2005 |
| EP | 1514544 A1 | 3/2005 |
| EP | 1535609 A1 | 6/2005 |
| EP | 1535610 A1 | 6/2005 |
| EP | 1555018 A1 | 7/2005 |
| FR | 1431689 | 3/1966 |
| FR | 2434143 | 3/1980 |
| GB | 1108393 | 12/1964 |
| GB | 1226438 | 3/1971 |
| JP | 58128365 A2 | 7/1983 |
| JP | 03288849 A2 | 12/1991 |

(Continued)

OTHER PUBLICATIONS

Carter et al., Chemotherapy of Cancer, second edition, John Wiley & Sons, N.Y., N.Y., 1981, pp. 362-365.*

(Continued)

*Primary Examiner*—Shailendra Kumar
(74) *Attorney, Agent, or Firm*—Herbert L. Ley, III; Jay Z. Zhang; Myriad IP Department

(57) ABSTRACT

Compounds and pharmaceutical compositions containing the same are provided, which are useful in therapeutic treatment or prevention of various diseases.

26 Claims, No Drawings

FOREIGN PATENT DOCUMENTS

| | | |
|---|---|---|
| JP | 04199047 A2 | 7/1992 |
| JP | 06161059 A2 | 6/1994 |
| JP | 06167782 A2 | 6/1994 |
| JP | 07175184 A2 | 7/1995 |
| JP | 07234484 A2 | 9/1995 |
| JP | 09268169 A2 | 10/1997 |
| JP | 09292684 A2 | 11/1997 |
| JP | 2943943 B2 | 8/1999 |
| NL | 6515918 | 6/1966 |
| SU | 697500 | 11/1979 |
| SU | 1587042 A1 | 8/1990 |
| SU | 1547248 A1 | 4/1991 |
| SU | 1547251 A1 | 4/1991 |
| WO | WO 9213828 A1 | 8/1992 |
| WO | WO 9401113 A1 | 1/1994 |
| WO | WO 9605170 A1 | 2/1996 |
| WO | WO 9641795 A1 | 12/1996 |
| WO | WO 9708135 A1 | 3/1997 |
| WO | WO 9731635 A1 | 9/1997 |
| WO | WO 9733873 A1 | 9/1997 |
| WO | WO 9803500 A1 | 1/1998 |
| WO | WO 9955663 A1 | 11/1999 |
| WO | WO 0003975 A2 | 1/2000 |
| WO | WO 0007979 A2 | 2/2000 |
| WO | WO 0123347 A1 | 4/2001 |
| WO | WO 0228819 A1 | 4/2002 |
| WO | WO 02076918 A1 | 10/2002 |
| WO | WO 2004002944 A1 | 1/2004 |
| WO | WO 2004006858 A2 | 1/2004 |
| WO | WO 2005007151 A1 | 1/2005 |

OTHER PUBLICATIONS

Burger, Medicinal Chemistry, Interscience Publishers, Inc., New York, 1960, pp. 74-77.

Dumas et al., "Synthesis and Structure Activity Relationships of Novel Small Molecule Cathepsin D Inhibitors", *Bioorganic & Medicinal Chemistry Letters*, Sep. 1999, 9(17):2531-2536.

Duwel et al., "2,6-Dihydroxybenzoic Acid Anilides as Fasciolicides", *Journal of Medicinal Chemistry*, May 1973, 16(5):433-436.

Endo et al., "Infrared spectra and intramolecular hydrogen bonding of some salicylanilides of pharmaceutical interest", *Bulletin of the Chemical Society of Japan*, 1982, 55(5):1564-1567.

Fernandez et al., "Photographic compounds and elements and processes using them", *Research Disclosure*, 1979, 177:45-50.

Gabrio et al., "Effects of sunlight on the behavior of rafoxanide", *Zeitschrift fuer Chemie*, 1977, 17(1):21.

Hamada et al., "On the antimicrobial activity and synthesis of salicylanilide derivatives", *Yakugaku Zasshi*, 1981, 101(7):633-641.

Ibrahim et al., "Efficient synthesis of 16-28 membered macrocyclic crown amides via ring closing metathesis", *Tetrahedron*, 2003, 59(37):7273-7282.

Kakiuchi et al., "Non-peptide inhibitors of HCV serine proteinase", *FEBS Letters*, 1998, 421(3):217-220.

Kondrat'ev et al., "Effectiveness of novel salicylanilide derivatives for the treatment of fascioliasis in livestock", *Doklady Vsesoyuznoi Akademii Sel'skokhozyaistvennykh Nauk imeni V.I. Lenina*, 1985, 9:32-34.

Liechti et al., "Salicylanilides as inhibitors of the protein tyrosine kinase epidermal growth factor receptor", *European Journal of Medicinal Chemistry*, 2004, 39(1):11-26.

Mikhailitsyn et al., "Search for new antiparasitic agents. I. Synthesis of halogen-containing benzamides and investigation of their acute toxicity", *Meditsinskaya Parazitologiya i Parazitamye Bolezni*, 1990, 6:52-53.

Mikhailitsyn et al., "Search for new antiparasitic agents. 7. The study of anthelmintic activity-structure relationships in new halogen-containing benzamides", *Meditsinskaya Parazitologiya i Parazitamye Bolezni*, 1991, 5:53-55.

Mikhailitsyn et al., "Search for new antiparasitic agents. 4. Antimalarial activity of N-(halonapthyloxy)-2-hydroxy-3,5-dihalobenzamides", *Meditsinskaya Parazitologiya i Parazitamye Bolezni*, 1991, 3:36-37.

Mikhailitsyn et al., "A search for new antiparasitic agents. 6. Synthesis of halobenzamides containing benzophenone or diphenyl sulfonic substituents at nitrogen and study of their acute toxicity", *Meditsinskaya Parazitologiya i Parazitarnye Bolezni*, 1991, 4:43-46.

Nara et al., "p-Azidosalicyl-5-amino-6-phenoxybenzimidazole Photolabels the N-terminal 63-103 Amino Acids of *Haemonchus contortus* β-Tublin 1", *Journal of Biological Chemistry*, Apr. 12, 1996, 271(15):8575-8581.

Ronova et al., "The effect of side substituents on rotation hindrance in polyheteroarylenes", *Russian Chemical Bulletin*, 1998, 47(7):1248-1256.

Takeuchi et al., "On the antimicrobial activity and syntheses of carbanilide and salicylanilide derivatives", *Yakugaku Zasshi*, 1982, 102(11):1023-1030.

Skvortsov et al. "Antitumor activity of CTFB, a novel anticancer agent, is associated with the down-regulation of nuclear factor-$_\kappa$B expression and proteasome activation in head and neck squamous carcinoma cell lines", *Molecular Cancer Therapeutics*, Jun. 2007, 6(6):1898-1908.

Database Accession No. 1964:23151. Profft et al., "Substituted salicylamides and their analgesic effect", Parmazie, 1962, 17(12):731-734. XP002513448.

Database Accession No. 2002:487387. Muto et al., "Preparation of Benzamides as inhibitors of production and release of inflammatory cytokines", Institute of Medicinal Molecular Design Inc., Japan, Jun. 27, 2002. XP-002513446.

Database Accession No. 2003:991336. Muto et al., "Preparation of hydroxybenzamide, naphthalenecarboxamide, and hydroxyheterocyclecarboxamide derivatives as anticancer agents", Institute of Medicinal Molecular Design, Inc., Japan, Dec. 18, 2003. XP002513449.

\* cited by examiner

COMPOUNDS, COMPOSITIONS, AND METHODS EMPLOYING SAME

CROSS REFERENCE TO RELATED APPLICATIONS

This application is a continuation-in-part of PCT/US2003/022183 filed Jul. 15, 2003, which claims the benefit of U.S. Provisional Application Ser. No. 60/396,266, filed on Jul. 15, 2002 and U.S. Provisional Application Ser. No. 60/396,773, filed Jul. 16, 2002, the contents of all of which are incorporated herein by reference in their entirety.

TECHNICAL FIELD OF THE INVENTION

The invention relates to compounds, pharmaceutical compositions and methods of employing such compounds and pharmaceutical compositions for purposes of therapeutic and/or prophylactic treatment of diseases and disorders.

TECHNICAL BACKGROUND OF THE INVENTION

Apoptosis, also known as programmed cell death, is an active process essential for normal development and functions of multicellular organisms. Typically, apoptosis involves isolated single cells and is characterized by DNA fragmentation, morphological changes of cells and nuclei including cell shrinkage, cell surface blebbing, exposure of phosphatidylserine on the cell surface, involution, contraction, chromatin condensation and fragmentation, and phagocytosis without cell infiltration or inflammation. See Honig and Rosenberg, *Am. J. Med.*, 108:317-330 (2000). Dysregulation of apoptosis can lead to various diseases and disorders. It is now well-known that reduced apoptosis may contribute to tumorigenesis and formation of cancer. Thus, induction of tumor cell apoptosis can be an effective approach in treating cancer. In addition, stimulation of endothelial cell apoptosis may prevent tumor blood supply and cause tumor regression. See Dimmeler and Zeiher, *Cir. Res.*, 87:434-439 (2000). Dysregulation of apoptosis is also an integral part of a wide range of autoimmune diseases and disorders. See Ravirajan et al., *Int. Rev. Immunol.*, 18:563-589 (1999). In addition, many neurological disorders involve apoptosis. During adulthood, there is little normal neuronal cell death. However, neurological diseases, particularly neurodegenerative diseases are often associated with excessive neural cell death. See Honig and Rosenberg, *Am. J. Med.*, 108:317-330 (2000). For example, Parkinson's disease is associated with the loss of substantia nigra pars compacta and sympathetic ganglia, while Alzheimer's disease is characterized with selective cell loss of entorhinal neurons, and hippocampal neurons, cortical neurons. See Honig and Rosenberg, *Am. J. Med.*, 108:317-330 (2000). Apoptosis also plays an important role in osteoporotic disorders including, but not limited to, postmenopausal osteoporosis, involutional osteoporosis, and glucocorticoid-induced osteoporosis. See Weinstein, et al., *Am. J. Med.*, 108:153-164 (2000). Apoptosis also has physiological significance in animal virus infection. See Kyama et al., *Microbes and Infection*, 2:1111-1117 (2000).

Degterev, Alexei, et al, "Identification of small-molecule inhibitors of interaction between the Bak BH3 domain and Bcl-$x_L$," *Nat. Cell Biol.*, 3:173-182 (2001), disclose apoptosis promoting compounds of the formulas:

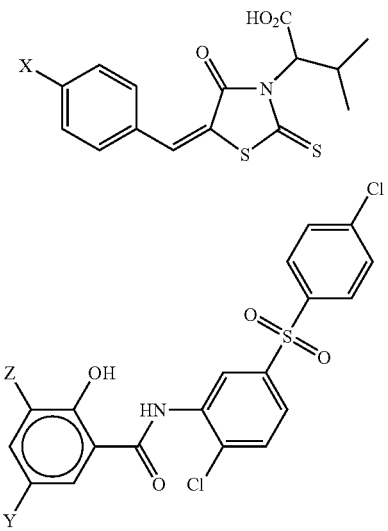

wherein X can be Br, Cl, or H, Y is Cl, or I, and Z is Br, or I. The compounds were shown via binding assay tests, to promote displacement of BH3 from a Bcl-$X_L$ fusion protein. The compounds were also shown to have apoptotic cytotoxicity when applied to Jurkat T lymphoma cells. The apoptotic cytotoxicity of the compounds quantitatively paralleled their in vitro Bcl-$X_L$ binding activities.

U.S. Pat. No. 6,284,783 discloses a method of inducing apoptosis in target cells of a subject by administering, to the subject a pharmaceutically effective amount of at least one compound of the formula:

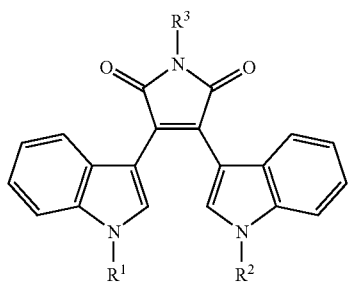

wherein: $R_1$ is hydrogen, $C_1$-$C_{12}$ alkyl, $C_1$-$C_{12}$ substituted alkyl, $C_3$-$C_7$ heterocycle, or $C_3$-$C_7$ substituted heterocycle, $R_2$ and $R_3$ are independently H or $C_1$-$C_{12}$ alkyl, and the pharmaceutically acceptable salts, esters, amides, and prodrugs thereof, wherein following the administration of the compound of Formula I, the target cell is caused to undergo apoptosis.

U.S. Pat. No. 6,316,462 discloses a method of treating cancer in a patient by inducing apoptosis with (1) a farnesyl protein transferase inhibiting amount of a fused-ring tricyclic benzocycloheptapyridine and (2) an additional Ras signaling pathway inhibitor. The farnesyl protein transferase inhibitor has a formula:

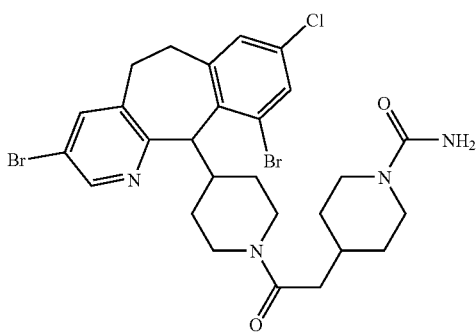

Despite of recent success in designing and identifying compounds that affect apoptosis, there is a continuing search for compounds capable of modulating apoptosis, and effective in treating diseases and disorders.

SUMMARY OF THE INVENTION

The present invention provides pro-apoptotic compounds, compositions and therapeutic treatment processes employing such pro-apoptotic compositions, comprising at least one compound of Formula 1, set forth below.

In particular, compounds of Formula 1 have the structure:

Formula 1

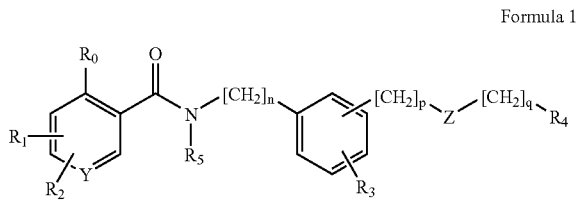

wherein Y is C or N;

Z is selected from the group consisting of a covalent bond, sulfur, i.e., —S—, oxygen, i.e., —O—, amino (e.g., primary, secondary, and tertiary amino), carbonyl, i.e., —CO—,

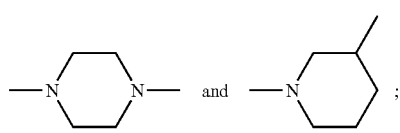

$R_0$ is selected from the group consisting of hydroxy, lower ($C_1$-$C_6$) alkoxy (which can be unsubstituted or substituted, e.g., hydroxyalkoxy, haloalkoxy), nitro, amide (e.g., formamide, acetamide, sulfonamide, alkylsulfonamide, and aryl sulfonamide);

$R_1$ and $R_2$ are positioned at the 3, 4 and/or 5 position (the amide side chain defining the 1 position), and are independently selected from the group consisting of hydrogen, hydrophobic substituents such as halo (e.g., F, Cl, Br, I), nitro, alkyl, aryl, heterocycle, haloalkyl and the like, formamido, formamidoalkyl, and alkoxy substituents, or at the 3 and 4 positions together form a substituted or unsubstituted fused ring having 3, 4, 5, or 6 carbon atoms;

$R_3$ represents from one to four substituents independently selected from the group consisting of hydrogen, hydrophobic substituents such as halo, alkyl (preferably lower ($C_1$-$C_6$) alkyl, haloalkyl, aryl, aralkyl, alkoxy, aryloxy, aralkoxy, a heterocycle, a heterocycle(oxy), or heterocycle(alkyl), cyano, and nitro substituents. Preferably, $R_3$ is haloalkyl (preferably trihaloalkyl, e.g., trifluoromethyl) or haloalkoxy (preferably trihaloalkoxy, e.g., trifluoromethoxy);

$R_4$ represents a substituent selected from the group consisting of hydrogen, alkyl, aryl, alkaryl, cycloalkyl, alkoxy, aryloxy, aralkoxy, heterocycle, heterocycle (oxy), and heterocycle(alkyl) substituents;

$R_5$ represents hydrogen or lower alkyl (e.g., methyl);

n, p and q are the same or different integers selected from the group consisting of 0, 1, 2 or 3.

In another aspect, the present invention provides a pharmaceutical composition comprising a compound of the present invention, or a therapeutically acceptable salt, ester, amide or hydrate thereof, in combination with a pharmaceutically acceptable carrier.

The present invention also provides a method of promoting apoptosis in a mammal in recognized need thereof comprising administering to the mammal, a pharmaceutical composition comprising a compound of the present invention or a pharmaceutically acceptable salt, ester, amide or hydrate thereof. Advantageously, the pharmaceutical composition is administered in an amount sufficient to promote apoptosis and/or to reduce the proliferation of abnormal cells, particularly tumor cells or proliferation of uncontrolled cells.

Another embodiment of the invention comprises the use of a compound of the present invention, or a pharmaceutically acceptable salt, ester or amide or hydrate thereof, in the manufacture of a medicament or pharmaceutical composition comprising the compound, or a therapeutically acceptable salt, ester or amide thereof, for promoting apoptosis in a mammal in recognized need thereof.

In yet another embodiment of the present invention, a method is provided for treating or preventing cancer or neoplastic diseases comprising identifying a mammal, particularly human patient in need of such treatment and administering a compound according to the present invention, or a pharmaceutically acceptable salt, ester, amide or hydrate thereof, or a pharmaceutical composition according to the present invention. Similarly, the compounds and compositions of the present invention can also be used in treating other diseases that benefit from promoting apoptosis, e.g., autoimmune diseases, viral infection, psoriasis, and the like, as discussed in detail below.

The foregoing and other advantages and features of the invention, and the manner in which the same are accomplished, will become more readily apparent upon consideration of the following detailed description of the invention taken in conjunction with the accompanying examples, which illustrate preferred and exemplary embodiments.

DETAILED DESCRIPTION OF THE INVENTION

The present invention provides novel compounds and pharmaceutical compositions which are useful in the treatment of diseases involving apoptosis impairment.

Unless specifically defined otherwise, chemical terms, and substituent names in particular, as used herein, have their normal meaning as understood in the art. The following terms are specifically defined for the sake of clarity.

Unless specifically stated otherwise or indicated by a bond symbol (dash or double dash), the connecting point to a recited group will be on the right-most stated group. Thus, for example, a hydroxyalkyl group is connected to the main structure through the alkyl and the hydroxyl is a substituent on the alkyl.

The term "alkyl," as used herein, represents a group of one to twelve carbon atoms derived from a straight or branched chain saturated hydrocarbon attached to the parent molecular moiety through a carbon atom. The term "lower," as applied to an alkyl or alkyl-containing group herein, means that the alkyl group is formed of one to six carbon atoms derived from a straight or branched chain saturated hydrocarbon. An alkyl group may be unsubstituted, or substituted at one or more substitutable position by one or more groups independently selected from halo (e.g., F, Cl, Br, I), alkoxy, aryloxy, amino, hydroxy, carboxy (e.g., carboxylic acid and esters thereof), nitro, cyano, thiol, alkylthio, aryl, heteroaryl, heterocyclo and carbocyloalkyl, etc. The term "alkoxyalkyl" refers to an alkyl group substituted with an alkoxy group.

The term "alkoxy," as used herein, represents an alkyl group (substituted or unsubstituted) attached to the parent molecular moiety through an oxygen atom, and further includes the alkylenedioxy group, i.e., the group —O-lower-alkyl-O— attached to a parent aryl, cycloalkyl, or heterocycle moiety through both of the oxygen atoms. "Lower alkoxy" refer to such groups containing from one to six carbon atoms, such as methoxy, ethoxy, propoxy, isopropoxy, butoxy, t-butoxy, trifluoromethoxy and the like.

The term "aryl," as used herein, represents a phenyl group or a bicycic or tricyclic fused ring system wherein one or more of the fused rings is a phenyl group. The aryl group can be optionally substituted with one, or a plurality of substituents independently selected from the group consisting of alkoxy, alkyl, arylalkoxy, aryloxy, halo (e.g., F, Cl, Br, I), haloalkoxy, haloalkyl, hydroxy, aralkyl, amino, alkylamino, a heterocycle, a heterocycle(oxy), or heterocycle(alkyl), carboxy (e.g., carboxylic acid and esters thereof), cyano, thiol, nitro substituents and the like.

The term "heteroaryl" as employed herein refers to groups having 5 to 14 ring atoms; 6, 10 or 14 π electrons shared in a cyclic array; and containing carbon atoms and 1 or more oxygen, nitrogen or sulfur heteroactoms.

Useful heteroaryl groups include thienyl (thiophenyl), benzo[b]thienyl, naphtho[2,3-b]thienyl, thianthrenyl, furyl (furanyl), isobenzofuranyl, chromenyl, xanthenyl, phenoxanthiinyl, pyrrolyl, including without limitation 2H-pyrrolyl, imidazolyl, pyrazolyl, pyridyl (pyridinyl), including without limitation 2-pyridyl, 3-pyridyl, and 4-pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalzinyl, naphthyridinyl, quinozalinyl, cinnolinyl, pteridinyl, carbazolyl, β-carbolinyl, phenanthridinyl, acrindinyl, perimidinyl, phenanthrolinyl, phenazinyl, isothiazolyl, phenothiazinyl, isoxazolyl, furazanyl, phenoxazinyl, 1,4-dihydroquinoxaline-2,3-dione, 7-aminoisocoumarin, pyrido[1,2-α]pyrimidin-4-one, pyrazolo[1,5-α]pyrimidinyl, including without limitation pyrazolo[1,5-α]pyrimidin-3-yl, 1,2-benzoisoxazol-3-yl, benzimidazolyl, 2-oxindolyl and 2-oxobenzimidazolyl. Where the heteroaryl group contains a nitrogen atom in a ring, such nitrogen atom may be in the form of an N-oxide, e.g., a pyridyl N-oxide, pyrazinyl N-oxide and pyrimidinyl N-oxide.

The term "aralkyl," as used herein, represents one or more aryl groups attached to one or more carbon atoms of an alkyl group, and being attached to the parent molecular moiety through a carbon atom of the alkyl group.

The term "heteroaralkyl" as used herein, means one or more heteroaryl groups attached to one or more carbon atoms of an alkyl group, and being attached to the parent molecular moiety through a carbon atom of the alkyl group.

The term "aryloxy," as used herein, represents an aryl group attached to the parent molecular moiety through an oxygen atom.

The term "aralkoxy," as used herein, represents at least one aryl group attached to one or more carbon atoms of an alkoxy group, attached to the parent molecular moiety through an oxygen atom.

The term "alkaryloxy," as used herein, represents an alkyl group attached to a carbon atom of an aryloxy group, attached to the parent molecular moiety through an oxygen atom.

The term "cycloalkyl," as used herein, represents a saturated or partially unsaturated ring system having three to twelve carbon atoms and one to three rings (e.g., monocyclic, bridged monocyclic, bicyclic, and spiro rings). Examples of cycloalkyl groups include cyclopropyl, cyclopentyl, bicyclo (3.1.1)heptyl, adamantyl, bicyclohexyl, bicyclooctyl, bicyclononyl, spirononyl and spirodecyl, and the like. The cycloalkyl groups of this invention can be optionally substituted with one, or a plurality of substituents independently selected from the group consisting of alkoxy, alkyl, arylalkoxy, aryloxy, halo, haloalkoxy, haloalkyl, hydroxy, aralkyl, amino, alkylamino, a heterocycle, a heterocycle(oxy), or heterocycle(alkyl), carboxy (e.g., carboxylic acid and esters thereof), cyano, thiol, nitro substituents and the like.

The term "alkanoyl" as used herein refers to an acyl radical derived from an alkanecarboxylic acid, particularly a lower alkanecarboxylic acid, and includes e.g., acetyl, propionyl, butyryl, valeryl, and 4-methylvaleryl.

The term "thiol" means —SH or a substituted thiol which results from substitution of the hydrogen with another suitable group such as alkyl, aryl, alkoxy, arylalkoxy, aryloxy, halo (e.g., F, Cl, Br, I), haloalkoxy, haloalkyl, hydroxy, aralkyl, amino, alkylamino, a heterocycle, a heterocycle (oxy), or heterocycle(alkyl), carboxy (e.g., carboxylic acid and esters thereof), cyano, nitro substituents and the like.

The term "amino" refers to unsubstituted amino (—NH$_2$), primary amino (i.e., mono-substituted amino), and secondary amino (i.e., di-substituted amino) groups. The optional substituents can be independently selected from the group consisting of alkyl (preferably lower alkyl), cycloalkyl, aryl, heteroaryl and heterocyclo, or two substituents in a secondary amino taken together with the nitrogen atom to which they are attached form a heterocyclic ring.

The term "alkylamino" as used herein, represents the group —N(R)$_2$ wherein one or both R groups are the same or different substituted or unsubstituted alkyl group, the alkylamino group being attached to the parent moiety through the nitrogen atom.

The term "amide," as used herein, represents the group, R—C(O)—N(H or alkyl or aryl)-, attached to the parent molecular moiety through the nitrogen atom, wherein R is substituent such as H, lower alkyl, and aryl. The term "formamide," or "formamido," as used herein, represents —NH-CHO attached to the parent moiety through the nitrogen atom.

The term "formamidoalkyl" as used herein, represents HCONH-(alkyl), or HCONH-(lower alkyl), attached to the parent moiety through a carbon atom of the alkyl group.

The term "sulfonamide," as used herein represents the group —SO$_2$NH— attached to the parent moiety through the nitrogen atom, wherein the H on the nitrogen atom can be substituted by e.g., lower alkyl or aryl.

The term "alkylsulfonamide," as used herein, represents (alkyl)-SO$_2$N(H or lower alkyl or aryl), or (lower alkyl)-SO$_2$N(H or lower alkyl or aryl)-, attached to the parent moiety through the nitrogen atom of the sulfonamide group.

The term "arylsulfonamide," as used herein, represents (aryl)-SO$_2$N(H or lower alkyl or aryl)-, attached to the parent moiety through the nitrogen atom of the sulfonamide group.

The term "halo," as used herein, represents F, Cl, Br, or I.

The term "cyano" as used herein, represents the group CN, attached to the parent moiety through the carbon atom.

The term "nitro" as used herein, represents the group NO$_2$ attached to the parent moiety through the nitrogen atom.

The term "haloalkyl" as used herein, represents an alkyl group substituted with one or more halogens (e.g., F, Cl, Br and I), attached to the parent moiety through a carbon atom of the halogen. "Lower haloalkyl" means the halo-substituted alkyl group has 1-6 carbon atoms.

The term "heterocycle," as used herein, represents a saturated or partially unsaturated monocyclic or a bicycic or tricyclic fused ring system having three to twelve carbon atoms and containing one, two or three heteroatoms independently selected from the group consisting of oxygen, nitrogen, and sulfur. The heterocycle group can be optionally substituted with one, or a plurality of substituents independently selected from the group consisting of alkoxy, alkyl, arylalkoxy, aryloxy, halo, haloalkoxy, haloalkyl, hydroxy, aralkyl, amino, alkylamino, a heterocycle, a heterocycle (oxy), or heterocycle(alkyl), cyano, nitro substituents and the like.

The term "heterocycle(oxy)," as used herein, represents an heterocycle group attached to the parent molecular moiety through an oxygen atom.

The term "heterocycle(alkyl)," as used herein, represents an heterocycle group attached to an alkyl group, attached to the parent molecular moiety through a carbon atom of the alkyl group.

The term "hydrophobic substituent" as used herein represents a substituent such as halo, alkyl, lower alkyl, haloalkyl, halo-lower-alkyl, di- or tri-haloalkyl, di- or tri-halo-lower-alkyl, aryl, haloalkyl, or the like which has a substituent hydrophobic parameter such that it increases (renders more hydrophobic) the overall water/octanol partition coefficient of the substituted parent molecule as compared to the unsubstituted parent molecule. The meaning of hydrophobic substituent, substituent hydrophobic parameter, and water/octanol partition coefficient are well known to the skilled artisan.

The term, "EC$_{50}$ cytotoxic response" as used herein, means a concentration of the active compound sufficient to achieve 50% cell death. The EC$_{50}$ cytotoxic response is considered to be pro-apoptotic when a positive apoptotic response can be observed upon examination of the cells under a test protocol designed to discriminate between cells with intact or damaged plasma membranes. One such protocol involves dual annexin V-FITC and propidium iodide (PI) staining. Flipping of phosphatidylserine to the outer leaflet of the plasma membrane is a characteristic of all apoptotic cells. AnnexinV is a serum protein that binds to phosphatidylserine in the presence of the divalent cations (calcium). PI is a DNA stain that is excluded from live cells and is used to discriminate between cells with intact or damaged plasma membranes.

The term "standard incubating conditions" as used herein, means an environment defined by a temperature of 37 degrees Celsius within a humidified chamber containing 5% CO$_2$.

As used herein, the phrase "treating . . . with . . . a compound" means either administering the compound to cells or an animal, or administering to cells or an animal the compound or another agent to cause the presence or formation of the compound inside the cells or the animal. Preferably, the methods of the present invention comprise administering to cells in vitro or to a warm-blood animal, particularly mammal, more particularly a human a pharmaceutical composition comprising an effective amount of a compound according to the present invention.

The present invention provides pro-apoptotic compounds, compositions and therapeutic treatment processes employing such pro-apoptotic compositions, comprising at least one compound of Formula 1, set forth below.

In particular, compounds of Formula 1 have the structure:

Formula 1

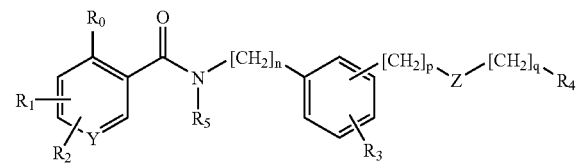

wherein Y is C or N;

Z is selected from the group consisting of a covalent bond, sulfur, i.e., —S—, oxygen, i.e., —O—, amino (e.g., primary, secondary, and tertiary amino), carbonyl, i.e., —CO—,

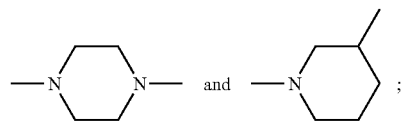

R$_0$ is selected from the group consisting of hydroxy, lower (C$_1$-C$_6$) alkoxy (which can be unsubstituted or substituted, e.g., hydroxyalkoxy, haloalkoxy), nitro, amide (e.g., formamide, acetamide), sulfonamide, alkylsulfonamide, and aryl sulfonamide;

R$_1$ and R$_2$ are positioned at the 3, 4 and/or 5 position (the amide side chain defining the 1 position), and are independently selected from the group consisting of hydrogen, hydrophobic substituents such as halo (e.g., F, Cl, Br, I), nitro, alkyl, aryl, heterocycle, haloalkyl and the like, formamido, formamidoalkyl, and alkoxy substituents, or at the 3 and 4 positions together form a substituted or unsubstituted fused ring having 3, 4, 5, or 6 carbon atoms;

R$_3$ represents from one to four substituents independently selected from the group consisting of hydrogen, hydrophobic substituents such as halo, alkyl (preferably lower (C$_1$-C$_6$) alkyl, haloalkyl, aryl, aralkyl, alkoxy, aryloxy, aralkoxy, a heterocycle, a heterocycle(oxy), or heterocycle(alkyl), cyano, and nitro substituents. Preferably, R$_3$ is haloalkyl (preferably trihaloalkyl, e.g., trifluoromethyl) or haloalkoxy (preferably trihaloalkoxy, e.g., trifluoromethoxy);

R$_4$ represents a substituent selected from the group consisting of haloalkyl, alkyl, aryl, aralkyl, cycloalkyl, alkoxy, aryloxy, aralkoxy, heterocycle, heterocycle (oxy), heteroaralkyl, and heterocycle(alkyl) substituents;

R$_5$ represents hydrogen or lower alkyl (e.g., methyl);

n, p and q are the same or different integers selected from the group consisting of 0, 1, 2 or 3. Preferably n is 0, and at least one of p and q is not 0.

In one preferred embodiment, the pro-apoptotic compounds have the following formula:

Formula 2

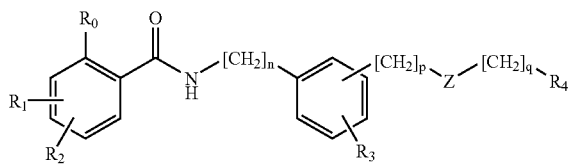

wherein Z is selected from the group consisting of a covalent bond, sulfur, i.e., —S—, oxygen, i.e., —O—, amino (e.g., primary, secondary, and tertiary amino), carbonyl, i.e., —CO—,

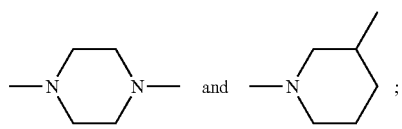

$R_0$ is selected from the group consisting of hydroxy, lower ($C_1$-$C_6$) alkoxy (which can be unsubstituted or substituted, e.g., hydroxyalkoxy, haloalkoxy), nitro, amide (e.g., formamide, acetamide, sulfonamide, alkylsulfonamide, and aryl sulfonamide);

$R_1$ and $R_2$ are positioned at the 3, 4 and/or 5 position (the amide side chain defining the 1 position), and are independently selected from the group consisting of hydrogen, hydrophobic substituents such as halo (e.g., F, Cl, Br, I), nitro, alkyl, aryl, heterocycle, haloalkyl and the like, formamido, formamidoalkyl, and alkoxy substituents, or at the 3 and 4 positions together form a substituted or unsubstituted fused ring;

$R_3$ represents from one to four substituents independently selected from the group consisting of hydrogen, hydrophobic substituents such as halo, alkyl (preferably lower ($C_{1-6}$) alkyl, haloalkyl, aryl, aralkyl, alkoxy, aryloxy, aralkoxy, a heterocycle, a heterocycle(oxy), or heterocycle(alkyl), cyano, and nitro substituents. Preferably, $R_3$ is haloalkyl (preferably trihaloalkyl, e.g., trifluoromethyl) or haloalkoxy (preferably trihaloalkoxy, e.g., trifluoromethoxy);

$R_4$ represents a substituent selected from the group consisting of haloalkyl, alkyl, aryl, alkaryl, cycloalkyl, alkoxy, aryloxy, aralkoxy, heterocycle, heterocycle(oxy), and heterocycle(alkyl) substituents. In preferred embodiments, $R_4$ represents haloalkyl, e.g., halo-substituted lower alkyl (preferably trihalo lower alkyl, e.g., trifluoromethyl); alkoxyalkoxy (including halo-substituted alkoxyalkoxy); $R_8$ as defined below; and $R_8$-Ak- or ($R_8R_9$)Ak-, wherein Ak is lower alkyl with a straight or branched chain substituted with $R_8$, or $R_8$ and $R_9$, $R_8$ and $R_9$ are independently selected from (1) cycloalkyl, (2) aryl such as benzene and naphthalene, (3) aryloxy, (4) a saturated or partially unsaturated or aromatic moncyclic 3, 4, 5, 6, or 7-membered heterocycle containing one or more N, O, or S, or (5) a saturated or partially unsaturated or aromatic biocyclic 8 to 12-membered heterocycle containing one or more N, O, or S, wherein the rings of the cycloalkyl, aryloxy, aryl and heterocycle may be substituted by one or more identical or different substituents selected from lower alkyl, halo, haloalkyl (e.g., halo-substituted lower alkyl, preferably trihalo lower alkyl, e.g., trifluoromethyl), alkoxy, alkoxyalkoxy, ($C_{1-6}$)-alkyl-O—C(O)—, ($C_{1-6}$)-alkyl-O—C(O)—($C_{1-3}$)-alkyl-, ($C_{1-6}$)-alkyl-O—C(O)—($C_{1-3}$)-alkene-, alkylsulfonyl (e.g., lower alkyl-$SO_2$—), halo-substituted lower alkoxy (preferably trihalo lower alkoxy, e.g., trifluoromethoxy), and halo-substituted aryl; and n, p and q are the same or different integers selected from the group consisting of 0, 1, 2 or 3. Preferably n is 0, and at least one of p and q is not 0.

In one preferred embodiment, the pro-apoptotic compositions of Formula 2, and therapeutic treatment processes employing same, comprise a compound of Formula 2a, set forth below:

Formula 2a

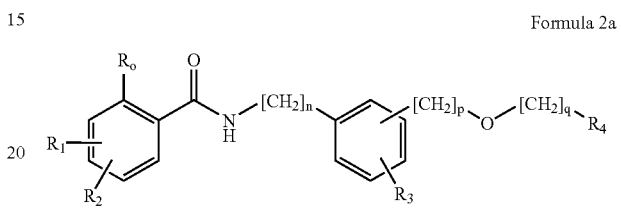

wherein $R_0$, $R_1$, $R_2$, $R_3$, $R_4$, n, p, and q have the same meanings as set forth above.

In another preferred embodiment, the pro-apoptotic compositions of Formula 2, and therapeutic treatment processes employing same, comprise a compound of Formula 1b, set forth below:

Formula 2b

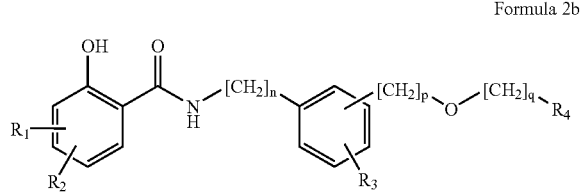

wherein $R_1$, $R_2$, $R_3$, $R_4$, n, p, and q have the same meanings as set forth above.

In another preferred embodiment, the pro-apoptotic compositions of Formula 2, and therapeutic treatment processes employing same, comprise a compound of Formula 2c, set forth below;

Formula 2c

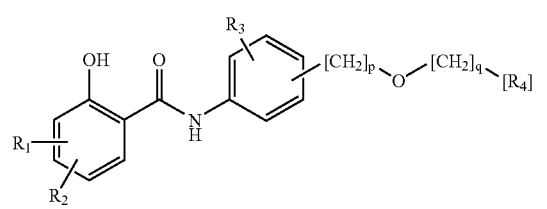

wherein $R_1$, $R_2$, $R_3$, $R_4$, p, and q have the same meanings as set forth above.

In another preferred embodiment, the pro-apoptotic compositions of Formula 2, and therapeutic treatment processes employing same, comprise a compound of Formula 2d, set forth below:

Formula 2d

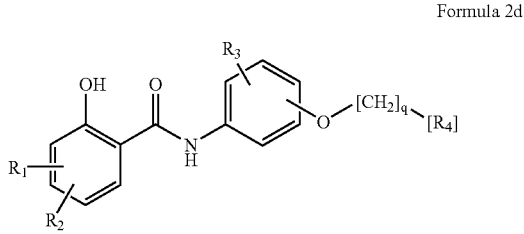

wherein $R_1$, $R_2$, $R_3$, $R_4$, and q have the same meanings as set forth above.

In yet another preferred embodiment, the pro-apoptotic compositions of Formula 2, and therapeutic treatment processes employing same, comprise a compound of Formula 2e, set forth below:

Formula 2e

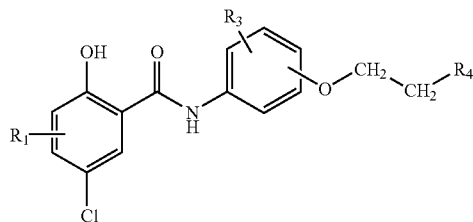

wherein $R_1$, $R_3$, and $R_4$, have the same meanings as set forth above.

In yet another preferred embodiment, the pro-apoptotic compositions of Formula 2, and therapeutic treatment processes employing same, comprise a compound of Formula 2f, set forth below:

Formula 2f

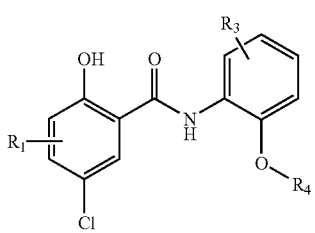

wherein $R_1$, $R_3$, and $R_4$, have the same meanings as set forth above. In a more preferred embodiment $R_3$ represents halo, haloalkyl, cyano or nitro. Even more preferably, $R_3$ trihalomethyl, halo or nitro. It is also preferred that $R_3$ is positioned para to —O—$R_4$.

In another preferred embodiment, the pro-apoptotic compositions of Formula 2, and therapeutic treatment processes employing same, comprise a compound of Formula 2g, set forth below:

Formula 2g

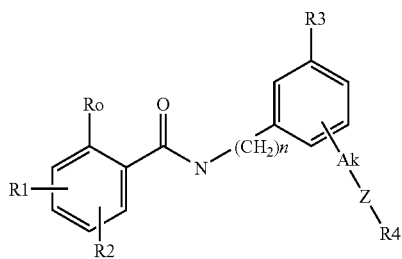

wherein

Z is oxygen, amino, sulfur,

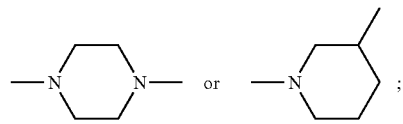

n is an integer of 0, 1, 2, or 3;

Ak is lower alkyl;

$R_0$ is hydroxy, lower ($C_1$-$C_6$) alkoxy, hydroxyalkoxy (e.g. hydroxymethoxy, hydroxyethoxy), nitro;

$R_1$ and $R_2$ are independently selected from hydrogen, halo, nitro, alkoxy, aryl, heterocycle, halo-substituted lower alkyl (preferably trihalo lower alkyl, e.g., trifluoromethyl), wherein $R_1$ and $R_2$ are not both hydrogen at the same time;

$R_3$ is halo, halo-substituted lower alkyl (preferably trihalo lower alkyl, e.g., trifluoromethyl), or haloalkoxy (preferably halo-substituted $C_1$-$C_6$ alkoxy, e.g., trihalo-substituted methoxy); and $R_4$ represents haloalkyl, e.g., halo-substituted lower alkyl (preferably trihalo lower alkyl, e.g., trifluoromethyl); alkoxyalkoxy (including halo-substituted alkoxyalkoxy); $R_8$ as defined below; and $R_8$-Ak- or ($R_8R_9$)-Ak-, wherein Ak is lower alkyl with a straight or branched chain, $R_8$ and $R_9$ are independently selected from (1) cycloalkyl, (2) aryl such as benzene and naphthalene, (3) aryloxy, (4) a saturated or partially unsaturated or aromatic moncyclic 3, 4, 5, 6, or 7-membered heterocycle containing one or more N, O, or S, or (5) a saturated or partially unsaturated or aromatic biocyclic 8 to 12-membered heterocycle containing one or more N, O, or S, wherein the rings of the cycloalkyl, aryloxy, aryl and heterocycle may be substituted by one or more identical or different substituents selected from lower alkyl, halo, haloalkyl (e.g., halo-substituted lower alkyl, preferably trihalo lower alkyl, e.g., trifluoromethyl), alkoxy, alkoxyalkoxy, ($C_{1-6}$)-alkyl-O—C-(O)-, ($C_{1-6}$)-alkyl-O—C(O)—($C_{1-3}$)-alkyl-, ($C_{1-6}$)-alkyl-O—C(O)—($C_{1-3}$)-alkene-, alkylsulfonyl (e.g., lower alkyl-$SO_2$—), halo-substituted lower alkoxy (preferably trihalo lower alkoxy, e.g., trifluoromethoxy), and halo-substituted aryl.

In a specific embodiment, the compounds of present invention have a formula:

Formula 2h

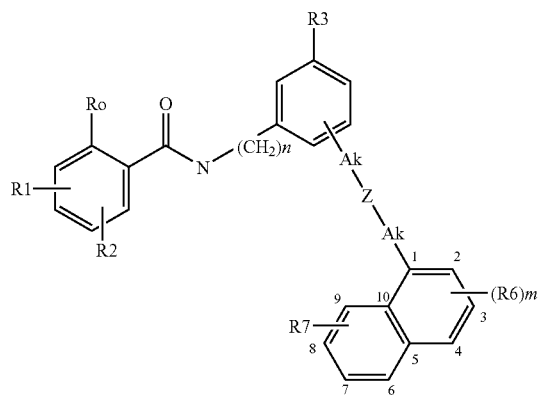

wherein
Z is oxygen, amino or sulfur;
n is an integer of 0, 1, 2, or 3;
Ak is lower alkyl;
$R_0$ is hydroxy, lower ($C_1$-$C_6$) alkoxy, hydroxyalkoxy, nitro, amide, sulfonamide, alkylsulfonamide, or aryl sulfonamide;
$R_1$ is hydrogen, halo, nitro, alkoxy, alkyl, aryl, heterocycle, haloalkyl, or amide;
$R_2$ is halo;
$R_3$ is halo, haloalkyl, or haloalkoxy;
$R_5$ is hydrogen or lower alkyl, preferably hydrogen;
$R_6$ is independently selected from F, Cl, Br, and I;
$R_7$ is hydrogen, halo, lower alkyl, alkoxy, or haloalkyl; and m is 1, 2, or 3, wherein all $R_6$ groups are positioned para, meta, or ortho to the group -Z-, i.e., at positions 2, 3, and/or 4. In specifically preferred embodiment, m is 1, $R_6$ is positioned para to -Z-, i.e., at position 4.

In another preferred embodiment, the pro-apoptotic compositions of Formula 2, and therapeutic treatment processes employing same, comprise a compound of Formula 2h, set forth below:

Formula 2i

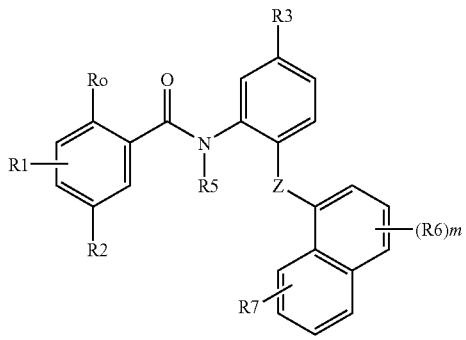

wherein Z is oxygen or amino or sulfur, preferably O, S or NH; $R_0$ is hydroxy, lower ($C_1$-$C_6$) alkoxy, hydroxyalkoxy, nitro, amide, sulfonamide, alkylsulfonamide, or aryl sulfonamide, and preferably is hydroxy; $R_1$ is H, halo, nitro, alkoxy, alkyl, aryl, heterocycle, haloalkyl, or amide, and preferably is H; $R_2$ is halo; $R_3$ is halo, haloalkyl, or haloalkoxy; $R_5$ is H or lower alkyl, preferably H; $R_6$ is independently selected from F, Cl, Br, and I; $R_7$ is H, halo, lower alkyl, alkoxy, or haloalkyl; and m is 1, 2, or 3, wherein all $R_6$ groups are positioned para, meta, or ortho to the group -Z-. In specifically preferred embodiment, m is 1, and $R_6$ is positioned para to -Z-.

In another preferred embodiment, the pro-apoptotic compositions of Formula 2, and therapeutic treatment processes employing same, comprise a compound of Formula 2j, set forth below:

Formula 2j

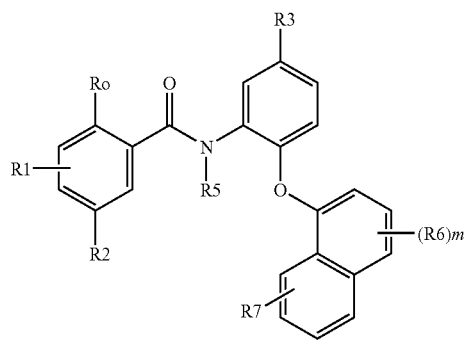

wherein $R_0$ is hydroxy, lower ($C_{1-6}$) alkoxy, hydroxyalkoxy, nitro, amide, sulfonamide, alkylsulfonamide, or aryl sulfonamide, and preferably is hydroxy; $R_1$ is H, halo, nitro, alkoxy, alkyl, aryl, heterocycle, haloalkyl, or amide, and preferably is H; $R_2$ is halo; $R_3$ is halo, halo-substituted lower alkyl (preferably trihalo lower alkyl, e.g., trifluoromethyl), or haloalkoxy (preferably halo-substituted $C_1$-$C_6$ alkoxy, e.g., trihalo-substituted methoxy);
$R_5$ is H or lower alkyl, preferably H; $R_6$ is independently selected from F, Cl, Br, and I;
$R_7$ is H, halo, lower alkyl, alkoxy, or haloalkyl; and m is 1, 2, or 3, wherein all $R_6$ groups are positioned para, meta, or ortho to the group —O—. In specifically preferred embodiments, m is 1, $R_6$ is positioned para to -O-.

In another preferred embodiment, the pro-apoptotic compositions of Formula 2, and therapeutic treatment processes employing same, comprise a compound of Formula 2k, set forth below:

Formula 2k

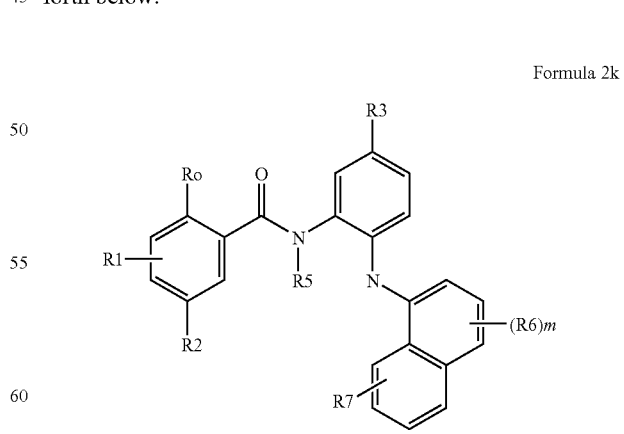

wherein $R_0$ is hydroxy, lower ($C_1$-$C_6$) alkoxy, hydroxyalkoxy, nitro, amide, sulfonamide, alkylsulfonamide, or aryl sulfonamide; $R_1$ is hydrogen, halo, nitro, alkoxy, alkyl, aryl, heterocycle, haloalkyl, or amide; $R_2$ is halo; $R_3$ is halo, halo-substituted lower alkyl (preferably trihalo lower alkyl, e.g., trifluoromethyl), or haloalkoxy (preferably halo-substituted $C_1$-$C_6$ alkoxy, e.g., trihalo-substituted methoxy); $R_5$ is hydrogen or lower alkyl, preferably hydrogen; $R_6$ is independently selected from F, Cl, Br, and I; $R_7$ is hydrogen, halo, lower alkyl, alkoxy, or haloalkyl; and m is 1, 2, or 3, wherein all $R_6$ groups are positioned para, meta, or ortho to the group —NH—. In specifically preferred embodiment, m is 1, $R_6$ is positioned para to —NH—.

In particularly preferred embodiments according to each and every embodiment and aspect of the invention as set forth above, Z is advantageously oxygen.

In additional particularly preferred embodiments according to each and every embodiment and aspect of the invention as set forth above, at least one of $R_1$ and $R_2$ is halo, more preferably, chloro, and more preferably a chloro substituent positioned para to $R_0$ (in formulas 1 and 1a) or to the hydroxy group (in Formulas 2b, 2c, 2d, 2e, and 2f).

In additional particularly preferred embodiments according to each and every embodiment and aspect of the invention as set forth above, in Formulas 2b, 2c, 2d, 2e, and 2f, $R_3$ represents an alkylhalo, halo, nitro or cyano substituent; and it is independently and concurrently preferred that $R_3$ is positioned para to the group containing $R_4$; and it is independently and concurrently preferred that p is zero.

In additional particularly preferred embodiments according to each and every embodiment and aspect of the invention as set forth above, at least one of $R_1$, $R_2$, $R_3$, $R_4$, is or comprises trihalomethyl, more preferably, trifluoromethyl.

In one embodiment, the compounds useful in the method of the present invention have a structure according to Formula 2L:

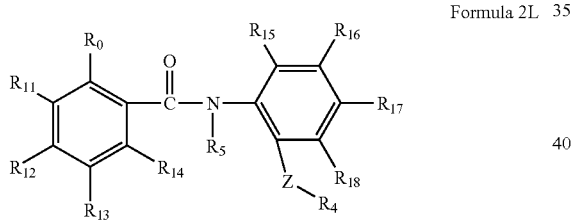

Formula 2L or pharmaceutically acceptable salts thereof, wherein,
$R_0$ is hydroxyl;
Z is O, N($R^z$) ($R^z$ is H or $C_{1-6}$ alkyl), or S, preferably O or N($R^z$), and more preferably O;
$R_5$ is H or $C_{1-6}$ alkyl;
$R_{11}$-$R_{18}$ are independently selected from
 (a) H, halo, $N_3$, nitro, hydroxy, thiol, sulfone, and CN,
 (b) $C_{1-6}$ alkyl, $C_{2-6}$ alkenyl, $C_{2-6}$ alkynyl, $C_{1-6}$ alkoxy, $C_{1-6}$ alkylthiol, $C_{2-6}$ alkenyloxy, $C_{2-6}$ alkynyloxy, $C_{1-6}$ haloalkyl, $C_{1-6}$ hydroxyalkyl, —($C_{1-6}$ alkyl-O—$C_{1-6}$ alkyl, $C_{1-6}$ alkylsulfonyl (i.e., —$SO_2$—$C_{1-6}$ alkyl), $C_{1-6}$ alkylsulfonamide, each of which being optionally substituted with 1-3 substituents wherein each substituent is independently halo, $N_3$, nitro, hydroxy, thiol, —CN, $C_{1-6}$ alkyl, $C_{1-6}$ haloalkyl, $C_{1-6}$ alkoxy, N($R^{50}$)($R^{51}$), —N($R^{50}$)C(=O)$R_{40}$, —N($R^{50}$)C(=O)N($R^{54}$)$R^{51}$), —C(=O)N($R^{50}$)($R^{51}$), —OC(=O)N($R^{50}$)($R^{51}$), —C(=O)$R_{40}$, —OC(=O)$R_{40}$, —C(=$G^1$)$R_{40}$, —$G^2$C(=$G^1$)$R_{40}$, —($R^{50}$)$G^2$C(=$G^1$)$R_{40}$, —C(=$G^1$)$G^2R_{41}$ or —$G^3$C(=$G^1$)$G^2R_{41}$,
 (c) carbocycle, heterocycle, aryl, and heteroaryl, each of which being optionally substituted with 1-3 substituents wherein each substituent is independently halo, $N_3$, nitro, hydroxy, thiol, sulfone, CN, $C_{1-6}$ alkyl, $C_{1-6}$ haloalkyl, $C_{1-6}$ alkoxy, $C_{1-6}$ hydroxyalkyl, $C_{1-6}$ alkylsulfonyl (i.e., —$SO_2$—$C_{1-6}$ alkyl), $C_{1-6}$ alkylsulfonamide, —N($R^{52}$)($R^{53}$), —N($R^{52}$)C(=O)$R_{42}$, —N($R^{52}$)C(=O)N($R^{55}$)($R^{53}$), —C(=O)N($R^{52}$)($R^{53}$), —OC(=O)N($R^{52}$)($R^{53}$), —C(=O)$R_{42}$, —OC(=O)$R_{42}$, —C(=$G^1$)$R_{42}$, —$G^2$C(=$G^1$)$R_{42}$, —$R^{52}$$G^2$C(=$G^1$)$R_{42}$, —C(=$G^1$)$G^2R_{43}$, or —$G^4$C(=$G^1$)$G^2R_{43}$,
 (d) —N($R^{50}$)($R^{51}$), —N($R^{50}$)C(=O)$R_{40}$, —N($R^{50}$)C(=O)N($R^{54}$)($R^{51}$), —C(=O)N($R^{50}$)($R^{51}$), —OC(=O)N($R^{50}$)($R^{51}$), —C(=O)$R_{40}$, —OC(=O)$R_{40}$, —C(=$G^1$)$R_{40}$, —$G^2$C(=$G^1$)$R_{40}$, —$R^{50}$$G^2$C(=$G^1$)$R_{40}$, —C(=$G^1$)$G^2R_{41}$ or —$G^3$C(=$G^1$)$G^2R_{41}$;

$R_4$ represents haloalkyl, e.g., halo-substituted lower alkyl (preferably trihalo lower alkyl, e.g., trifluoromethyl); ($C_{2-6}$ alkoxy)$C_{2-6}$ alkyl; -Ak-O—$R_8$; -Ak-$R_8$ or -Ak($R_8R_9$), wherein Ak is lower alkyl with a straight or branched chain, $R_8$ and $R_9$ are independently selected from (1) cycloalkyl, (2) aryl (e.g., benzene and naphthalene), (3) heterocycle, e.g., a saturated or partially unsaturated moncyclic 3, 4, 5, 6, or 7-membered heterocycle containing one or more N, O, or S, or (4) heteroaryl, e.g., a monocyclic or biocyclic 6 to 12-membered aromatic ring or fused ring containing one or more N, O, or S; each of $R_4$ being optionally substituted by one or more, e.g., 1-5, substituents independently selected from
 (a) H, halo, $N_3$, nitro, hydroxy, thiol, sulfone, and CN,
 (b) $C_{1-6}$ alkyl, $C_{2-6}$ alkenyl, $C_{2-6}$ alkynyl, $C_{1-6}$ alkoxy, $C_{1-6}$ alkylthiol, $C_{2-6}$ alkenyloxy, $C_{2-6}$ alkynyloxy, $C_{1-6}$ haloalkyl, $C_{1-6}$ hydroxyalkyl, $C_{1-6}$ alkyl-O—$C_{1-6}$ alkyl-, $C_{1-6}$ alkylsulfonyl (i.e., $C_{1-6}$ alkyl-$SO_2$—), $C_{1-6}$ alkylsulfonamide, each of which being optionally substituted with 1-3 substituents wherein each substituent is independently halo, $N_3$, nitro, hydroxy, thiol, —CN, $C_{1-6}$ alkyl, $C_{1-6}$ haloalkyl, $C_{1-6}$ alkoxy, carbocycle, heterocycle, aryl, heteroaryl, —N($R^{50}$)($R^{51}$), —N($R^{50}$)C(=O)$R_{40}$, —N($R^{50}$)C(=O)N($R^{54}$)($R^{51}$), —C(=O)N($R^{50}$)($R^{51}$), —OC(=O)N($R^{50}$)($R^{51}$), —C(=O)$R_{40}$, —OC(=O)$R_{40}$, —C(=$G^1$)$R_{40}$, —$G^2$C(=$G^1$)$R_{40}$, —($R^{50}$)$G^2$C(=$G^1$)$R_{40}$, —C(=$G^1$)$G^2R_{41}$ or —$G^3$C(=$G^1$)$G^2R_{41}$,
 (c) carbocycle, heterocycle, aryl, heteroaryl, carbocycloxy, heterocycloxy, aryloxy, heteroaryloxy, each of which being optionally substituted with 1-3 substituents wherein each substituent is independently halo, $N_3$, nitro, hydroxy, thiol, sulfone, CN, $C_{1-6}$ alkyl, $C_{1-6}$ haloalkyl, $C_{1-6}$ alkoxy, $C_{1-6}$ hydroxyalkyl, $C_{1-6}$ alkylsulfonyl (i.e., $C_{1-6}$ alkyl-$SO_2$—), $C_{1-6}$ alkylsulfonamide, carbocycle, heterocycle, aryl, heteroaryl, —N($R^{52}$)($R^{53}$), —N($R^{52}$)C(=O)$R_{42}$, —N($R^{52}$)C(=O)N($R^{55}$)($R^{53}$), —C(=O)N($R^{52}$)($R^{53}$), —OC(=O)N($R^{52}$)($R^{53}$), —C(=O)$R_{42}$, —OC(=O)$R_{42}$, —C(=$G^1$)$R_{42}$, —$G^2$C(=$G^1$)$R_{42}$, —$R^{52}$$G^2$C(=$G^1$)$R_{42}$, —C(=$G^1$)$G^2R_{43}$, or —$G^4$C(=$G^1$)$G^2R_{43}$,
 (d) —N($R^{50}$)($R^{51}$), —N($R_{50}$)C(=O)$R_{40}$, —N($R^{50}$)C(=O)N($R^{54}$)($R^{51}$), —C(=O)N($R^{50}$)($R^{51}$), —OC(=O)N$^{50}$)($R^{51}$), C(=O)$R_{40}$, —C(=O)$R_{40}$, —OC(=O)$R_{40}$, —C(=$G^1$)$R_{40}$, —$G^2$C(=$G^1$)$R_{40}$, —($R^{50}$)$G^2$C(=$G^1$)$R_{40}$, —C(=$G^1$)$G^2R_{41}$ or —$G^3$C(=$G^1$)$G^2R_{41}$;

$G^1$ is S or N; $G^2$ and $G^3$ are independently S or N($R^{50}$); $G^4$ is N($R^{52}$);

$R_{40}$ is selected from: H, —OH, $C_{1-6}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy and $C_{1-6}$ alkylthiol, wherein $R_{40}$ is optionally substituted with from one to three substituents independently selected from halo, $N_3$, nitro, hydroxy, thiol, CN, $C_{1-6}$ alkyl;

$R_{41}$ is H, $C_{1-6}$ alkyl, $C_{2-6}$ alkenyl or $C_{2-6}$ alkynyl, wherein $R_4$ is optionally substituted with from one to three substituents independently selected from halo, $N_3$, nitro, hydroxy, thiol, CN, $C_{1-6}$ alkyl;

$R_{42}$ is selected from: H, —OH, $C_{1-6}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy, and $C_{1-6}$ alkylthiol, wherein $R_{42}$ is optionally substituted with from one to three substituents independently selected from halo, $N_3$, nitro, hydroxy, thiol, CN and $C_{1-6}$ alkyl;

$R_{43}$ is H, $C_{1-6}$ alkyl, $C_{2-6}$ alkenyl or $C_{2-6}$ alkynyl, wherein $R_{43}$ is optionally substituted with from one to three substituents independently selected from halo, $N_3$, nitro, hydroxy, thiol, CN and $C_{1-6}$ alkyl;

$R^{50}$, $R^{51}$ and $R^{54}$ are independently H, OH($R^{50}$ and $R^{51}$ are not both OH), $C_{1-10}$ alkyl, $C_{2-10}$ alkenyl, $C_{2-10}$ alkynyl, $C_{1-10}$ alkoxy, $C_{1-10}$ alkylthiol, $C_{2-10}$ alkenyloxy, $C_{2-10}$ alkynyloxy, $C_{1-10}$ haloalkyl, $C_{2-6}$ hydroxyalkyl, $C_{1-6}$ alkyl-O—$C_{1-6}$ alkyl-, wherein $R^{50}$ and $R^{51}$ each is optionally substituted with 1-3 substituents wherein each substituent is independently halo, $N_3$, nitro, hydroxy, thiol, CN, $C_{1-6}$ alkyl, $C_{1-6}$ haloalkyl, $C_{1-6}$ alkoxy, —C(=O)N($R^{54}$)($R^{55}$), $R_{44}$C(=O)— or —N($R^{54}$)($R^{55}$), wherein $R^{54}$ and $R^{55}$ are independently H, OH or $C_{1-4}$ alkyl, and wherein $R_{44}$ is H or $C_{1-4}$ alkyl; and $R^{52}$, $R^{53}$ and $R^{55}$ are independently H, OH($R^{52}$ and $R^{53}$ are not both OH), $C_{1-10}$ alkyl, $C_{2-10}$ alkenyl, $C_{2-10}$ alkynyl, $C_{1-10}$ alkoxy, $C_{1-10}$ alkylthiol, $C_{2-10}$ alkenyloxy, $C_{2-10}$ alkynyloxy, $C_{1-10}$ haloalkyl, $C_{2-6}$ hydroxyalkyl, $C_{1-6}$ alkyl-O—$C_{1-6}$ alkyl-, or $R^{52}$ and $R^{53}$ together with the nitrogen atom to which they are both linked form a 3, 4, 5 or 6-membered heterocycle (e.g., piperidinyl, pyrrolidinyl, and morpholinyl), wherein $R^{52}$ and $R^{53}$ each is optionally substituted with 1-3 substituents wherein each substituent is independently halo, $N_3$, nitro, hydroxy, thiol, CN, $C_{1-6}$ alkyl, $C_{1-6}$ haloalkyl, $C_{1-6}$ alkoxy, —C(=O)N($R^{54}$)($R^{55}$), $R_{44}$C(=O)— or —N($R^{54}$)($R^{55}$), wherein $R^{54}$ and $R^{55}$ are independently H, OH or $C_{1-4}$ alkyl, and wherein $R_{44}$ is H or $C_{1-4}$ alkyl.

In preferred embodiments of the compounds of Formula 2L,

Z is O, —$NR^z$ ($R^z$ is H or $C_{1-4}$ alkyl), or S, preferably O;

$R_4$ is $C_{1-6}$ haloalkyl, —$R^{31}$—W—$R^{32}$ or —$R^{31}$—$R^{33}$;

$R^{31}$ is $C_{2-6}$ alkyl optionally substituted with an aryl group;

W is O, —$NR^z$ ($R^z$ is H or $C_{1-4}$ alkyl), or S, preferably O;

$R^{32}$ is (a) $C_{2-6}$ alkyl optionally substituted with 1-3 substituents selected from halo, $C_{2-6}$ alkyoxy, or (b) phenyl optionally substituted with halo;

$R^{33}$ is cycloalkyl, heterocycle, aryl or heteroaryl, each of which being optionally substituted with one to three substituents selected from halo, $C_{1-6}$ alkyl, $C_{1-6}$ haloalkyl (e.g., trifluoromethyl), $C_{1-6}$ alkoxy, $C_{1-6}$ haloalkoxy (e.g., trifluoromethoxy), $C_{1-6}$ alkylsulfonyl (i.e., —$SO_2$—$C_{1-6}$ alkyl), —$R^{34}$—C(=O)$R^{35}$, —OC(=O)$R_{34}$, —N($R^{36}$)($R^{37}$) and aryl;

$R^{34}$ is $C_{1-6}$ alkyl; $R^{35}$ is $C_{1-6}$ alkoxy; and $R^{36}$ and $R^{37}$ are independently H or $C_{1-6}$ alkyl.

In a more preferred embodiment, the compounds of Formula 2L have the following structure:

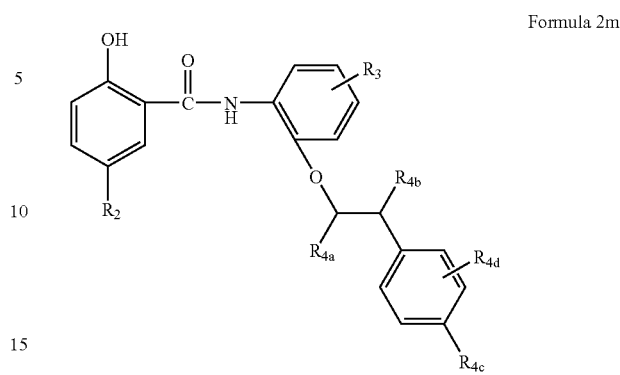

Formula 2m or pharmaceutically acceptable salts thereof, wherein, $R_2$ and $R_3$ are independently halo (preferably F or Cl) or $C_{1-6}$ haloalkyl (preferably trifluoromethyl);

$R_{4a}$ and $R_{4b}$ are independently $C_{1-6}$ alkyl;

$R_{4c}$ is halo or $C_{1-4}$ haloalkyl; and $R_{4d}$ is H or halo. Preferably, $R_3$ is at the para position to the —O—.

In specific embodiments, the compounds are selected from the following:

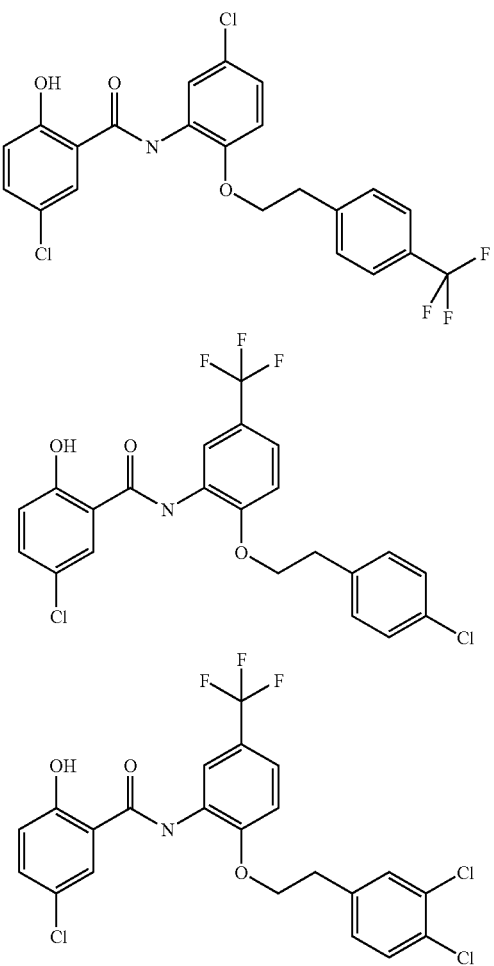

-continued

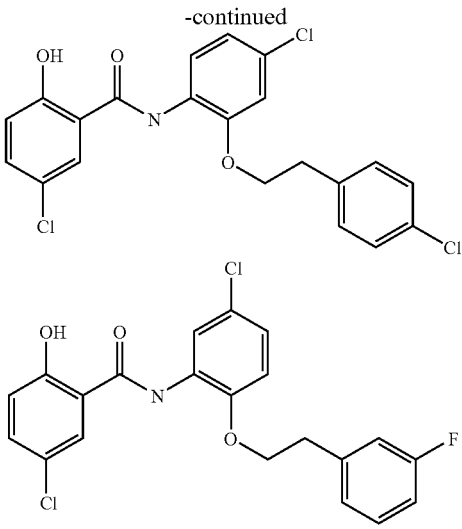

In accordance with another embodiment, the compounds useful in the present invention are according to Formula 2n:

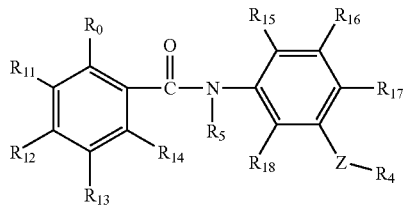

Formula 2n or pharmaceutically acceptable salts thereof, wherein,
$R_0$ is hydroxyl;
Z is O, $N(R^z)$ ($R^z$ is H or $C_{1-6}$ alkyl), or S, preferably O or $N(R^z)$, and more preferably O;
$R_5$ is H or $C_{1-6}$ alkyl;
$R_{11}$-$R_{18}$ are independently selected from
(a) H, halo, $N_3$, nitro, hydroxy, thiol, sulfone, and CN,
(b) $C_{1-6}$ alkyl, $C_{2-6}$ alkenyl, $C_{2-6}$ alkynyl, $C_{1-6}$ alkoxy, $C_{1-6}$ alkylthiol, $C_{2-6}$ alkenyloxy, $C_{2-6}$ alkynyloxy, $C_{1-6}$ haloalkyl, $C_{1-6}$ hydroxyalkyl, —$C_{1-6}$ alkyl-O—$C_{1-6}$ alkyl, $C_{1-6}$ alkylsulfonyl (i.e., —$SO_2$—$C_{1-6}$ alkyl), $C_{1-6}$ alkylsulfonamide, each of which being optionally substituted with 1-3b substituents wherein each substituent is independently halo, $N_3$, nitro, hydroxy, thiol, CN, $C_{1-6}$ alkyl, $C_{1-6}$ haloalkyl, $C_{1-6}$ alkoxy, —$N(R^{50})(R^{51})$, —$N(R^{50})C(=O)R_{40}$, —$N(R^{50})C(=O)N(R^{54})(R^{51})$, —$C(=O)N(R^{50})(R^{51})$, —$OC(=O)N(R^{50})(R^{51})$, —$C(=O)R_{40}$, —$OC(=O)R_{40}$, —$C(=G^1)R_{40}$, —$G^2C(=G^1)R_{40}$, —$(R^{50})G^2C(=G^1)R_{40}$, —$C(=G^1)G^2R_{41}$ or —$G^3C(=G^1)G^2R_{41}$,
(c) carbocycle, heterocycle, aryl, and heteroaryl, each of which being optionally substituted with 1-3 substituents wherein each substituent is independently halo, $N_3$, nitro, hydroxy, thiol, sulfone, CN, $C_{1-6}$ alkyl, $C_{1-6}$ haloalkyl, $C_{1-6}$ alkoxy, $C_{1-6}$ hydroxyalkyl, $C_{1-6}$ alkylsulfonyl (i.e., —$SO_2$—$C_{1-6}$ alkyl), $C_{1-6}$ alkylsulfonamide, —$N(R^{52})(R^{53})$, —$N(R^{52})C(=O)R_{42}$, —$N(R^{52})C(=O)N(R^{55})(R^{53})$, —$C(=O)N(R^{52})(R^{53})$, —$OC(=O)N(R^{52})(R^{53})$, —$C(=O)R_{42}$, —$OC(=O)R_{42}$, —$C(=G^1)R_{42}$, —$G^2C(=G^1)R_{42}$, —$R^{52})G^2C(=G^1)R_{42}$, —$C(=G^1)G^2R_{43}$, or —$G^4C(=G^1)G^2R_{43}$,
(d) —$N(R^{50})(R^{51})$, —$N(R^{50})C(=O)R_{40}$, —$N(R^{50})C(=O)N(R^{54})(R^{51})$, —$C(=O)N(R^{50})(R^{51})$, —$OC(=O)N(R^{50})(R^{51})$, —$C(=O)R_{40}$, —$OC(=O)R_{40}$, —$C(=G^1)R_{40}$, —$G^2C(=G^1)R_{40}$, —$(R^{50})G^2C(=G^1)R_{40}$, —$C(=G^1)G^2R_{41}$ or —$G^3C(=G^1)G^2R_{41}$;
$R_4$ represents haloalkyl, e.g., halo-substituted lower alkyl (preferably trihalo lower alkyl, e.g., trifluoromethyl); ($C_{2-6}$ alkoxy)$C_{2-6}$ alkyl; -Ak-O—$R_8$; -Ak-$R_8$ or -Ak($R_8R_9$), wherein Ak is lower alkyl with a straight or branched chain, and preferably $C_{2-6}$ alkyl, $R_8$ and $R_9$ are independently selected from (1) cycloalkyl, (2) aryl (e.g., benzene and naphthalene), (3) heterocycle, e.g., a saturated or partially unsaturated monocyclic 3, 4, 5, 6, or 7-membered heterocycle containing one or more N, O, or S, or (4) heteroaryl, e.g., a monocyclic or bicyclic 6 to 12-membered aromatic ring or fused ring containing one or more N, O, or S; each of the $R_4$ moieties being optionally substituted by one or more, e.g., 1-5, substituents independently selected from
(a) halo, $N_3$, nitro, hydroxy, thiol, sulfone, and CN,
(b) $C_{1-6}$ alkyl, $C_{2-6}$ alkenyl, $C_{2-6}$ alkynyl, $C_{1-6}$ alkoxy, $C_{1-6}$ alkylthiol, $C_{2-6}$ alkenyloxy, $C_{2-6}$ alkynyloxy, $C_{1-6}$ haloalkyl, $C_{1-6}$ hydroxyalkyl, $C_{1-6}$ alkyl-O—$C_{1-6}$ alkyl-, $C_{1-6}$ alkylsulfonyl (i.e., —$SO_2$—$C_{1-6}$ alkyl), $C_{1-6}$ alkylsulfonamide, each of which being optionally substituted with 1-3 substituents wherein each substituent is independently halo, $N_3$, nitro, hydroxy, thiol, CN, $C_{1-6}$ alkyl, $C_{1-6}$ haloalkyl, $C_{1-6}$ alkoxy, carbocycle, heterocycle, aryl, heteroaryl, —$N(R_{50})(R^{51})$, —$N(R^{50})C(=O)R_{40}$, —$N(R^{50})C(=O)N(R^{54})(R^{51})$, —$C(=O)N(R^{50})(R^{51})$, —$OC(=O)N(R^{50})(R^{51})$, —$C(=O)R_{40}$, —$OC(=O)R_{40}$, —$C(=G^1)R_{40}$, —$G^2C(=G^1)R_{40}$, —$R^{50})G^2C(=G^1)R_{40}$, —$C(=G^1)G^2R_{41}$, or —$G^3C(=G^1)G^2R_{41}$,
(c) carbocycle, heterocycle, aryl, heteroaryl, carbocycloxy, heterocycloxy, aryloxy, heteroaryloxy, each of which being optionally substituted with 1-3 substituents wherein each substituent is independently halo, $N_3$, nitro, hydroxy, thiol, sulfone, CN, $C_{1-6}$ alkyl, $C_{1-6}$ haloalkyl, $C_{1-6}$ alkoxy, $C_{1-6}$ hydroxyalkyl, $C_{1-6}$ alkylsulfonyl (i.e., —$SO_2$—$C_{1-6}$ alkyl), $C_{1-6}$ alkylsulfonamide, carbocycle, heterocycle, aryl, heteroaryl, —$N(R^{52})(R^{53})$, —$N(R^{52})C(=O)R_{42}$, —$N(R^{52})C(=O)N(R^{55})(R^{53})$, —$C(=O)N(R^{52})(R^{53})$, —$OC(=O)N(R^{52})(R^{53})$, —$C(=O)R_{42}$, —$OC(=O)R_{42}$, —$C(=G^1)R_{42}$, —$G^2C(=G^1)R_{42}$, —$(R^{52})G^2C(=G^1)R_{42}$, —$C(=G^1)G^2R_{43}$, or —$G^4C(=G^1)G^2R_{43}$,
(d) —$N(R^{50})(R^{51})$, —$N(R^{50})C(=O)R_{40}$, —$N(R^{50})C(=O)N(R^{54})(R^{51})$, —$C(=O)N(R^{50})(R^{51})$, —$OC(=O)N(R^{50})(R^{51})$, —$C(=O)R_{40}$, —$OC(=O)R_{40}$, —$C(=G^1)R_{40}$, —$G^2C(=G^1)R_{40}$, —$(R^{50})G^2C(=G^1)R_{40}$, —$C(=G^1)G^2R_{41}$ or —$G^3C(=G^1)G^2R_{41}$;
$G^1$ is S or N; $G^2$ and $G^3$ are independently S or $N(R^{50})$; $G^4$ is $N(R^{52})$;
$R_{40}$ is selected from: H, OH, $C_{1-6}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy and $C_{1-6}$ alkylthiol, wherein $R_{40}$ is optionally substituted with from one to three substituents independently selected from halo, $N_3$, nitro, hydroxy, thiol, CN, $C_{1-6}$ alkyl;
$R_{41}$ is H, $C_{1-6}$ alkyl, $C_{2-6}$ alkenyl or $C_{2-6}$ alkynyl, wherein $R_{41}$, is optionally substituted with from one to three substituents independently selected from halo, $N_3$, nitro, hydroxy, thiol, CN, $C_{1-6}$ alkyl;
$R_{42}$ is selected from: H, OH, $C_{1-6}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy, and $C_{1-6}$ alkylthiol, wherein $R_{42}$ is optionally substituted with from one to three substituents independently selected from halo, $N_3$, nitro, hydroxy, thiol, CN and $C_{1-6}$ alkyl;

$R_{43}$ is H, $C_{1-6}$ alkyl, $C_{2-6}$ alkenyl or $C_{2-6}$ alkynyl, wherein $R_{43}$ is optionally substituted with from one to three substituents independently selected from halo, $N_3$, nitro, hydroxy, thiol, CN and $C_{1-6}$ alkyl;

$R^{50}$, $R^{51}$ and $R^{54}$ are independently H, OH($R_{50}$ and $R_{51}$ are not both OH), $C_{1-10}$ alkyl, $C_{2-10}$ alkenyl, $C_{2-10}$ alkynyl, $C_{1-10}$ alkoxy, $C_{1-10}$ alkylthiol, $C_{2-10}$ alkenyloxy, $C_{2-10}$ alkynyloxy, $C_{1-10}$ haloalkyl, $C_{2-6}$ hydroxyalkyl, $C_{1-6}$ alkyl-O—$C_{1-6}$ alkyl-, wherein $R^{50}$ and $R^{51}$ each is optionally substituted with 1-3 substituents wherein each substituent is independently halo, $N_3$, nitro, hydroxy, thiol, CN, $C_{1-6}$ alkyl, $C_{1-6}$ haloalkyl, $C_{1-6}$ alkoxy, —C(=O)N($R^{54}$)(55), $R_{44}$C(=O)— or —N($R^{54}$)(55), wherein $R^{54}$ and $R^{55}$ are independently H, OH or $C_{1-4}$ alkyl, and wherein $R_{44}$ is H or $C_{1-4}$ alkyl; and $R^{52}$, $R^{53}$ and $R^{55}$ are independently H, OH($R^{52}$ and $R^{53}$ are not both OH), $C_{1-10}$ alkyl, $C_{2-10}$ alkenyl, $C_{2-10}$ alkynyl, $C_{1-10}$ alkoxy, $C_{1-10}$ alkylthiol, $C_{2-10}$ alkenyloxy, $C_{2-10}$ alkynyloxy, $C_{1-10}$ haloalkyl, $C_{2-6}$ hydroxyalkyl, $C_{1-6}$ alkyl-O—$C_{1-6}$ alkyl-, or $R^{52}$ and $R^{53}$ together with the nitrogen atom to which they are both linked form a 3, 4, 5 or 6-membered heterocycle (e.g., piperidinyl, pyrrolidinyl, and morpholinyl), wherein $R^{52}$ and $R^{53}$ each is optionally substituted with 1-3 substituents wherein each substituent is independently halo, $N_3$, nitro, hydroxy, thiol, CN, $C_{1-6}$ alkyl, $C_{1-6}$ haloalkyl, $C_{1-6}$ alkoxy, —C(=O)N($R^{54}$)($R^{55}$), $R_{44}$C(=O)— or —N($R^{54}$)($R^{55}$), wherein $R^{54}$ and $R^{55}$ are independently H, OH or $C_{1-4}$ alkyl, and wherein $R_{44}$ is H or $C_{1-4}$ alkyl.

Preferably, in the compounds of Formula 2n, $R_{13}$ is not H or nitro, and preferably is halo, e.g., Cl. Also preferably, the -Ak- moiety in $R_4$ is $C_{2-6}$ alkylene, and $R_8$ or $R_9$ or both are substituted with a substituent defined above for $R_4$. Also preferably $R_{11}$, is not nitro, and preferably is H.

In preferred embodiments of the compounds of Formula 2n,

Z is O, —$NR^z$ ($R^z$ is H or $C_{1-4}$ alkyl), or S, preferably O;

$R_4$ is $C_{1-6}$ haloalkyl, —$R^{31}$—W—$R_{32}$, or —$R^{31}$—$R^{33}$;

wherein $R^{31}$ is $C_{2-6}$ alkyl optionally substituted with an aryl group;

W is O, —$NR^z$ ($R^z$ is H or $C_{1-4}$ alkyl), or S, preferably O;

$R^{32}$ is (a) $C_{2-6}$ alkyl optionally substituted with 1-3 substituents selected from halo, $C_{2-6}$ alkyoxy, or (b) phenyl optionally substituted with halo;

$R^{33}$ is cycloalkyl, heterocycle, aryl or heteroaryl, each of which being optionally substituted with one to three substituents selected from halo, $C_{1-6}$ alkyl, $C_{1-6}$ haloalkyl (e.g., trifluoromethyl), $C_{1-6}$ alkoxy, $C_{1-6}$ haloalkoxy (e.g., trifluoromethoxy), $C_{1-6}$ alkylsulfonyl (i.e., —$SO_2$—$C_{1-6}$ alkyl), —$R^{34}$—C(=O)$R^{35}$, —C(=O)$R_{34}$, —N($R^{36}$)($R^{37}$) and aryl;

$R^{34}$ is $C_{1-6}$ alkyl; $R^{35}$ is $C_{1-6}$ alkoxy; and $R^{36}$ and $R^{37}$ are independently H or $C_{1-6}$ alkyl.

In a more preferred embodiment, the compounds of 2n have the following structure:

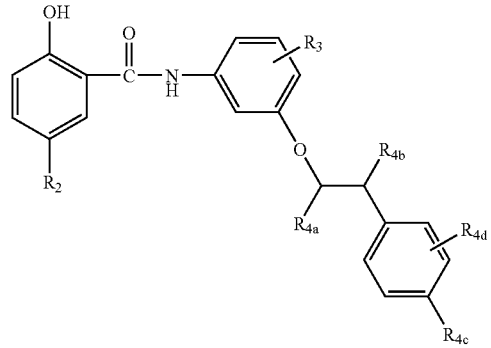

Formula 2o

Or pharmaceutically acceptable salts thereof, wherein, $R_2$ and $R_3$ are independently halo (preferably F or Cl) or $C_{1-6}$ haloalkyl (preferably trifluoromethyl);

$R_{4a}$ and $R_{4b}$ are independently $C_{1-6}$ alkyl;

$R_{4c}$ is halo or $C_{1-4}$ haloalkyl;

$R_{4d}$ is H or halo; and preferably, $R_3$ is at the meta position, relative to the —O— and —N—.

The compounds useful in the methods of the present invention also includes those having the following Formula 2p:

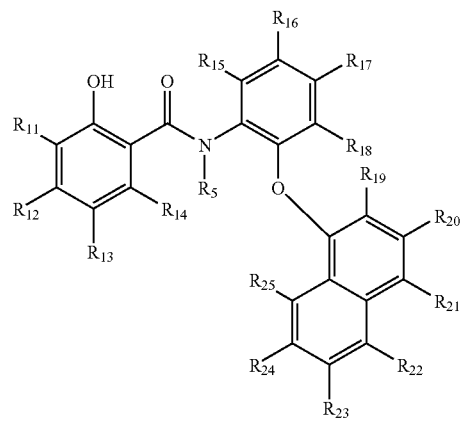

Formula 2p or pharmaceutically acceptable salt, wherein $R_5$ is H or $C_{1-6}$ alkyl, preferably H;

$R_{11}$-$R_{25}$ are independently selected from (a) H, halo, $N_3$, nitro, hydroxy, thiol, sulfone, and CN, (b) $C_{1-6}$ alkyl, $C_{2-6}$ alkenyl, $C_{2-6}$ alkynyl, $C_{1-6}$ alkoxy, $C_{1-6}$ alkylthiol, $C_{2-6}$ alkenyloxy, $C_{2-6}$ alkynyloxy, $C_{1-6}$ haloalkyl, $C_{1-6}$ hydroxyalkyl, —$C_{1-6}$ alkyl-O—$C_{1-6}$ alkyl, $C_{1-6}$ alkylsulfonyl (i.e., —$SO_2$—$C_{1-6}$ alkyl), $C_{1-6}$ alkylsulfonamide, each of which being optionally substituted with 1-3 substituents wherein each substituent is independently halo, $N_3$, nitro, hydroxy, thiol, —CN, $C_{1-6}$ alkyl, $C_{1-6}$ haloalkyl, $C_{1-6}$ alkoxy, —N($R^{50}$)($R^{51}$), —N($R^{50}$)C(=O)$R_{40}$, —N($R^{50}$)C(=O)N($R^{54}$)($R^{51}$), —C(=O)N($R^{50}$)($R^{51}$), —OC(=O)N($R^{50}$)($R^{51}$), —C(=O)$R_{40}$, —OC(=O)$R_{40}$, —C(=$G^1$)$R_{40}$, —$G^2$C(=$G^1$)$R_{40}$, —($R^{50}$)$G^2$C(=$G^1$)$R_{40}$, —C(=$G^1$)$G^2R_{41}$ or —$G^3$C(=$G^1$)$G^2R_{41}$, (c) carbocycle, heterocycle, aryl, and heteroaryl, each of which being optionally substituted with 1-3 substituents wherein each substituent is independently halo, $N_3$, nitro, hydroxy, thiol, sulfone, CN, $C_{1-6}$ alkyl, $C_{1-6}$ haloalkyl, $C_{1-6}$ alkoxy, $C_{1-6}$ hydroxyalkyl, $C_{1-6}$ alkylsulfonyl (i.e., —$SO_2$—$C_{1-6}$ alkyl), $C_{1-6}$ alkylsulfonamide, —$N(R^{52})(R^{53})$, —$N(R^{52})C(=O)R_{42}$, —$N(R^{52})C(=O)N(R^{55})(R^{53})$, —$C(=O)N(R^{52})(R^{53})$, —$OC(=O)N(R^{52})(R^{53})$, —$C(=O)R_{42}$, —$OC(=O)R_{42}$, —$C(=G^1)R_{42}$, —$G^2C(=G^1)R_{42}$, —$(R^{52})G^2C(=G^1)R_{42}$, —$C(=G^1)G^2R_{43}$, or —$G^4C(=G^1)G^2R_{43}$, (d) —$N(R^{50})(R^{51})$, —$N(R^{50})C(=O)R_{40}$, —$N(R^{50})C(=O)N(R^{54})(R^{51})$, —$C(=O)N(R^{50})(R^{51})$, —$OC(=O)N(R^{50})(R^{51})$, —$C(=O)R_{40}$, —$OC(=O)R_{40}$, —$C(=G^1)R_{40}$, —$G^2C(=G^1)R_{40}$, —$(R^{50})G^2C(=G^1)R_{40}$, —$C(=G^1)G^2R_{41}$ or $G^3C(=G^1)G^2R_{41}$;

$G^1$ is S or N; $G^2$ and $G^3$ are independently S or $N(R^{50})$; $G^4$ is $N(R^{52})$;

$R_{40}$ is selected from: H, —OH, $C_{1-6}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy and $C_{1-6}$ alkylthiol, wherein $R_{40}$ is optionally substituted with from one to three substituents independently selected from halo, $N_3$, nitro, hydroxy, thiol, CN, $C_{1-6}$ alkyl;

$R_{41}$ is H, $C_{1-6}$ alkyl, $C_{2-6}$ alkenyl or $C_{2-6}$ alkynyl, wherein $R_4$, is optionally substituted with from one to three substituents independently selected from halo, $N_3$, nitro, hydroxy, thiol, CN, $C_{1-6}$ alkyl;

$R_{42}$ is selected from: H, —OH, $C_{1-6}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy, and $C_{1-6}$ alkylthiol, wherein $R_{42}$ is optionally substituted with from one to three substituents independently selected from halo, $N_3$, nitro, hydroxy, thiol, CN and $C_{1-6}$ alkyl;

$R_{43}$ is H, $C_{1-6}$ alkyl, $C_{2-6}$ alkenyl or $C_{2-6}$ alkynyl, wherein $R_{43}$ is optionally substituted with from one to three substituents independently selected from halo, $N_3$, nitro, hydroxy, thiol, CN and $C_{1-6}$ alkyl;

$R^{50}$, $R^{51}$ and $R^{54}$ are independently H, OH($R^{50}$ and $R^{51}$ are not both OH), $C_{1-10}$ alkyl, $C_{2-10}$ alkenyl, $C_{2-10}$ alkynyl, $C_{1-10}$ alkoxy, $C_{1-10}$ alkylthiol, $C_{2-10}$ alkenyloxy, $C_{2-10}$ alkynyloxy, $C_{1-10}$ haloalkyl, $C_{2-6}$ hydroxyalkyl, $C_{1-6}$ alkyl-O—$C_{1-6}$ alkyl-, wherein $R^{50}$ and $R^{51}$ each is optionally substituted with 1-3 substituents wherein each substituent is independently halo, $N_3$, nitro, hydroxy, thiol, CN, $C_{1-6}$ alkyl, $C_{1-6}$ haloalkyl, $C_{1-6}$ alkoxy, —$C(=O)N(R^{54})(R^{55})$, $R_{44}C(=O)$— or —$N(R^{54})(R^{55})$, wherein $R^{54}$ and $R^{55}$ are independently H, OH or $C_{1-4}$ alkyl, and wherein $R_{44}$ is H or $C_{1-4}$ alkyl; and $R^{52}$, $R^{53}$ and $R^{55}$ are independently H, OH($R^{52}$ and $R^{53}$ are not both OH), $C_{1-10}$ alkyl, $C_{2-10}$ alkenyl, $C_{2-10}$ alkynyl, $C_{1-10}$ alkoxy, $C_{1-10}$ alkylthiol, $C_{2-10}$ alkenyloxy, $C_{2-10}$ alkynyloxy, $C_{1-10}$ haloalkyl, $C_{2-6}$ hydroxyalkyl, $C_{1-6}$ alkyl-O—$C_{1-6}$ alkyl-, or $R^{52}$ and $R^{53}$ together with the nitrogen atom to which they are both linked form a 3, 4, 5 or 6-membered heterocycle (e.g., piperidinyl, pyrrolidinyl, and morpholinyl), wherein $R^{52}$ and $R^{53}$ each is optionally substituted with 1-3 substituents wherein each substituent is independently halo, $N_3$, nitro, hydroxy, thiol, CN, $C_{1-6}$ alkyl, $C_{1-6}$ haloalkyl, $C_{1-6}$ alkoxy, —$C(=O)N(R^{54})(R^{55})$, $R_{44}C(=O)$— or —$N(R^{54})(R^{55})$, wherein $R^{54}$ and $R^{55}$ are independently H, OH or $C_{1-4}$ alkyl, and wherein $R_{44}$ is H or $C_{1-4}$ alkyl.

Preferably, in the compounds of Formula 2p, at least one of $R_{19}$-$R_{25}$ is not H, and preferably is selected from Cl, Br, I, or $C_{1-6}$ haloalkyl. More preferably, at least one of $R_{19}$-$R_{25}$ is Cl. In most preferred embodiments, in the compounds of Formula 2p, $R_{21}$, is Cl, Br, I, or $C_{1-6}$ haloalkyl, preferably Cl.

In preferred embodiments, $R_{11}$, $R_{12}$ and $R_{14}$ are H; $R_{13}$ is halo, preferably Cl; $R_{21}$ is halo, preferably Cl.

In more preferred embodiments of the compounds of Formula 2p, $R_{11}$, $R_{12}$ and $R_{14}$ are H; $R_{13}$ is halo, preferably Cl; $R_{15}$-$R_{18}$ are independently H, F, Cl, Br, I, $C_{1-3}$ haloalkyl (e.g., trifluoromethyl); $R_{21}$, is Cl, Br, I, or $C_{1-3}$ haloalkyl, preferably Cl; and $R_{19}$, $R_{20}$, $R_{22}$-$R_{25}$ are independently H, F, Cl, Br, I, $C_{1-6}$ alkyl, $C_{1-3}$ haloalkyl (e.g., trifluoromethyl).

In specific embodiments, the compounds are:

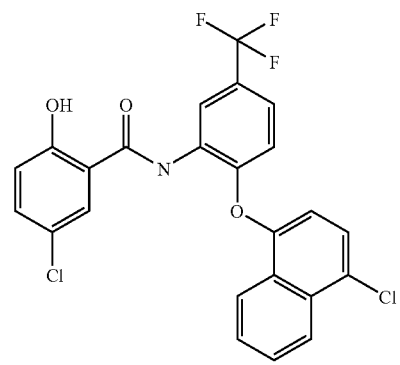

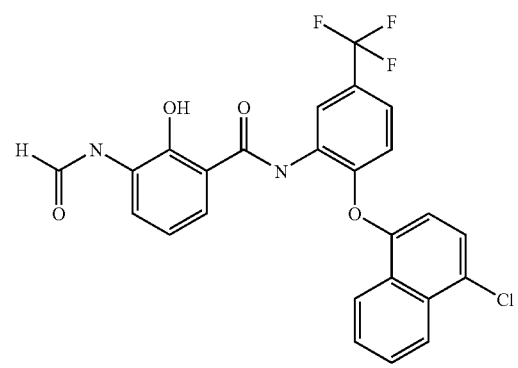

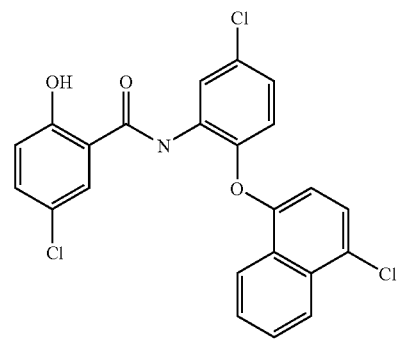

The compounds useful in the methods of the present invention also include those having the following Formula 2q:

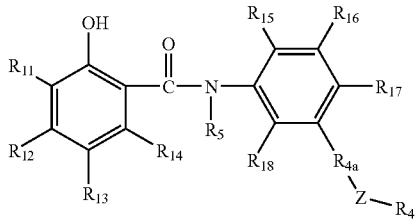

Formula 2q or pharmaceutically acceptable salts thereof, wherein

Z is O, N($R^z$) ($R^z$ is H or $C_{1-6}$ alkyl), or S, preferably O or N($R^z$), and more preferably O;

$R_{4a}$ is $C_{1-6}$ alkylene, preferably $C_{2-6}$ alkylene;

$R_5$ is H or $C_{1-6}$ alkyl, preferably H;

$R_{11}$-$R_{18}$ are independently selected from (a) H, halo, $N_3$, nitro, hydroxy, thiol, sulfone, and CN, (b) $C_{1-6}$ alkyl, $C_{2-6}$ alkenyl, $C_{2-6}$ alkynyl, $C_{1-6}$ alkoxy, $C_{1-6}$ alkylthiol, $C_{2-6}$ alkenyloxy, $C_{2-6}$ alkynyloxy, $C_{1-6}$ haloalkyl, $C_{1-6}$ hydroxyalkyl, —$C_{1-6}$ alkyl-O—$C_{1-6}$ alkyl, $C_{1-6}$ alkylsulfonyl (i.e., —$SO_2$—$C_{1-6}$ alkyl), $C_{1-6}$ alkylsulfonamide, each of which being optionally substituted with 1-3 substituents wherein each substituent is independently halo, $N_3$, nitro, hydroxy, thiol, —CN, $C_{1-6}$ alkyl, $C_{1-6}$ haloalkyl, $C_{1-6}$ alkoxy, —N($R^{50}$)($R^{51}$), —N($R^{50}$)C(=O)$R_{40}$, —N($R^{50}$)C(=O)N($R^{54}$)($R^{51}$), —C(=O)N($R^{50}$)($R^{51}$), —OC(=O)N($R^{50}$)($R_{51}$), —C(=O)$R_{40}$, —OC(=O)$R_{40}$, —C(=$G^1$)$R_{40}$, —$G^2$C(=$G^1$)$R_{40}$, —$R^{50}$$G^2$C(=$G^1$)$R_{40}$, —C(=$G^1$)$G^2R_{41}$ or —$G^3$C(=$G^1$)$G^2R_{41}$, (c) carbocycle, heterocycle, aryl, and heteroaryl, each of which being optionally substituted with 1-3 substituents wherein each substituent is independently halo, $N_3$, nitro, hydroxy, thiol, sulfone, CN, $C_{1-6}$ alkyl, $C_{1-6}$ haloalkyl, $C_{1-6}$ alkoxy, $C_{1-6}$ hydroxyalkyl, $C_{1-6}$ alkylsulfonyl (i.e., —$SO_2$—$C_{1-6}$ alkyl), $C_{1-6}$ alkylsulfonamide, —N($R^{52}$)($R^{53}$), —N($R^{52}$)C(=O)$R_{42}$, —N($R^{52}$)C(=O)N($R^{55}$)($R_{53}$), —C(=O)N($R^{52}$)($R^{53}$), —OC(=O)N($R^{52}$)($R^{53}$), —C(=O)$R_{42}$, —OC(=O)$R_{42}$, —C(=$G^1$)$R_{42}$, $G^2$C(=$G^1$)$R_{42}$, $R^{52}$$G^2$C(=$G^1$)$R_{42}$, —C(=$G^1$)$G^2R_{43}$, or —$G^4$C(=$G^1$)$G^2R_{43}$, (d) —N($R^{50}$)($R^{51}$), —N($R^{50}$)C(=O)$R_{40}$, —N($R^{50}$)C(=O)N($R^{54}$)($R^{51}$), —C(=O)N($R^{50}$)($R^{51}$), —OC(=O)N($R^{50}$)($R^{51}$), —C(=O)$R_{40}$, —OC(=O)$R_{40}$, —C(=$G^1$)$R_{40}$, —$G^2$C(=$G^1$)$R_{40}$, —($R^{50}$)$G^2$C(=$G^1$)$R_{40}$, —C(=$G^1$)$G^2R_{41}$ or —$G^3$C(=$G^1$)$G^2R_{41}$;

$R_4$ represents $C_{1-6}$ haloalkyl, e.g., halo-substituted lower alkyl (preferably trihalo lower alkyl, e.g., trifluoromethyl); ($C_{2-6}$ alkoxy)$C_{2-6}$ alkyl; $R_8$; -Ak-O—$R_8$; -Ak-$R_8$ or -Ak($R_8R_9$), wherein Ak is lower alkyl with a straight or branched chain, $R_8$ and $R_9$ are independently selected from (1) cycloalkyl, (2) aryl (e.g., benzene and naphthalene), (3) heterocycle, e.g., a saturated or partially unsaturated moncyclic 3, 4, 5, 6, or 7-membered heterocycle containing one or more N, O, or S, or (4) heteroaryl, e.g., a monocyclic or biocyclic 6 to 12-membered aromatic ring or fused ring containing one or more N, O, or S; each being optionally substituted by one or more, e.g., 1-5, substituents independently selected from (a) halo, $N_3$, nitro, hydroxy, thiol, sulfone, and CN, (b) $C_{1-6}$ alkyl, $C_{2-6}$ alkenyl, $C_{2-6}$ alkynyl, $C_{1-6}$ alkoxy, $C_{1-6}$ alkylthiol, $C_{2-6}$ alkenyloxy, $C_{2-6}$ alkynyloxy, $C_{1-6}$ haloalkyl, $C_{1-6}$ hydroxyalkyl, $C_{1-6}$ alkyl-O—$C_{1-6}$ alkyl-, $C_{1-6}$ alkylsulfonyl (i.e., $C_{1-6}$ alkyl-$SO_2$—), $C_{1-6}$ alkylsulfonamide, each of which being optionally substituted with 1-3 substituents wherein each substituent is independently halo, $N_3$, nitro, hydroxy, thiol, —CN, $C_{1-6}$ alkyl, $C_{1-6}$ haloalkyl, $C_{1-6}$ alkoxy, carbocycle, heterocycle, aryl, heteroaryl, —N($R^{50}$)($R_{51}$), —N($R^{50}$)C(=O)$R_{40}$, —N($R^{50}$)C(=O)N($R^{54}$)($R^{51}$), —C(=O)N($R^{50}$)($R_{51}$), —OC(=O)N($R^{50}$)($R^{51}$), —C(=O)$R_{40}$, —OC(=O)$R_{40}$, —C(=$G^1$)$R_{40}$, —$G^2$C(=$G^1$)$R_{40}$, —($R^{50}$)$G^2$C(=$G^1$)$R_{40}$, —C(=$G^1$)$G^2R_{41}$ or —$G^3$C(=$G^1$)$G^2R_{41}$, (c) carbocycle, heterocycle, aryl, heteroaryl, carbocycloxy, heterocycloxy, aryloxy, heteroaryloxy, each of which being optionally substituted with 1-3 substituents wherein each substituent is independently halo, $N_3$, nitro, hydroxy, thiol, sulfone, CN, $C_{1-6}$ alkyl, $C_{1-6}$ haloalkyl, $C_{1-6}$ alkoxy, $C_{1-6}$ hydroxyalkyl, $C_{1-6}$ alkylsulfonyl (i.e., $C_{1-6}$ alkyl-$SO_2$—), $C_{1-6}$ alkylsulfonamide, carbocycle, heterocycle, aryl, heteroaryl, —N($R^{52}$)($R^{53}$), —N($R^{52}$)C(=O)$R_{42}$, —N($R^{52}$)C(=O)N($R^{55}$)($R^{53}$), —C(=O)N($R^{52}$)($R^{53}$), —OC(=O)N($R^{52}$)($R^{53}$), —C(=O)$R_{42}$, —OC(=O)$R_{42}$, —C(=$G^1$)$R_{42}$, —$G^2$C(=$G^1$)$R_{42}$, —($R^{52}$)$G^2$C(=$G^1$)$R_{42}$, —C(=$G^1$)$G^2R_{43}$, or $G^4$C(=$G^1$)$G^2R_{43}$;

(d) —N($R^{50}$)($R^{51}$), —N($R_{50}$)C(=O)$R_{40}$, —N($R^{50}$)C(=O)N($R^{54}$)($R^{51}$), —C(=O)N($R^{50}$)($R^{51}$), —OC(=O)N($R^{50}$)($R^{51}$), —C(=O)$R_{40}$, —OC(=O)$R_{40}$, —C(=$G^1$)$R_{40}$, —$G^2$C(=$G^1$)$R_{40}$, —($R^{50}$)$G^2$C(=$G^1$)$R_{40}$, —C(=$G^1$)$G^2R_{41}$ or —$G^3$C(=$G^1$)$G^2R_{41}$;

$G^1$ is S or N; $G^2$ and $G^3$ are independently S or N($R^{50}$); $G^4$ is N($R^{52}$);

$R_{40}$ is selected from: H, —OH, $C_{1-6}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy and $C_{1-6}$ alkylthiol, wherein $R_{40}$ is optionally substituted with from one to three substituents independently selected from halo, $N_3$, nitro, hydroxy, thiol, CN, $C_{1-6}$ alkyl; $R_{41}$ is H, $C_{1-6}$ alkyl, $C_{2-6}$ alkenyl or $C_{2-6}$ alkynyl, wherein $R_{41}$ is optionally substituted with from one to three substituents independently selected from halo, $N_3$, nitro, hydroxy, thiol, CN, $C_{1-6}$ alkyl;

$R_{42}$ is selected from: H, —OH, $C_{1-6}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy, and $C_{1-6}$ alkylthiol, wherein $R_{42}$ is optionally substituted with from one to three substituents independently selected from halo, $N_3$, nitro, hydroxy, thiol, CN and $C_{1-6}$ alkyl;

$R_{43}$ is H, $C_{1-6}$ alkyl, $C_{2-6}$ alkenyl or $C_{2-6}$ alkynyl, wherein $R_{43}$ is optionally substituted with from one to three substituents independently selected from halo, $N_3$, nitro, hydroxy, thiol, CN and $C_{1-6}$ alkyl;

$R^{50}$, $R^{51}$ and $R^{54}$ are independently H, OH($R^{50}$ and $R^{51}$ are not both OH), $C_{1-10}$ alkyl, $C_{2-10}$ alkenyl, $C_{2-10}$ alkynyl, $C_{1-10}$ alkoxy, $C_{1-10}$ alkylthiol, $C_{2-10}$ alkenyloxy, $C_{2-10}$ alkynyloxy, $C_{1-10}$ haloalkyl, $C_{2-6}$ hydroxyalkyl, $C_{1-6}$ alkyl-O—$C_{1-6}$ alkyl-, wherein $R^{50}$ and $R^{51}$ each is optionally substituted with 1-3 substituents wherein each substituent is independently halo, $N_3$, nitro, hydroxy, thiol, CN, $C_{1-6}$ alkyl, $C_{1-6}$ haloalkyl, $C_{1-6}$ alkoxy, —C(=O)N($R^{54}$)($R^{55}$), $R_{44}$C(=O)— or —N($R^{54}$)($R^{55}$), wherein $R^{54}$ and $R^{55}$ are independently H, OH or $C_{1-4}$ alkyl, and wherein $R_{44}$ is H or $C_{1-4}$ alkyl; and $R^{52}$, $R^{53}$ and $R^{55}$ are independently H, OH($R^{52}$ and $R^{53}$ are not both OH), $C_{1-10}$ alkyl, $C_{2-10}$ alkenyl, $C_{2-10}$ alkynyl, $C_{1-10}$ alkoxy, $C_{1-10}$ alkylthiol, $C_{2-10}$ alkenyloxy, $C_{2-10}$ alkynyloxy, $C_{1-10}$ haloalkyl, $C_{2-6}$ hydroxyalkyl, $C_{1-6}$ alkyl-O—$C_{1-6}$ alkyl-, or $R^{52}$ and $R^{53}$ together with the nitrogen atom to which they are both linked form a 3, 4, 5 or 6-membered heterocycle (e.g., piperidinyl, pyrrolidinyl, and morpholinyl), wherein $R^{52}$ and $R^{53}$ each is optionally substituted with 1-3 substituents wherein each substituent is independently halo, $N_3$, nitro, hydroxy, thiol, CN, $C_{1-6}$ alkyl, $C_{1-6}$ haloalkyl, $C_{1-6}$ alkoxy, —C(=O)N($R^{54}$)($R^{55}$), $R_{44}$C(=O)— or —N($R^{54}$)($R^{55}$), wherein $R^{54}$ and $R^{55}$ are independently H, OH or $C_{1-4}$ alkyl, and wherein $R_{44}$ is H or $C_{1-4}$ alkyl;

with the proviso that when Z is S, $R_4$ is not bicyclic heteroaryl, preferably not heteroaryl.

Preferably, in the compounds of Formula 2q, $R_{13}$ is not H or nitro, and preferably is halo.

In preferred embodiments, in the compounds of Formula 2q,

Z is O, —$NR^z$ ($R^z$ is H or $C_{1-4}$ alkyl), or S, preferably O or NH;
$R_{4a}$ is —$CH_2$— or —$CH_2CH_2$—;
$R_4$ is aryl, aralkyl or heteroaralkyl, each being optionally substituted with one to three substituents selected from F, Cl, Br, I, $C_{1-6}$ alkyl, and $C_{1-6}$ lower alkoxy;
$R_{11}$, $R_{12}$, and $R_{14}$-$R_{18}$ are H; and
$R_{13}$ is halo.

The compounds useful in the methods of the present invention also include those having the following Formula 2r:

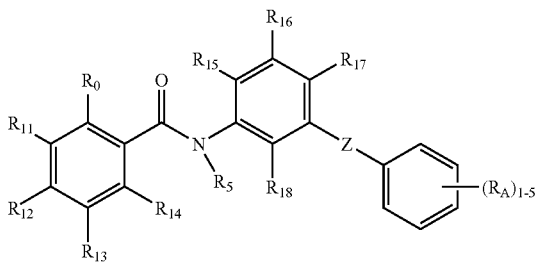

Formula 2r or pharmaceutically acceptable salts thereof, wherein $R_0$ is hydroxyl;
Z is O, N($R^z$) ($R^z$ is H or $C_{1-6}$ alkyl), or S, preferably O or N($R^z$), and more preferably O;
$R_5$ is H or $C_{1-6}$ alkyl;
$R_{11}$-$R_{18}$ are independently selected from
(a) H, halo, $N_3$, nitro, hydroxy, thiol, sulfone, and CN,
(b) $C_{1-6}$ alkyl, $C_{2-6}$ alkenyl, $C_{2-6}$ alkynyl, $C_{1-6}$ alkoxy, $C_{1-6}$ alkylthiol, $C_{2-6}$ alkenyloxy, $C_{2-6}$ alkynyloxy, $C_{1-6}$ haloalkyl, $C_{1-6}$ hydroxyalkyl, —$C_{1-6}$ alkyl-O—$C_{1-6}$ alkyl, $C_{1-6}$ alkylsulfonyl (i.e., —$SO_2$—$C_{1-6}$ alkyl), $C_{1-6}$ alkylsulfonamide, each of which being optionally substituted with 1-3 substituents wherein each substituent is independently halo, $N_3$, nitro, hydroxy, thiol, —CN, $C_{1-6}$ alkyl, $C_{1-6}$ haloalkyl, $C_{1-6}$ alkoxy, —N($R^{50}$)($R^{51}$), —N($R^{50}$)C(=O)$R_{40}$, —N($R^{50}$)C(=O)N($R^{54}$)($R^{51}$), —C(=O)N($R^{50}$)($R^{51}$), —OC(=O)N($R^{50}$)($R^{51}$), —C(=O)$R_{40}$, —OC(=O)$R_{40}$, —C(=$G^1$)$R_{40}$, —$G^2$C(=$G^1$)$R_{40}$, —($R^{50}$)$G^2$C(=$G^1$)$R_{40}$, —C(=$G^1$)$G^2R_{41}$ or —$G^3$C(=$G^1$)$G^2R_{41}$,
(c) carbocycle, heterocycle, aryl, and heteroaryl, each of which being optionally substituted with 1-3 substituents wherein each substituent is independently halo, $N_3$, nitro, hydroxy, thiol, sulfone, CN, $C_{1-6}$ alkyl, $C_{1-6}$ haloalkyl, $C_{1-6}$ alkoxy, $C_{1-6}$ hydroxyalkyl, $C_{1-6}$ alkylsulfonyl (i.e., —$SO_2$—$C_{1-6}$ alkyl), $C_{1-6}$ alkylsulfonamide, —N($R^{52}$)($R^{53}$), —N($R^{52}$)C(=O)$R_{42}$, —N($R^{52}$)C(=O)N($R^{55}$)($R^{53}$), —C(=O)N($R^{52}$)($R^{53}$), —OC(=O)N($R^{52}$)($R^{53}$), —C(=O)$R_{42}$, —OC(=O)$R_{42}$, —C(=$G^1$)$R_{42}$, —$G^2$C(=$G^1$)$R_{42}$, —($R^{52}$)$G^2$C(=$G^1$)$R_{42}$, —C(=$G^1$)$G^2R_{43}$, or —$G^4$C(=$G^1$)$G^2R_{43}$,
(d) —N($R^{50}$)($R^{51}$), —N($R^{50}$)C(=O)$R_{40}$, —N($R^{50}$)C(=O)N($R^{54}$)($R^{51}$), —C(=O)N($R^{50}$)($R^{51}$), —OC(=O)N($R^{50}$)($R^{51}$), —C(=O)$R_{40}$, —OC(=O)$R_{40}$, —C(=$G^1$)$R_{40}$, —$G^2$C(=$G^1$)$R_{40}$, —($R^{50}$)$G^2$C(=$G^1$)$R_{40}$, —C(=$G^1$)$G^2R_{41}$ or —$G^3$C(=$G^1$)$G^2R_{41}$;

each $R_A$ when present is selected from the group consisting of
(a) halo, $N_3$, nitro, hydroxy, thiol, sulfone, and CN,
(b) $C_{1-6}$ alkyl, $C_{2-6}$ alkenyl, $C_{2-6}$ alkynyl, $C_{1-6}$ alkoxy, $C_{1-6}$ alkylthiol, $C_{2-6}$ alkenyloxy, $C_{2-6}$ alkynyloxy, $C_{1-6}$ haloalkyl, $C_{1-6}$ hydroxyalkyl, $C_{1-6}$ alkyl-O—$C_{1-6}$ alkyl-, $C_{1-6}$ alkylsulfonyl (i.e., $C_{1-6}$ alkyl-$SO_2$—), $C_{1-6}$ alkylsulfonamide, each of which being optionally substituted with 1-3 substituents wherein each substituent is independently halo, $N_3$, nitro, hydroxy, thiol, —CN, $C_{1-6}$ alkyl, $C_{1-6}$ haloalkyl, $C_{1-6}$ alkoxy, carbocycle, heterocycle, aryl, heteroaryl, —N($R^{50}$)($R^{51}$), —N($R^{50}$)C(=O)$R_{40}$, —N($R^{50}$)C(=O)N($R^{54}$)($R^{51}$), —C(=O)N($R^{50}$)($R^{51}$), —OC(=O)N($R^{50}$)($R^{51}$), —C(=O)$R_{40}$, —OC(=O)$R_{40}$, —C(=$G^1$)$R_{40}$, —$G^2$C(=$G^1$)$R_{40}$, —($R^{50}$)$G^2$C(=$G^1$)$R_{40}$, —C(=$G^1$)$G^2R_{41}$ or —$G^3$C(=$G^1$)$G^2R_{41}$,
(c) carbocycle, heterocycle, aryl, heteroaryl, carbocycloxy, heterocycloxy, aryloxy, heteroaryloxy, each of which being optionally substituted with 1-3 substituents wherein each substituent is independently halo, $N_3$, nitro, hydroxy, thiol, sulfone, CN, $C_{1-6}$ alkyl, $C_{1-6}$ haloalkyl, $C_{1-6}$ alkoxy, $C_{1-6}$ hydroxyalkyl, $C_{1-6}$ alkylsulfonyl (i.e., $C_{1-6}$ alkyl-$SO_2$—), $C_{1-6}$ alkylsulfonamide, carbocycle, heterocycle, aryl, heteroaryl, —N($R^{52}$)($R^{53}$), —N($R^{52}$)C(=O)$R_{42}$, —N($R^{52}$)C(=O)N($R^{55}$)($R^{53}$), —C(=O)N($R^{52}$)($R^{53}$), —OC(=O)N($R^{52}$)($R^{53}$), —C(=O)$R_{42}$, —OC(=O)$R_{42}$, —C(=$G^1$)$R_{42}$, —$G^2$C(=$G^1$)$R_{42}$, —($R^{52}$)$G^2$C(=$G^1$)$R_{42}$, —C(=$G^1$)$G^2R_{43}$, or —$G^4$C(=$G^1$)$G^2R_{43}$,
(d) —N($R^{50}$)($R^{51}$), —N($R^{50}$)C(=O)$R_{40}$, —N($R^{50}$)C(=O)N($R^{54}$)($R^{51}$), —C(=O)N($R^{50}$)($R^{51}$), —OC(=O)N($R^{50}$)($R^{51}$), —C(=O)$R_{40}$, —OC(=O)$R_{40}$, —C(=$G^1$)$R_{40}$, —$G^2$C(=$G^1$)$R_{40}$, —($R^{50}$)$G^2$C(=$G^1$)$R_{40}$, —C(=$G^1$)$G^2R_{41}$ or —$G^3$C(=$G^1$)$G^2R_{41}$;
(e) two adjacent $R_A$ can be taken together to form a carbocyclic, heterocyclic, aryl, or heteroaryl ring fused to the phenyl ring where the resultant bicyclic ring system is substituted with 1-3 substitutents selected from the group consisting of halo, $N_3$, nitro, hydroxy, thiol, sulfone, CN, $C_{1-6}$ alkyl, $C_{1-6}$ haloalkyl, $C_{1-6}$ alkoxy, $C_{1-6}$ hydroxyalkyl, $C_{1-6}$ alkylsulfonyl (i.e., $C_{1-6}$ alkyl-$SO_2$—), $C_{1-6}$ alkylsulfonamide, carbocycle, heterocycle, aryl, heteroaryl, —N($R^{52}$)($R^{53}$), —N($R^{52}$)C(=O)$R_{42}$, —N($R^{52}$)C(=O)N($R^{55}$)($R^{53}$), —C(=O)N($R^{52}$)($R^{53}$), —OC(=O)N($R^{52}$)($R^{53}$), —C(=O)$R_{42}$, —OC(=O)$R_{42}$, —C(=$G^1$)$R_{42}$, —$G^2$C(=$G^1$)$R_{42}$, —($R^{52}$)$G^2$C(=$G^1$)$R_{42}$, —C(=$G^1$)$G^2R_{43}$, or —$G^4$C(=$G^1$)$G^2R_{43}$, —N($R^{50}$)($R^{51}$), —N($R^{50}$)C(=O)$R_{40}$, —N($R^{50}$)C(=O)N($R^{54}$)($R^{51}$), —C(=O)N($R^{50}$)($R^{51}$), —OC(=O)N($R^{50}$)($R^{51}$), —C(=O)$R_{40}$, —OC(=O)$R_{40}$, —C(=$G^1$)$R_{40}$, —$G^2$C(=$G^1$)$R_{40}$, —($R^{50}$)$G^2$C(=$G^1$)$R_{40}$, —C(=$G^1$)$G^2R_{41}$ or —$G^3$C(=$G^1$)$G^2R_{41}$;

with the provision that the compound is not 5-chloro-N-[3-(2,4-dichlorophenoxy)-5-(trifluoromethyl)phenyl]-2-hydroxy-benzamide, 5-chloro-2-hydroxy-N-(2-methoxy-5- phenoxyphenyl)-benzamide, or 5-chloro-2-hydroxy-N-[3-(2-naphthalenyloxy)-5-(trifluoromethyl)phenyl]-benzamide. Also preferably, the compound is not 5-chloro-N-[3-(2,4-dichlorophenoxy)-5-(trifluoromethyl)phenyl]-2-hydroxy-benzamide, 3-bromo-5-chloro-N-[2-chloro-5-[(1-chloro-2-naphthalenyl)oxy]phenyl]-2-hydroxy-benzamide, 2-hydroxy-N-[3-[4-[(2-hydroxybenzoyl)amino]phenoxy]phenyl]-benzamide, N-[3-(2-chloro-4-nitrophenoxy)phenyl]-2-hydroxy-benzamide, 2-hydroxy-N-[3-(4-nitrophenoxy)phenyl]-benzamide, N-[2-chloro-5-[2-chloro-4-(trifluoromethyl)phenoxy]phenyl]-2-hydroxybenzamide, N-[3-(3,5-dichlorophenoxy)phenyl]-4-ethoxy-2-hydroxy-benzamide.

In preferred embodiments, $R_{11}$ is not nitro or —NC(═O) (formyl amino), $R_{13}$ is not nitro, and $R_{11}$, and $R_{13}$ are not the same halo. Preferably $R_{13}$ is not H. More preferably $R_{11}$ is H.

In a preferred embodiment of the compounds of Formula 2r, Z is O and $R_{13}$ is halo. In another preferred embodiment of the compounds of Formula 2r $R_{16}$ is —CF$_3$.

In one embodiment, compounds of the invention include those of Formula 2r$^a$ and Formula 2r$^b$ Formula 2r$^a$

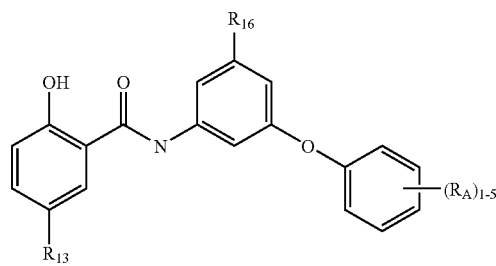

Formula 2r$^b$

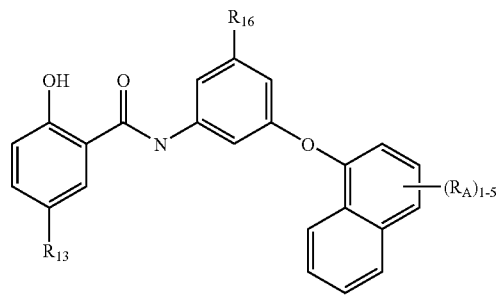

or pharmaceutically acceptable salts thereof, wherein
$R_{13}$ is a halo;
$R_{16}$ is selected from the group consisting of hydrogen, halo, $C_{1-6}$ alkyl, $C_{1-6}$ haloalkyl, and $C_{1-6}$ alkoxy; and
each $R_A$ is independently selected from the group consisting of halo, $N_3$, nitro, hydroxy, thiol, sulfone, CN, $C_{1-6}$ alkyl, $C_{1-6}$ haloalkyl, $C_{1-6}$ alkoxy, $C_{1-6}$ hydroxyalkyl, $C_{1-6}$ alkylsulfonyl (i.e., $C_{1-6}$ alkyl-SO$_2$—), $C_{1-6}$ alkylsulfonamide, carbocycle, heterocycle, aryl, heteroaryl, —N(R$^{52}$)(R$^{53}$), —N(R$^{52}$)C(═O)R$_{42}$, —N(R$^{52}$)C(═O)N(R$^{55}$)(R$^{53}$), —C(═O)N(R$^{52}$)(R$^{53}$), —OC(═O)N(R$^{52}$)(R$^{53}$), —C(═O)R$_{42}$, —OC(═O)R$_{42}$, —C(═G$^1$)R$_{42}$, —G$^2$C(═G$^1$)R$_{42}$, —(R$^{52}$)G$^2$C(═G$^1$)R$_{42}$, —C(═G$^1$)G$^2$R$_{43}$, or —G$^4$C(═G$^1$)G$^2$R$_{43}$, —N(R$^{50}$)(R$^{51}$), —N(R$^{50}$)C(═O)R$_{40}$, —N(R$^{50}$)C(═O)N(R$^{54}$)(R$^{51}$), —C(═O)N(R$^{50}$)(R$^{51}$), —OC(═O)N(R$^{50}$)(R$^{51}$), —C(═O)R$_{40}$, —OC(═O)R$_{40}$, —C(═G$^1$)R$_{40}$, —G$^2$C(═G$^1$)R$_{40}$, —C(═G$^1$)R$_{40}$, —(R$^{50}$)G$^2$C(═G$^1$)R$_{40}$, —C(═G$^1$)G$^2$R$_{41}$ and —G$^3$C(═G$^1$)G$^2$R$_{41}$;

provided that the compound is not 5-chloro-N-[3-(2,4-dichlorophenoxy)-5-(trifluoromethyl)phenyl]-2-hydroxy-benzamide.

In an embodiment, the invention provides a compound slected from the following:

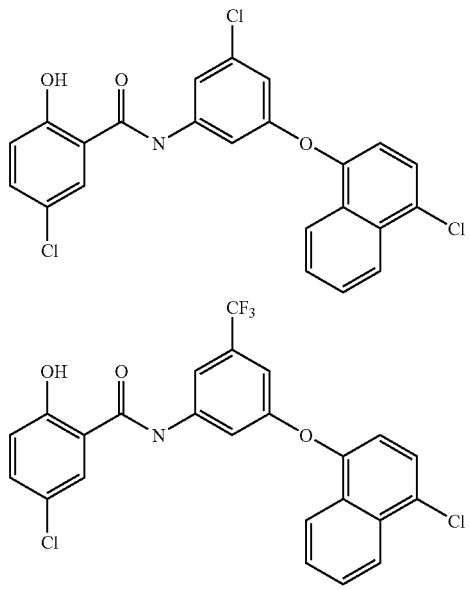

or a pharmaceutically acceptable salt thereof.

In another embodiment, the compounds useful in the methods of the present invention also include those having a structure according to Formula 2s:

Formula 2s

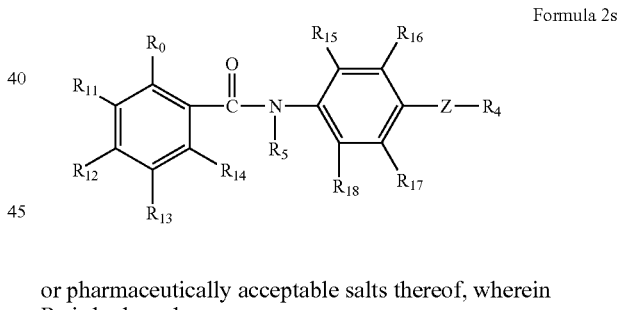

or pharmaceutically acceptable salts thereof, wherein
$R_0$ is hydroxyl;
Z is O, N(R$^z$) (R$^z$ is H or $C_{1-6}$ alkyl), or S, preferably O and N(R$^z$) (R$^z$ is H or $C_{1-6}$ alkyl), and more preferably O;
$R_5$ is H or $C_{1-6}$ alkyl;
$R_{11}$-$R_{18}$ are independently selected from
(a) H, halo, $N_3$, nitro, hydroxy, thiol, sulfone, and CN,
(b) $C_{1-6}$ alkyl, $C_{2-6}$ alkenyl, $C_{2-6}$ alkynyl, $C_{1-6}$ alkoxy, $C_{1-6}$ alkylthio, $C_{2-6}$ alkenyloxy, $C_{2-6}$ alkynyloxy, $C_{1-6}$ haloalkyl, $C_{1-6}$ hydroxyalkyl, —$C_{1-6}$ alkyl-O—$C_{1-6}$ alkyl, $C_{1-6}$ alkylsulfonyl (i.e., —SO$_2$—$C_{1-6}$ alkyl), $C_{1-6}$ alkylsulfonamide, each of which being optionally substituted with 1-3 substituents wherein each substituent is independently halo, $N_3$, nitro, hydroxy, thiol, CN, $C_{1-6}$ alkyl, $C_{1-6}$ haloalkyl, $C_{1-6}$ alkoxy, —N(R$^{50}$)(R$^{51}$), —N(R$^{50}$)C(═O)$_{40}$, —N(R$^{50}$)C(═O)N(R$^{54}$)(R$^{51}$), —C(═O)N(R$^{50}$)(R$^{51}$), —OC(═O)N(R$^{50}$)(R$^{51}$), —C(═O)R$_{40}$, —OC(═O)R$_{40}$, —C(═G$^1$)R$_{40}$, —G$^2$C(═G$^1$)R$_{40}$, —(R$^{50}$)G$^2$C(═G$^1$)R$_{40}$, —C(═G$^1$)G$^2$R$_{41}$ or —G$^3$C(═G$^1$)G$^2$R$_{41}$, (c) carbocycle, heterocycle, aryl, and heteroaryl, each of which being optionally substituted with 1-3 substituents wherein each substituent is independently $N_3$, nitro, hydroxy, thiol, sulfone, CN, $C_{1-6}$ alkyl, $C_{1-6}$ haloalkyl, $C_{1-6}$ alkoxy, $C_{1-6}$ hydroxyalkyl, $C_{1-6}$ alkylsulfonyl (i.e., $-SO_2-C_{1-6}$ alkyl), $C_{1-6}$ alkylsulfonamide, $-N(R^{52})(R^{53})$, $-N(R^{52})C(=O)R_{42}$, $-N(R^{52})C(=O)N(R^{55})(R^{53})$, $-C(=O)N(R^{52})(R^{53})$, $-OC(=O)N(R^{52})(R^{53})$, $-C(=O)R_{42}$, $-OC(=O)R_{42}$, $-C(=G^1)R_{42}$, $-G^2C(=G^1)R_{42}$, $-(R^{52})G^2C(=G^1)R_{42}$, $-C(=G^1)G^2R_{43}$, or $-G^4C(=G^1)G^2R_{43}$, (d) $-N(R^{50})(R^{51})$, $-N(R^{50})C(=O)R_{40}$, $-N(R^{50})C(=O)N(R^{54})(R^{51})$, $-C(=O)N(R^{50})(R^{51})$, $-OC(=O)N(R^{50})(R^{51})$, $-C(=O)R_{40}$, $-OC(=O)_{40}$, $-C(=G^1)R_{40}$, $-G^2C(=G^1)R_{40}$, $-(R^{50})G^2C(=G^1)R_{40}$, $-C(=G^1)G^2R_{41}$ or $-G^3C(=G^1)G^2R_{41}$;

$R_4$ represents (1) haloalkyl; (2) $(C_{2-6}$ alkoxy$)C_{2-6}$ alkyl; (3) -Ak—O—$R_8$, -Ak-$R_8$ or -Ak($R_8R_9$), wherein Ak is $C_{2-6}$ alkylene, $R_8$ and $R_9$ are independently selected from cycloalkyl, aryl, heterocycle or heteroaryl; each being optionally substituted by one or more substituents independently selected from (a) halo, $N_3$, nitro, hydroxy, thiol, sulfone, and CN, (b) $C_{1-6}$ alkyl, $C_{2-6}$ alkenyl, $C_{2-6}$ alkynyl, $C_{1-6}$ alkoxy, $C_{1-6}$ alkylthiol, $C_{2-6}$ alkenyloxy, $C_{2-6}$ alkynyloxy, $C_{1-6}$ haloalkyl, $C_{1-6}$ hydroxyalkyl, $C_{1-6}$ alkyl-O—$C_{1-6}$ alkyl-, $C_{1-6}$ alkylsulfonyl, $C_{1-6}$ alkylsulfonamide, each of which being optionally substituted with 1-3 substituents wherein each substituent is independently halo, $N_3$, nitro, hydroxy, thiol, CN, $C_{1-6}$ alkyl, $C_{1-6}$ haloalkyl, $C_{1-6}$ alkoxy, carbocycle, heterocycle, aryl, heteroaryl, $-N(R^{50})(R^{51})$, $-N(R^{50})C(=O)R_{40}$, $-N(R^{50})C(=O)N(R^{54})(R^{51})$, $-C(=O)N(R^{50})(R^{51})$, $-OC(=O)N(R_{50})(R^{51})$, $-C(=O)R_{40}$, $-OC(=O)R_{40}$, $-C(=G^1)R_{40}$, $-G^2C(=G^1)R_{40}$, $-(R^{50})G^2C(=G^1)R_{40}$, $-C(=G^1)G^2R_{41}$ or $-G^3C(=G^1)G^2R_{41}$, (c) carbocycle, heterocycle, aryl, heteroaryl, carbocycloxy, heterocycloxy, aryloxy, heteroaryloxy, each of which being optionally substituted with 1-3 substituents wherein each substituent is independently halo, $N_3$, nitro, hydroxy, thiol, sulfone, CN, $C_{1-6}$ alkyl, $C_{1-6}$ haloalkyl, $C_{1-6}$ alkoxy, $C_{1-6}$ hydroxyalkyl, $C_{1-6}$ alkylsulfonyl, $C_{1-6}$ alkylsulfonamide, carbocycle, heterocycle, aryl, heteroaryl, $-N(R^{52})(R^{53})$, $-N(R^{52})C(=O)R_{42}$, $-N(R^{52})C(=O)N(R^{55})(R^{53})$, $-C(=O)N(R^{52})(R^{53})$, $-OC(=O)N(R_{52})(R^{53})$, $-C(=O)R_{42}$, $-OC(=O)R_{42}$, $-C(=G^1)R_{42}$, $-G^2C(=G^1)R_{42}$, $-(R^{52})G^2C(=G^1)R_{42}$, $-C(=G^1)G^2R_{43}$, or $-G^4C(=G^1)G^2R_{43}$, (d) $-N(R^{50})(R^{51})$, $-N(R^{50})C(=O)R_{40}$, $-N(R^{50})C(=O)N(R^{54})R^{51})$, $-C(=O)N(R^{50})(R^{51})$, $-OC(=O)N(R^{50})(R^{51})$, $-C(=O)R_{40}$, $-OC(=O)R_{40}$, $-C(=G^1)R_{40}$, $-G^2C(=G^1)R_{40}$, $-(R^{50})G^2C(=G^1)R_{40}$, $-C(=G^1)G^2R_{41}$ or $-G^3C(=G^1)G^2R_{41}$;

$G^1$ is S or N; $G^2$ and $G^3$ are independently S or $N(R^{50})$; $G^4$ is $N(R^{52})$;

$R_{40}$ is selected from: H, OH, $C_1$alkyl, $C_{2-6}$ alkenyl, $C_{2-6}$ alkynyl, $C_{1-6}$ alkoxy, $C_{2-6}$ alkenyloxy, $C_{2-6}$ alkynyloxy and $C_{1-6}$ alkylthio, wherein $R_{40}$ is optionally substituted with from one to three substituents independently selected from halo, $N_3$, nitro, hydroxy, thiol, CN, $C_{1-6}$ alkyl;

$R_{41}$ is H, $C_{1-6}$ alkyl, $C_{2-6}$ alkenyl or $C_{2-6}$ alkynyl, wherein $R_{41}$ is optionally substituted with from one to three substituents independently selected from halo, $N_3$, nitro, hydroxy, thiol, CN, $C_{1-6}$ alkyl;

$R_{42}$ is selected from: H, OH, $C_{1-6}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy, and $C_{1-6}$ alkylthiol, wherein $R_{42}$ is optionally substituted with from one to three substituents independently selected from halo, $N_3$, nitro, hydroxy, thiol, CN and $C_{1-6}$ alkyl;

$R_{43}$ is H, $C_{1-6}$ alkyl, $C_{2-6}$ alkenyl or $C_{2-6}$ alkynyl, wherein $R_{43}$ is optionally substituted with from one to three substituents independently selected from halo, $N_3$, nitro, hydroxy, thiol, CN and $C_{1-6}$ alkyl;

$R^{50}$, $R^{51}$ and $R^{54}$ are independently H, OH($R^{50}$ and $R^{51}$ are not both OH), $C_{1-10}$ alkyl, $C_{2-10}$ alkenyl, $C_{2-10}$ alkynyl, $C_{1-10}$ alkoxy, $C_{1-10}$ alkylthiol, $C_{2-10}$ alkenyloxy, $C_{2-10}$ alkynyloxy, $C_{1-10}$ haloalkyl, $C_{2-6}$ hydroxyalkyl, $C_{1-6}$ alkyl-O—$C_{1-6}$ alkyl-, wherein $R^{50}$ and $R^{51}$ each is optionally substituted with 1-3 substituents wherein each substituent is independently halo, $N_3$, nitro, hydroxy, thiol, CN, $C_{1-6}$ alkyl, $C_{1-6}$ haloalkyl, $C_{1-6}$ alkoxy, $-C(=O)N(R^{54})(R^{55})$, $R_{44}C(=O)-$ or $-N(R^{54})(R^{55})$, wherein $R^{54}$ and $R^{55}$ are independently H, OH or $C_{1-4}$ alkyl, and wherein $R_{44}$ is H or $C_{1-4}$ alkyl; and $R^{52}$, $R^{53}$ and $R^{55}$ are independently H, OH($R^{52}$ and $R^{53}$ are not both OH), $C_{1-10}$ alkyl, $C_{2-10}$ alkenyl, $C_{2-10}$ alkynyl, $C_{1-10}$ alkoxy, $C_{1-10}$ alkylthiol, $C_{2-10}$ alkenyloxy, $C_{2-10}$ alkynyloxy, $C_{1-10}$ haloalkyl, $C_{2-6}$ hydroxyalkyl, $C_{1-6}$ alkyl-O—$C_{1-6}$ alkyl-, or $R^{52}$ and $R^{53}$ together with the nitrogen atom to which they are both linked form a 3, 4, 5 or 6-membered heterocycle (e.g., piperidinyl, pyrrolidinyl, and morpholinyl), wherein $R^{52}$ and $R^{53}$ each is optionally substituted with 1-3 substituents wherein each substituent is independently halo, $N_3$, nitro, hydroxy, thiol, CN, $C_{1-6}$ alkyl, $C_{1-6}$ haloalkyl, $C_{1-6}$ alkoxy, $-C(=O)N(R^{54})(R^{55})$, $R_{44}C(=O)-$ or $-N(R^{54})(R^{55})$, wherein $R^{54}$ and $R^{55}$ are independently H, OH or $C_{1-4}$ alkyl, and wherein $R_{44}$ is H or $C_{1-4}$ alkyl.

Preferably, $R_8$ or $R_9$ or both are substituted with one or more said substituents defined for $R_4$. In preferred embodiments, $R_{13}$ is not H, nitro, $CF_3$ or CN. In all embodiments, preferably $R_{13}$ is halo, and $R_{11}$, $R_{12}$, and $R_{14}$ are H.

In another aspect, compounds are provided according to Formula 3:

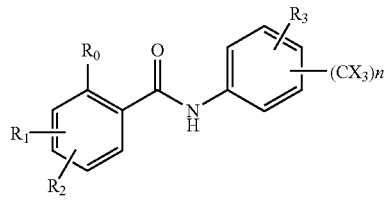

Formula 3 wherein $R_0$ is selected from the group consisting of hydroxy, lower ($C_1$-$C_6$) alkoxy (which can be unsubstituted or substituted, e.g., hydroxyalkoxy, haloalkoxy, preferably hydroxymethoxy), acetylamide, sulfonamide, alkylsulfonamide, and aryl sulfonamide;

$R_1$ and $R_2$ are positioned at the 3, 4 and/or 5 position (the amide side chain defining the 1 position), and are independently selected from the group consisting of hydrogen, hydrophobic substituents such as halo (e.g., F, Cl, Br, I), nitro, alkyl, aryl, heterocycle, haloalkyl and the like, formamido, formamidoalkyl, and alkoxy substituents, or at the 3 and 4 positions together form a substituted or unsubstituted fused ring having 3, 4, 5, or 6 carbon atoms;

$R_3$ represents from one to four substituents independently selected from the group consisting of hydrogen, hydrophobic substituents such as halo, alkyl (preferably lower ($C_1$-$C_6$) alkyl, haloalkyl, aryl, aralkyl, alkoxy, aryloxy, aralkoxy, a heterocycle, a heterocycle(oxy), or heterocycle(alkyl), cyano, and nitro substituents. Preferably, $R_3$ is haloalkyl (preferably trihaloalkyl, e.g., trifluoromethyl) or haloalkoxy (preferably trihaloalkoxy, e.g., trifluoromethoxy);

X represents halo (e.g., F, Cl, Br, I); and n is an integer selected from the group consisting of 1, 2, or 3.

In one preferred embodiment, the pro-apoptotic compounds have the formula 3a, shown below:

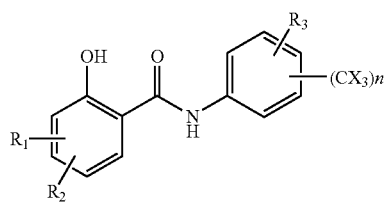

Formula 3a wherein $R_1$ and $R_2$ are independently selected from the group consisting of hydrogen, hydrophobic substituents such as halo, alkyl, aryl, haloalkyl and the like, formamido, formamidoalkyl, and alkoxy substituents, positioned at the 3,4 and/or 5 position (the amide side chain defining the 1 position);

$R_3$ represents hydrogen, halo, alkyl, cycloalkyl, aryl, or aralkyl;

X represents halo;

and n is an integer selected from the group consisting of 1, 2, or 3.

In another preferred embodiment, the pro-apoptotic compositions of Formula 3, and therapeutic treatment processes employing same, comprise a compound of Formula 3b, set forth below:

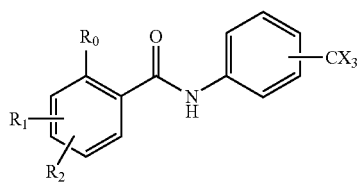

Formula 3b wherein $R_0$, $R_1$, $R_2$, and X are as defined above.

In another preferred embodiment, the pro-apoptotic compositions of Formula 3, and therapeutic treatment processes employing same, comprise a compound of Formula 3c, set forth below:

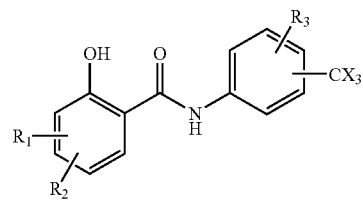

Formula 3c wherein $R_1$, $R_2$, $R_3$, X and n are as defined above.

According to another aspect, the present invention provides pro-apoptotic compounds, compositions and therapeutic treatment processes employing such pro-apoptotic compositions, comprising at least one compound of Formula 4, set forth below.

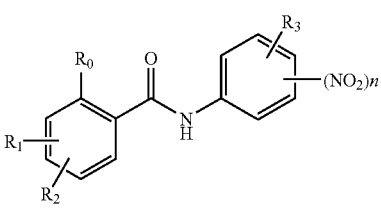

Formula 4 wherein $R_0$ is selected from the group consisting of hydroxy, lower ($C_1$-$C_6$) alkoxy (which can be unsubstituted or substituted, e.g., hydroxyalkoxy, haloalkoxy, preferably hydroxymethoxy), acetylamide, sulfonamide, alkylsulfonamide, and aryl sulfonamide;

$R_1$ and $R_2$ are independently selected from the group consisting of hydrogen, hydrophobic substituents such as halo, alkyl, aryl, haloalkyl and the like, formamido, formamidoalkyl, and alkoxy substituents, positioned at the 3,4 and/or 5 position (the amide side chain defining the 1 position);

$R_3$ represents hydrogen halo, alkyl, cycloalkyl, aryl, or aralkyl.

and n is an integer selected from the group consisting of 1, 2, or 3.

In one preferred embodiment, the pro-apoptotic compounds have the formula 4a, shown below:

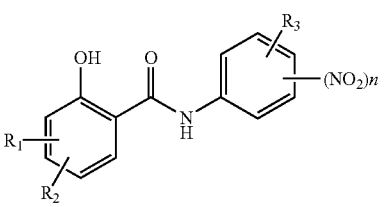

Formula 4a wherein $R_1$ and $R_2$ are independently selected from the group consisting of hydrogen, hydrophobic substituents such as halo, alkyl, aryl, haloalkyl and the like, formamido, formamidoalkyl, and alkoxy substituents, positioned at the 3,4 and/or 5 position (the amide side chain defining the 1 position);

$R_3$ represents hydrogen, halo, alkyl, cycloalkyl, aryl, or aralkyl.

and n is an integer selected from the group consisting of 1, 2, or 3.

In another preferred embodiment, the pro-apoptotic compositions of Formula 4, and therapeutic treatment processes employing same, comprise a compound of Formula 4b, set forth below:

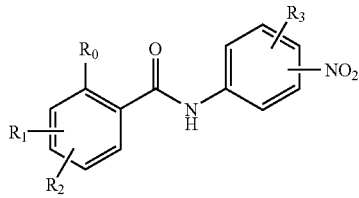

Formula 4b wherein $R_0$, $R_1$, $R_2$, $R_3$, and n are as defined above.

In another preferred embodiment, the pro-apoptotic compositions of Formula 4, and therapeutic treatment processes employing same, comprise a compound of Formula 4c, set forth below:

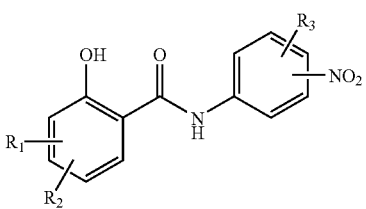

Formula 4c wherein $R_1$, $R_2$, $R_3$, and n are as defined above.

According to another aspect, the present invention provides pro-apoptotic compounds, compositions and therapeutic treatment processes employing such pro-apoptotic compositions, comprising at least one compound of Formula 5, set forth below.

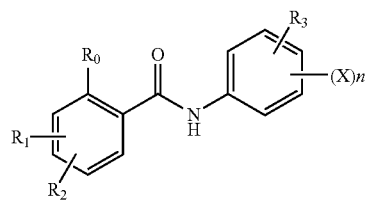

Formula 5 wherein $R_0$ is selected from the group consisting of hydroxy, lower ($C_1$-$C_6$) alkoxy (which can be unsubstituted or substituted, e.g., hydroxyalkoxy, haloalkoxy, preferably hydroxymethoxy), acetylamide, sulfonamide, alkylsulfonamide, and aryl sulfonamide;

$R_1$ and $R_2$ are independently selected from the group consisting of hydrogen, hydrophobic substituents such as halo, alkyl, aryl, haloalkyl and the like, formamido, formamidoalkyl, and alkoxy substituents, positioned at the 3,4 and/or 5 position (the amide side chain defining the 1 position);

$R_3$ represents hydrogen halo, alkyl, cycloalkyl, aryl, or aralkyl;

X represents halo;

and n is an integer selected from the group consisting of 1, 2, or 3.

In one preferred embodiment, the pro-apoptotic compounds have the formula 5a, shown below:

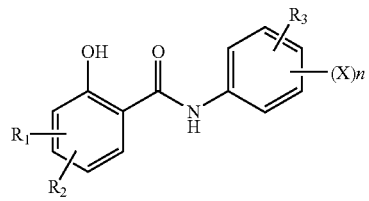

Formula 5a wherein $R_1$ and $R_2$ are independently selected from the group consisting of hydrogen, hydrophobic substituents such as halo, alkyl, aryl, haloalkyl and the like, formamido, formamidoalkyl, and alkoxy substituents, positioned at the 3,4 and/or 5 position (the amide side chain defining the 1 position);

$R_3$ represents hydrogen, halo, alkyl, cycloalkyl, aryl, or aralkyl;

X represents halo;

and n is an integer selected from the group consisting of 1, 2, or 3.

In another preferred embodiment, the pro-apoptotic compositions of Formula 5, and therapeutic treatment processes employing same, comprise a compound of Formula 3b, set forth below:

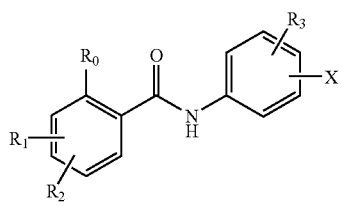

Formula 5b wherein $R_0$, $R_1$, $R_2$, $R_3$, X, and n are as defined above.

In another preferred embodiment, the pro-apoptotic compositions of Formula 5, and therapeutic treatment processes employing same, comprise a compound of Formula 5c, set forth below:

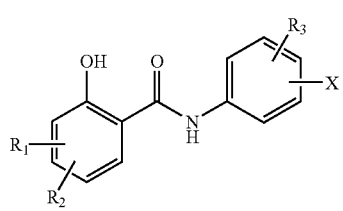

Formula 5c wherein $R_1$, $R_2$, $R_3$, X, and n are as defined above.

The structures of some representative compounds are provided in Table 1 below:

TABLE 1

| Compound No. | Structure |
|---|---|
| 1 | 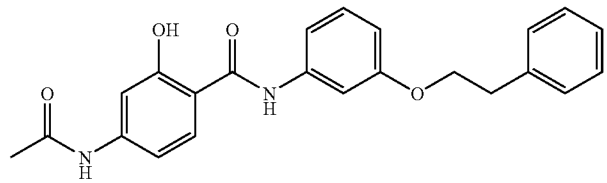 |
| 2 | 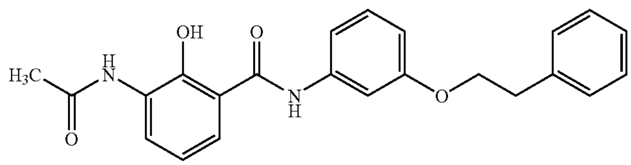 |
| 3 | 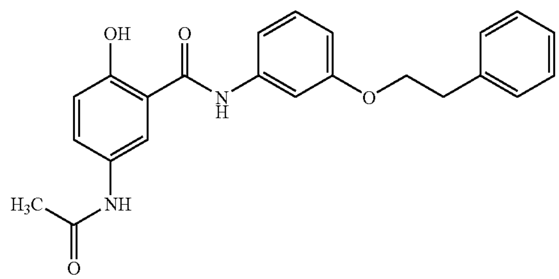 |
| 4 | 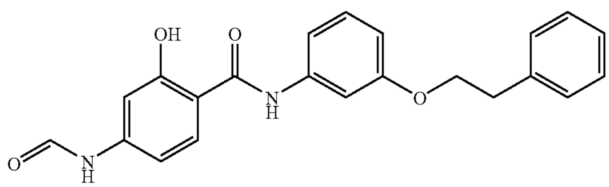 |
| 5 | 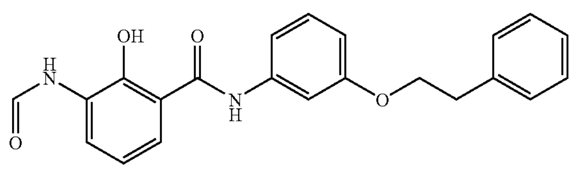 |
| 6 | 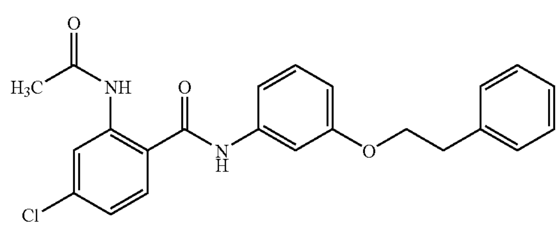 |
| 7 | 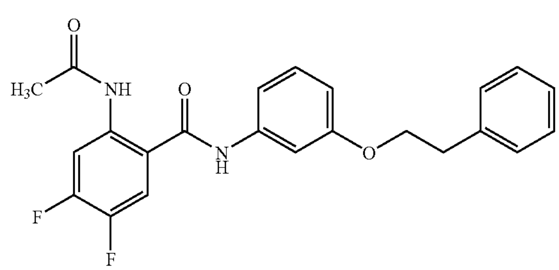 |

-continued
8 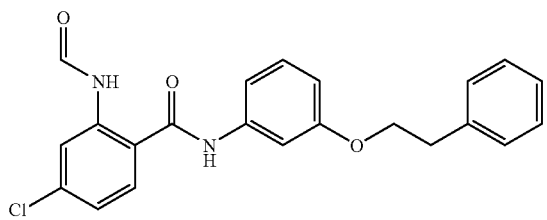
9 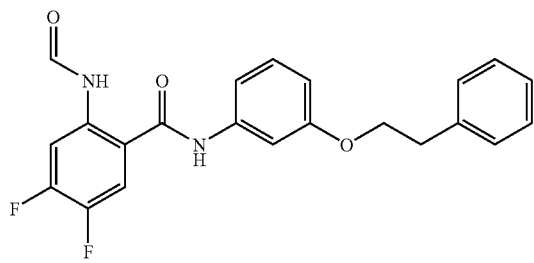
10 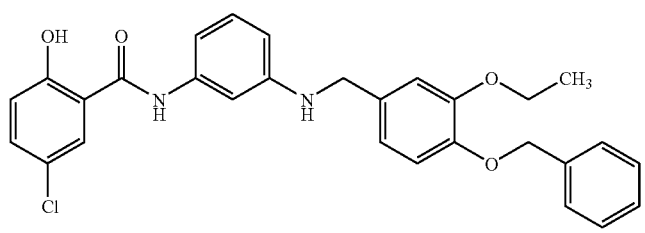
11 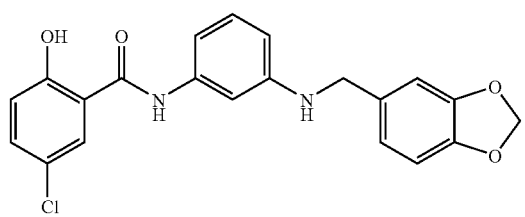
12 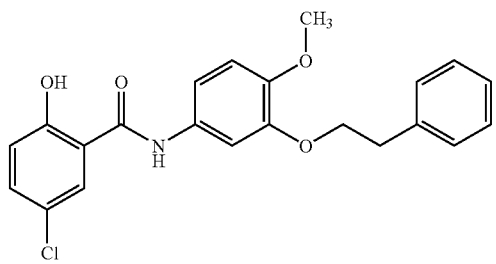
13 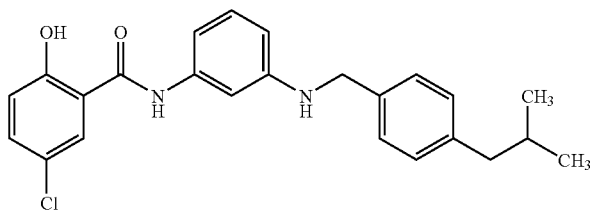

-continued
14
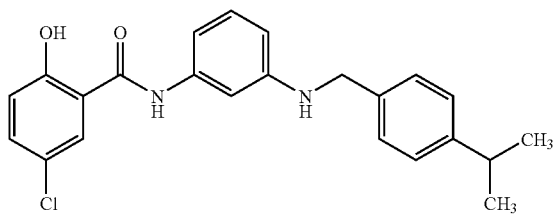
15
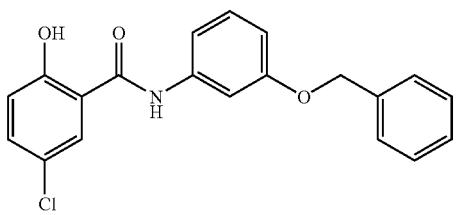
16
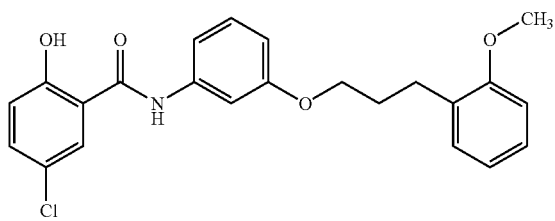
17
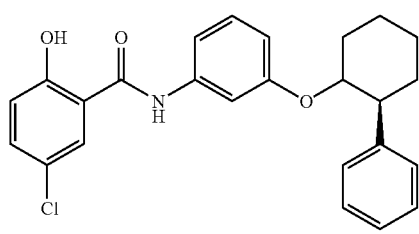
18
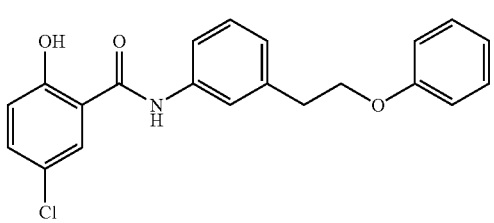
19
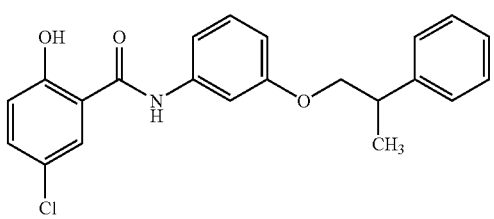
20
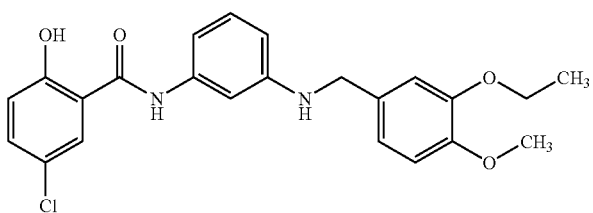

-continued
21 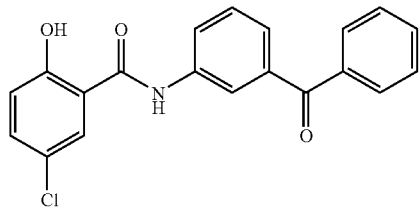
22 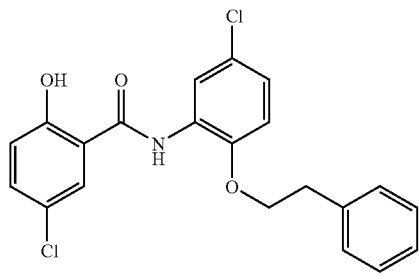
23 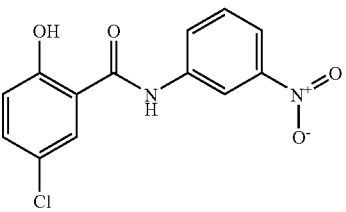
24 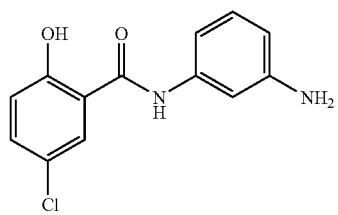
25 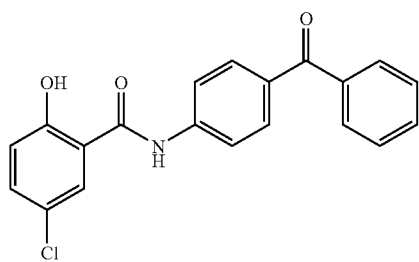
26 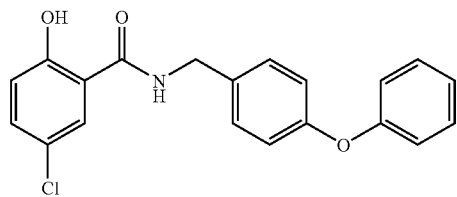
27 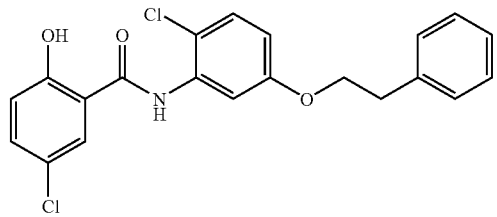

-continued
28 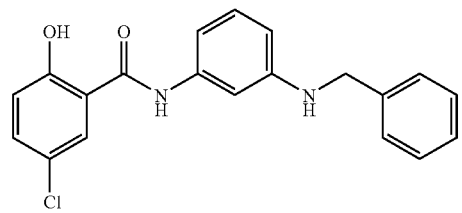
29 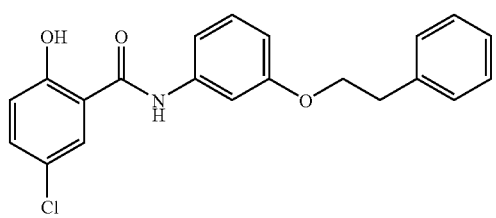
30 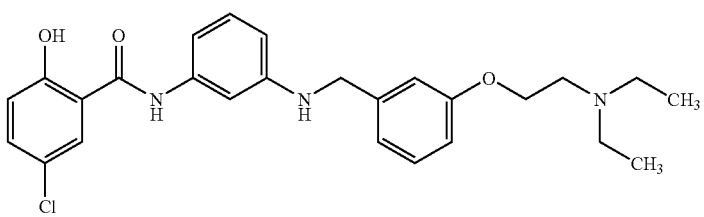
31 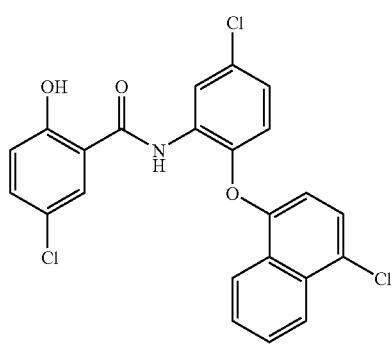
32 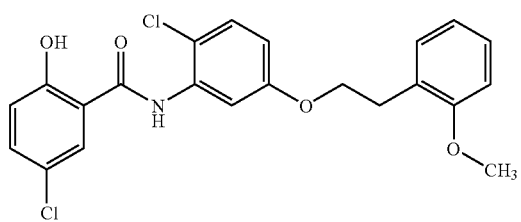
33 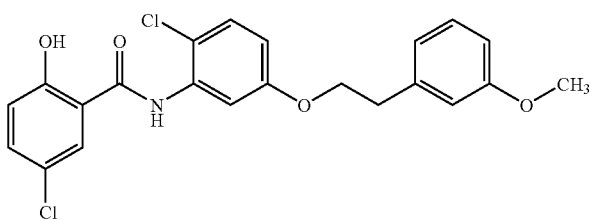

-continued
34 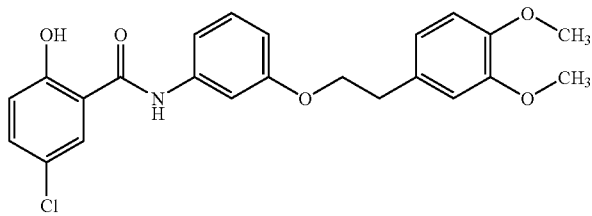
35 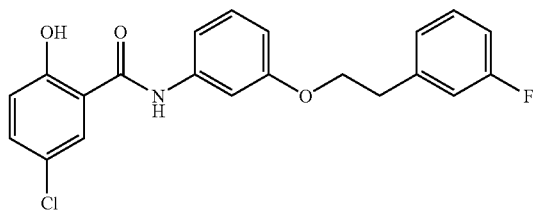
36 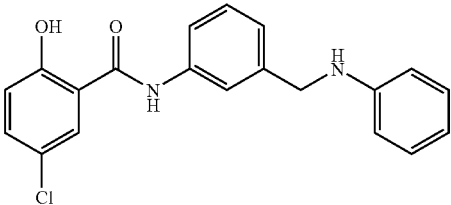
37 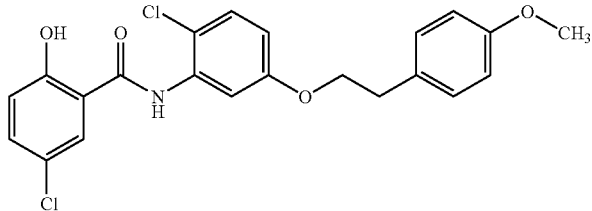
38 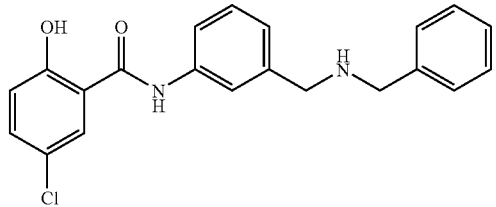
39 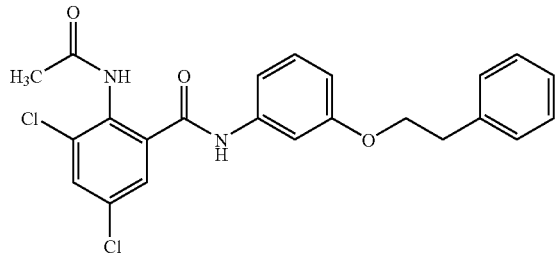

-continued
40
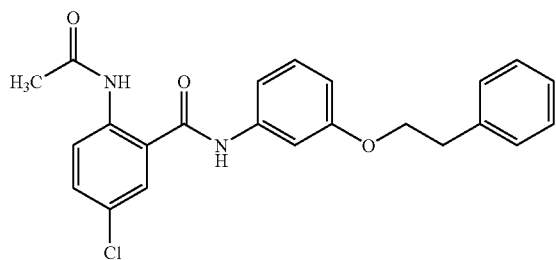
41
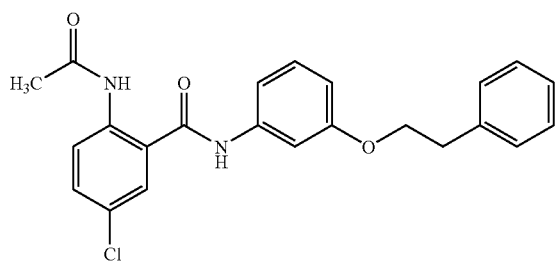
42
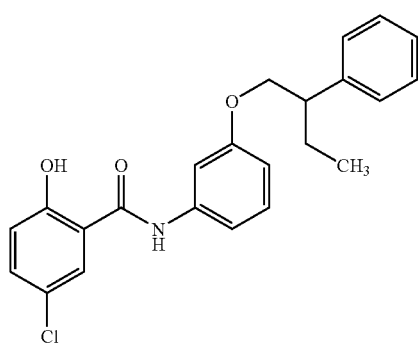
43
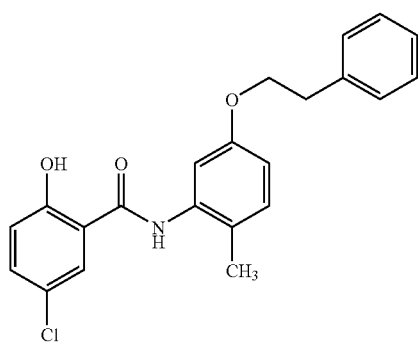
44
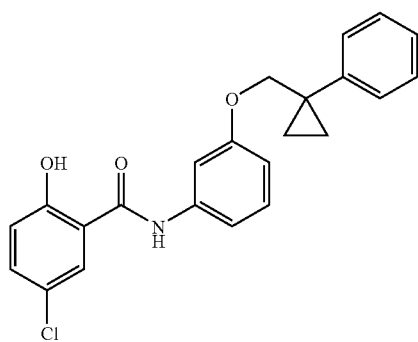

-continued
45
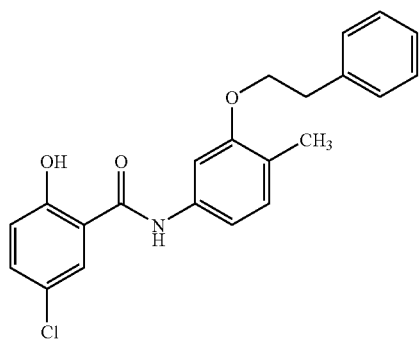
46
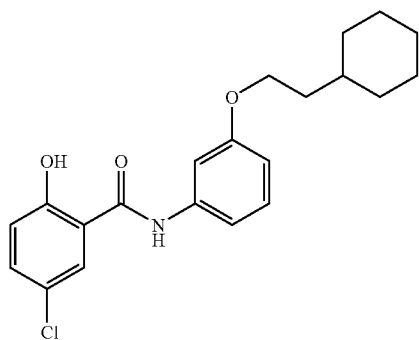
47
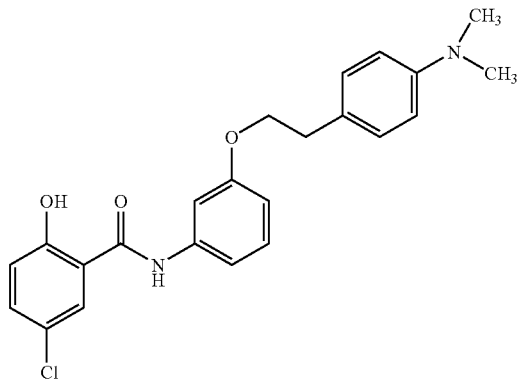
48
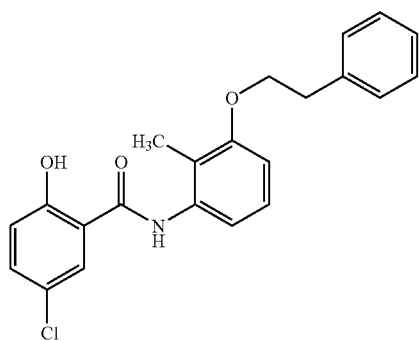

-continued
| | |
|---|---|
| 49 | 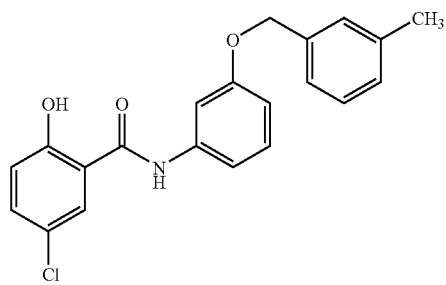 |
| 50 | 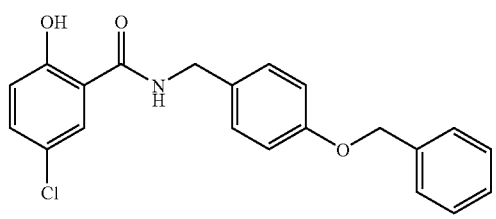 |
| 51 | 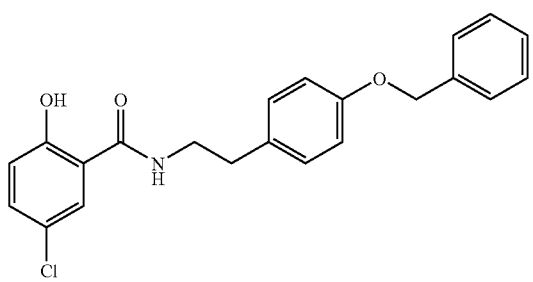 |
| 52 | 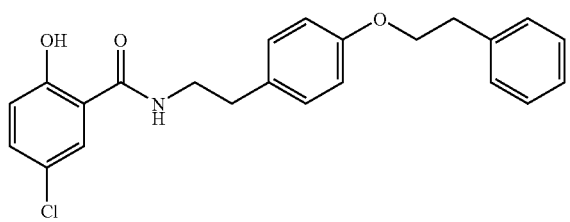 |
| 53 | 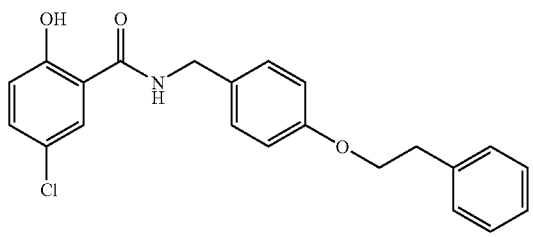 |
| 54 | 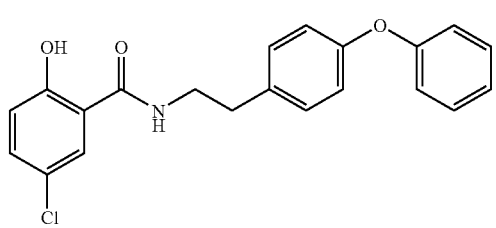 |

-continued
| | |
|---|---|
| 55 | 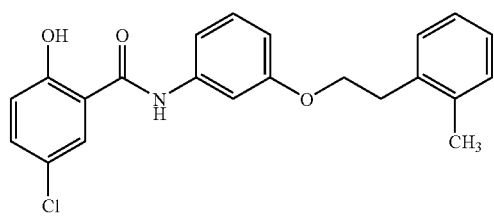 |
| 56 | 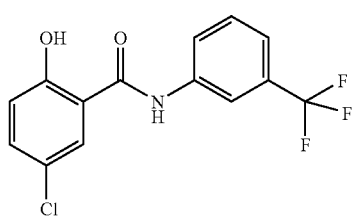 |
| 57 | 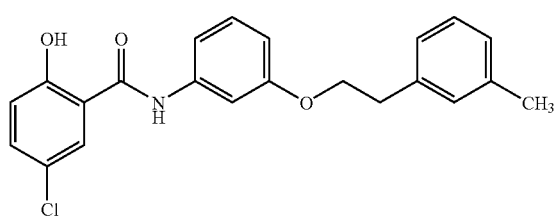 |
| 58 | 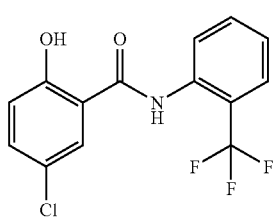 |
| 59 | 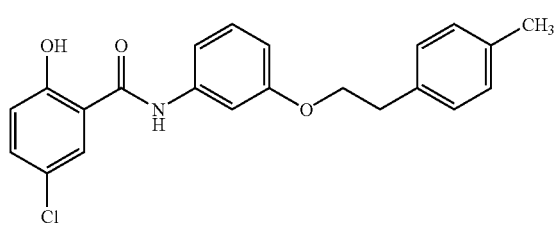 |
| 60 | 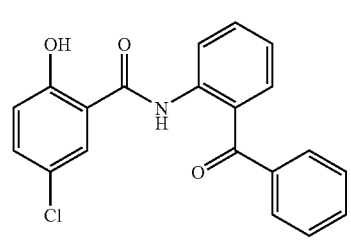 |
| 61 | 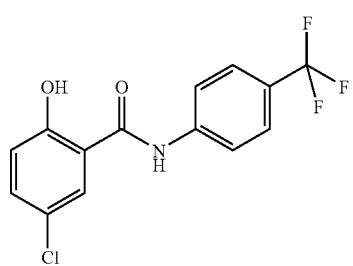 |

-continued
| | |
|---|---|
| 62 | 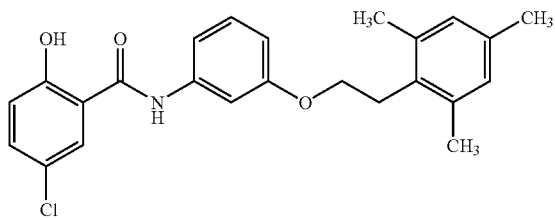 |
| 63 | 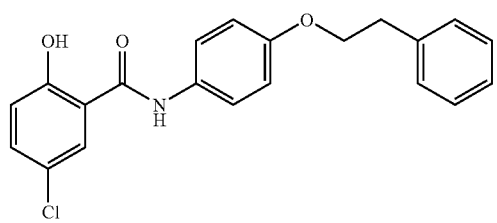 |
| 64 | 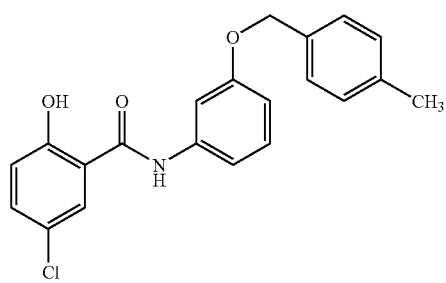 |
| 65 | 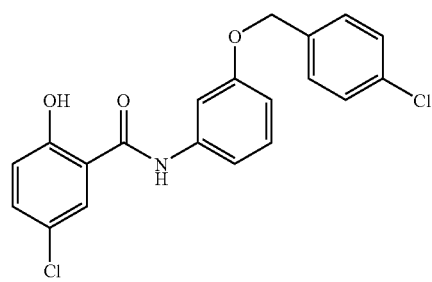 |
| 66 | 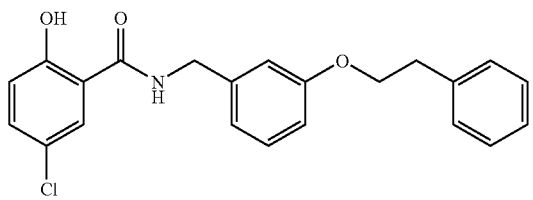 |
| 67 | 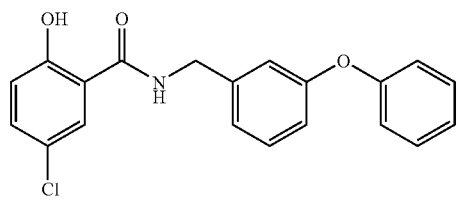 |

-continued
68 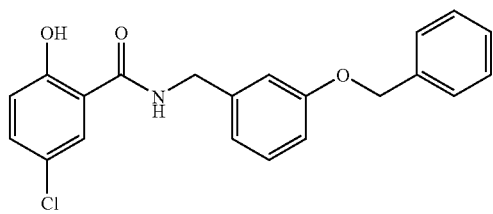
69 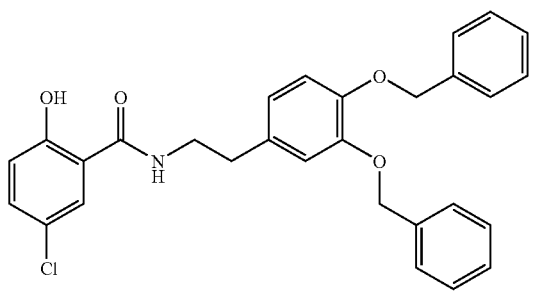
70 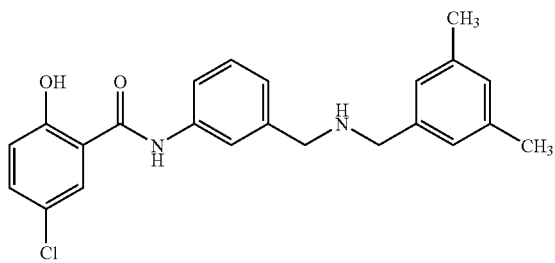
71 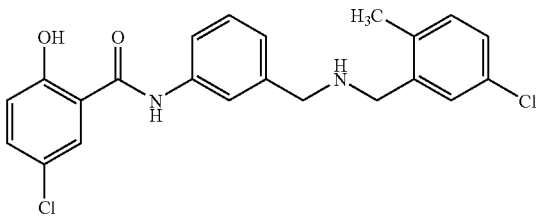
72 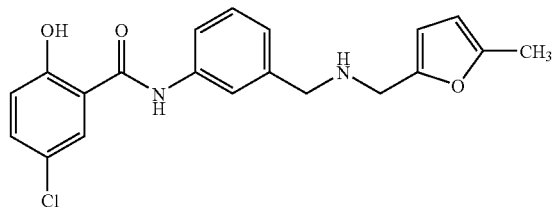
73 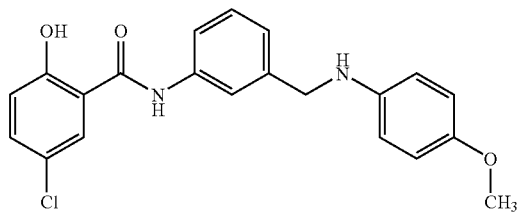

-continued
74 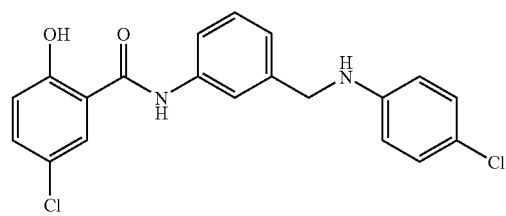
75 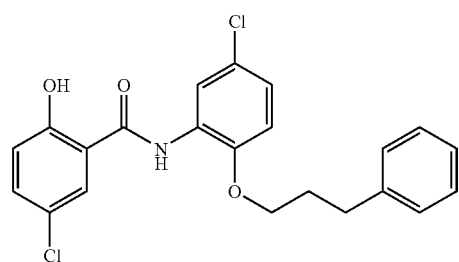
76 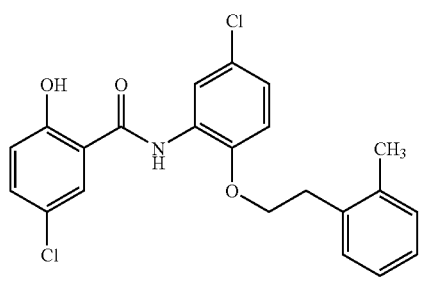
77 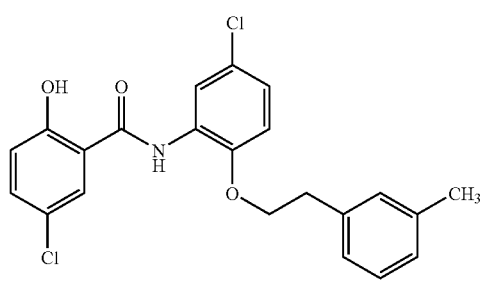
78 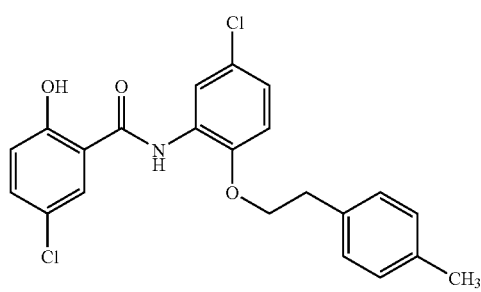
79 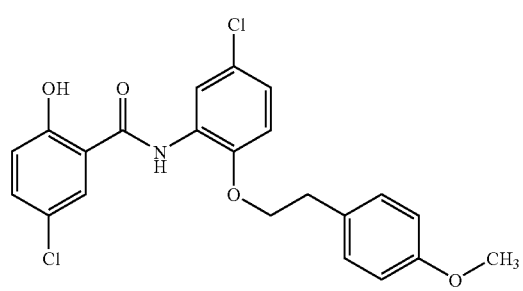

| | |
|---|---|
| 80 | 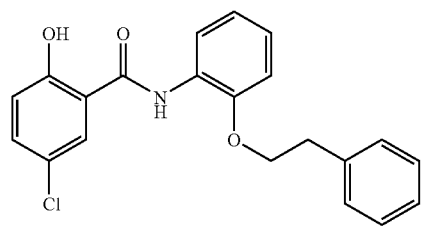 |
| 81 | 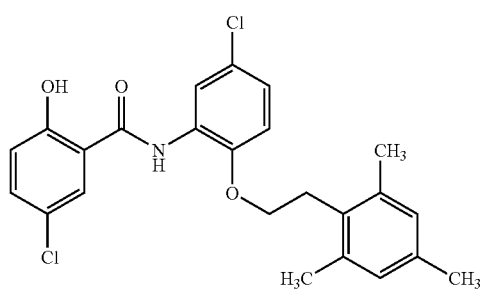 |
| 82 | 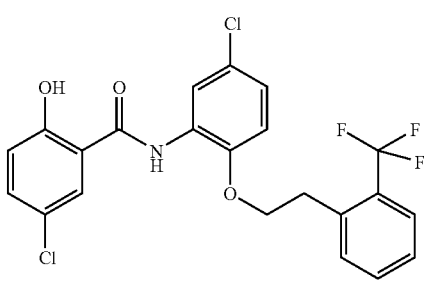 |
| 83 | 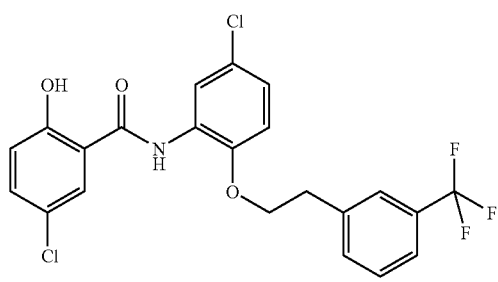 |
| 84 | 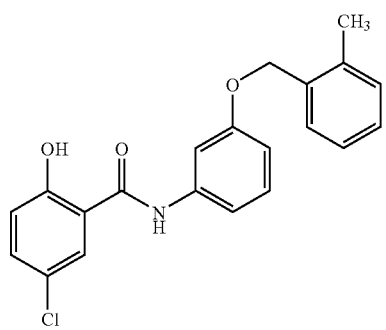 |

-continued
85 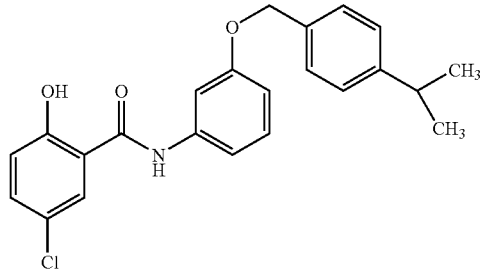
86 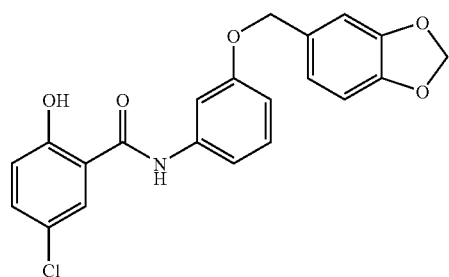
87 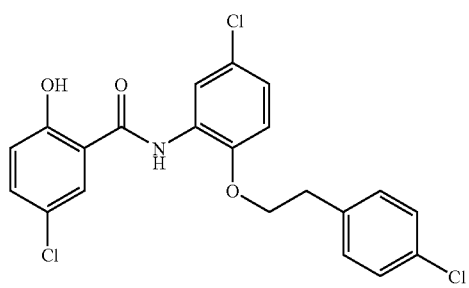
88 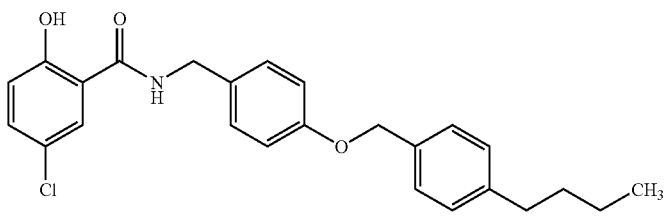
89 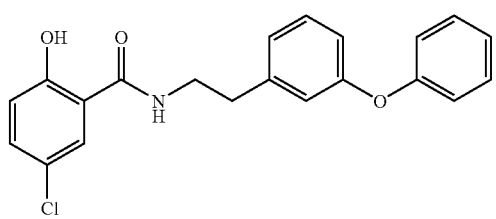
90 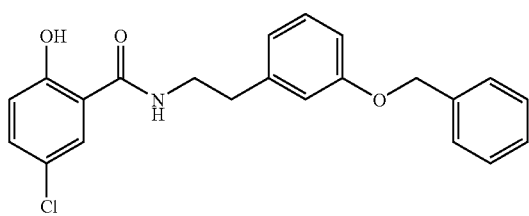

-continued
| | |
|---|---|
| 91 | 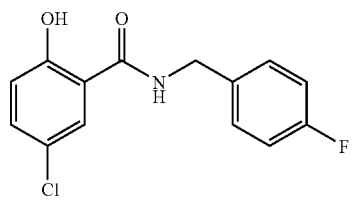 |
| 92 | 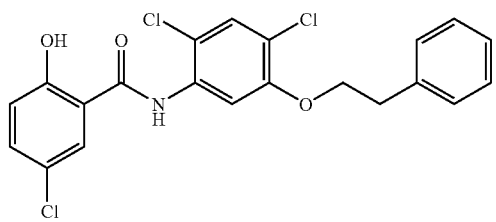 |
| 93 | 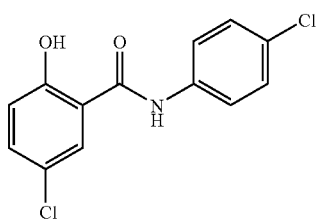 |
| 94 | 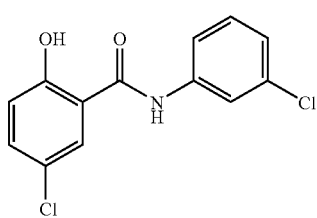 |
| 95 | 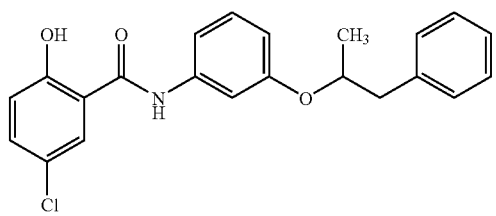 |
| 96 | 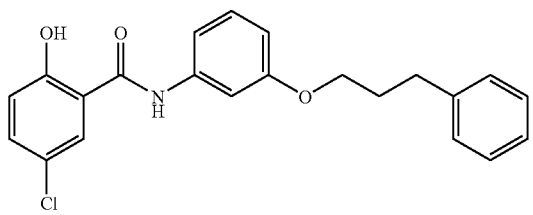 |
| 97 | 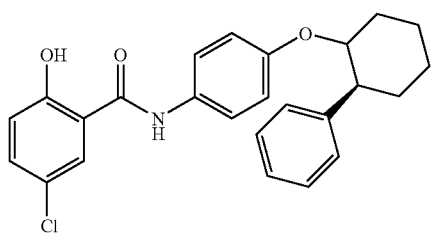 |

-continued
98 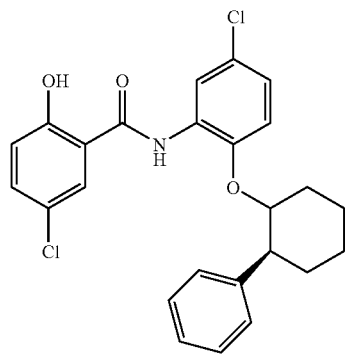
99 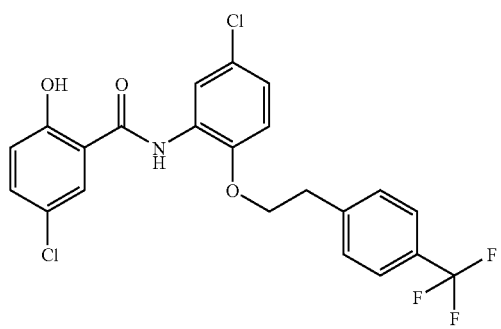
100 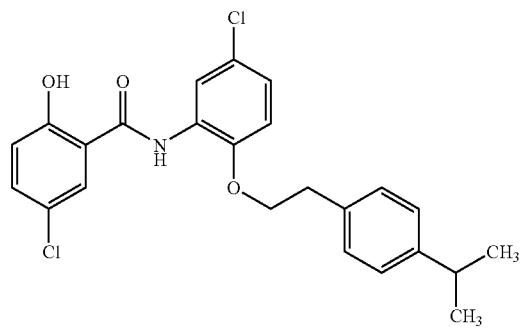
101 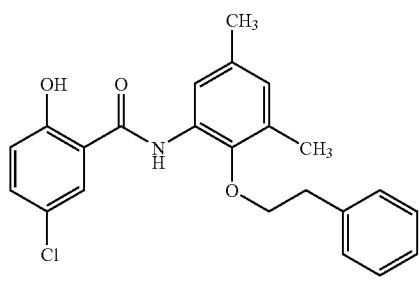
102 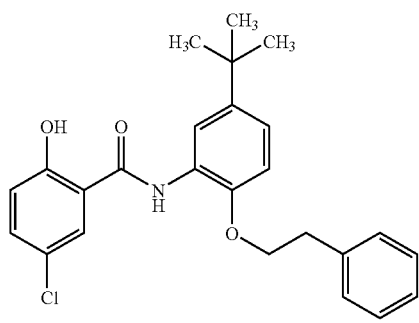

-continued
103 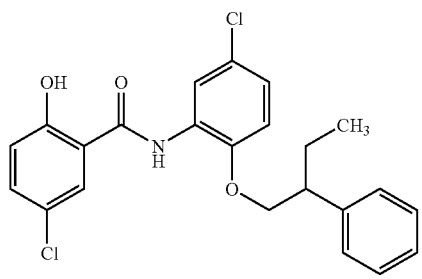
104 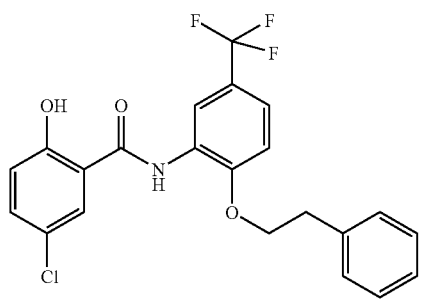
105 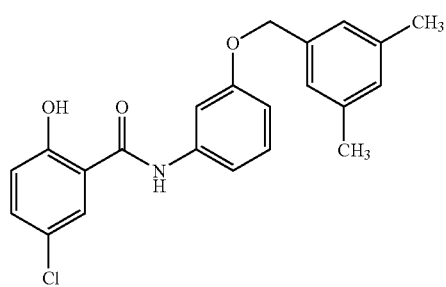
106 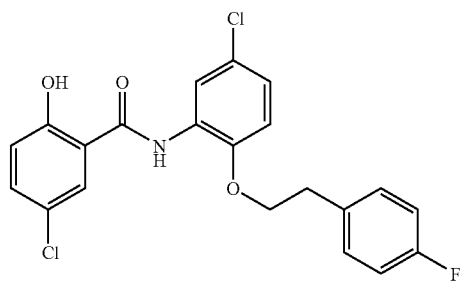
107 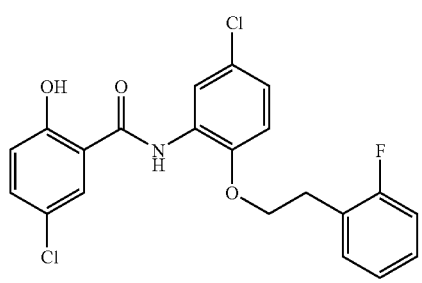

-continued
108 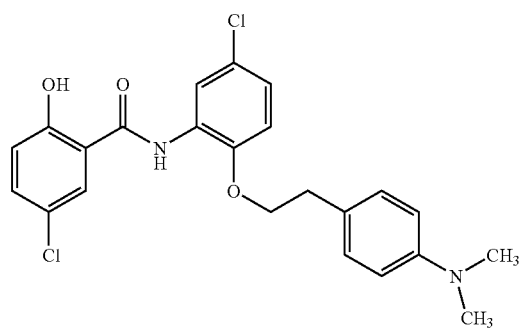
109 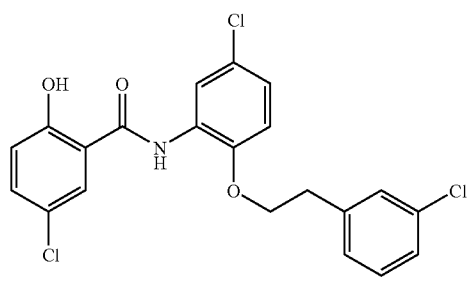
110 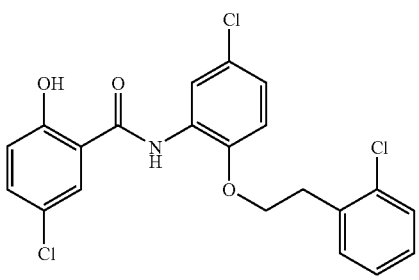
111 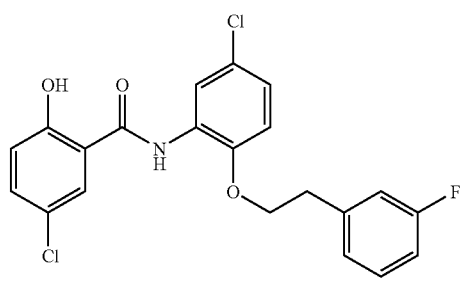
112 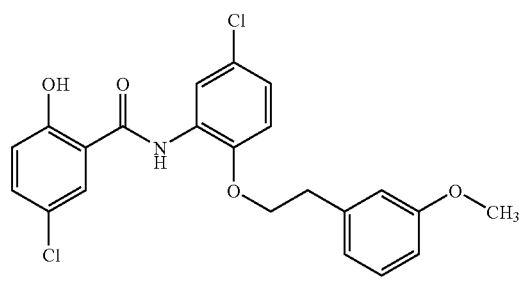

-continued
113 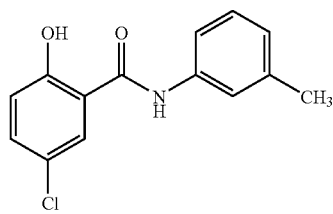
114 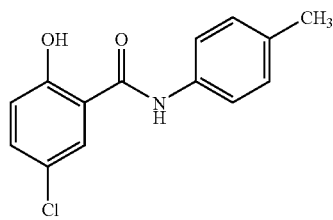
115 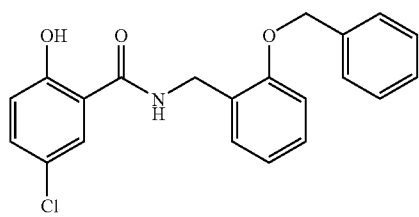
116 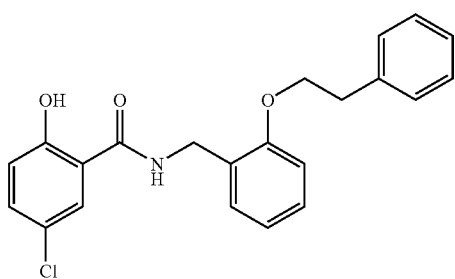
117 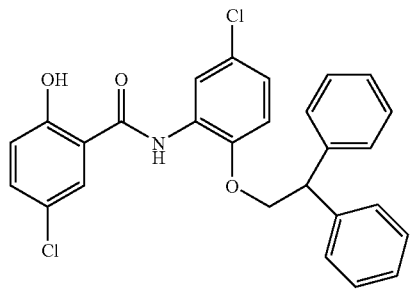
118 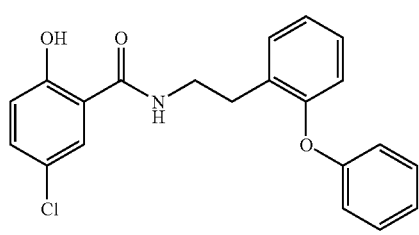

-continued
| | |
|---|---|
| 119 | 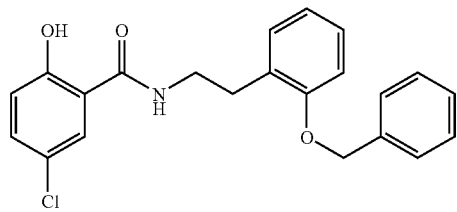 |
| 120 | 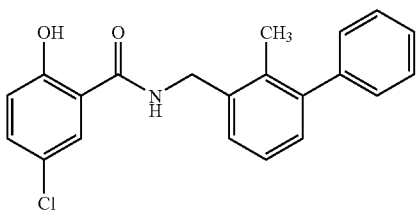 |
| 121 | 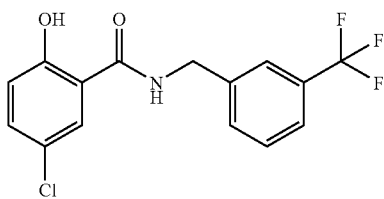 |
| 122 | 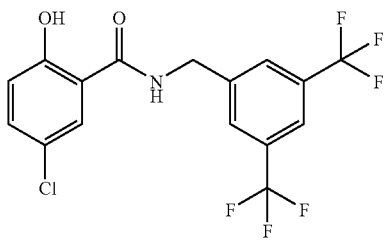 |
| 123 | 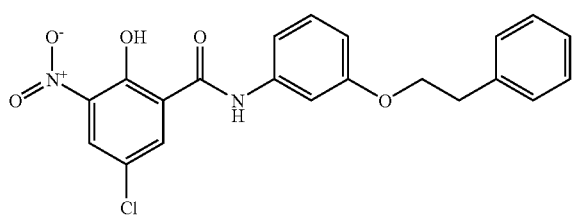 |
| 124 | 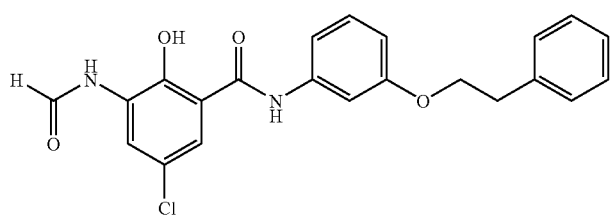 |
| 125 | 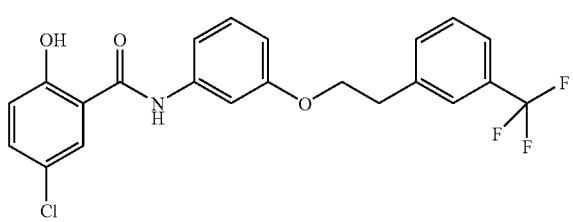 |

126 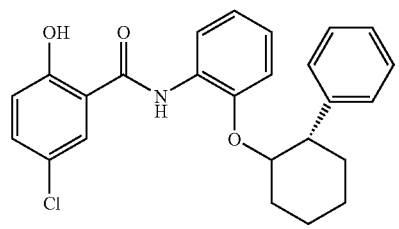
127 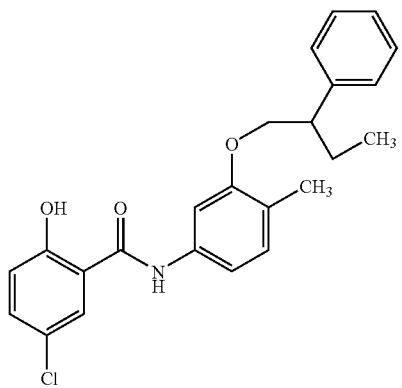
128 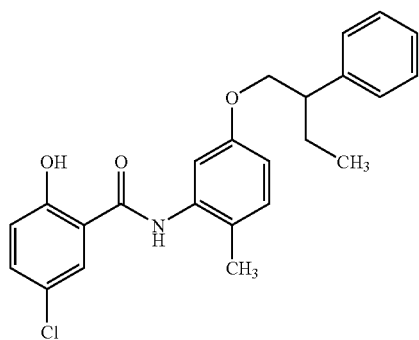
129 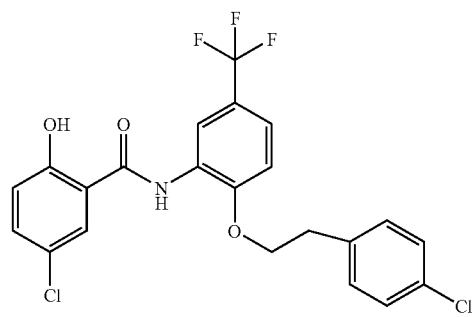

-continued
130
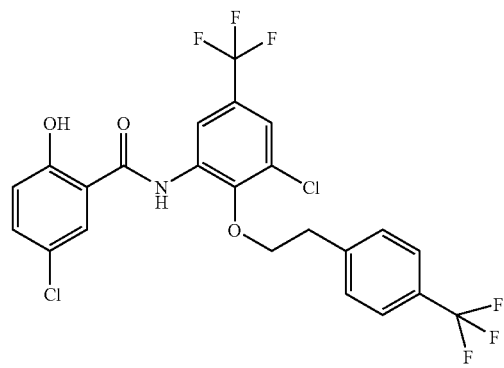
131
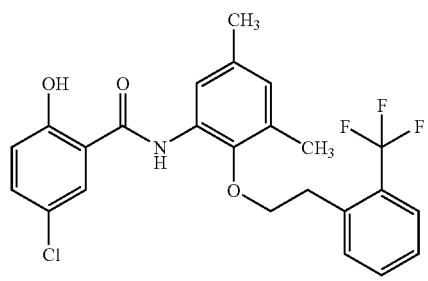
132
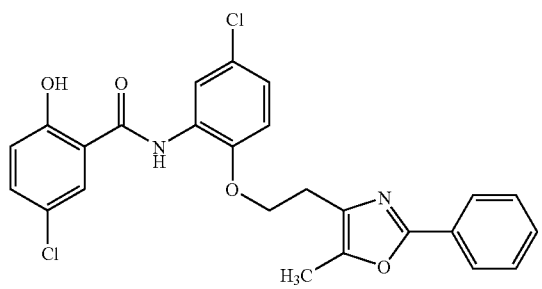
133
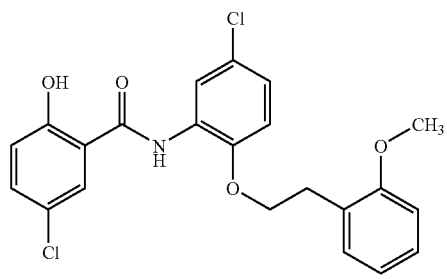
134
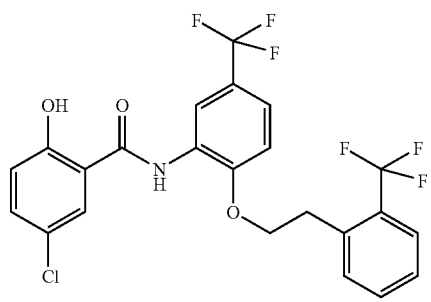

-continued
135
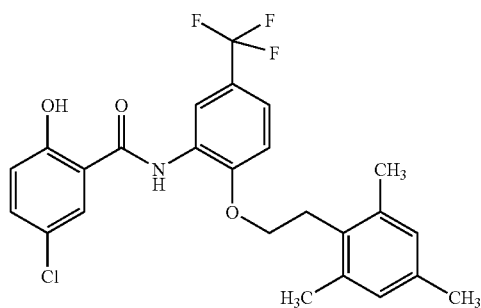
136
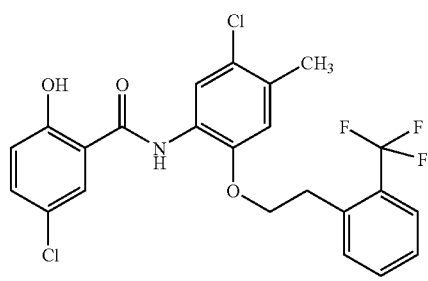
137
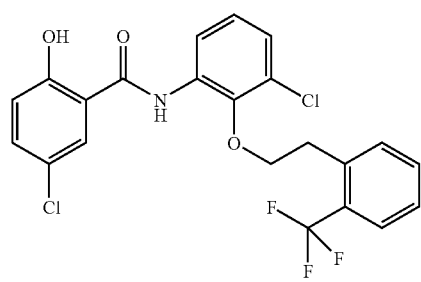
138
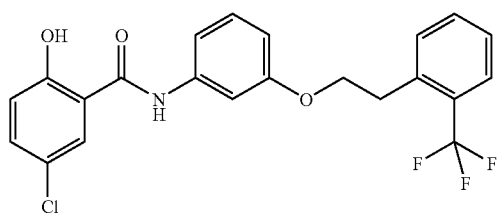
139
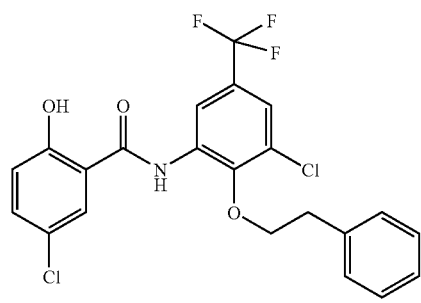

-continued
140 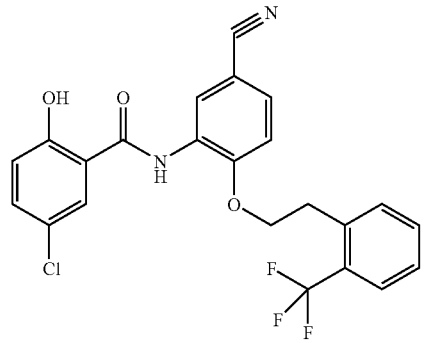
141 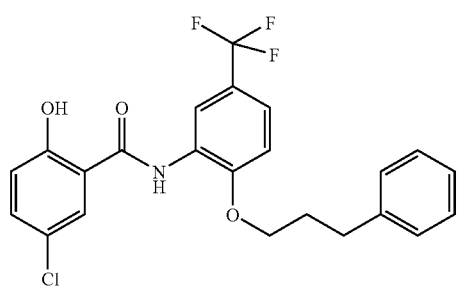
142 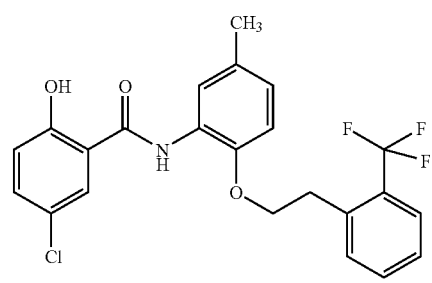
143 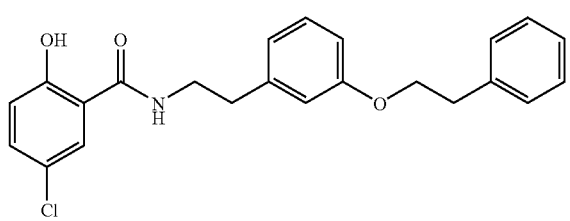
144 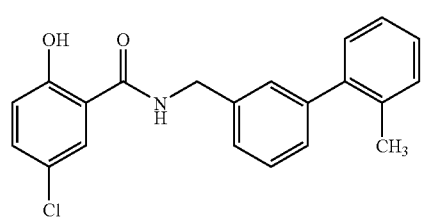
145 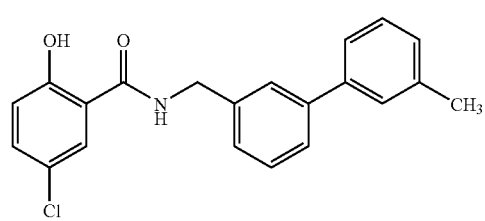

-continued
146 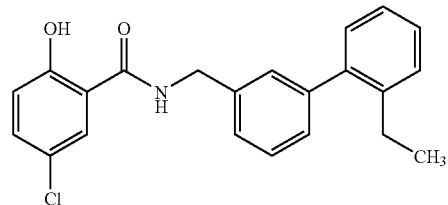
147 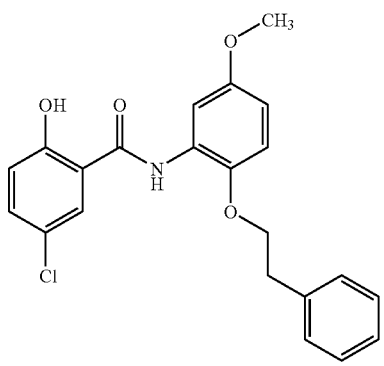
148 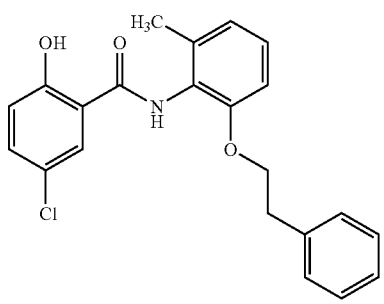
149 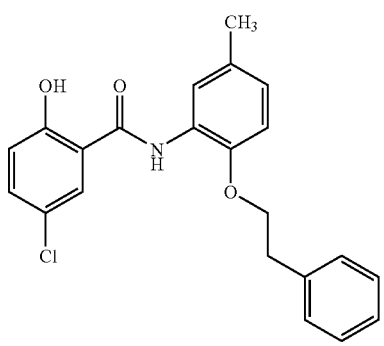
150 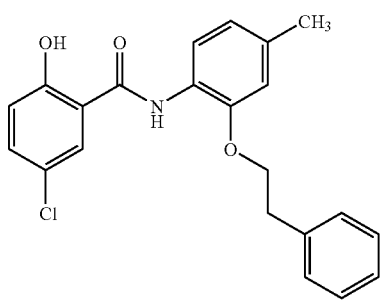

-continued
151 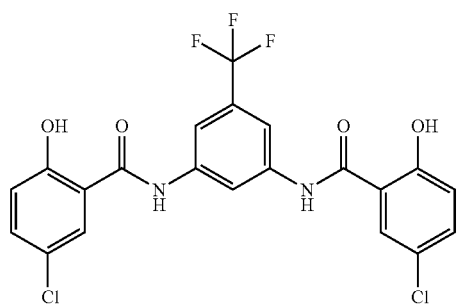
152 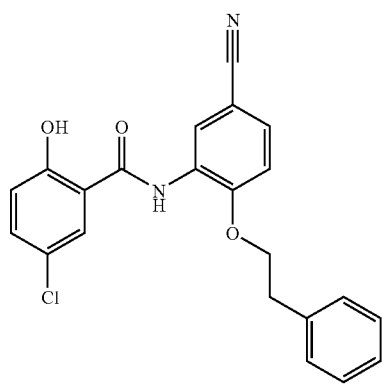
153 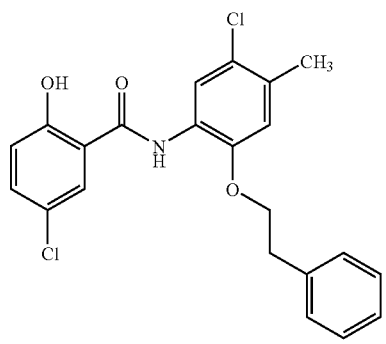
154 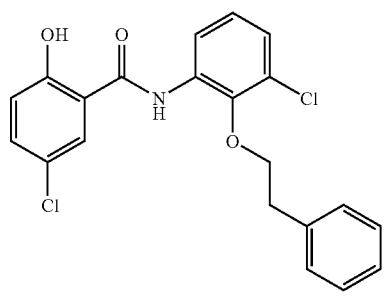

-continued
155
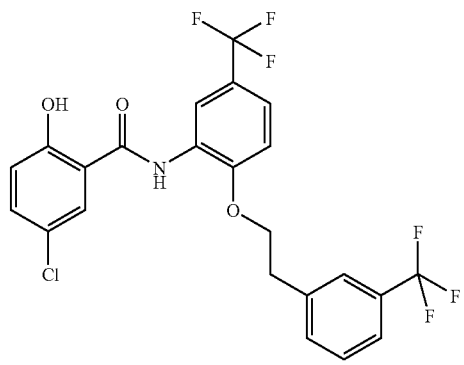
156
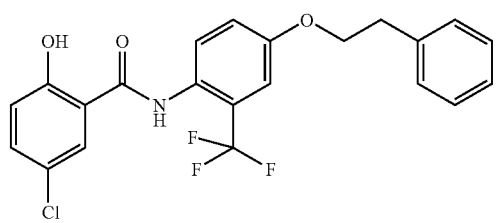
157
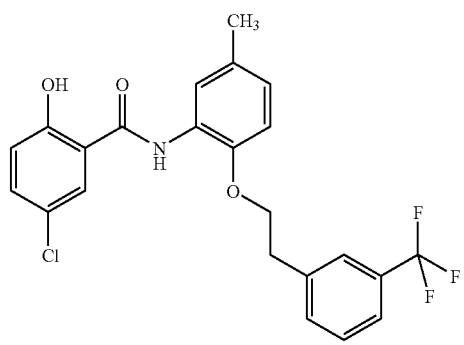
158
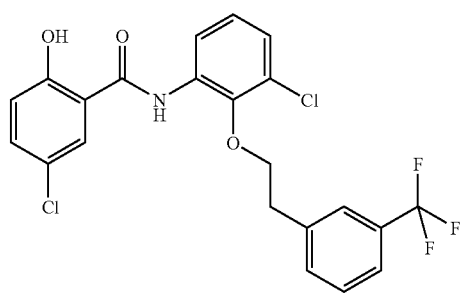
159
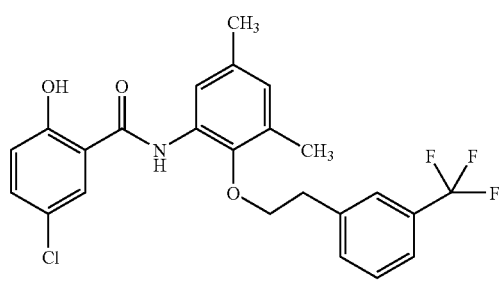

-continued
160
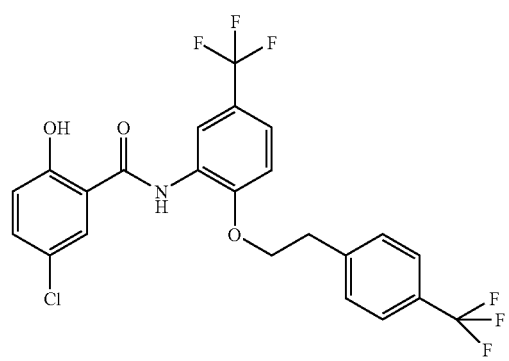
161
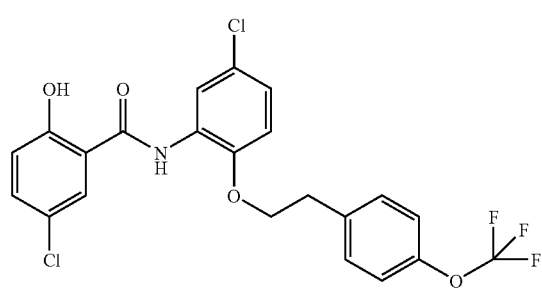
162
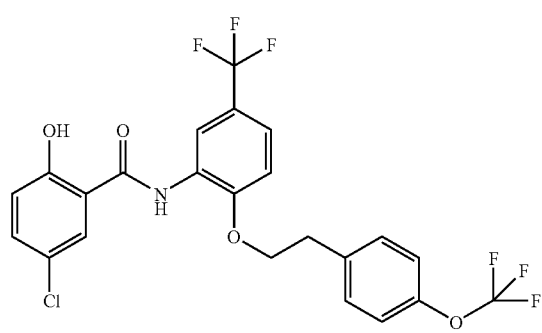
163
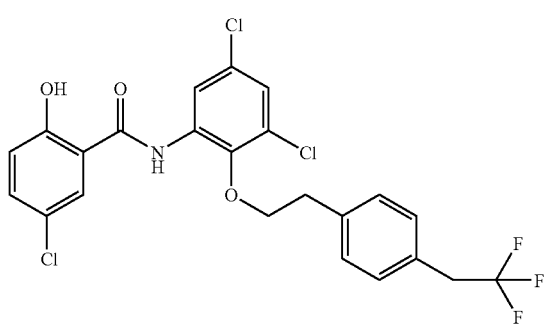

-continued
164
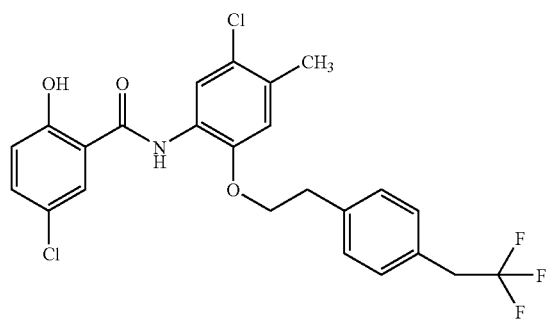
165
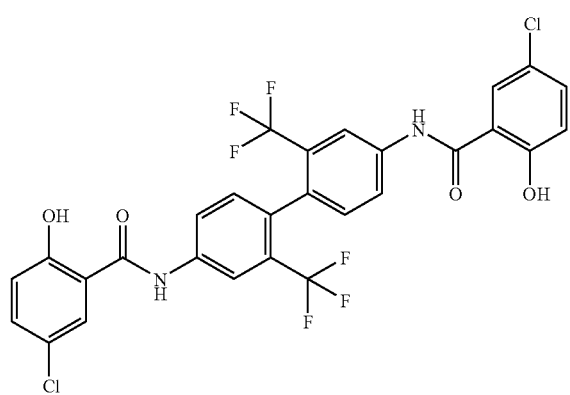
166
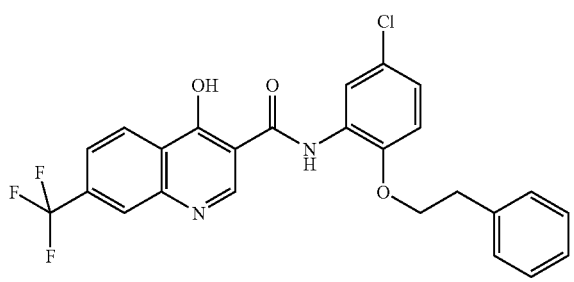
167
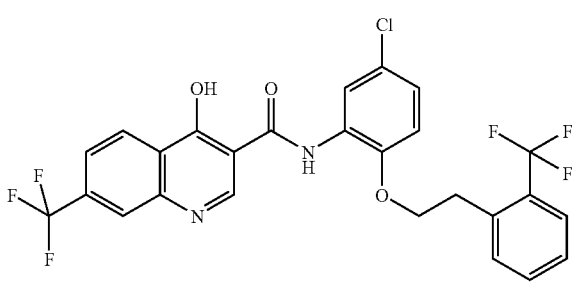
168
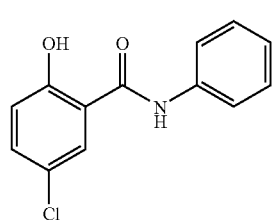

-continued
169 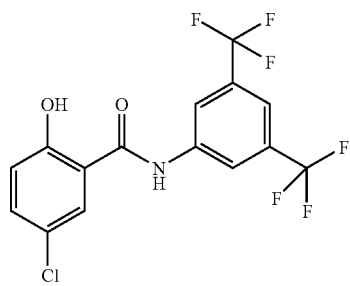
170 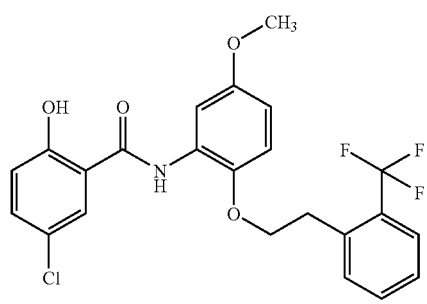
171 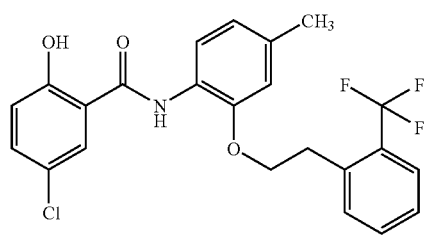
172 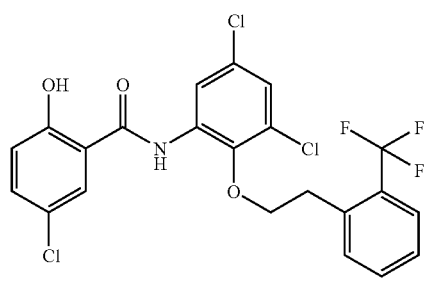
173 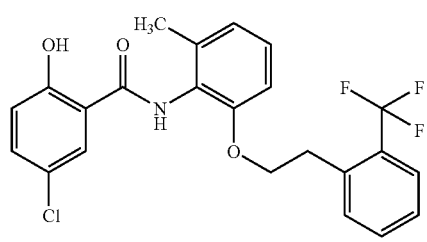
174 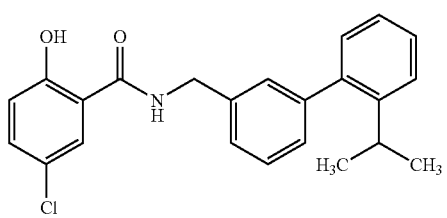

-continued
175 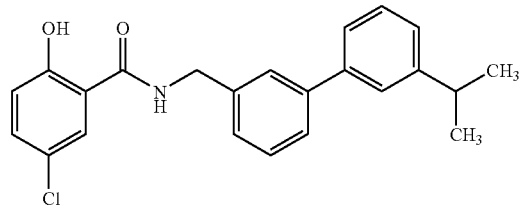
176 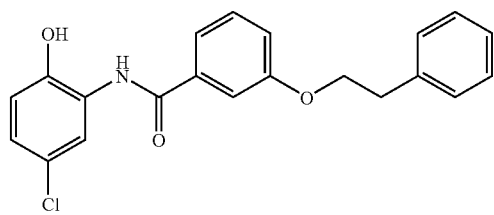
177 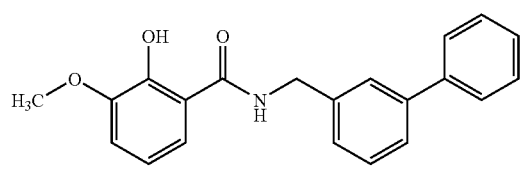
178 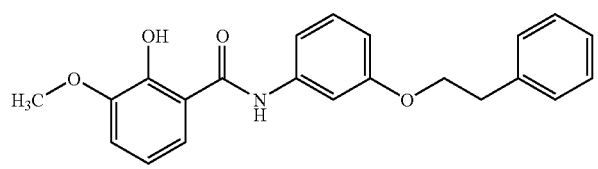
179 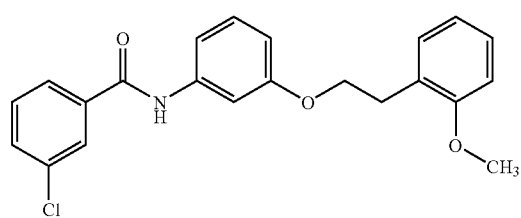
180 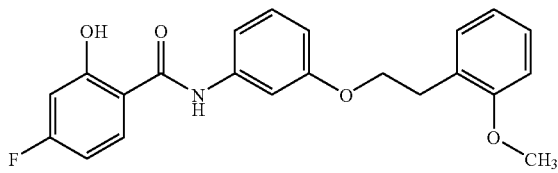
181 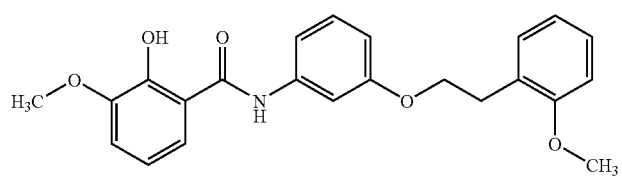
182 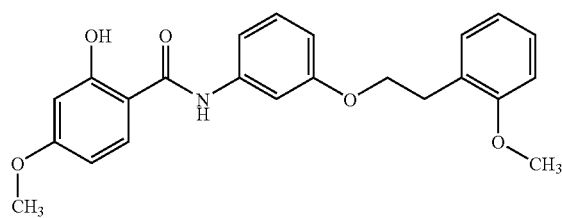

-continued
183
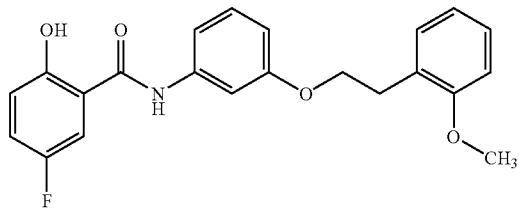
184
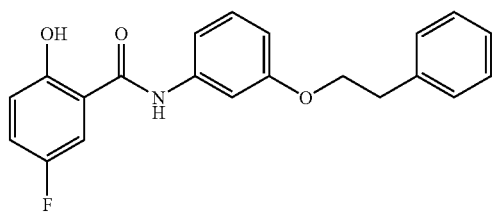
185
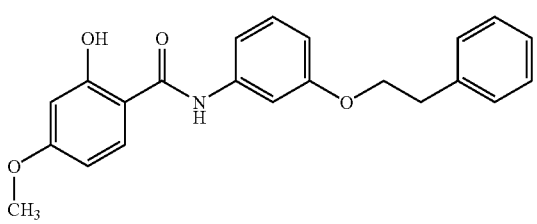
186
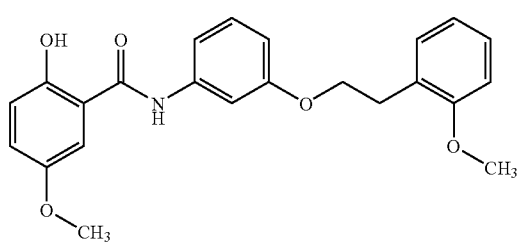
187
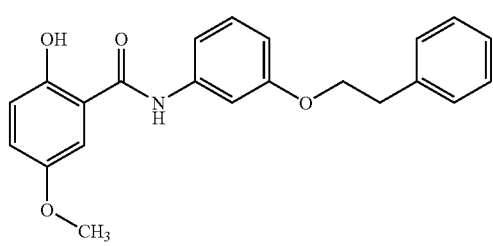
188
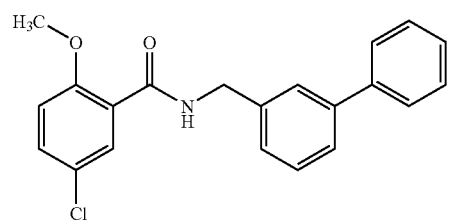
189
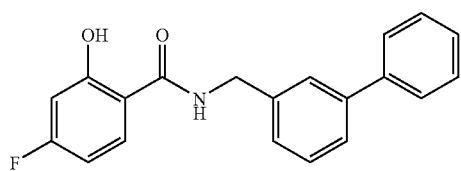

-continued
| | |
|---|---|
| 190 | 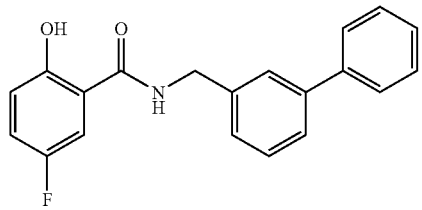 |
| 191 | 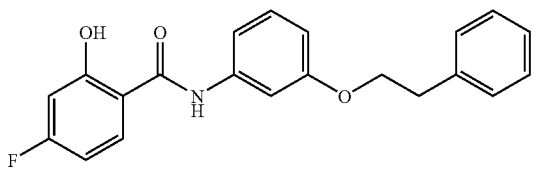 |
| 192 | 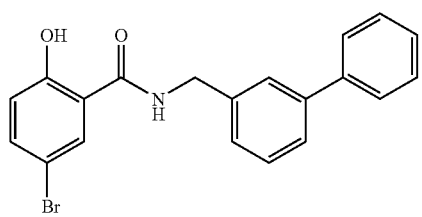 |
| 193 | 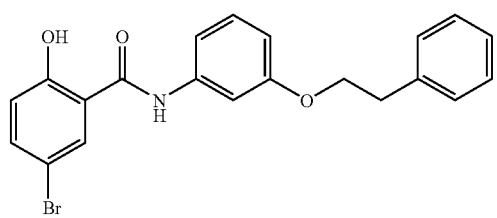 |
| 194 | 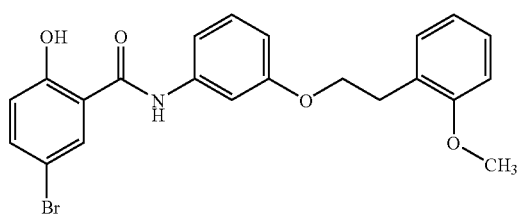 |
| 195 | 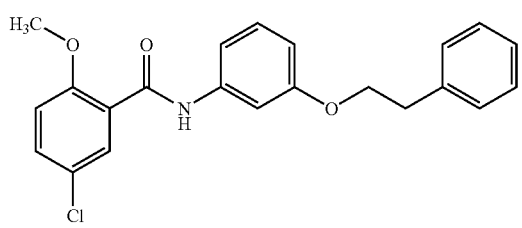 |
| 196 | 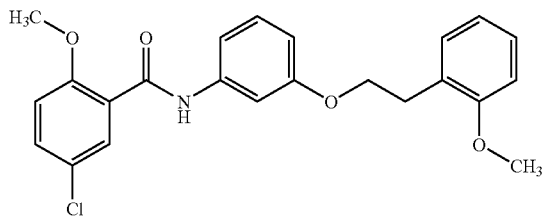 |

-continued
| | |
|---|---|
| 197 | 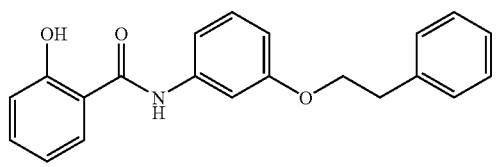 |
| 198 | 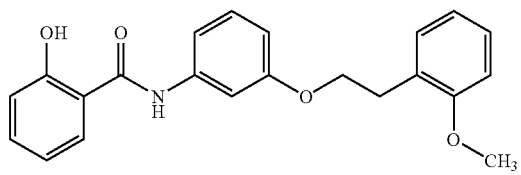 |
| 199 | 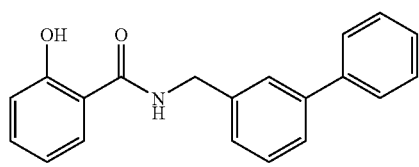 |
| 200 | 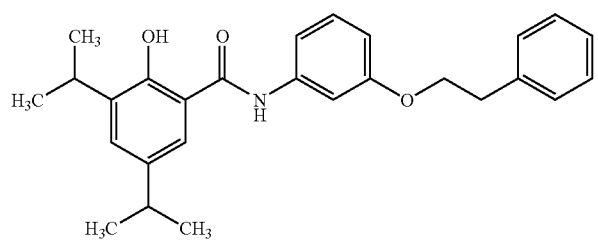 |
| 201 | 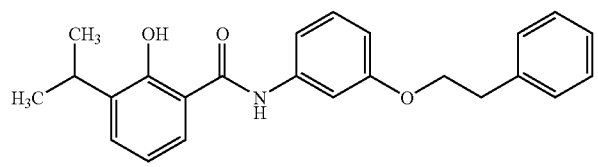 |
| 202 | 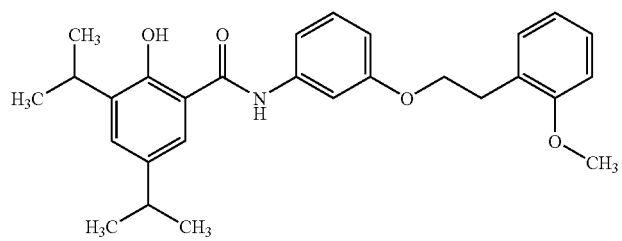 |
| 203 | 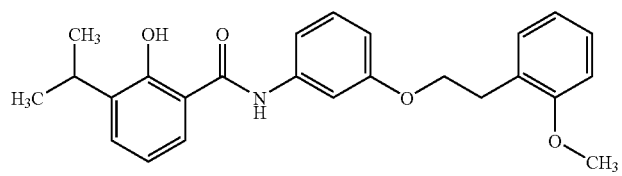 |
| 204 | 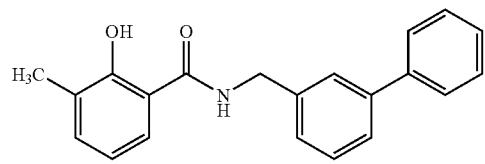 |

-continued
| | |
|---|---|
| 205 | 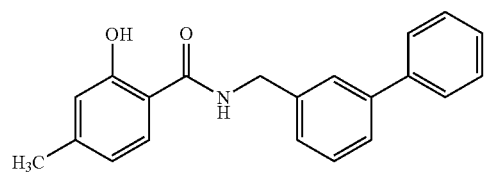 |
| 206 | 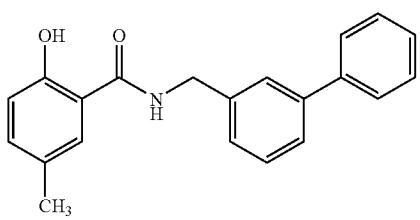 |
| 207 | 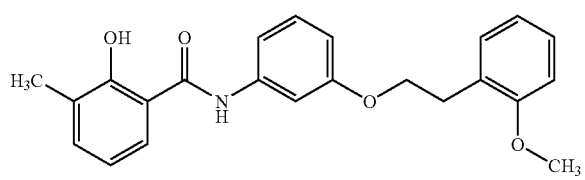 |
| 208 |  |
| 209 | 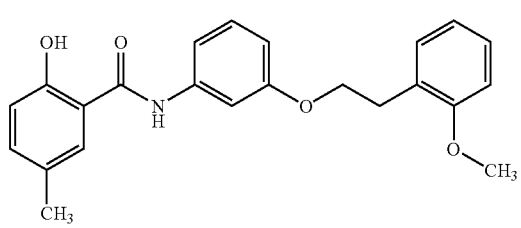 |
| 210 | 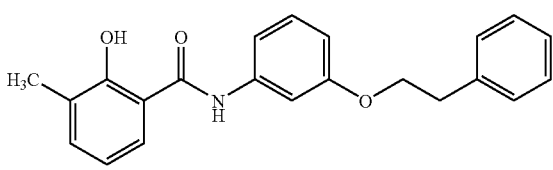 |
| 211 | 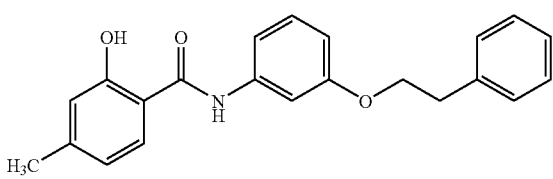 |
| 212 | 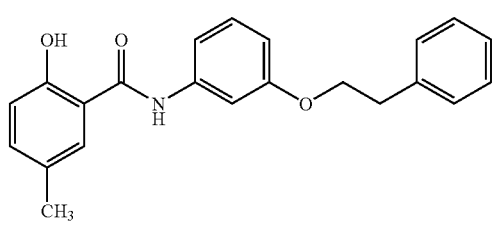 |

-continued
| | |
|---|---|
| 213 | 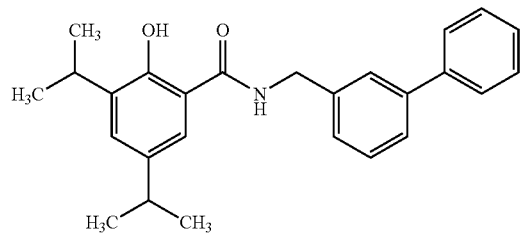 |
| 214 | 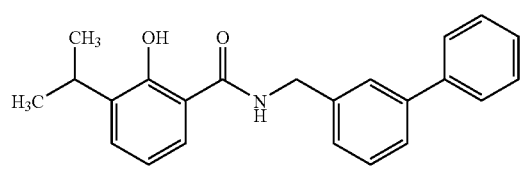 |
| 215 | 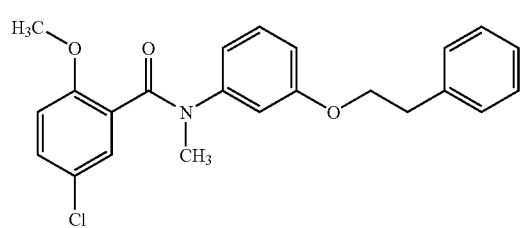 |
| 216 | 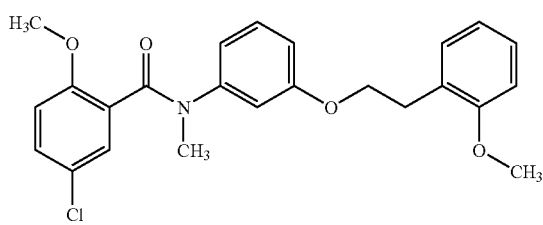 |
| 217 | 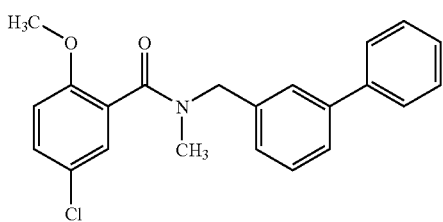 |
| 218 | 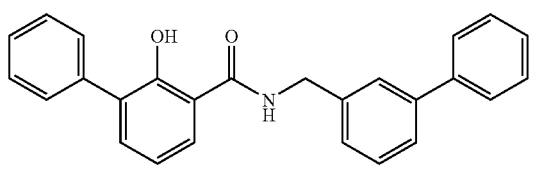 |
| 219 | 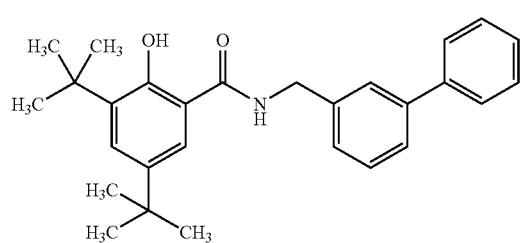 |

-continued
220
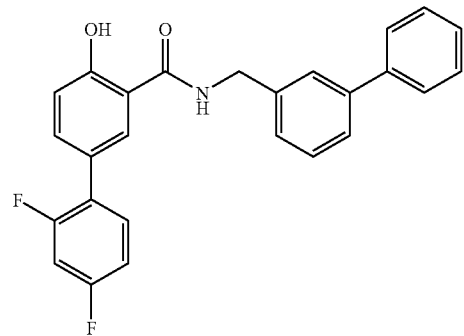
221
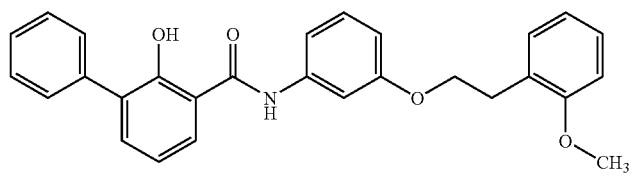
222
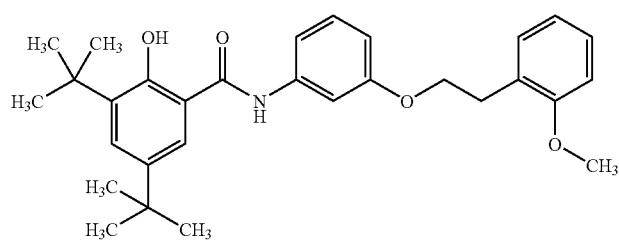
223
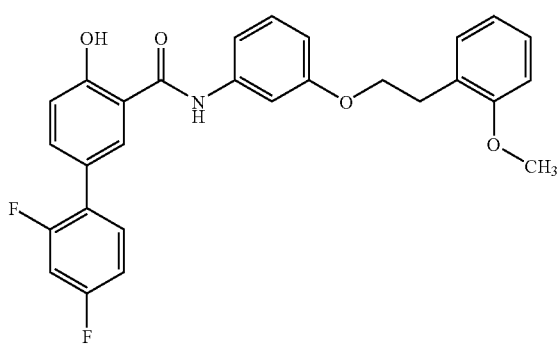
224
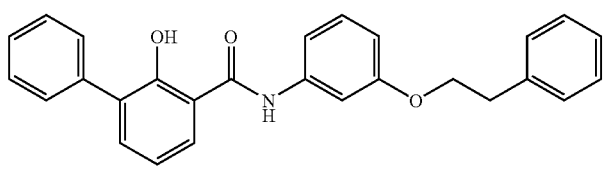
225
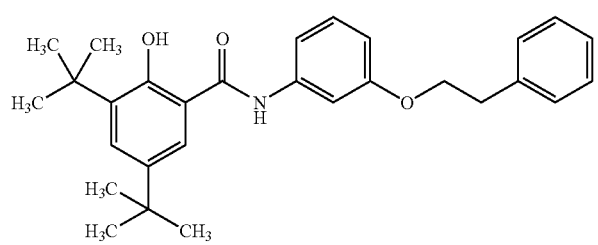

-continued
226
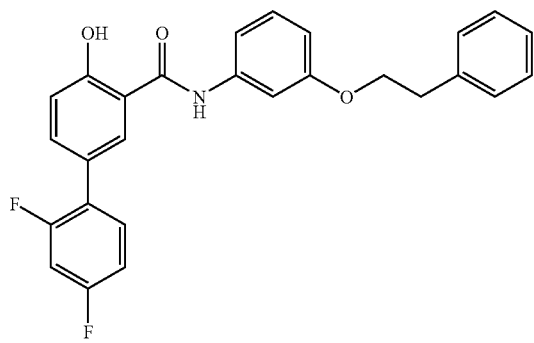
227
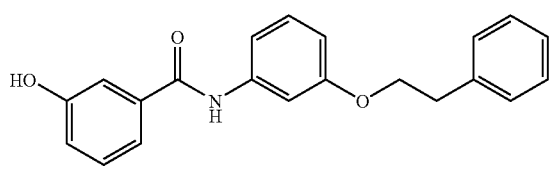
228
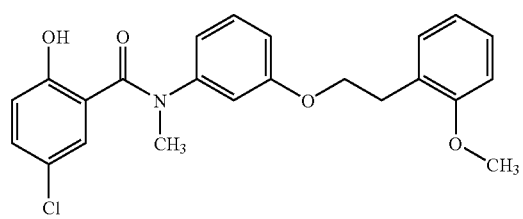
229
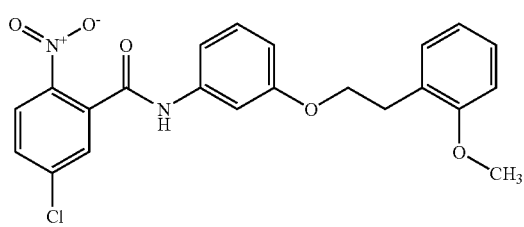
230
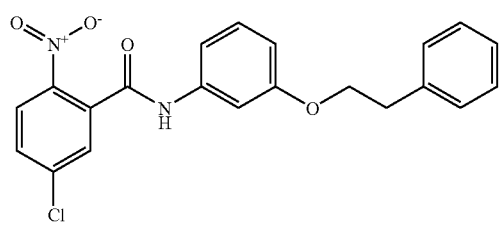
231
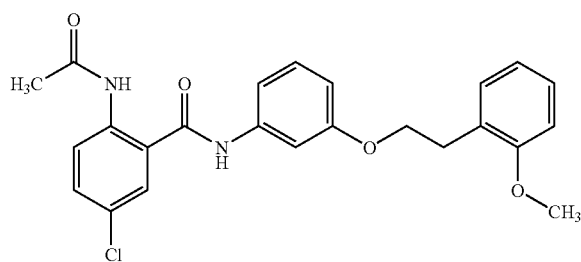

-continued
232 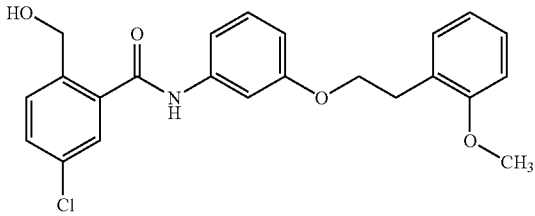
233 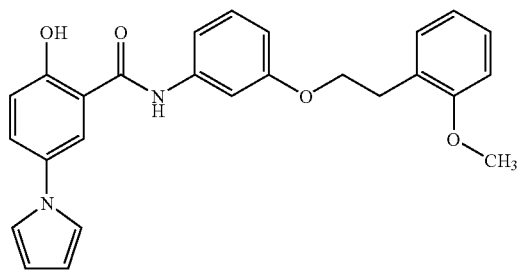
234 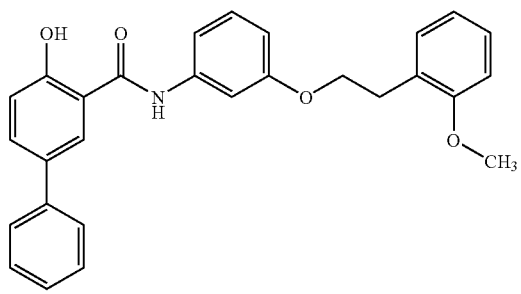
235 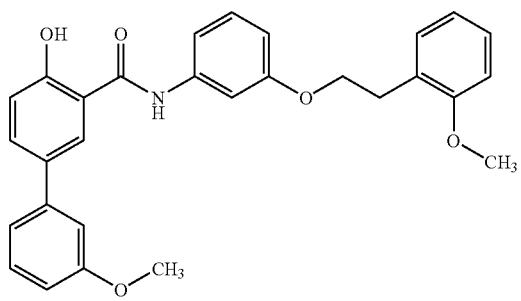
236 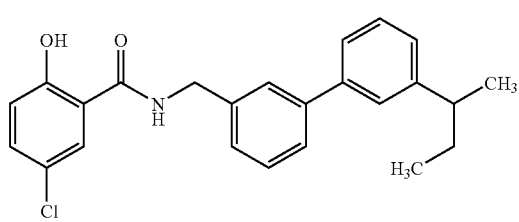
237 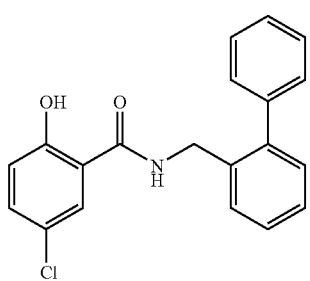

238 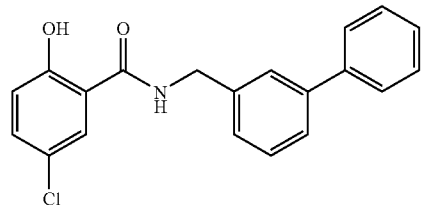
239 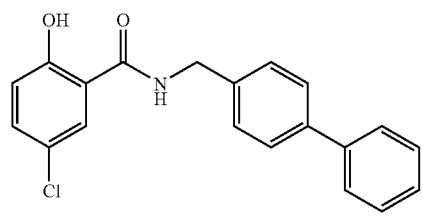
240 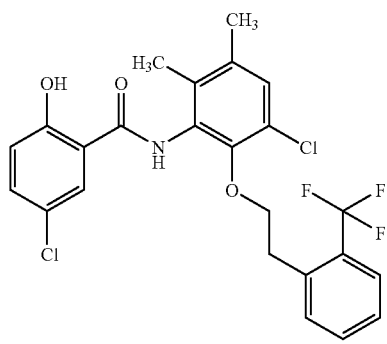
241 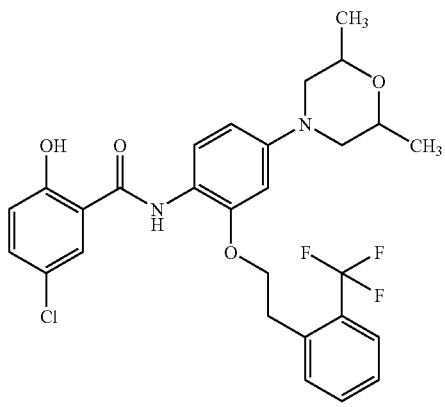
242 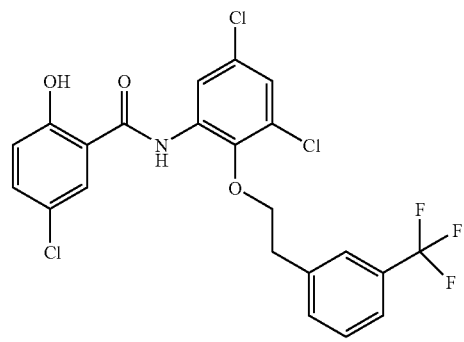

243 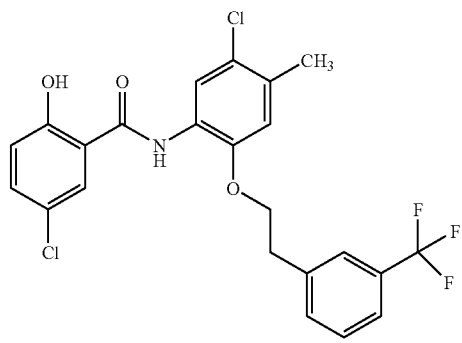
244 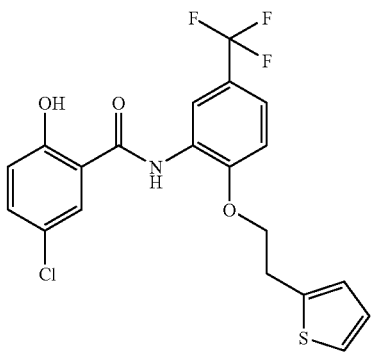
245 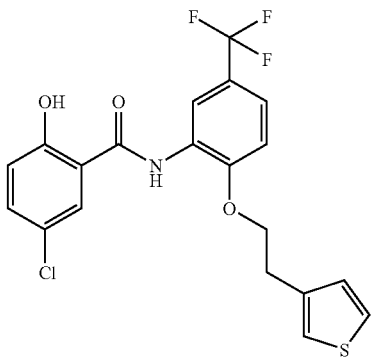
246 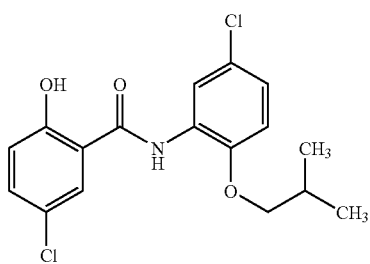

-continued
247 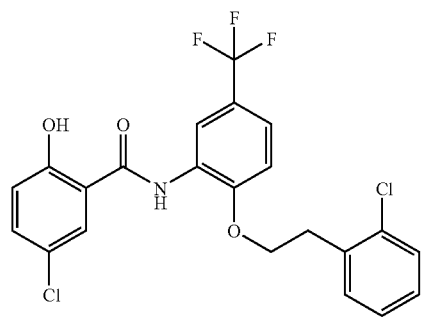
248 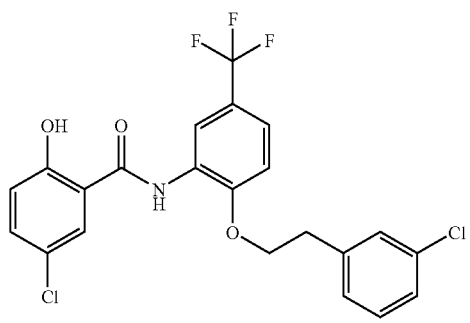
249 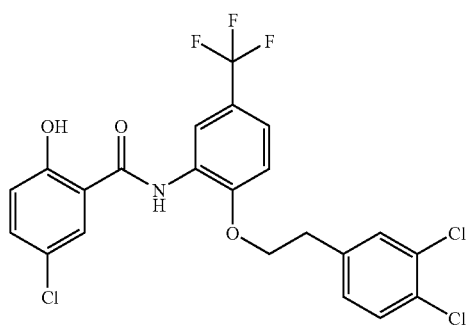
250 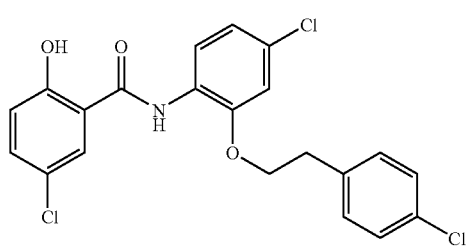
251 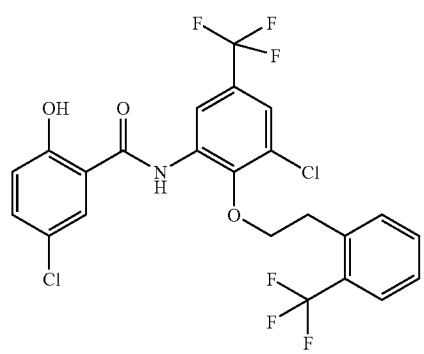

-continued
252
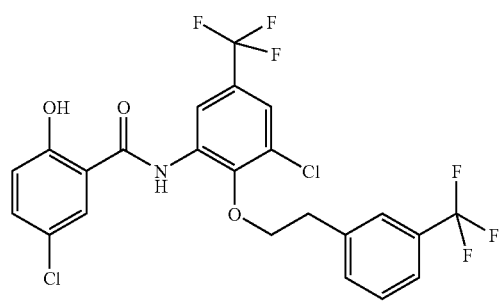
253
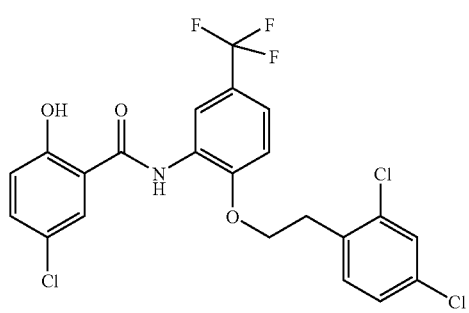
254
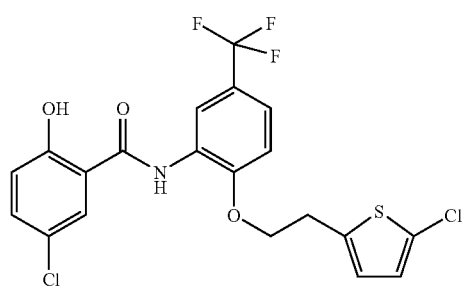
255
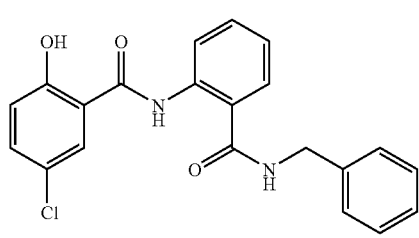
256
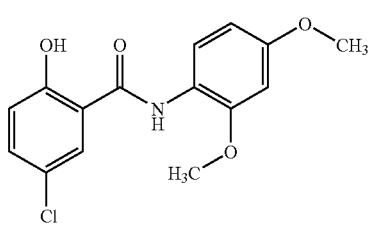

-continued
257 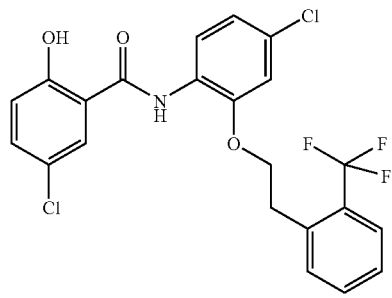
258 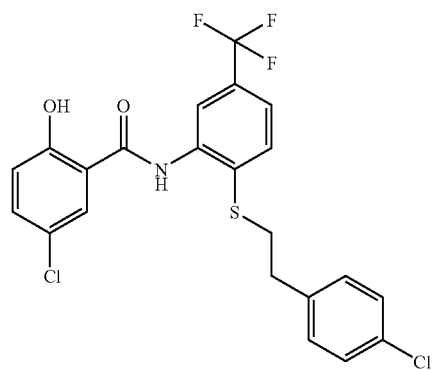
259 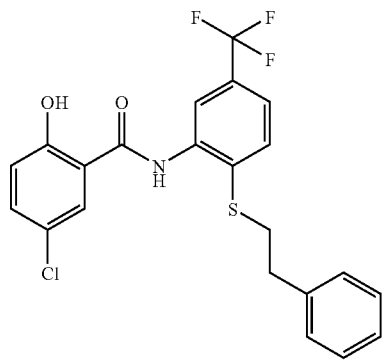
260 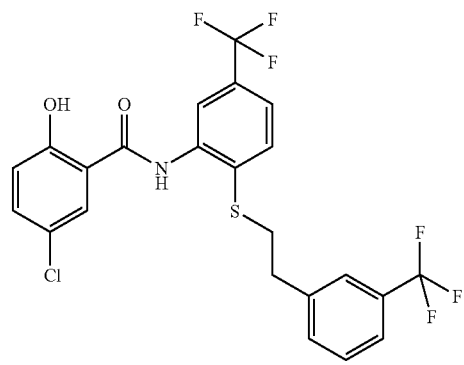

-continued
261
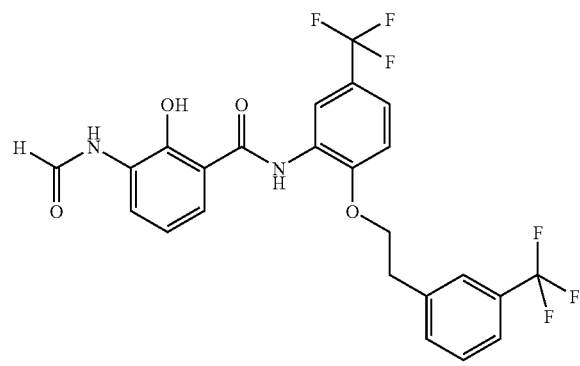
262
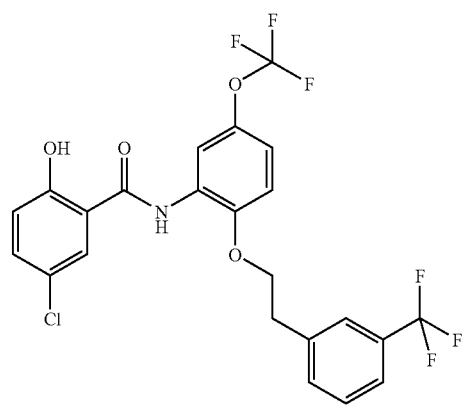
263
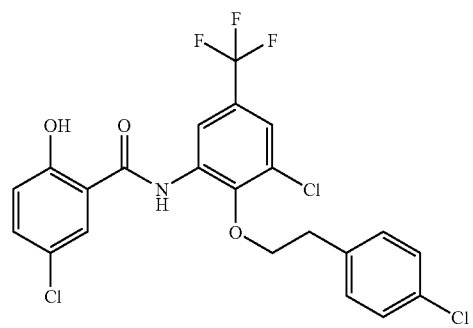
264
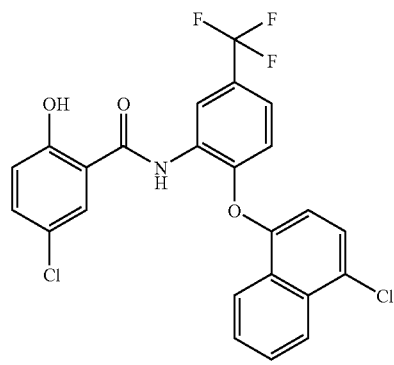

-continued
265
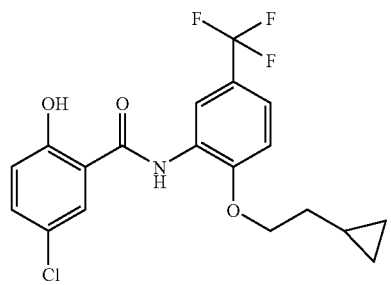
266
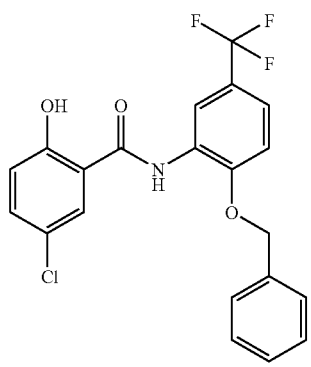
267
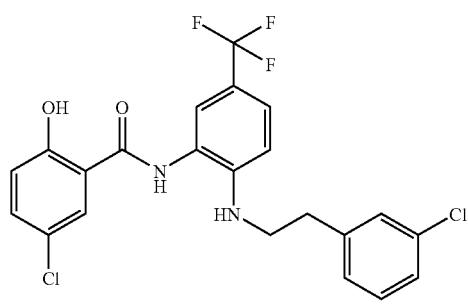
268
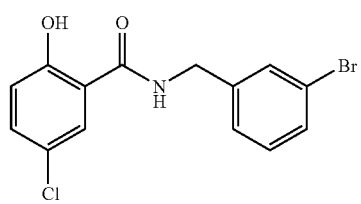
269
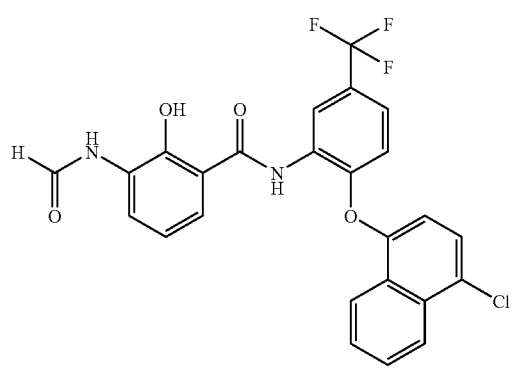

-continued
270 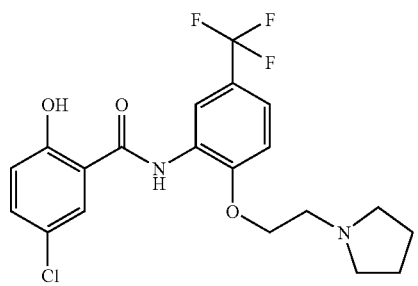
271 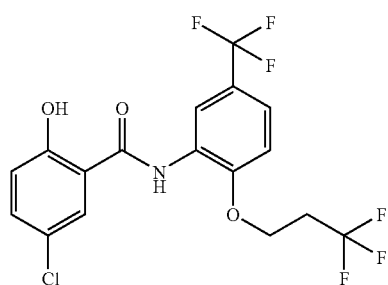
272 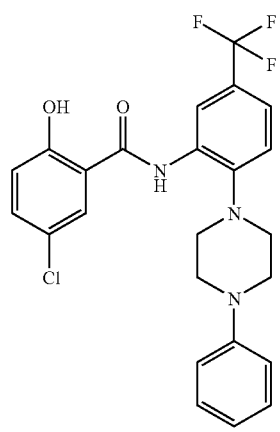
273 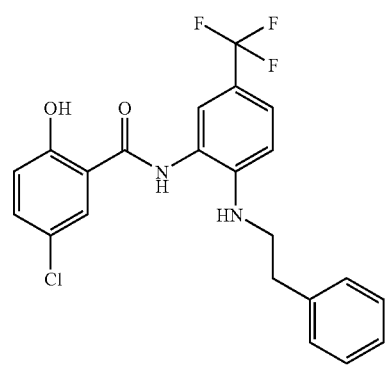

-continued
274
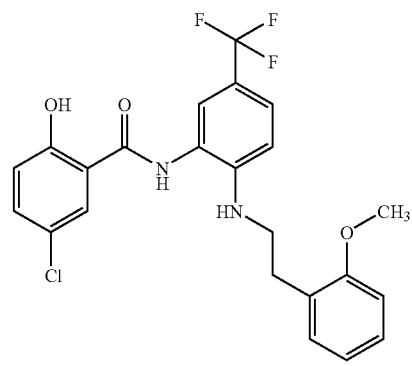
275
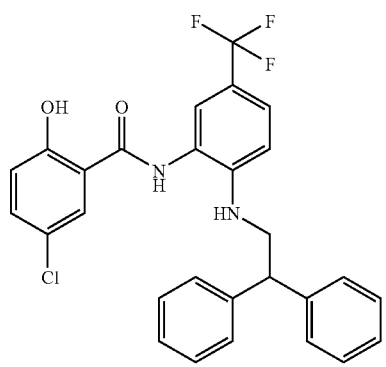
276
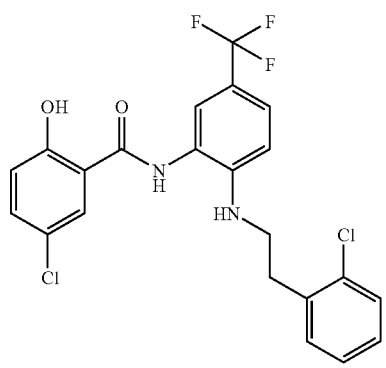
277
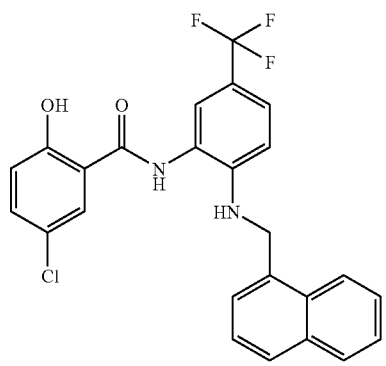

-continued
278 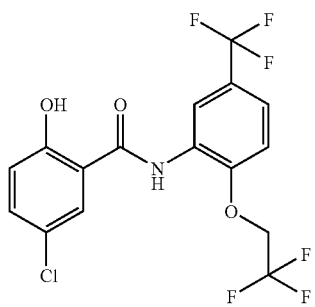
279 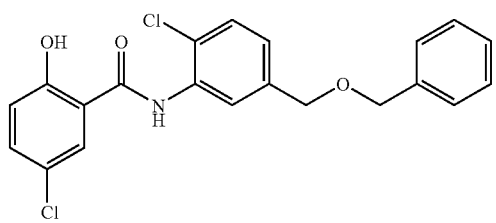
280 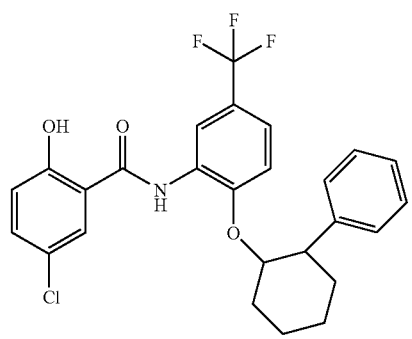
281 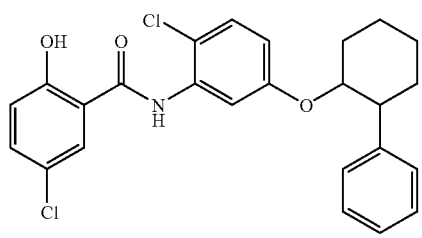
282 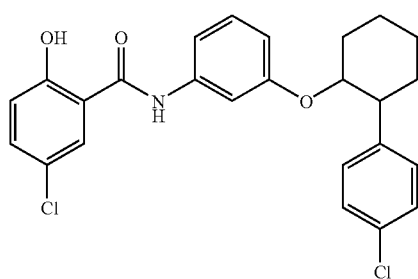

283 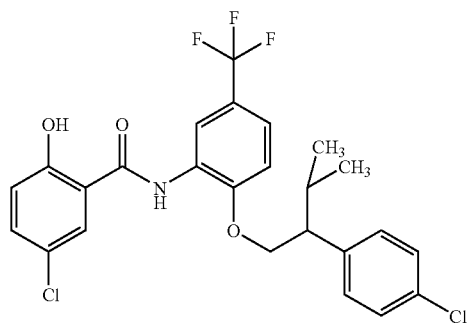
284 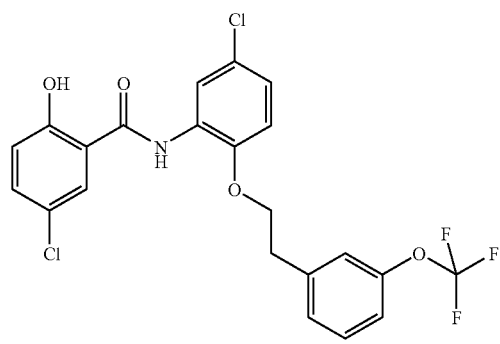
285 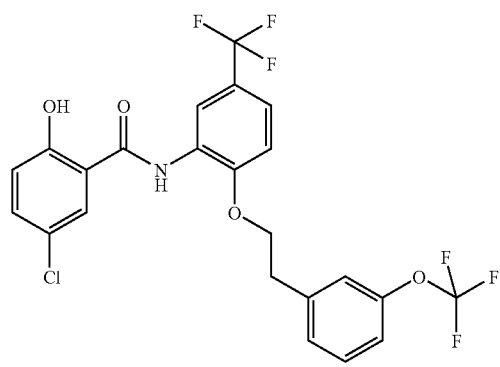
286 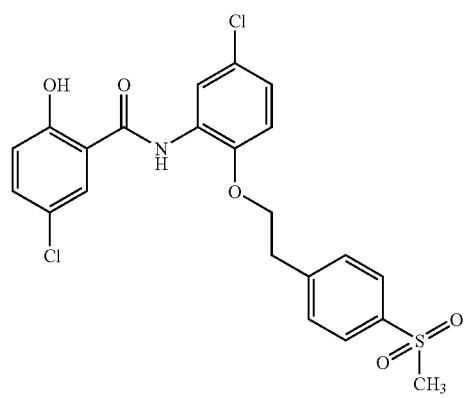

| | |
|---|---|
| 287 | 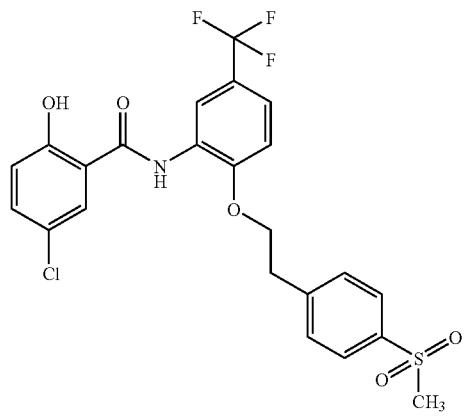 |
| 288 | 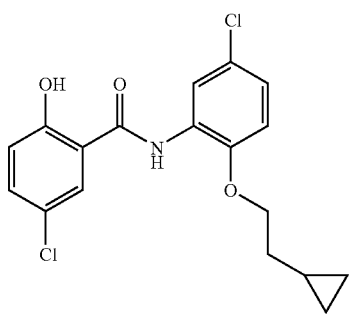 |
| 289 | 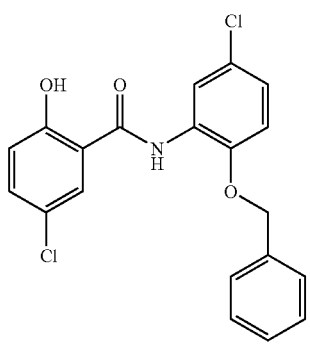 |
| 290 | 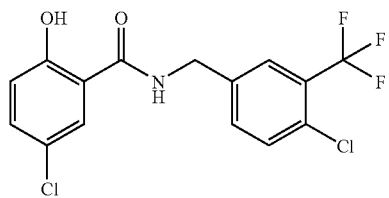 |
| 291 | 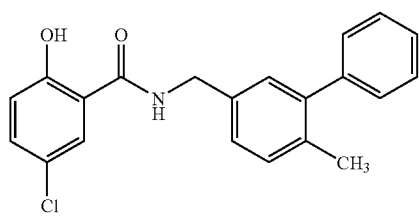 |

-continued
292 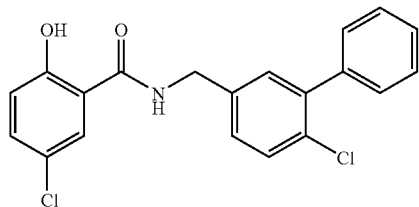
293 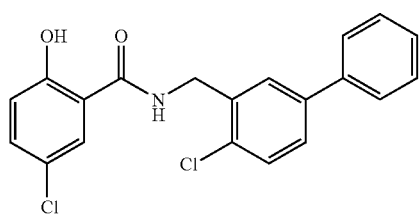
294 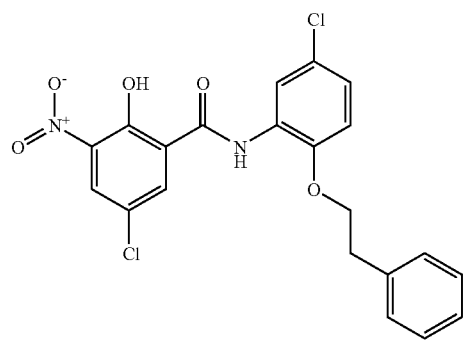
295 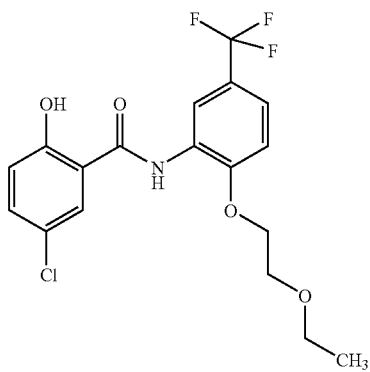
296 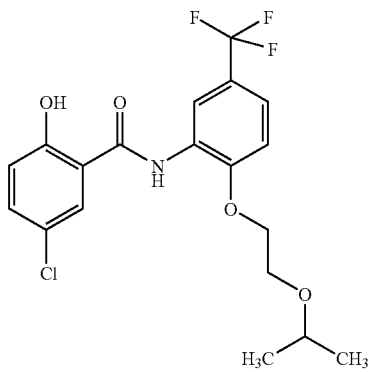

297 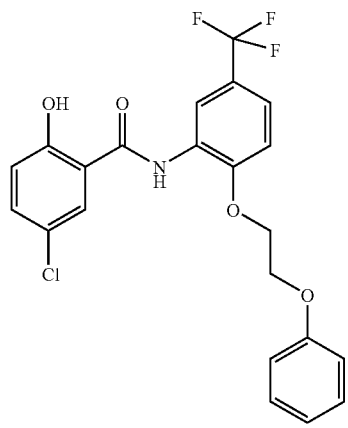
298 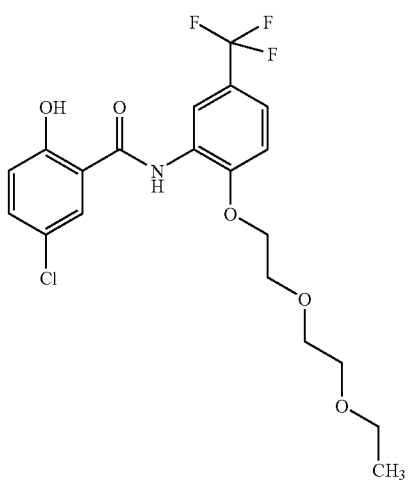
299 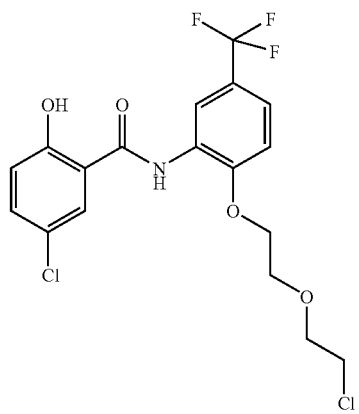

-continued
300 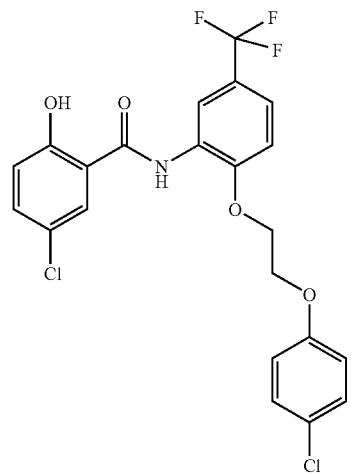
301 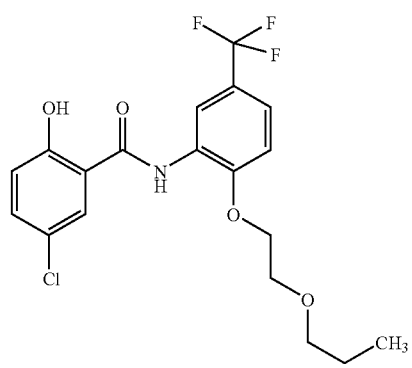
302 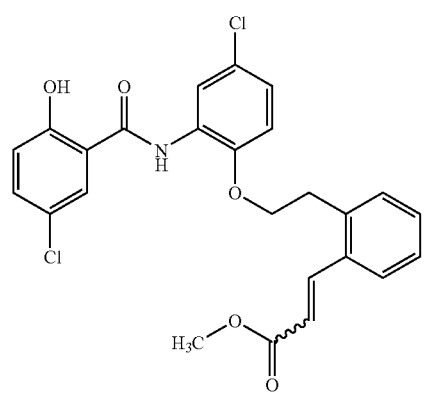
303 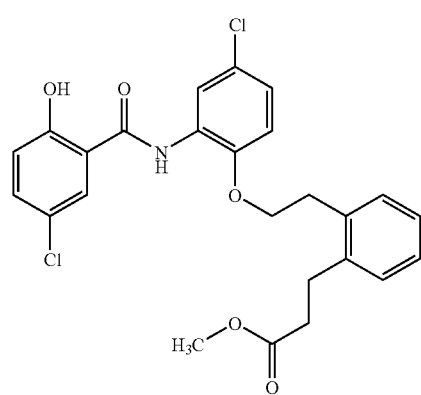

-continued
304
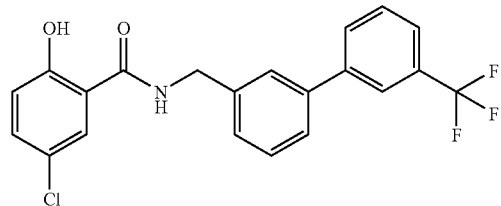
305
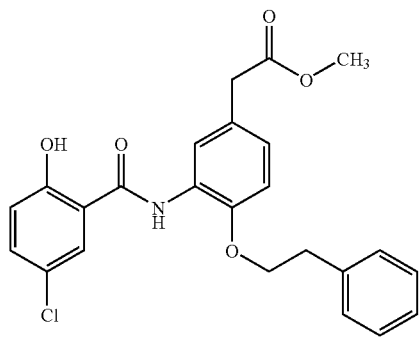
306
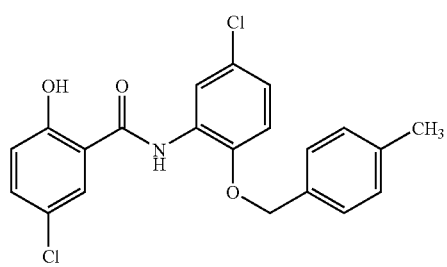
307
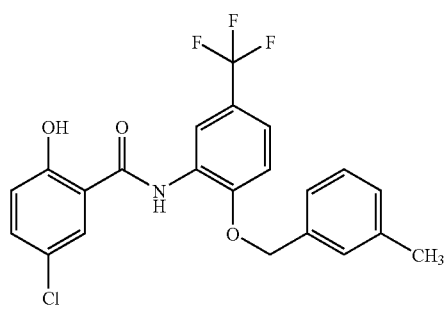
308
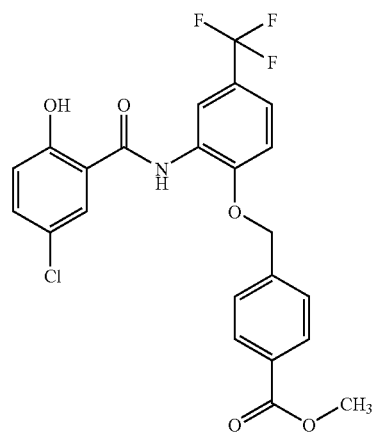

-continued
| | |
|---|---|
| 309 | 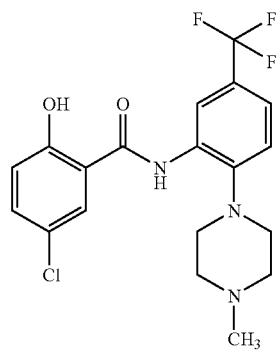 |
| 310 | 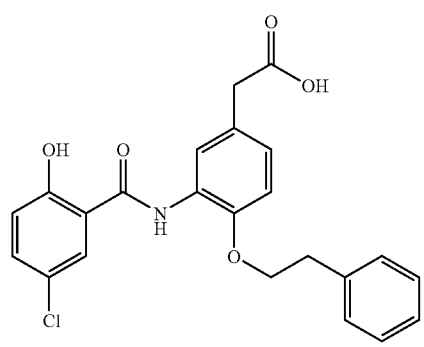 |
| | |
|---|---|
| 311 | 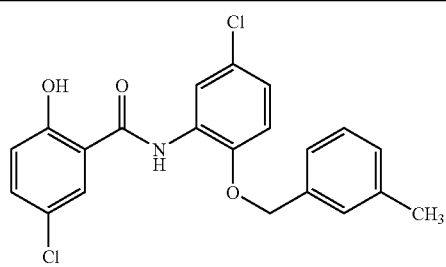 |
| 312 | 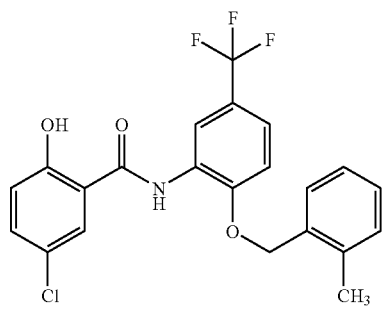 |
| 313 | 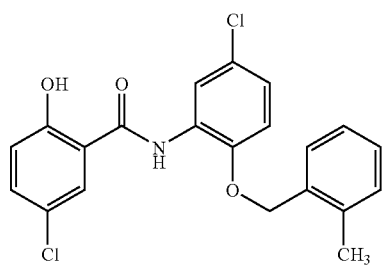 |

-continued
| | |
|---|---|
| 314 | 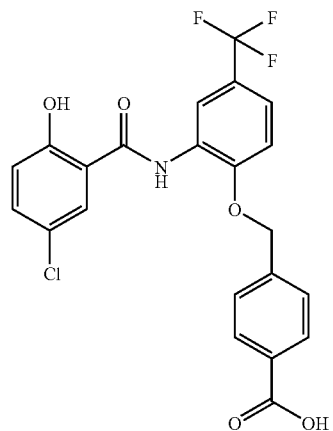 |
| 315 | 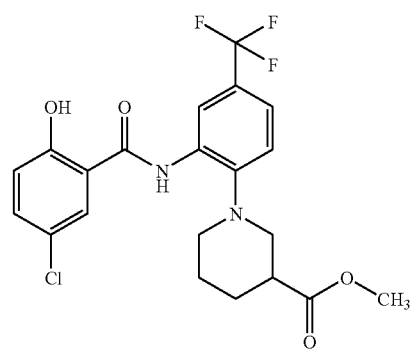 |
| 316 | 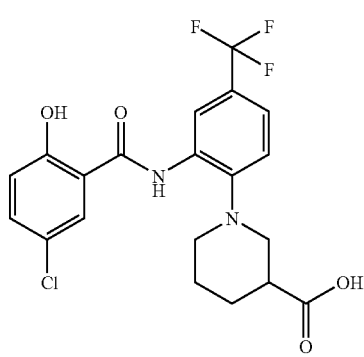 |
| 317 | 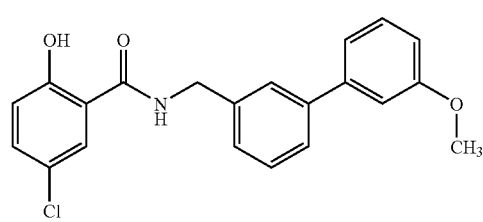 |
| 318 | 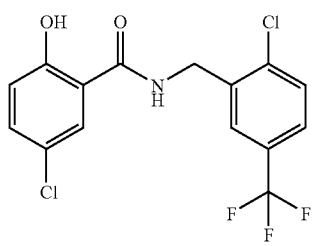 |

-continued
319 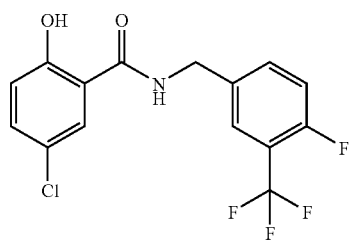
320 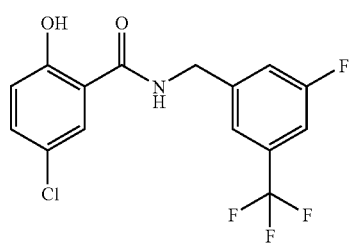
321 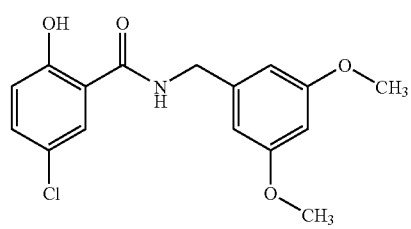
322 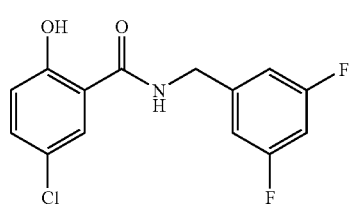
323 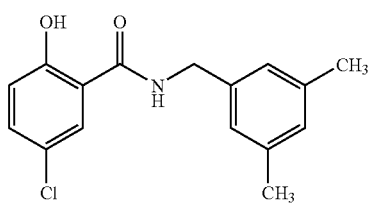
324 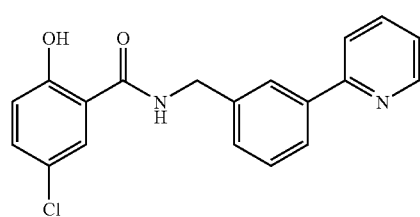

-continued
| | |
|---|---|
| 325 | 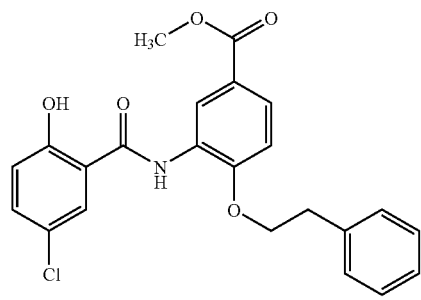 |
| 326 | 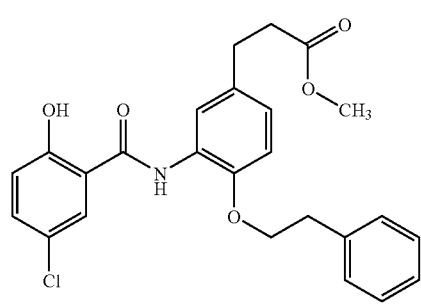 |
| 327 | 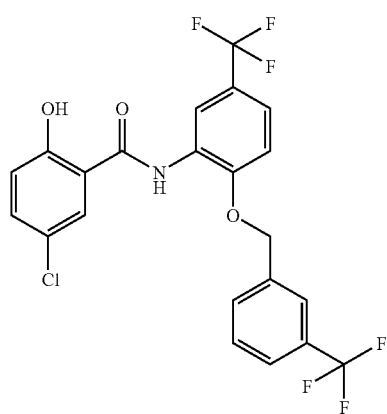 |
| 328 | 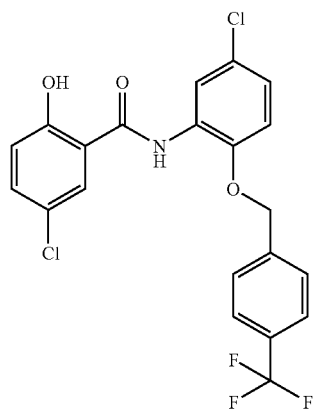 |

-continued
329
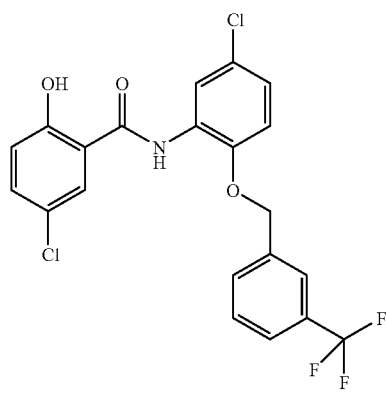
330
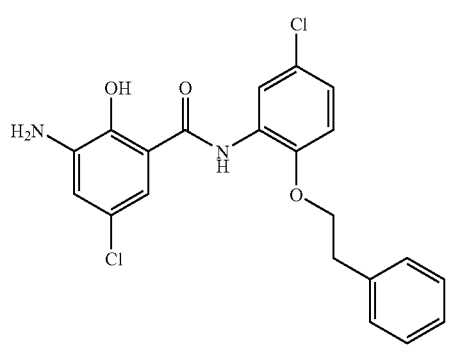
331
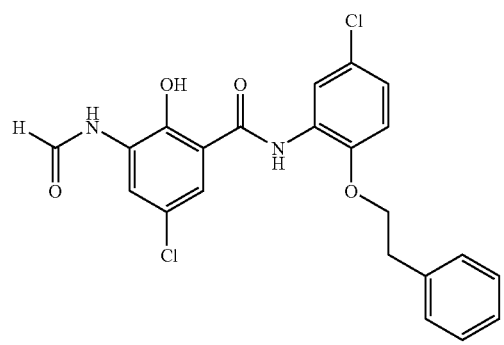
332
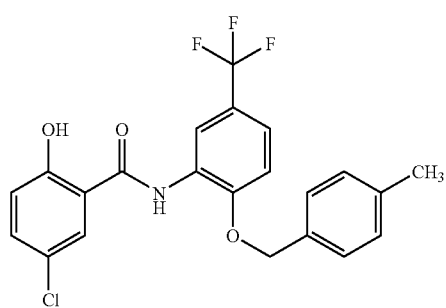

-continued
333
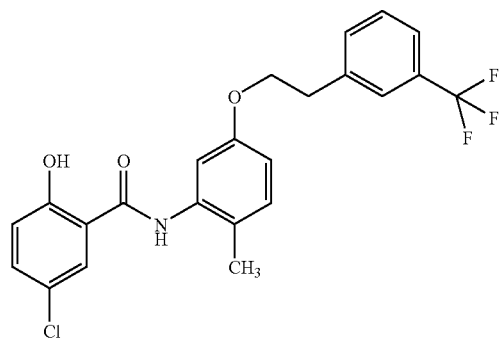
334
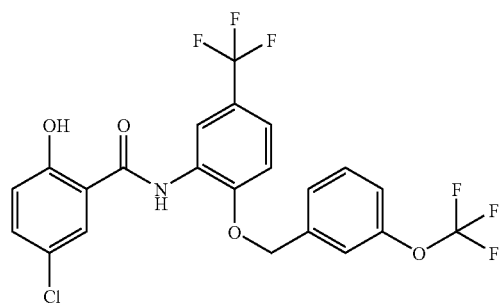
335
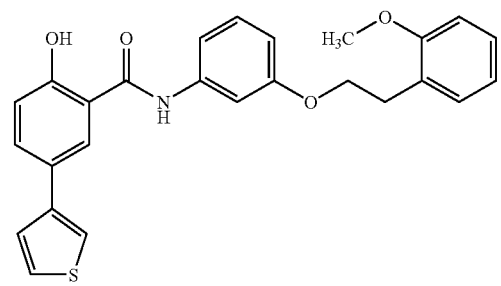
336
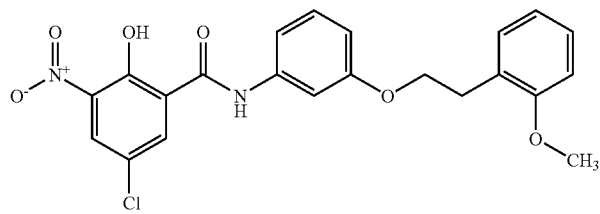
337
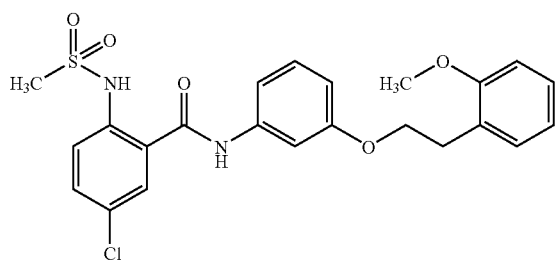

338 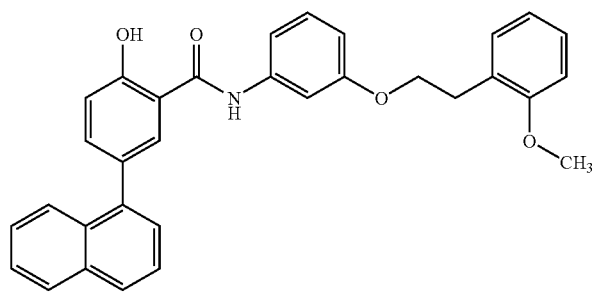
339 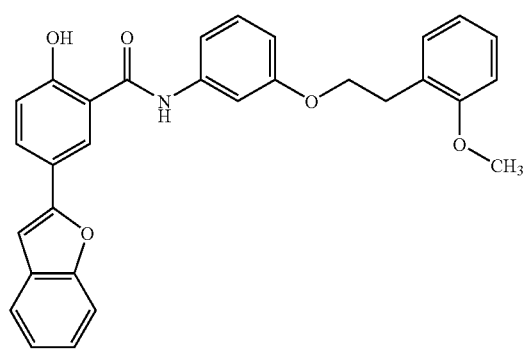
340 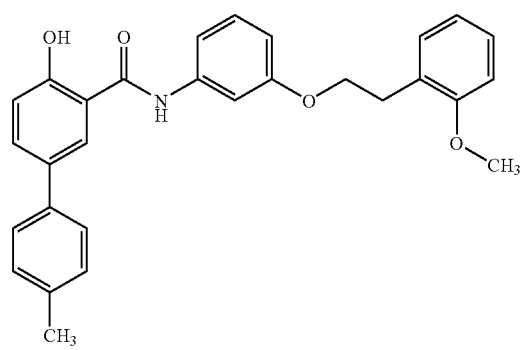
341 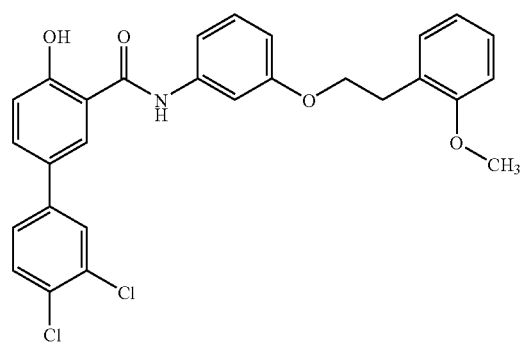

-continued
342 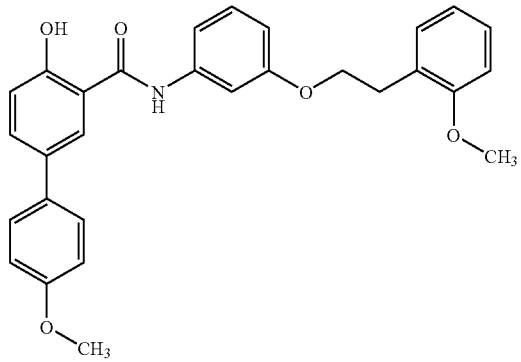
343 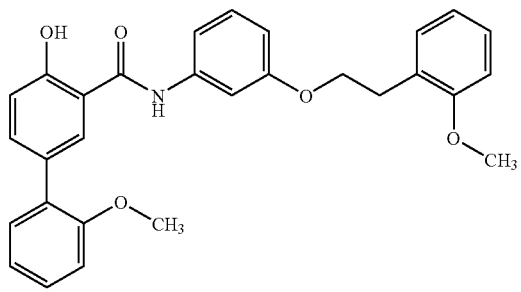
344 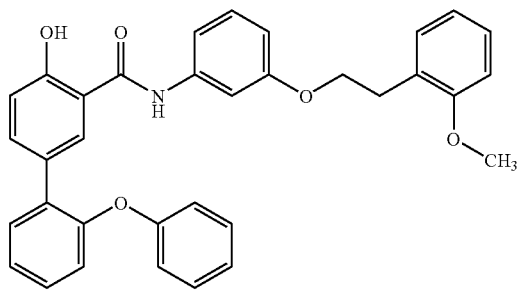
345 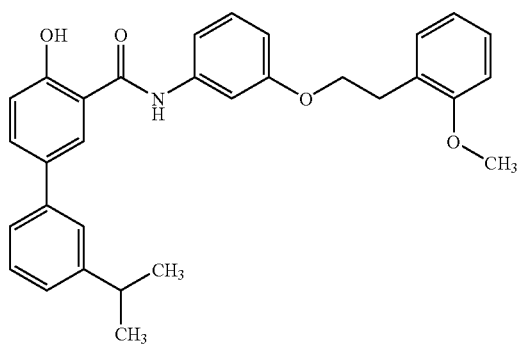
346 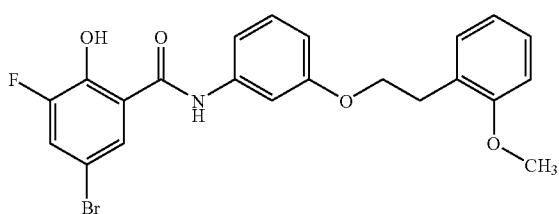

-continued
347 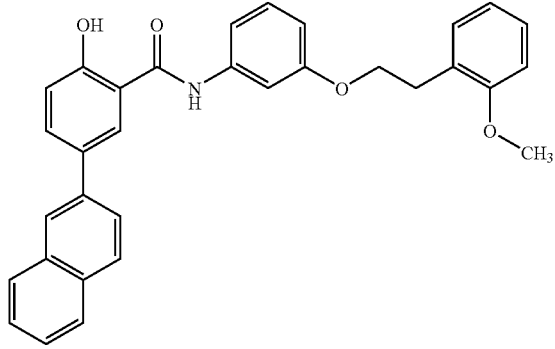
348 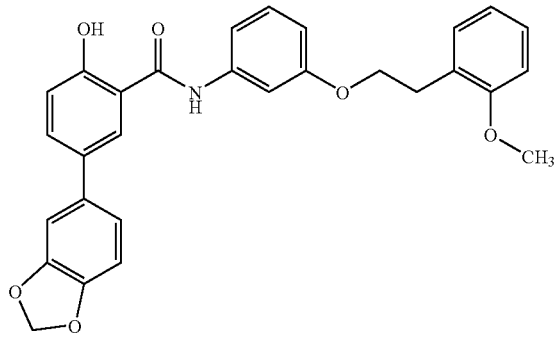
349 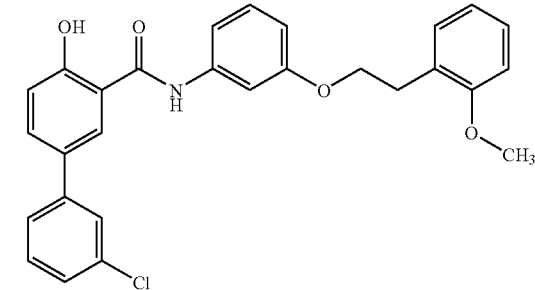
350 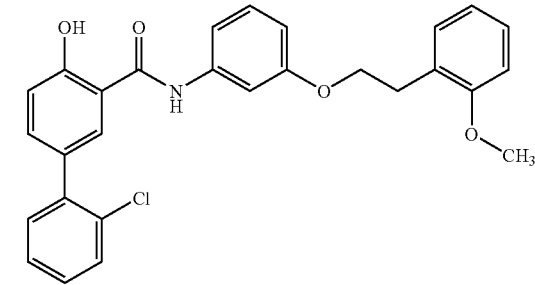
351 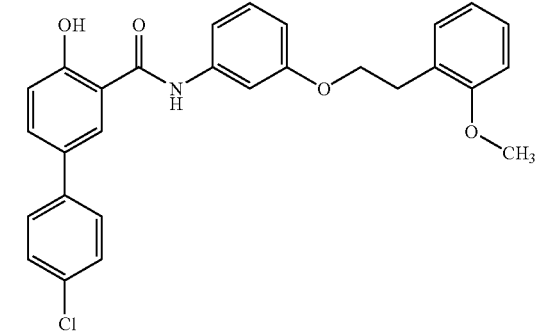

| | |
|---|---|
| 352 | 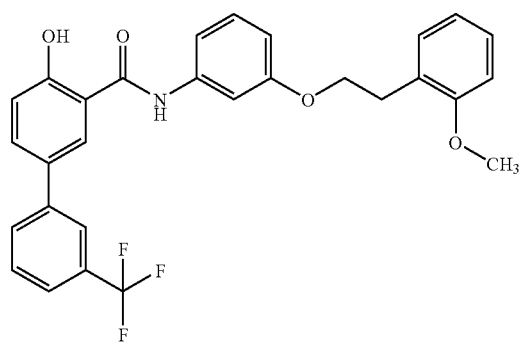 |
| 353 | 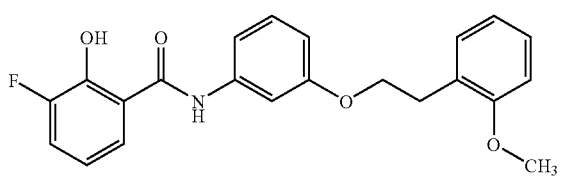 |
| 354 | 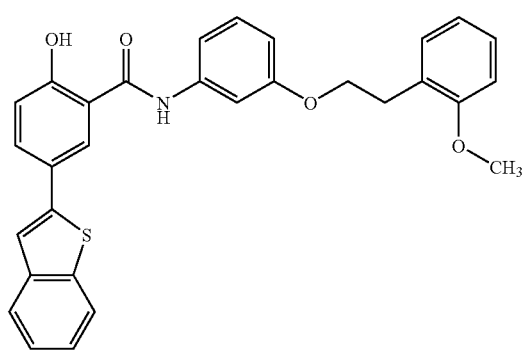 |
| 355 | 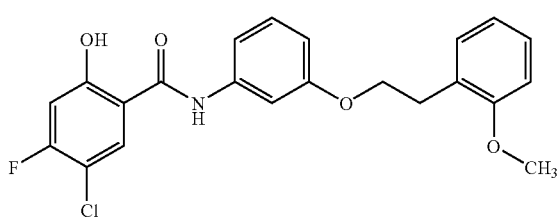 |
| 356 | 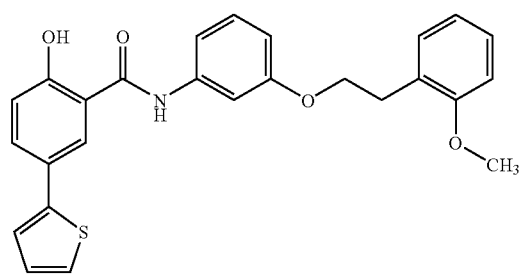 |

| | |
|---|---|
| 357 | 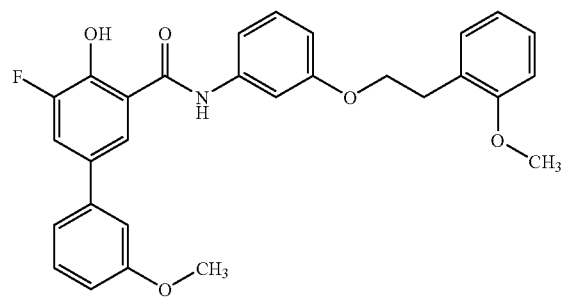 |
| 358 | 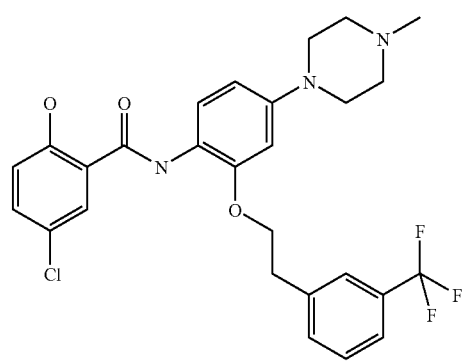 |
| 359 | 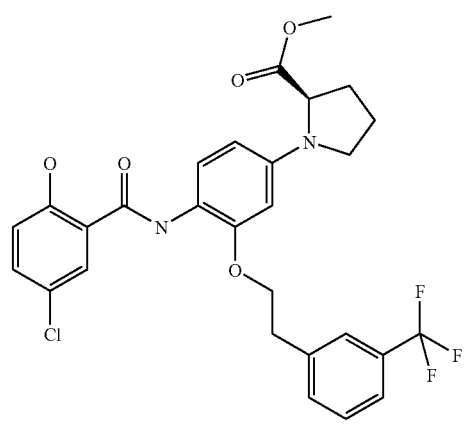 |
| 360 | 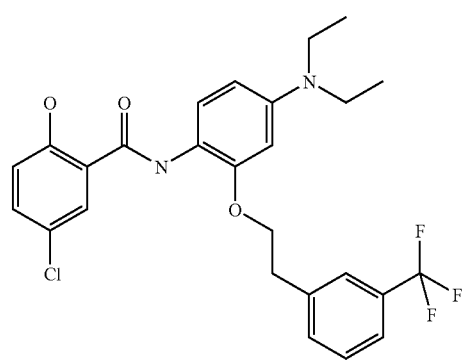 |

-continued
| | |
|---|---|
| 361 | 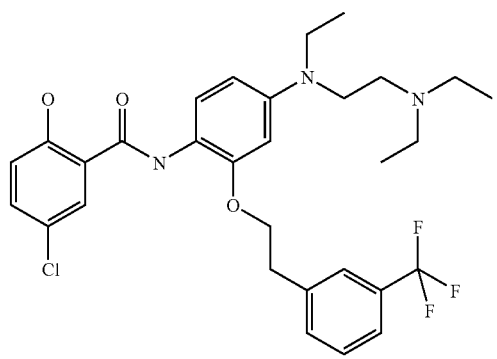 |
| 362 | 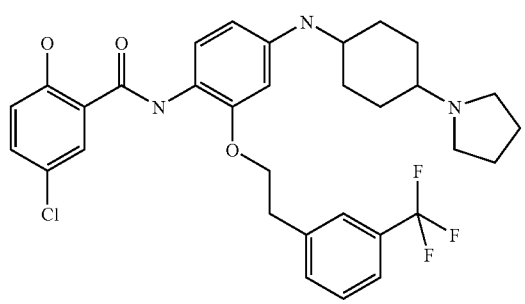 |
| 363 | 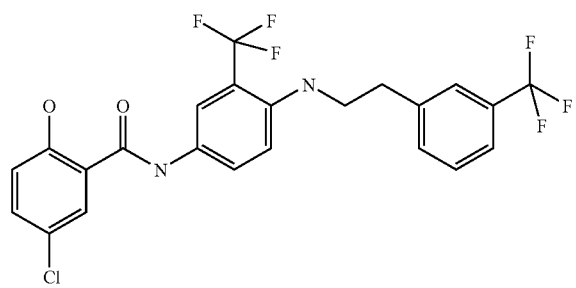 |
| 364 | 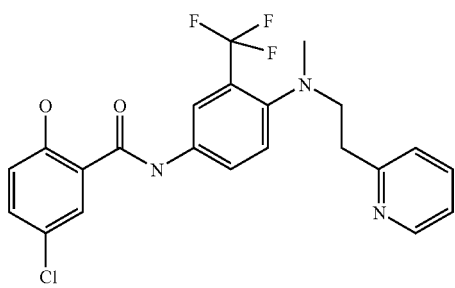 |
| 365 | 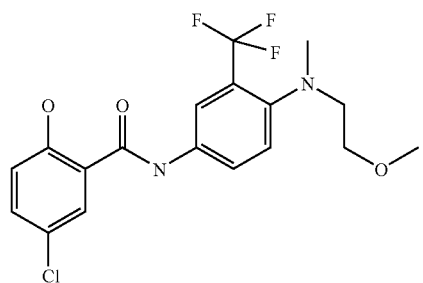 |

| | |
|---|---|
| 366 | 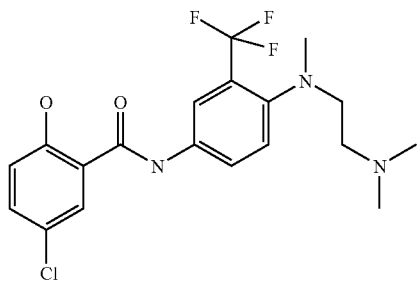 |
| 367 | 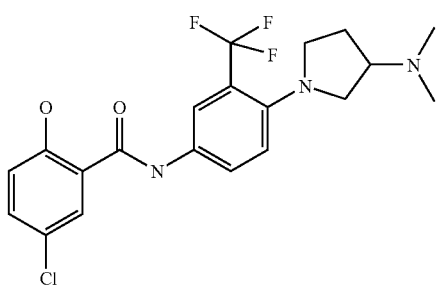 |
| 368 | 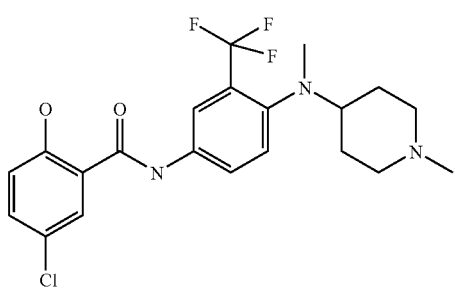 |
| 369 | 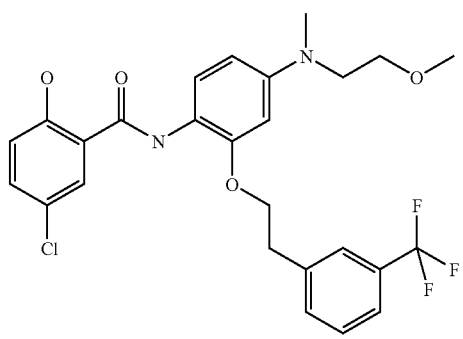 |
| 370 | 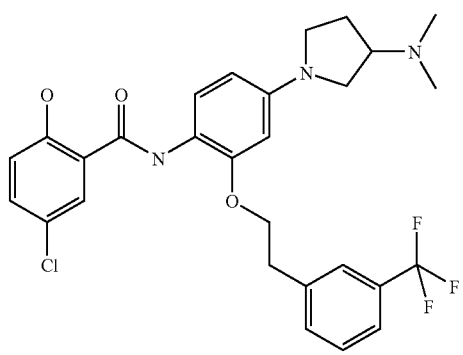 |

-continued
371
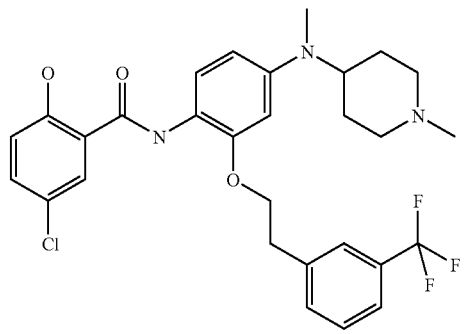
372
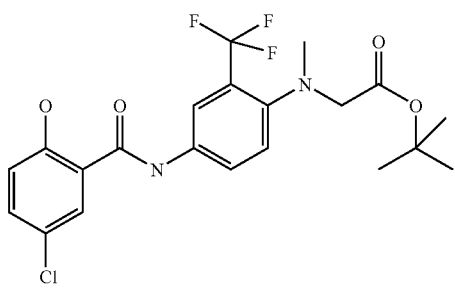
373
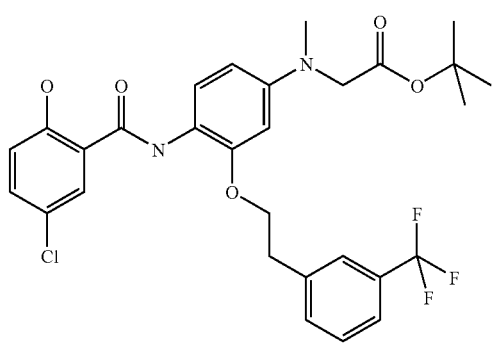
374
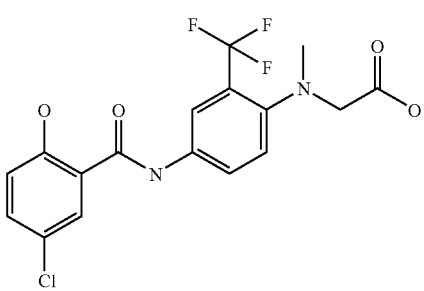
375
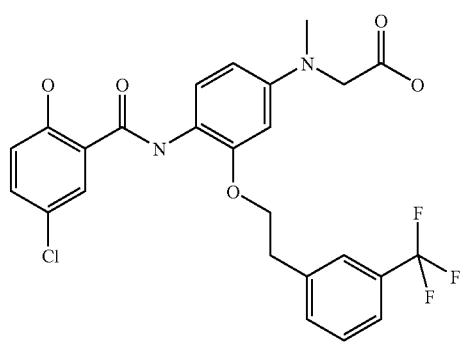

-continued

376

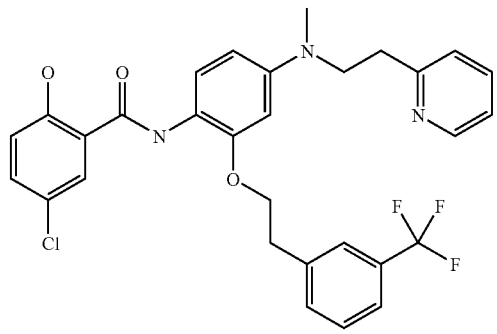

377

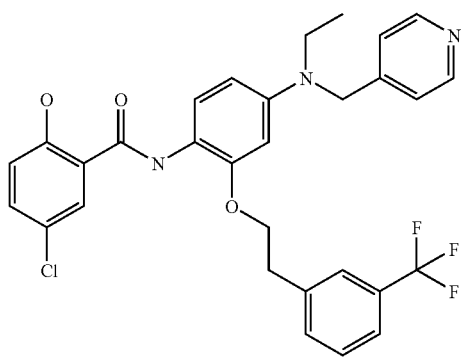

Pharmaceutically Acceptable Compositions, Formulations, and Salts, Esters, and Amides The term "pharmaceutically acceptable" as applied to compositions, formulations, salts, esters, amides or hydrates of the invention and/or used in methods of the invention refers to compositions, formulations, salts, esters, amides, or hydrates which are, within the scope of sound medical judgment, suitable for use in contact with the tissues of humans and lower animals without undue toxicity, irritation, allergic, or a like negative response that exceeds a reasonable risk/therapeutic benefit ratio. More simply, "pharmaceutically acceptable" compositions, formulations, salts, esters, amides, hydrates are compositions, formulations, salts, esters, amides, hydrates suitable for administration to a patient. Accordingly, the present invention also extends to pharmaceutically acceptable compositions, formulations, salts, and esters containing the pro-apoptotic compounds of the present invention.

In particular, pharmaceutically acceptable salts are generally known in the art, and in the case of the present invention, include relatively non-toxic, organic or inorganic salts of the compounds of the present invention. Examples of such salts include, but are not limited to, acid addition salts such as hydrochloride salts, sulfate salts, bisulfate salts, borate salts, nitrate salts, acetate salts, phosphate salts, hydrobromide salts, laurylsulfonate salts, glucoheptonate salts, oxalate salts, oleate salts, laurate salts, stearate salts, palmitate salts, valerate salts, benzoate salts, naphthylate salts, mesylate salts, tosylate salts, citrate salts, lactate salts, maleate salts, succinate salts, tartrate salts, fumarate salts, and the like. See, e.g., Berge, et al., J. Pharm. Sci., 66:1-19 (1977). In addition, pharmaceutically acceptable salts also include basic salts such as alkali metal salts, alkaline earth salts, and ammonium salts. For example, pharmaceutically acceptable basic salts include salts of aluminum, calcium, lithium, magnesium, potassium, sodium, zinc, and the like. In addition, organic salts may also be used including, e.g., salts of lysine, N,N'-dibenzylethylenediamine, chloroprocaine, choline, diethanolamine, ethylenediamine, meglumine (N-methylglucamine), procaine and tris. The basic nitrogen-containing groups in the compounds of the present invention can be quaternized with various organic agents including, e.g., alkyl halides (such as lower alkyl halide including methyl, ethyl, propyl, and butyl chlorides, bromides and iodides), long chain halides (e.g., decyl, lauryl, myristyl and stearyl chlorides, bromides and iodides), aralkyl halides (e.g., benzyl and phenethyl bromides), dialkyl sulfates (e.g., dimethyl, diethyl, dibutyl and diamyl sulfates).

The pharmaceutically acceptable salts of the compounds of the present invention also can exist in the form of solvates, e.g., with water, methanol, ethanol, dimethylformamide, ethyl acetate, and the like, and mixtures thereof.

Pharmaceutically acceptable esters can be made by reacting a hydroxyl group in the compounds of the present invention with a pharmaceutically acceptable organic acid, or by reacting a carboxylic acid group in the compounds with a pharmaceutically acceptable alcohol such as methanol, ethanol, propanol, etc. For example, when $R_0$ in the formulas provided above is hydroxyl or hydroxyl alkoxy, the hydroxyl group may be reacted with an acid to form an ester bond thereby forming an acid salt. The organic acids used to form acid addition salts described above can all be useful. Pharmaceutically acceptable amides can be prepared by reacting an amino functional group of the compounds of the above formulas with a pharmaceutically acceptable organic acid, as will be apparent to skilled artisans.

For oral delivery, the active compounds can be incorporated into a formulation that includes pharmaceutically acceptable carriers such as binders (e.g., gelatin, cellulose, gum tragacanth), excipients (e.g., starch, lactose), lubricants (e.g., magnesium stearate, silicon dioxide), disintegrating agents (e.g., alginate, Primogel, and corn starch), and sweetening or flavoring agents (e.g., glucose, sucrose, saccharin, methyl salicylate, and peppermint). The formulation can be orally delivered in the form of enclosed gelatin capsules or compressed tablets. Capsules and tablets can be prepared in any conventional techniques. The capsules and tablets can also be coated with various coatings known in the art to modify the flavors, tastes, colors, and shapes of the capsules and tablets. In addition, liquid carriers such as fatty oil can also be included in capsules.

Suitable oral formulations can also be in the form of suspension, syrup, chewing gum, wafer, elixir, and the like. If desired, conventional agents for modifying flavors, tastes, colors, and shapes of the special forms can also be included. In addition, for convenient administration by enteral feeding tube in patients unable to swallow, the active compounds can be dissolved in an acceptable lipophilic vegetable oil vehicle such as olive oil, corn oil and safflower oil.

The active compounds can also be administered parenterally in the form of solution or suspension, or in lyophilized form capable of conversion into a solution or suspension form before use. In such formulations, diluents or pharmaceutically acceptable carriers such as sterile water and physiological saline buffer can be used. Other conventional solvents, pH buffers, stabilizers, anti-bacterial agents, surfactants, and antioxidants can all be included. For example, useful components include sodium chloride, acetate, citrate or phosphate buffers, glycerin, dextrose, fixed oils, methyl parabens, polyethylene glycol, propylene glycol, sodium bisulfate, benzyl alcohol, ascorbic acid, and the like. The parenteral formulations can be stored in any conventional containers such as vials and ampoules.

Routes of topical administration include nasal, bucal, mucosal, rectal, or vaginal applications. For topical administration, the active compounds can be formulated into lotions, creams, ointments, gels, powders, pastes, sprays, suspensions, drops and aerosols. Thus, one or more thickening agents, humectants, and stabilizing agents can be included in the formulations. Examples of such agents include, but are not limited to, polyethylene glycol, sorbitol, xanthan gum, petrolatum, beeswax, or mineral oil, lanolin, squalene, and the like. A special form of topical administration is delivery by a transdermal patch. Methods for preparing transdermal patches are disclosed, e.g., in Brown, et al., *Annual Review of Medicine*, 39:221-229 (1988), which is incorporated herein by reference.

Subcutaneous implantation for sustained release of the active compounds may also be a suitable route of administration. This entails surgical procedures for implanting an active compound in any suitable formulation into a subcutaneous space, e.g., beneath the anterior abdominal wall. See, e.g., Wilson et al., *J. Clin. Psych*. 45:242-247 (1984). Hydrogels can be used as a carrier for the sustained release of the active compounds. Hydrogels are generally known in the art. They are typically made by crosslinking high molecular weight biocompatible polymers into a network that swells in water to form a gel like material. Preferably, hydrogels is biodegradable or biosorbable. For purposes of this invention, hydrogels made of polyethylene glycols, collagen, or poly(glycolic-co-L-lactic acid) may be useful. See, e.g., Phillips et al., *J. Pharmaceut. Sci*. 73:1718-1720 (1984).

The active compounds can also be conjugated, to a water soluble non-immunogenic non-peptidic high molecular weight polymer to form a polymer conjugate. For example, an active compound is covalently linked to polyethylene glycol to form a conjugate. Typically, such a conjugate exhibits improved solubility, stability, and reduced toxicity and immunogenicity. Thus, when administered to a patient, the active compound in the conjugate can have a longer half-life in the body, and exhibit better efficacy. See generally, Burnham, *Am. J. Hosp. Pharm*., 15:210-218 (1994). PEGylated proteins are currently being used in protein replacement therapies and for other therapeutic uses. For example, PEGylated interferon (PEG-INTRON A®) is clinically used for treating Hepatitis C. PEGylated adenosine deaminase (ADAGEN®) is being used to treat severe combined immunodeficiency disease (SCIDS). PEGylated L-asparaginase (ONCAPSPAR®) is being used to treat acute lymphoblastic leukemia (ALL). It is preferred that the covalent linkage between the polymer and the active compound and/or the polymer itself is hydrolytically degradable under physiological conditions. Such conjugates known as "prodrugs" can readily release the active compound inside the body. In general, the term "prodrug," refers to compounds which are transformed, in vivo, to parent compounds of the active compound for example, by hydrolysis in blood. Controlled release of an active compound can also be achieved by incorporating the active ingredient into microcapsules, nanocapsules, or hydrogels generally known in the art.

Liposomes can also be used as pharmaceutically acceptable carriers for the active compounds of the present invention. Liposomes are micelles made of various lipids such as cholesterol, phospholipids, fatty acids, and derivatives thereof. Various modified lipids can also be used. Liposomes can reduce the toxicity of the active compounds, and increase their stability. Methods for preparing liposomal suspensions containing active ingredients therein are generally known in the art. See, e.g., U.S. Pat. No. 4,522,811; Prescott, Ed., *Methods in Cell Biology*, Volume XIV, Academic Press, New York, N.Y. (1976).

Therapeutic Pro-Apoptotic Treatments

As indicated previously, apoptosis, or 'programmed cell death', is an active process essential for normal development and functions of multi-cellular organisms. Apoptosis typically involves isolated single cells and is characterized by DNA fragmentation, morphological changes of cells and nuclei including cell shrinkage, cell surface blebbing, exposure of phosphatidylserine on the cell surface, involution, contraction, chromatin condensation and fragmentation, and phagocytosis without cell infiltration or inflammation. See Honig and Rosenberg, *Am. J. Med*., 108:317-330 (2000). These characteristics are typically used as markers for assaying apoptosis and can be used in cell-based assays for identifying apoptosis. Many techniques have been developed in the art for detecting such apoptosis markers including, e.g., examining DNA ladders, detecting free DNA ends or breaks under TdT-mediated dUTP nick end labeling (TUNEL) or in situ end labeling (ISEL), determining chromatin clumping by bisbenzimide stain or acridine orange stain, observation under light or electron microscopy, immunochemistry analysis of apoptosis-specific proteins, Western blot analysis of caspase-3 cleavage, etc.

Dysregulation of apoptosis can lead to various diseases and disorders. It is now understood that reduced apoptosis may contribute to tumorigenesis and formation of cancer. Thus, induction of tumor cell apoptosis is now a commonly accepted effective approach in treating cancer. In addition, stimulation of endothelial cell apoptosis may prevent tumor blood supply and cause tumor regression. See Dimmeler and Zeiher, *Cir. Res*., 87:434-439 (2000). Dysregulation of apoptosis is also an integral part of a wide range of autoimmune diseases and disorders. See Ravirajan et al., *Int. Rev. Immunol.*, 18:563-589 (1999). In addition, many neurological disorders involve apoptosis.

Apoptosis also plays an important role in osteoporotic disorders including, but not limited to, postmenopausal osteoporosis, involutional osteoporosis, and glucocorticoid-induced osteoporosis. See Weinstein, et al., *Am. J. Med.*, 108:153-164 (2000). Generally, under normal conditions, the balance between bone formation, bone resorption, bone cell proliferation and apoptosis maintains nearly constant bone mass. The imbalance of such processes leads to abnormal bone remodeling, and thus osteoporosis and other bone-related diseases. It has been suggested that treatment or prevention of osteoporosis may be achieved by promotion of osteoclast apoptosis. See Weinstein, et al., *Am. J. Med.*, 108:153-164 (2000).

Apoptosis also has physiological significance in animal virus infection. See Kyama et al., *Microbes and Infection*, 2:1111-1117 (2000). Apoptosis of cells infected with viruses may slow the viral multiplication process, although animal viruses typically are able to escape apoptosis of the infected cells. However, it has been suggested that apoptosis of the infected cells triggers the phagocytosis of the dying cells by macrophages. This phagocytosis prevents the leakage of toxic substances that are mediators of dysregulated inflammatory reactions. As a result, dysregulated inflammatory reactions are prevented while specific immune responses against the viruses are initiated at the viral infection site. See Kyama et al., *Microbes and Infection*, 2:1111-1117 (2000).

Thus, the present invention provides a method of promoting apoptosis of mammalian cells, particularly human cells, comprising administering to the cells, a pharmaceutical composition comprising a compound of the present invention or a pharmaceutically acceptable salt, ester, amide or hydrate thereof. Advantageously, the pharmaceutical composition is administered in an amount sufficient to promote apoptosis and/or to reduce the proliferation of abnormal cells, particularly tumor cells or proliferation of uncontrolled cells.

Specifically, the present invention provides a method of promoting apoptosis in a mammal, particularly a human, in recognized need thereof comprising administering to the mammal, a pharmaceutical composition comprising a compound of the present invention or a pharmaceutically acceptable salt, ester, amide or hydrate thereof. Advantageously, the pharmaceutical composition is administered in an amount sufficient to promote apoptosis and/or to reduce the proliferation of abnormal cells, particularly tumor cells or proliferation of uncontrolled cells.

Another embodiment of the invention comprises the use of a compound of the present invention, or a pharmaceutically acceptable salt, ester or amide or hydrate thereof, in the manufacture of a medicament or pharmaceutical composition comprising the compound, or a therapeutically acceptable salt, ester or amide or hydrate thereof, for promoting apoptosis in a mammal in recognized need thereof.

In yet another embodiment of the present invention, a method is provided for treating or preventing cancer or neoplastic diseases comprising identifying a mammal, particularly human patient in need of such treatment and administering a compound according to the present invention, or a pharmaceutically acceptable salt, ester, amide or hydrate thereof, or a pharmaceutical composition according to the present invention. Similarly, the compounds and compositions of the present invention can also be used in treating other diseases which benefit from promoting apoptosis, e.g., autoimmune diseases, viral infection, psoriasis, and the like, as discussed in detail above.

In particularly preferred embodiments according to each and every embodiment and aspect of the invention as set forth above, the compound of the present invention, is selected to have a pro-apoptotic efficacy sufficient to achieve an $EC_{50}$ cytotoxic response, at a concentration of about 50 µM (micromolar) or less, when applied for a period of 72 hours at standard incubating conditions, to a cell culture formed of cells selected from the group consisting of LNCaP, OVCAR-3, and SW480, e.g., as assayed in Example below. More preferably, the compound has a pro-apoptotic $EC_{50}$ efficacy under the above time and incubation conditions, and with respect to the specified cells, at a concentration of 25 µM or less, even more preferably at a concentration of 10 µM or less, and most preferably at a concentration of 5 µM or less.

Thus, the therapeutic treatment methods and compositions according to the present invention can be applicable to a variety of tumors, i.e., abnormal growth, whether cancerous (malignant) or noncancerous (benign), and whether primary tumors or secondary tumors. Such disorders include but are not limited to lung cancers such as bronchogenic carcinoma (e.g., squamous cell carcinoma, small cell carcinoma, large cell carcinoma, and adenocarcinoma), alveolar cell carcinoma, bronchial adenoma, chondromatous hamartoma (noncancerous), and sarcoma (cancerous); heart tumors such as myxoma, fibromas and rhabdomyomas; bone tumors such as osteochondromas, condromas, chondroblastomas, chondromyxoid fibromas, osteoid osteomas, giant cell tumors, chondrosarcoma, multiple myeloma, osteosarcoma, fibrosarcomas, malignant fibrous histiocytomas, Ewing's tumor (Ewing's sarcoma), and reticulum cell sarcoma; brain tumors such as gliomas (e.g., glioblastoma multiforme), anaplastic astrocytomas, astrocytomas, and oligodendrogliomas, medulloblastomas, chordoma, Schwannomas, ependymomas, meningiomas, pituitary adenoma, pinealoma, osteomas, and hemangioblastomas, craniopharyngiomas, chordomas, germinomas, teratomas, dermoid cysts, and angiomas; various oral cancers; tumors in digestive system such as leiomyoma, epidermoid carcinoma, adenocarcinoma, leiomyosarcoma, stomach adenocarcinomas, intestinal lipomas, intestinal neurofibromas, intestinal fibromas, polyps in large intestine, familial polyposis such as Gardner's syndrome and Peutz-Jeghers syndrome, colorectal cancers (including colon cancer and rectal cancer); liver cancers such as hepatocellular adenomas, hemangioma, hepatocellular carcinoma, fibrolamellar carcinoma, cholangiocarcinoma, hepatoblastoma, and angiosarcoma; kidney tumors such as kidney adenocarcinoma, renal cell carcinoma, hypemephroma, and transitional cell carcinoma of the renal pelvis; bladder cancers; tumors in blood system including acute lymphocytic (lymphoblastic) leukemia, acute myeloid (myelocytic, myelogenous, myeloblastic, myelomonocytic) leukemia, chronic lymphocytic leukemia (e.g., Sézary syndrome and hairy cell leukemia), chronic myelocytic (myeloid, myelogenous, granulocytic) leukemia, Hodgkin's lymphoma, non-Hodgkin's lymphoma, mycosis flugoides, and myeloproliferative disorders (including myeloproliferative disorders are polycythemia vera, myelofibrosis, thrombocythemia, and chronic myelocytic leukemia); skin cancers such as basal cell carcinoma, squamous cell carcinoma, melanoma, Kaposi's sarcoma, and Paget's disease; head and neck cancers; eye-related cancers such as retinoblastoma and intraocular melanocarcinoma; male reproductive system cancers such as benign prostatic hyperplasia, prostate cancer, and testicular cancers (e.g., seminoma, teratoma, embryonal carcinoma, and choriocarcinoma); breast cancer; female reproductive system cancers such as uterus cancer (endometrial carcinoma), cervical cancer (cervical carcinoma), cancer of the ovaries (ovarian carcinoma), vulvar carcinoma, vaginal carcinoma, fallopian tube cancer, and hydatidiform mole; thyroid cancer (including papillary, follicular, anaplastic, or medullary cancer); pheochromocytomas (adrenal gland); noncancerous growths of the parathyroid glands; cancerous or noncancerous growths of the pancreas; etc.

Specifically, breast cancers, colon cancers, prostate cancers, lung cancers and skin cancers may be amenable to the treatment by the methods and compositions of the present invention. In addition, pre-malignant conditions may also be treated by the methods of the present invention to prevent or stop the progression of such conditions towards malignancy, or cause regression of the premalignant conditions. Examples of pre-malignant conditions include hyperplasia, dysplasia, and metaplasia.

Thus, the term "treating cancer" as used herein, specifically refers to administering therapeutic agents to a patient diagnosed of cancer, i.e., having established cancer in the patient, to inhibit the further growth or spread of the malignant cells in the cancerous tissue, and/or to cause the death of the malignant cells. The term "treating cancer" also encompasses treating a patient having pre-malignant symptoms or physiological conditions, in order to mitigate or stop the progression of, or cause regression of, the pre-malignant conditions.

The methods and compositions of the present invention may also be useful in treating or preventing other diseases and disorders caused by abnormal cell proliferation (hyperproliferation or dysproliferation), e.g., keloid, liver cirrhosis, psoriasis, etc.

Additionally, the methods and compositions of the invention may be used in treating or preventing autoimmune diseases and disorders including, but not limited to, rheumatoid arthritis, systemic lupus erythematosus (SLE), Sjogren's syndrome, Canale-Smith syndrome, psoriasis, scleroderma, dermatomyositis, polymyositis, Behcet's syndrome, skin-related autoimmue diseases such as bullus pemphigoid, IgA dermatosis, pemphigus vulgaris, pemphigus foliaceus, dermatitis herpetiformis, contact dermatitis, autoimmune allopecia, erythema nodosa, and epidermolysis bullous aquisita, drug-induced hemotologic autoimmune disorders, autoimmue thrombocytopenic purpura, autoimmune neutropenia, systemic sclerosis, multiple sclerosis, imflammatory demyelinating, diabetes mellitus, autoimmune polyglandular syndromes, vasculitides, Wegener's granulomatosis, Hashimoto's disease, multinodular goitre, Grave's disease, autoimmune encephalomyelitis (EAE), demyelinating diseases, etc.

The methods and compositions of the invention may also be used for treating or preventing osteoporotic disorders such as postmenopausal osteoporosis, involutional osteoporosis, and glucocorticoid-induced osteoporosis.

In addition, the methods and compositions of the present invention may also be useful in treating or preventing diseases or disorders associated with viral infection in animals, particularly humans. Such viral infection can be caused by viruses including, but not limited to, hepatitis A, hepatitis B, hepatitis C, hepatitis E virus, hepatitis G virus, human foamy virus, human herpes viruses (e.g., human herpes virus 1, human herpes virus 2, human herpes virus 4/Epstein Barr virus, human herpes virus 5, human herpes virus 7), human papilloma virus, human parechovirus 2, human T-cell lymphotropic virus, Measles virus, Rubella virus, Semliki Forest virus, West Nile virus, Colorado tick fever virus, foot-and-mouth disease virus, Marburg virus, polyomavirus, TT virus, Lassa virus, lymphocytic choriomeningitis virus, vesicular stomatitis virus, influenza viruses, human parainfluenza viruses, respiratory syncytial virus, herpes simplex virus, herpes zoster virus, varicella virus, cytomegalovirus, variola virus, encephalitis, and various human retroviruses, etc.

As used herein, the term "HBV infection" generally encompasses infection of a human by any strain or serotype of hepatitis B virus, including acute hepatitis B infection and chronic hepatitis B infection. Thus, the treatment of HBV infection means the treatment of a person who is a carrier of any strain or serotype of hepatitis B virus or a person who is diagnosed of active hepatitis B to reduce the HBV viral load in the person or to alleviate one or more symptoms associated with HBV infection and/or hepatitis B, including, e.g., nausea and vomiting, loss of appetite, fatigue, muscle and joint aches, elevated transaminase blood levels, increased prothrombin time, jaundice (yellow discoloration of the eyes and body) and dark urine. A carrier of HBV may be identified by any methods known in the art. For example, a person can be identified as HBV carrier on the basis that the person is anti-HBV antibody positive (e.g., based on hepatitis B core antibody or hepatitis B surface antibody), or is HBV-positive (e.g., based on hepatitis B surface antigens (HBeAg or HbsAg) or HBV RNA or DNA) or has symptoms of hepatitis B infection or hepatitis B. That is, "treating HBV infection" should be understood as treating a patient who is at any one of the several stages of HBV infection progression. In addition, the term "treating HBV infection" will also encompass treating suspected infection by HBV after suspected past exposure to HBV by, e.g., contact with HBV-contaminated blood, blood transfusion, exchange of body fluids, "unsafe" sex with an infected person, accidental needle stick, receiving a tattoo or acupuncture with contaminated instruments, or transmission of the virus from a mother to a baby during pregnancy, delivery or shortly thereafter. The term "treating HBV infection" will also encompass treating a person who is free of HBV infection but is believed to be at risk of infection by HBV.

The term "preventing hepatitis B" as used herein means preventing in a patient who has HBV infection or is suspected to have HBV infection or is at risk of HBV infection, from developing hepatitis B (which are characterized by more serious hepatitis-defining symptoms), cirrhosis, or hepatocellular carcinoma.

In another specific embodiment, the present invention provides methods for treating or preventing HCV infection and hepatitis C. As used herein, the term "HCV infection" generally encompasses infection of a human by any types or subtypes of hepatitis C virus, including acute hepatitis C infection and chronic hepatitis C infection. Thus, treating HCV infection means the treatment of a person who is a carrier of any types or subtypes of hepatitis C virus or a person who is diagnosed of active hepatitis C to reduce the HCV viral load in the person or to alleviate one or more symptoms associated with HCV infection and/or hepatitis C. A carrier of HCV may be identified by any methods known in the art. For example, a person can be identified as HCV carrier on the basis that the person is anti-HCV antibody positive, or is HCV-positive (e.g., based on HCV RNA or DNA) or has symptoms of hepatitis C infection or hepatitis C (e.g., elevated serum transaminases). That is, "treating HCV infection" should be understood as treating a patient who is at any one of the several stages of HCV infection progression. In addition, the term "treating HCV infection" will also encompass treating suspected infection by HCV after suspected past exposure to HCV by, e.g., contact with HCV-contaminated blood, blood transfusion, exchange of body fluids, "unsafe" sex with an infected person, accidental needle stick, receiving a tattoo or acupuncture with contaminated instruments, or transmission of the virus from a mother to a baby during pregnancy, delivery or shortly thereafter. The term "treating HCV infection" will also encompass treating a person who is free of HCV infection but is believed to be at risk of infection by HCV. The term of "preventing HCV" as used herein means preventing in a patient who has HCV infection or is suspected to have HCV infection or is at risk of HCV infection from developing hepatitis C (which is characterized by more serious hepatitis-defining symptoms), cirrhosis, or hepatocellular carcinoma.

Still further, the methods and compositions of the present invention may also be applied to treatment of benign proliferative conditions including, but not limited to, diabetic proliferative retinopathy, idiopathic fibrotic diseases such as fibrosing alveolitis, and vascular smooth muscle proliferation following balloon antioplasty that can lead to re-stenosis.

Combination Therapy

Pro-apototic compounds and compositions of the present invention can desirably be administered in combination with other pharmaceutically compatible therapeutic agents. For example, when used in the treatment of solid tumors, compounds of the present invention can be administered with chemotherapeutic agents such as alpha inteferon, COMP (cyclophosphamide, vincristine, methotrexate, and prednisone), etoposide, mBACOD (methortrexate, bleomycin, doxorubicin, cyclophosphamide, vincristine, and dexamethasone), PRO-MACE/MOpp (prednisone, methotrexate (with leucovin rescue), doxorubicin, cyclophosphamide, taxol, etoposide/mechlorethamine, yincristine, prednisone, and procarbazine), vincristine, vinblastine, angioinhibins, TNP-470, pentosan polysulfate, platelet factor 4, angiostatin, LM-609, SU-101, CM-101, Techgalan, thalidomide, SP-PG, and the like.

By "pharmaceutically compatible" it is meant that the other therapeutic agent will not interact or react with the above composition, directly or indirectly, in such a way as to adversely affect the effect of the treatment, or to cause any significant adverse side reaction in the patient. The active compounds of this invention are administered at a therapeutically effective amount to achieve the desired therapeutic effect without causing any serious adverse effects in the patient treated.

Pro-apototic compounds and compositions of the present invention can also desirably be administered in combination with other therapeutic treatments including conventional surgery to remove a tumor, radiation and/or chemotherapy treatments wherein a compound or composition of the present invention can be administered to extend the dormancy of micrometastases and to stabilize and inhibit the growth of any residual primary tumor.

Dosage and Delivery

The active compounds of this invention are typically administered in combination with a pharmaceutically acceptable carrier through any appropriate routes such as parenteral, oral, or topical administration, in a therapeutically acceptable amount. The active compounds are further desirably administered in a therapeutically effective amount, i.e., in an amount sufficient to promote/induce apoptosis and/or to reduce the proliferation of abnormal cells.

Generally, the toxicity profile and therapeutic efficacy of the therapeutic agents can be determined by standard pharmaceutical procedures in suitable cell models or animal models. As is known in the art, the $LD_{50}$ represents the dose lethal to about 50% of a tested population. The $ED_{50}$ is a parameter indicating the dose therapeutically effective in about 50% of a tested population. Both $LD_{50}$ and $ED_{50}$ can be determined in cell models and animal models. In addition, the $IC_{50}$ may also be obtained in cell models and animal models, which stands for the circulating plasma concentration that is effective in achieving about 50% of the maximal inhibition of the symptoms of a disease or disorder. Such data may be used in designing a dosage range for clinical trials in humans. Typically, as will be apparent to skilled artisans, the dosage range for human use should be designed such that the range centers around the $ED_{50}$ and/or $IC_{50}$, but remains significantly below the $LD_{50}$ dosage level, as determined from cell or animal models.

Typically, the pro-apoptotic compounds and compositions of the invention can be effective at an amount of from about 0.05 mg to about 4000 mg per day, preferably from about 0.1 mg to about 2000 mg per day. However, the amount can vary with the body weight of the patient treated and the state of disease conditions. The active ingredient may be administered at once, or may be divided into a number of smaller doses to be administered at predetermined intervals of time. The $EC_{50}$ values discussed previously can desirably be used to identify specific pro-apoptotic compounds and compositions that can be used within predetermined, desirable dosage ranges.

In the case of combination therapy, a therapeutically effective amount of another therapeutic compound can be administered in a separate pharmaceutical composition, or alternatively included in the pharmaceutical composition according to the present invention. The pharmacology and toxicology of other therapeutic compositions are known in the art. See e.g., *Physicians Desk Reference*, Medical Economics, Montvale, N.J.; and *The Merck Index*, Merck & Co., Rahway, N.J. The therapeutically effective amounts and suitable unit dosage ranges of such compounds used in art can be equally applicable in the present invention.

It should be understood that the dosage ranges set forth above are exemplary only and are not intended to limit the scope of this invention. The therapeutically effective amount for each active compound can vary with factors including but not limited to the activity of the compound used, stability of the active compound in the patient's body, the severity of the conditions to be alleviated, the total weight of the patient treated, the route of administration, the ease of absorption, distribution, and excretion of the active compound by the body, the age and sensitivity of the patient to be treated, and the like, as will be apparent to a skilled artisan. The amount of administration can also be adjusted as the various factors change over time.

Preparation of compounds and compositions according to the invention can be readily accomplished employing synthetic processes well known to those skilled in the art. Reference may be made to U.S. Pat. No. 3,674,850 (which is incorporated herein by reference), which discloses preparation of various substituted salicylanilides, and to related patents and disclosures.

For example, compounds of Formula 1 can be made by the following scheme:

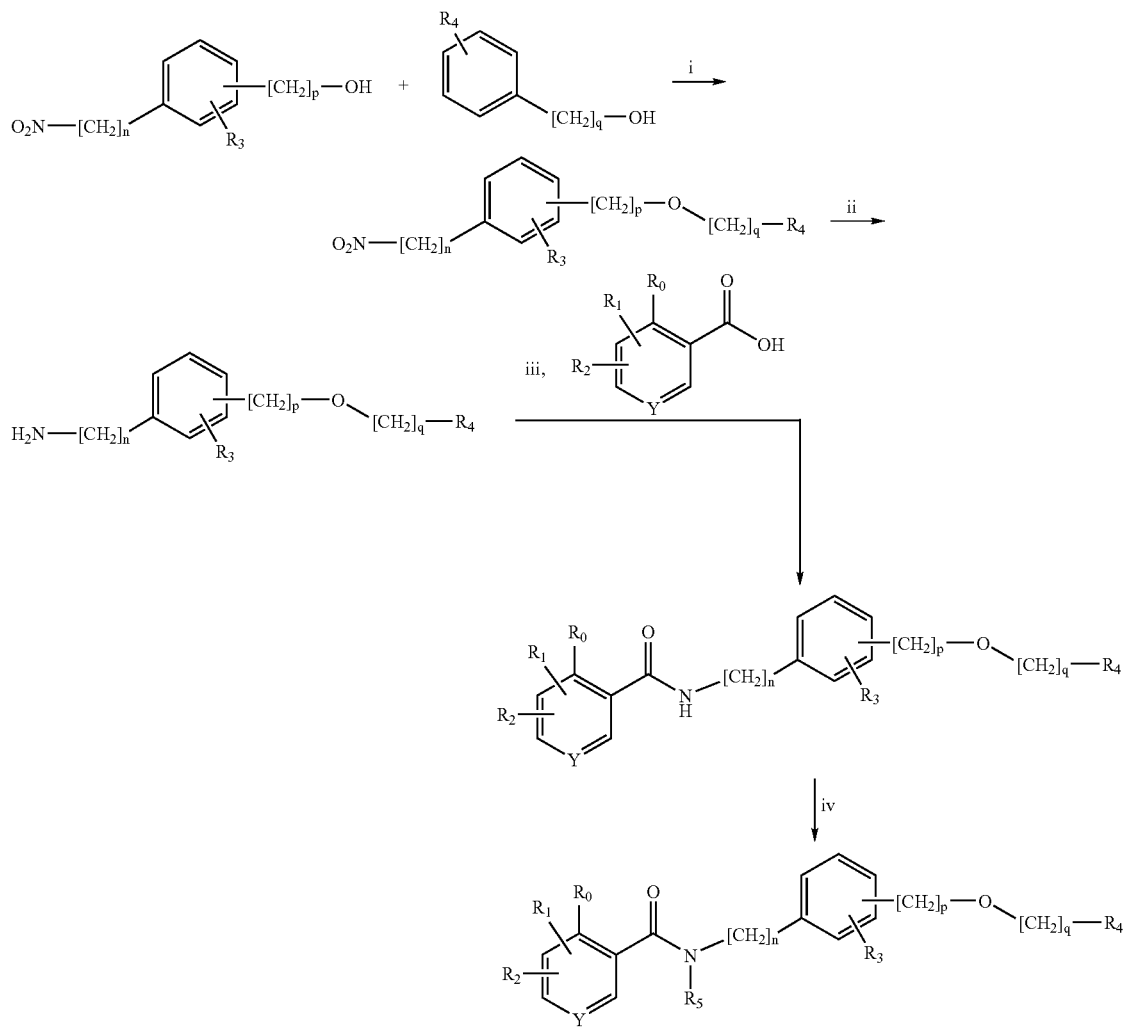

i. DEAD/PPh3/THF/0-25° C.  ii. SnCl2•2H2O/EtOH/75° C. or 5% Pt—C/HCOONH4/CH3OH  iii. Tetraethyl pyrophosphite/Toluene/135° C. or CDI/DMP  iv. R5X/Base/DMF In the above synthesis scheme, X is halo, and the various other substituents and symbols are as specified in Formula 1 above.

The following examples further illustrate various preferred aspects of the present invention. In the examples the methods and materials set forth below were used to evaluate compounds and compositions of the invention.

EXAMPLE 1

Synthesis of 5-Chloro-2-hydroxy-N-(3-phenethyloxyphenyl)benzamide

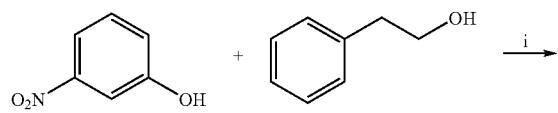

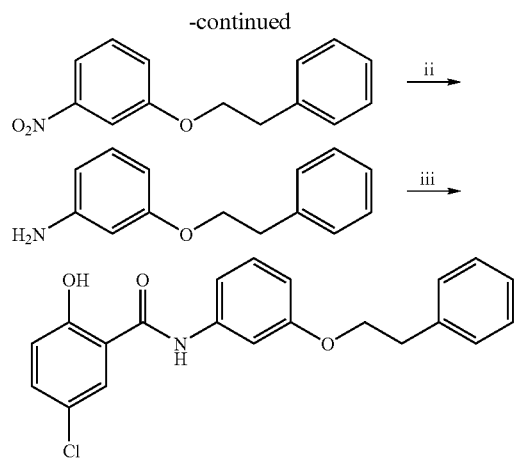

i. DEAD/PPh3/THF/0-25° C.  ii. SnCl2•2H2O/EtOH/75° C.
iii. 5-Chlorosalicylic acid/Tetraethyl pyrophosphite/Toluene/ 135° C.

To a solution of 3-nitrrophenol (1.5 g, 10.78 mmol) and triphenyl phosphine (4.24 g, 16.17 mmo) in anhydrous THF (30 mL) was added DEAD (2.25 g, 12.93 mmol) in THF (2.5 mL) and phenethyl alcohol (1.31 g, 10.78 mmol) in THF (2.5 mL) at 0° C. simultaneously. The temperature of the reaction mixture was raised slowly to room temperature and stirring continued further at room temperature overnight. At the end of this period diluted with Ethyl acetate (100 mL) and washed with water (2×50 mL), dried ($Na_2SO_4$), filtered and the solvent was evaporated. The residu was chromatographed over silica gel using a mixture of ethyl acetate and hexane (2:8) to afford title product (1.80 g, 69%). $^1$H NMR ($CDCl_3$) δ 3.12 (t, 2H), 4.22 (t, 2H), 7.10-7.49 (m, 7H), 7.70-7.90 (m, 2H).

A mixture of Step 1 product (1.80 g, 7.39 mmol) and stannous chloride dihydrate (4.16 g, 18.47 mmol) in ethanol was refluxed for 3 h. At the end of period solvent was evaporated, to the residue 2N NaOH (30 mL) was added and extracted with ethyl acetate (2×150 mL). The combined ethyl acetate layer was washed with water (2×75 mL), dried (Na2SO4), filtered and the solvent was evaporated to dryness to give the amine. The crude product was sufficiently pure enough to use for the next step and was used without any further purification. $^1$H NMR ($CDCl_3$) δ 3.10 (t, 2H), 3.60 (bs, 2H), 4.20 (t, 2H), 6.18-6.40 (m, 3H), 7.10 (t, 1H), 7.20-7.39 (m, 5H).

A mixture of material from step 2 (0.102 g, 0.48 mmol), 5-chlorosalicylic acid (0.083 g, 0.48 mmol) and tetraethyl pyrophosphite (0.136g, 0.53 mmol) in toluene (5 mL) was refluxed for 6 h. The reaction mixture was cooled to 30° C. and diluted with ethyl acetate (50 mL) and washed with 1N HCl (20 mL) followed by water (2×50 mL). The organic layer was dried (Na2SO4), filtered and the solvent was evaporated to dryness. The resultant crude material was chromatographed over silica gel using a mixture of ethyl acetate and hexane (2:8) to afford title product (0.092 g, 52%). $^1$H NMR ($CDCl_3$) δ 3.10 (t, 2H), 4.25 (t, 2H), 6.80 (d, 1H), 6.90-7.20 (m, 1H), 7.30-7.60 (m, 9H), 7.80 (bs, 1H), 11.92 (s, 1H).

EXAMPLE 2

Synthesis of 5-Chloro-N-(5-chloro-2-phenethyloxyphenyl)-2-hydroxybenzamide

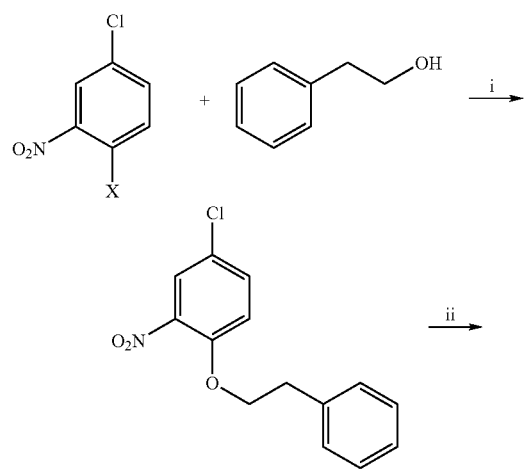

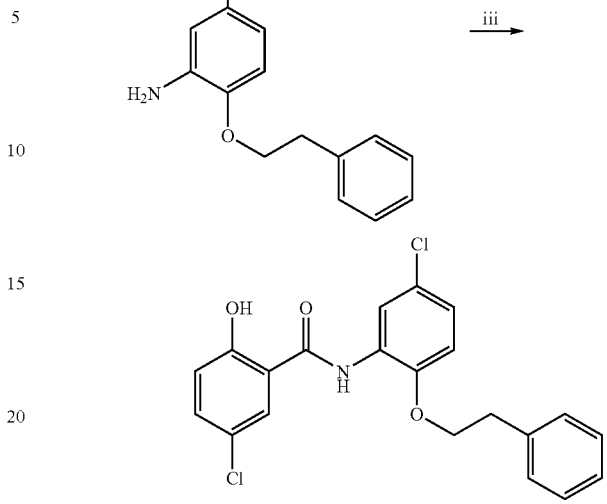

i. DEAD/PPh$_3$/THF/0-25° C. ii. SnCl$_2$•2H$_2$O/EtOH/75° C.
iii. 5-Chlorosalicylic acid/Tetraethyl pyrophosphite/Toluene/135° C.

To a solution of 4-Chloro-3-nitrophenol (0.6 g, 3.457 mmol) and triphenyl phosphine (0.997 g, 3.802 mmol) in anhydrous THF (25 mL) was added DEAD (0.662 g, 3.802 mmol) in THF (2.5 mL) and phenethyl alcohol (0.464 g, 3.802 mmol) in THF (2.5 mL) at 0° C. simultaneously. The temperature of the reaction mixture was raised slowly to room temperature and stirring continued further at room temperature overnight. At the end of this period diluted with Ethyl acetate (100 mL) and washed with water (2×50 mL), dried ($Na_2SO_4$), filtered and the solvent was evaporated. The residue was chromatographed over silica gel using a mixture of ethyl acetate and hexane (2:8) to afford title product (0.92 g, 95%). $^1$H NMR ($CDCl_3$) δ 3.14 (t, 2H), 4.26 (t, 2H), 6.96 (d, 1H), 7.24-7.33 (m, 6H), 7.81 (d, 1H).

A mixture of Step 1 Product (0.3 g, 1.08 mmol) and stannous chloride dihydrate (0.974g, 4.32 mmol) in ethanol was refluxed for 3 h. At the end of period solvent was evaporated, to the residue 2N NaOH (20 mL) was added and extracted with ethyl acetate (2×75 mL). The combined ethy acetate layer was washed with water (2×75 mL), dried ($Na_2SO_4$), filtered and the solvent was evaporated to dryness. The crude product was sufficiently pure enough to use for the next step and was used without any further purification. $^1$H NMR ($CDCl_3$) δ 3.11 (t, 2H), 3.77 (bs, 2H), 4.18 (t, 2H), 6.64-6.68 (m, 3H), 7.24-7.33 (m, 5H).

A mixture of material from step 2 (0.178 g, 0.718 mmol), 5-chlorosalicylic acid (0.124 g, 0.718 mmol) and tetraethyl pyrophosphite (0.204g, 0.790 mmol) in toluene (5 mL) was refluxed for 6 h. The reaction mixture was cooled to 30° C. and diluted with ethyl acetate (50 mL) and washed with 1N HCl (20 mL) followed by water (2×50 mL). The organic layer was dried ($Na_2SO_4$), filtered and the solvent was evaporated to dryness. The resultant crude material was chromatographed over silica gel using a mixture of ethyl acetate and hexane (2:8) to afford title product (0.085 g, 29%). $^1$H NMR (CDCl$_3$) δ 3.17 (t, 2H), 4.37 (t, 2H), 6.85-7.41 (m, 10H), 8.35 (s, 1H), 8.40 (s, 1H), 11.82 (s, 1H).

EXAMPLE 3

5-Chloro-N-[2-(4-chloronaphthalen-yloxy)-5-chlorophenyl]-2-hydroxybenzamide

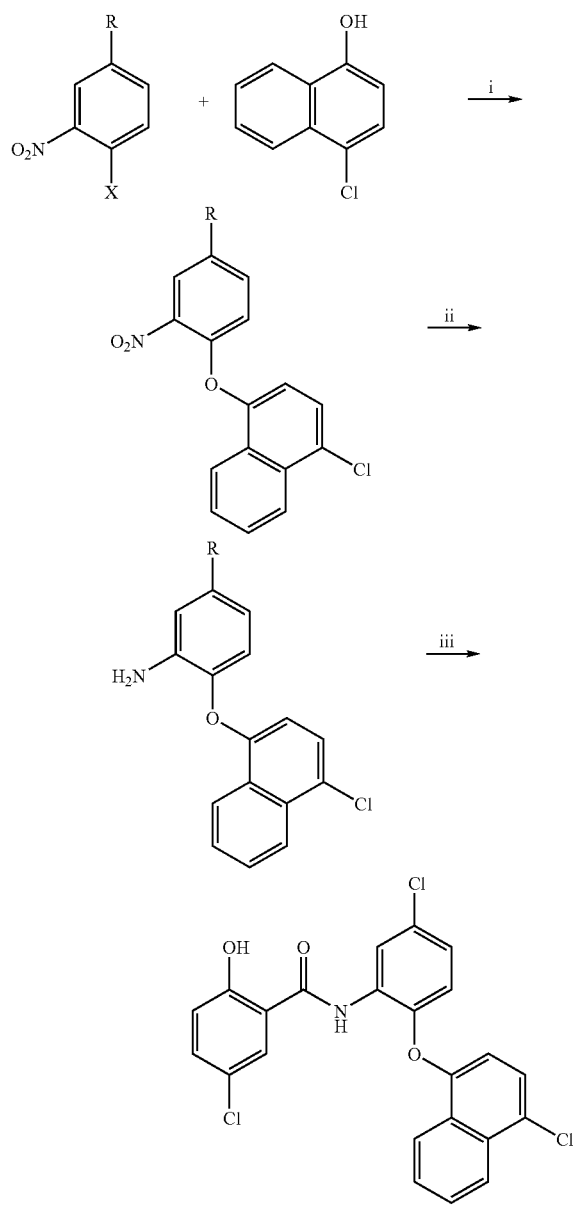

i. Potassium tert-butoxide/THF/80° C. ii. HCOONH$_4$/Pt—C/CH$_3$OH/70° C. iii. 5-Chlorosalicylic acid/tetraethyl pyrophosphite/Toluene/130° C.

A solution of 2,5-dichloronitrobenzene (5.0 g, 26.04 mmol), 4-chloronapphthol (5.11 g 28.64 mmol) in anhydrous THF (20 mL) was added 28.5 mL Potassium tert-butoxide (1M sol in THF) over 20 min period at 25° C. The dark reaction mixture was refluxed overnight. After cooling, the reaction mixture was diluted with Water (50 mL) and ethyl acetate (200 mL). The ethyl acetate layer was washed with water (100 mL) and brine (100 mL), dried (Na$_2$SO$_4$), filtered and solvent evaporated to dryness to give nitro compound in quantitative yield. $^1$H NMR (CDCl$_3$) δ 6.87 (d, 1H), 6.93 (d, 1H), 7.40-6.69 (m, 4H), 8.00 (s, 1H), 8.13 (d, 1H), 8.30 (d, 1H).

A mixture of a step 1 material (3.8 g, 11.37 mmol), ammonium formate (4.30 g, 68.23 mmol) and 5% Pt—C (1.0 g) in methanol was refluxed overnight. After cooling, the catalyst was removed by filtration through Celite and washed with methanol (2×25 mL). The filtrate was concentrated and the resulting solid was dissolved in dichloromethane (100 mL) an water (100 mL). The dichloromethane layer was washed with brine (100 mL), dried (Na$_2$SO$_4$), filtered and solvent was evaporated to dryness to afford amine (3.2 g, 93%). $^1$H NMR (CDCl$_3$) δ 3.19 (bs, 2H), 6.53-6.85 (m, 4H), 7.60 (d, 1H), 7.61-7.66 (m, 2H), 8.25-8.33 (m, 2H).

The title compound (5.4 g, 48%) was prepared from the step 2 material and 5-chlorosalicylic acid by procedure similar to that described for step 3 in Example 1. $^1$H NMR (d$_6$-DMSO) δ 6.78-7.00 (m, 4H), 7.21 (d, 1H), 7.53-7.79 (m, 3H), 8.04 (s, 1H), 8.26 (d, 2H), 8.75 (d, 1H), 11.14 (s, 1H), 11.24 (s, 1H)

EXAMPLE 4

Synthesis of 5-Chloro-2-hydroxy-N-(4-phenoxybenzyl)benzamide

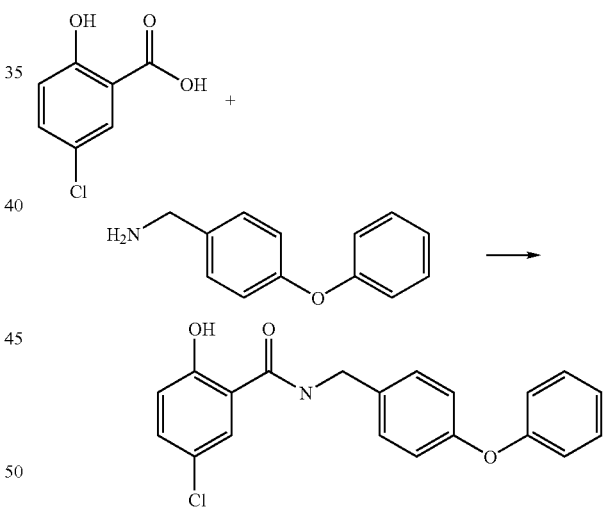

To a solution of 5-chlorocsalicyclic acid in anhydrous DMF (5 mL) was added CDI (0.167 g, 1.043 mmol), at 25° C. under nitrogen atmosphere. The reaction mixture was stirred for another 2 h at 25° C. To the above reaction mixture 4-phenoxy benzylamine was added and stirring continued overnight. At the end of this period 2N HCl (20 mL) was added and extracted with ethyl acetate (2×20 mL). The combined ethyl acetate layer was washed with water (2×30 mL), dried (Na$_2$SO$_4$), filtered and solvent was evaporated. The resulting crude material was chromatographed over silica gel using mixture of ethyl acetate and hexanes (3:7) to give title product (0.121 g, 27%). $^1$H NMR (CDCl$_3$) δ 4.60 (d, 2H), 6.44 (bs, 1H), 6.90-7.37 (m, 12H), 12.21 (s, 1H),

EXAMPLE 5

Synthesis of 5-Chloro-N-[3-(3-ethoxy-4-methoxy-benzylamino)phenyl]-2-hydrxybenzamide

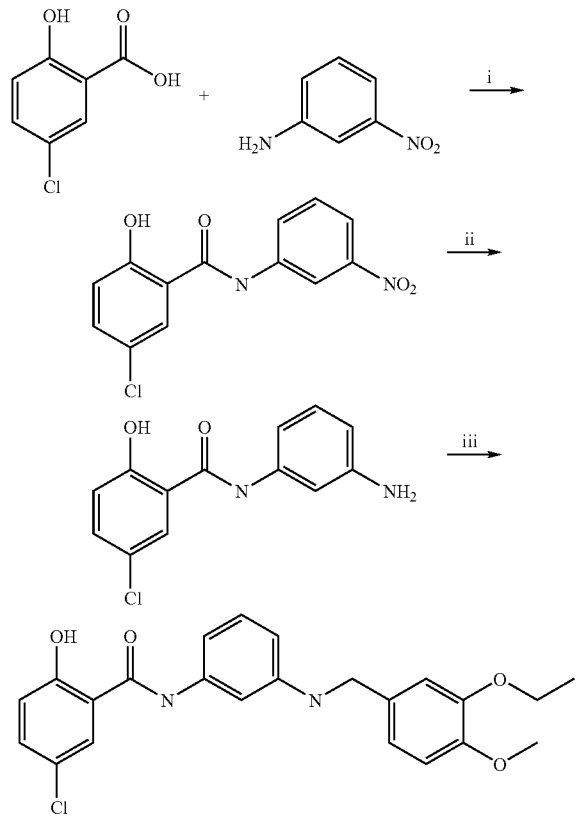

i. Tetraethyl pyrophosphite/Toluene/135° C.  ii. 5% Pt—C/HCOONH₄/CH₃OH/70°
iii. (a) 3-ethoxy-4-methoxy-benzaldehyde/CH₃OH/NaBH₃CN/RT The Step 1 compound (1.6 g, 63%) was prepared by an analogous procedure described for step 3 in Example 1 from 5-chlorosalicylic acid (1.5 g, 8.692 mmol) and 3-nitroaniline (1.44 g, 10.43 mmol). $^1$H NMR (CDCl₃+d₆-DMSO) δ 6.97 (d, 1H), 7.35-7.57 (m, 3H), 7.98 (d, 1H), 8.15-8.24 (m, 1H), 8.67 (s, 1H), 10.55 (s, 1H), 11.91 (s, The step 2 product (0.85 g, 95%) was prepared by a similar procedure described for step 2 in scheme 1 using product of step 1 (1.0 g, 3.416 mmol), HCOONH₄ (1.24 g, 17.683 mmol) and 5% Pt—C (110 mg). $^1$H NMR (CDCl₃) δ 3.88 (bs, 2H), 6.49 (d, 1H), 6.92-7.35 (m, 5H), 8.05 (d, 1H), 9.80 (s, 1H), 12.00 (bs, 1H).

In Step 3, a mixture of the product of step 2 (0.08 g, 0.305 mmol) and 3-ethoxy-4-methoxybenzaldehyde (0.054 g, 0.305 mmol) in absolute ethanol (4 mL) was added 4 drops acetic acid and the mixture was refluxed for 6 h. At the end of this period the reaction was cooled to 25° C. and sodium cyanoborohydride was added. After stirring for further 2 h at 25° C., solvent was evaporated, water (20 mL) was added and extracted with ethyl acetate (75 mL). The ethyl acetate layer was dried (Na₂SO₄), filtered and solvent evaporated. The resulting crude product was chromatographed over silica gel using a mixture of ethyl acetate and hexanes (3:7) to give title product (0.098 g, 75%). $^1$H NMR (CDCl₃+d₆-DMSO) δ 1.49 (t, 3H), 3.88 (s, 3H), 4.11 (q, 2H), 4.29 (s, 2H), 4.63 (bs, 1H), 6.30-6.63 (m, 1H), 6.70-7.70 (m, 8H), 8.13 (s, 1H), 10.00 (s, 1H), 12.10 (s, 1H),

EXAMPLE 6

Synthesis of 5-Chloro-2-hydroxy-N-(3-Methylphenyl)benzamide

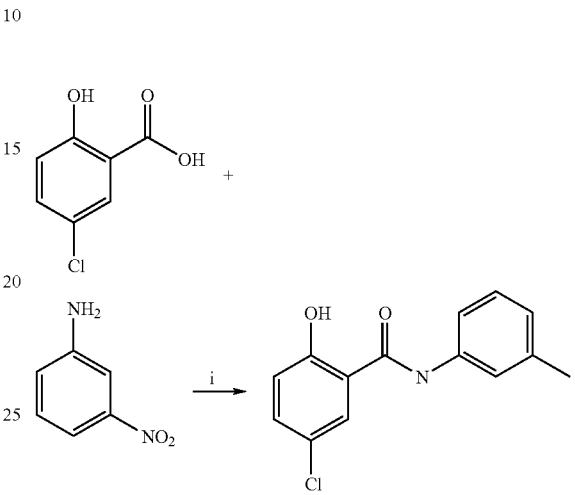

i. Tetraethyl pyrophosphite/Toluene/130° C.

A mixture of 5-Chlorosalicylic acid (0.338 g, 1.9 mmol), m-Toluidine (0.2 g, 1.9 mmol) and Tetraethyl pyrophosphite (0.53 g, 2.0 mmol) in dry toluene was refluxed 7 hrs under nitrogen atmosphere. It was diluted with ethyl acetate, washed with HCl (10%) and then with water (3×30 mL). The organic layer was dried (Na₂SO₄), filtered and evaporated under vacuum. The resulting crude material was purified by column chromatography over SiO₂ using mixture of ethyl acetate and hexanes (2:8) to give title compound (0.134 g,) $^1$H NMR (CDCl₃/DMSO-d₆) δ 2.38 (s, 3H), 6.89-7.03 (m, 2H), 7.19-7.59 (m, 4H), 8.08 (d, 1H), 9.92 (bs, 1H), 12.05 (s, 1H).

EXAMPLE 7

Synthesis of 5-Chloro-2-hydroxy-N-{4-[(2-methoxy-ethyl)-methylamino]-3-trifluoromethylphenyl}benzamide

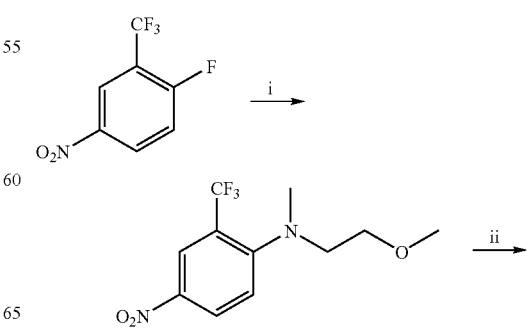

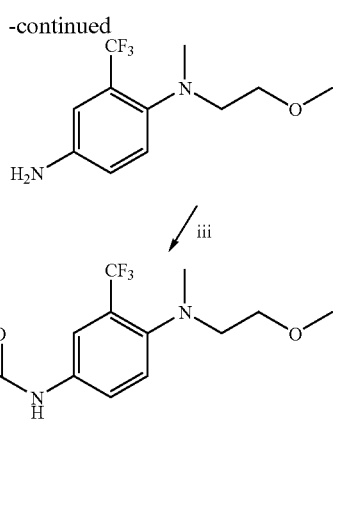

Reagents: i. Et₃N, DMF, N-(2-methoxyethyl)methylamine. ii. Pd/C, MeOH. iii. 5-chlorosalacyclic acid, tetraethylpyrophosphite toluene.

Step 1: Synthesis of (2-methoxyethyl)-methyl-(4-nitro-2-trifluoromethyl-phenyl) amine. Dissolved 2-fluoro-5-nitrobenzotrifluoride (250 mg, 1.2 mmol) in DMF (4 mL) and added triethylamine (242 mg, 2.39 mmol). N-(2-methoxyethyl)methylamine (179 mg, 1.32 mmol) was added to the reaction mixture and it was stirred overnight at ambient temperature. The reaction mixture was poured into water and extracted with EtOAc (2×). The combined organic washes were washed with brine and dried over Na₂SO₄. After concentration the remaining residue was purified by column chromatography (100% CHCl₃ to 1:1 MeOH:CHCl₃) to give the title compound. MS 265 [M–H]⁻, 267 [M+H]⁺.

Step 2: Synthesis of 1-[N-(2-Methoxyethyl)-N-methyl]-2-trifluoromethylbenzene-1,4-diamine. Dissolved (2-methoxyethyl)-methyl-(4-nitro-2-trifluoromethyl-phenyl) amine (325 mg) in MeOH (5 mL), and the solution was degassed with N₂ followed by the addition of Pd/C (10%, catalytic). The mixture was placed under an atmosphere of H₂ at atmospheric pressure and was stirred overnight at ambient temperature. The reaction mixture was filtered through celite and concentrated. The title compound was used as is in the following reaction.

Step 3: Synthesis of 5-Chloro-2-hydroxy-N-{4-[(2-methoxyethyl)-methylamino]-3-trifluoromethylphenyl} benzamide. Dissolved 1-[N-(2-Methoxyethyl)-N-methyl]-2-trifluoromethylbenzene-1,4-diamine (~1.03 mmol, crude from above) and 5-chlorosalicylic acid (178 mg, 1.03 mmol) in toluene (5 mL). Tetraethylpyrophosphite (293 mg, 1.14 mmol) was added and the mixture was warmed to reflux for 18 h. The reaction mixture was poured into water and extracted EtOAc. The organic extract was washed with brine and dried over Na₂SO₄. The title compound was purified by prep-LC to yield 194 mg. ¹H NMR (CDCl₃) δ 3.06 (t, 3H), 3.16 (t, 2H), 3.32 (s, 3H), 3.49 (t, 2H), 7.00 (d, 1H), 7.40 (m, 3H), 7.50 (m, 2H), 7.76 (s, 1H), 11.67 (s, 1H).

EXAMPLE 8

Synthesis of 5-Chloro-2-hydroxy-N-{4-[(2-methoxyethyl)-methylamino]-2-[2-(3-trifluoromethylphenyl)ethoxy]phenyl}benzamide

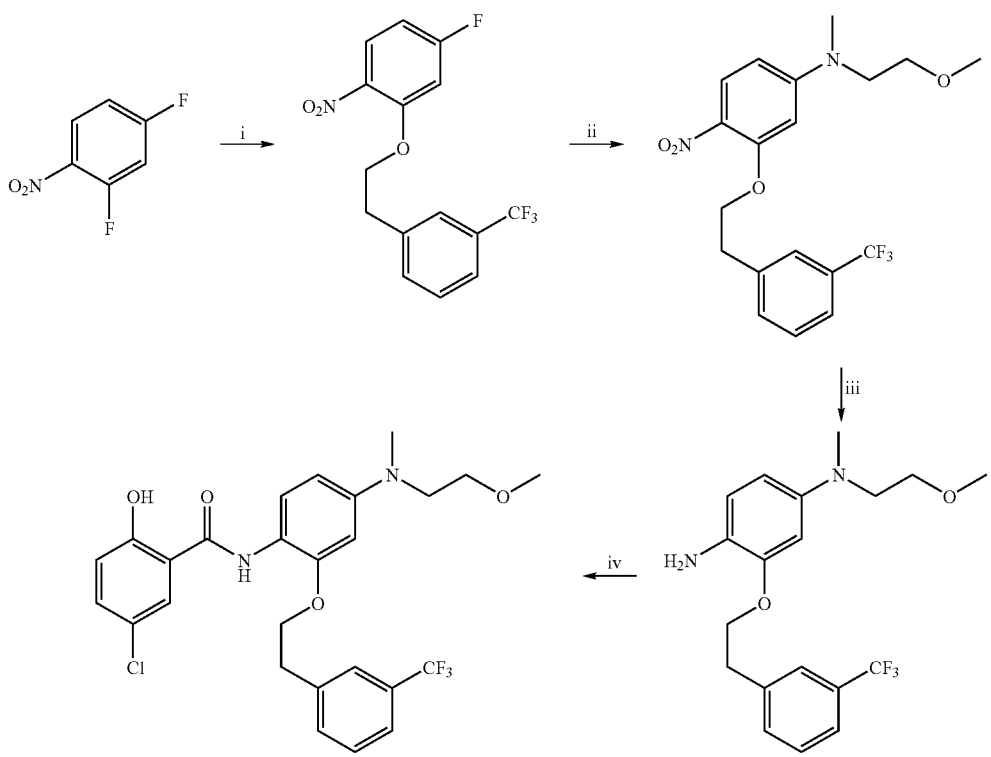

Reagents: i. 3-(trifluoromethyl)phenethyl alcohol, potassium tert-butoxide, THF.
ii. N-(2-methoxyethyl)methylamine, DMF. iii. Pd/C, MeOH. iv. 5-chlorosalicyclic acid, tetraethylpyrophosphite, toluene.

Step 1: Synthesis of 4-Fluoro-1-nitro-2-[2-(3-trifluoromethylphenyl)ethoxy]benzene. Dissolved 3-(trifluoromethyl)phenethyl alcohol (657 mg, 3.46 mmol) in THF (5 mL). After cooling to 0° C., potassium tert-butoxide (1M THF, 4.08 mmol, 4.08 mL) was added and the mixture was warmed to ambient temperature and stirred for 30 min. The reaction mixture was cooled to −78° C., and 2,4-difluoronitrobenzene (500 mg, 3.14 mmol) was added. The reaction mixture was allowed to slowly warm to ambient temperature. The mixture was poured into H2O and extracted with EtOAc (2×). The combined organics were washed with brine and dried over Na2SO4. The title compound was purified by crystallization from a EtOAc:Hexane mixture.

Step 2: Synthesis of (2-Methoxyethyl)methyl-{4-nitro-3-[2-(3-trifluoromethylphenyl)ethoxy]-phenyl}amine: Dissolved 4-fluoro-1-nitro-2-[2-(3-trifluoromethylphenyl)ethoxy]benzene (200 mg, 0.61 mmol) in DMF (1 mL) and added N-(2-methoxyethyl)methylamine (270 mg, 3.04 mmol). Reaction Mixture was warmed to 60° C. and stirred for 18 h. The reaction mixture was poured into H₂O and extracted with EtOAc (2×). The combined organics were washed with brine and dried over Na2SO4. The title compound was carried on crude to the next step.

Step 3: Synthesis of N-(4-(2-Methoxy-ethyl)-N-(4-methyl-2-[2-(3-trifluoromethylphenyl)-ethoxy]benzene-1,4-diamine: Dissolved (2-Methoxyethyl)methyl-{4-nitro-3-[2-(3-trifluoromethylphenyl)ethoxy]-phenyl}amine (0.61 mmol) in MeOH (5 mL) and the solution was degassed with N₂ followed by the addition of Pd/C (10%, catalytic). The mixture was placed under an atmosphere of H₂ at atmospheric pressure and was stirred overnight at ambient temperature. The reaction mixture was filtered through celite and concentrated. The title compound was used as is in the following reaction.

Step 4: Synthesis of 5-Chloro-2-hydroxy-N-{4-[(2-methoxyethyl)-methylamino]-2-[2-(3-trifluoromethylphenyl)ethoxy]phenyl}benzamide: Dissolved N-(4-(2-Methoxyethyl)-N-(4-methyl-2-[2-(3-trifluoromethylphenyl)-ethoxy]benzene-1,4-diamine (Q 0.60 mmol, crude from above) and 5-chlorosalicylic acid (103 mg, 0.60 mmol) in toluene (3 mL). Tetraethylpyrophosphite (170 mg, 0.66 mmol) was added and the mixture was warmed to reflux for 18 h. The reaction mixture was poured into water and extracted EtOAc. The organic extract was washed with brine and dried over Na₂SO₄. The title compound was purified by prep-LC. ¹H NMR (CDCl₃) δ 3.12 (s, 3H), 3.24 (t, 2H), 3.33 (s, 3H), 3.57 (bs, 4H), 4.42 (t,2H), 6.65 (dd, 1H), 6.99 (t, 2H), 7.38 (m, 5H), 8.26 (d, 2H).

In addition, compound No. 18 can be synthesized according the following

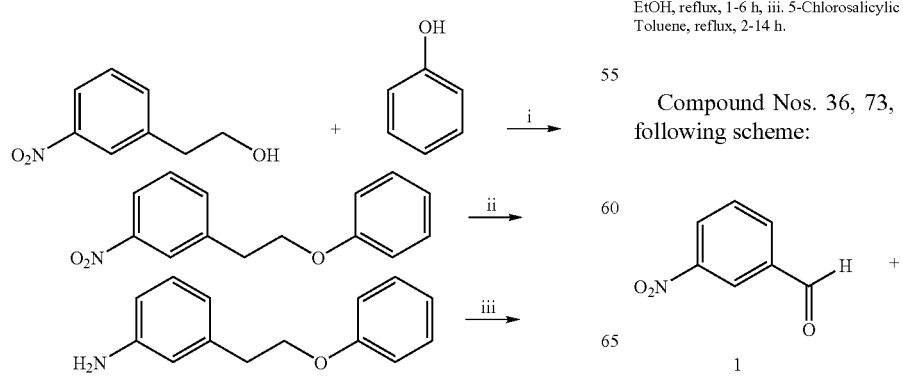

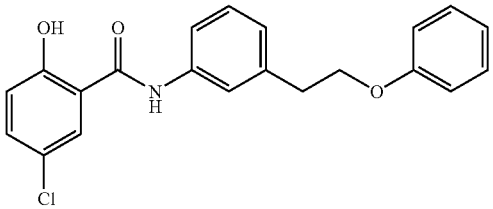

Reagents: i. DEAD, PPh₃, THF, 0-25° C., 16 h, ii. SnCl₂•H₂O, EtOH, reflux, 2-6 h, iii. 5-Chlorosalicylic acid, Tetraethyl pyrophosphite, Toluene, reflux, 2-14 h.

Compound Nos. 38, 70, 71, 72 can be synthesized according the following schemes:

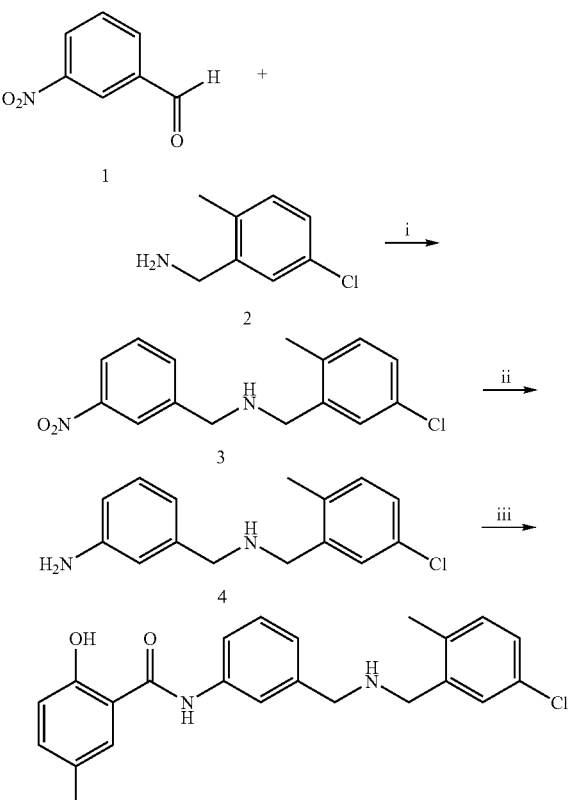

Reagents: i. NaCNBH₃, AcOH, MeOH, 2-16 h, rt ii. SnCl₂•2H₂O (3 eq), EtOH, reflux, 1-6 h, iii. 5-Chlorosalicylic acid, Tetraethyl pyrophosphite, Toluene, reflux, 2-14 h.

Compound Nos. 36, 73, 74 can be synthesized with the following scheme:

-continued

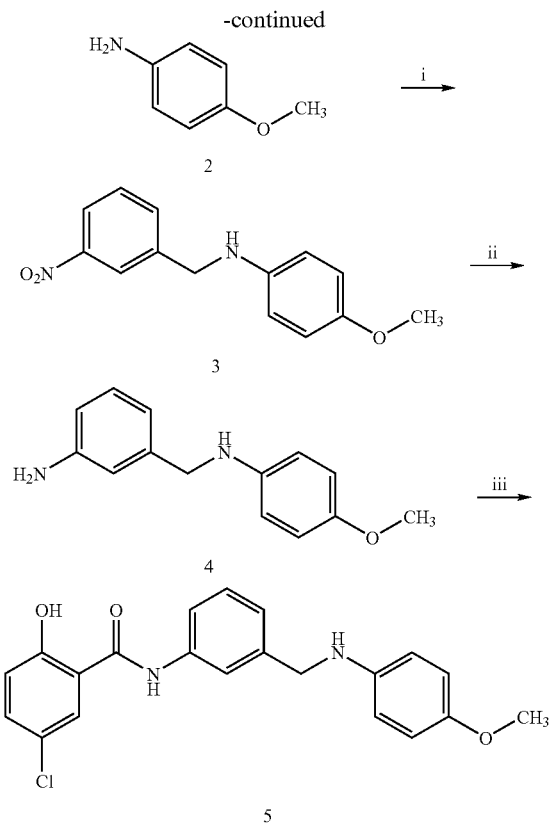

Reagents: i. NaCNBH₃, AcOH, MeOH, 2-16 h, rt ii. SnCl₂•2H₂O (3 eq), EtOH, reflux, 1-6 h, iii. 5-Chlorosalicylic acid, Tetraethyl pyrophosphite, Toluene, reflux, 2-14 h.

Using the methods described above and substituting the appropriate starting materials, other example compounds in Table 1 were similarly prepared and are summarized below in Table 2 and Table 3.

TABLE 2

| Example # | ¹H NMR(CDCl₃) δ |
|---|---|
| 5 | 3.2(t, 2H), 4.2(t, 2H), 6.20-8.60(m, 15H), 12.7(s, 1H) |
| 11 | 4.24(d, 2H), 4.52(bs, 1H), 5.94(s, 2H), 6.22-6.56(m, 1H) 6.52-7.04(m, 8H), 7.09(s, 1H), 9.92(s, 1H), 12.06(s, 1H) |
| 12 | 3.18(t, 2H), 3.87(s, 3H), 4.24(t, 2H), 6.62-7.58(m, 11H), 7.72(s, 1H), 11.92(s, 1H) |
| 15 | 5.12(s, 2H), 6.65-8.10(m, 13H), 11.85(s, 1H) |
| 16 | (CDCl₃+d₆-DMSO) 2.07(m, 2H), 2.79(t, 2H), 3.81(s, 3H), 3.98(t, 2H), 6.39-7.80(m, 10H), 8.13(s, 1H), 10.17(s, 1H), 12.04(s, 1H) |
| 17 | 1.58-2.31(m, 8H), 2.82-2.87(m, 1H), 4.59(bs, 1H), 6.61(d, 1H), 6.96-7.66(m, 12H), 11.87(s, 1H) |
| 18 | (CDCl₃+d₆-DMSO) 3.09(t, 2H), 4.17(t, 2H), 6.52-8.62(m, 12H), 9.66(bs, 1H), 12.00(s, 1H) |
| 19 | 1.43(d, 3H), 3.86-4.85(m, 3H), 6.55-7.90(m, 12H), 11.86(s, 1H) |
| 22 | 3.17(t, 2H), 4.37(t, 2H), 6.84-7.42(m, 9H), 8.32-8.40(m, 2H), 11.82(s, 1H) |
| 26 | 4.60(d, 2H), 6.44(bs, 1H), 6.90-7.37(m, 12H), 12.21(s, 1H) |
| 28 | 4.19(bs, 1H), 4.36(s, 2H), 6.50-7.71(m, 13H), 11.94(s, 1H) |
| 31 | (CDCl₃+d₆-DMSO); 6.76-6.97(m, 5H), 7.21-7.24(m, 1H), 7.48-7.71(m, 2H), 8.04(d, 1H), 8.08-8.76(m, 2H), 8.77(s, 1H), 11.00(s, 1H), 11.08(s, 1H) |

TABLE 2-continued

| Example # | ¹H NMR(CDCl₃) δ |
|---|---|
| 33 | 3.09(t, 2H), 3.81(s, 3H), 4.20(t, 2H), 6.67-7.02(m, 5H), 7.22-7.50(m, 4H), 8.06(d, 1H), 8.43(s, 1H), 11.73(s, 1H) |
| 41 | 2.2(s, 3H), 3.1(t, 2H), 4.2(t, 2H), 6.70-7.90(m, 12H), 8.5(s, 1H), 10.50(s, 1H) |
| 42 | 0.91(t, 3H), 1.64-1.83(m, 1H), 1.97-2.15(m, 1H), 2.94-3.09(m, 1H), 4.06-4.20(m, 2H), 6.76(dd, 1H), 7.02(d, 1H), 7.09(dd, 1H), 7.18-7.53(m, 9H), 7.88(bs, 1H), 11.88(s, 1H) |
| 44 | 0.98-1.09(m, 4H), 4.08(s, 2H), 6.73(dd, 1H), 6.96-7.50(m, 11H), 7.76(bs, 1H), 11.86(bs, 1H) |
| 49 | 2.38(s, 3H), 5.05(s, 2H), 6.93-7.52(m, 11H), 9.91(bs, 1H), 12.00(s, 1H) |
| 50 | 4.51(d, 2H), 5.10(s, 2H), 6.35(bs, 1H), 6.85-7.05(m, 3H), 7.15-7.65(m, 9H), 12.21(s, 1H) |
| 53 | 3.08(t, 2H), 4.14(t, 2H), 4.53(d, 2H), 6.34(bs, 1H), 6.86-6.94(m, 5H), 7.22-7.33(m, 7H), 12.22(s, 1H) |
| 54 | 2.90(t, 2H), 3.69(t, 2H), 6.21(bs, 1H), 6.90-7.54(m, 12H), 12.26(s, 1H) |
| 70 | 2.32(s, 6H), 4.54(d, 4H), 6.34(bs, 1H), 6.93-6.96(m, 6H), 7.26-7.29(m, 5H), 12.25(s, 1H) |
| 74 | (CDCl₃+d₆-DMSO) 4.32(d, 2H), 5.06(bs, 1H), 6.53(d, 2H), 6.73-7.34(m, 5H), 7.55-7.69(m, 3H), 8.12(d, 1H), 10.23(s, 1H), 12.03(s, 1H) |
| 95 | 1.30(d, 3H), 2.85(dd, 1H), 3.10(dd, 1H) 4.61(m, 1H), 6.65(d, 1H), 6.92(d, 1H), 6.95-7.41(m, 8H), 7.74(d, 1H), 8.10(s, 1H), 10.23(s, 1H), 12.02(1H) |
| 98 | 1.52-1.68(m, 8H), 2.19-2.27(m, 1H), 4.82(s, 1H), 6.51-7.49(m, 10H), 8.35(s, 1H), 8.60(s, 1H), 11.84(s, 1H) |
| 124 | 3.10(t, 2H), 4.20(t, 2H), 6.76(d, 1H), 7.06(d, 1H), 7.25-7.33(m, 8H), 7.95(bs, 2H), 8.55(s, 1H), 8.59(s, 1H), 12.71(s, 1H) |
| 179 | 3.13(t, 2H), 3.85(s, 3H), 4.18(s, 2H), 6.74(d, 1H), 6.86-6.93(m, 2H), 7.08(d, 1H), 7.21-7.54(m, 6H), 7.69-7.74(m, 2H), 7.84(bs, 1H) |
| 237 | 4.62(d, 2H), 6.10(bs, 1H), 6.87-6.90(m, 2H), 7.26-7.48(m, 10H), 12.10(s, 1H) |
| 238 | 4.69(d, 2H), 6.49(bs, 1H), 6.96(d, 1H), 7.31-7.59(m, 11H), 12.20(s, 1H) |
| 239 | 4.67(d, 2H), 6.49(bs, 1H), 7.32-7.61(m, 11H), 12.20(s, 1H) |
| 241 | 1.25(s, 3H), 1.28(s, 3H), 2.41(t, 2H), 3.37-3.41(m, 4H), 3.78-3.82(m, 2H), 4.36(t, 2H), 6.49-6.54(m, 2H), 6.98(d, 1H), 7.25-7.45(m, 5H), 7.67(d, 1H), 8.09(d, 1H), 8.16(s, 1H), 12.06(s, 1H) |
| 244 | 3.43(t, 2H), 4.41(t, 2H), 6.96-7.43(m, 8H), 8.52 9s, 1H), 8.69(s, 1H), 11.78(s, 1H) |
| 246 | 1.13(d, 6H), 2.22-2.27(m, 1H), 3.87(d, 2H), 6.83-7.44(m, 5H), 8.45(d, 1H), 8.73(bs, 1H), 11.88(s, 1H) |
| 247 | 3.35(t, 2H), 4.47(t, 2H), 6.99-7.44(m, 9H), 8.43(s, 1H), 8.65(s, 1H), 11.73(s, 1H) |
| 248 | 3.19(t, 2H), 4.43(t, 2H), 6.98-7.43(m, 9H), 8.42(bs, 1H), 8.69(s, 1H), 11.74(s, 1H) |
| 249 | 3.18(t, 2H), 4.43(t, 2H), 6.99-7.42(m, 8H), 8.41(bs, 1H), 8.69(1H), 11.73(bs, 1H) |
| 250 | 3.17(t, 2H), 4.25(t, 2H), 6.90-7.33(m, 7H), 7.57(s, 1H), 8.01(d, 1H), 8.36(d, 1H), 10.48(bs, 1H), 11.30(1H) |
| 258 | 2.68(t, 2H), 3.01(t, 2H), 6.58-7.00(m, 8H), 7.21(d, 1H), 8.23(s, 1H), 8.66(s, 1H), 11.06(s, 1H) |
| 259 | 2.89(t, 2H), 3.26(t, 2H), 6.91-7.42(m, 9H), 7.66(d, 1H), 8.72(s, 1H), 9.16(s, 1H), 11.77(s, 1H) |
| 264 | 6.79(d, 1H), 6.99(d, 1H), 7.07(d, 1H), 7.28-7.35(m, 3H), 7.57-7.72(m, 3H), 8.03(d, 1H), 8.34(d, 1H), 8.75(s, 1H), 8.85(s, 1H), 11.63(s, 1H) |
| 265 | 0.19-0.21(m, 2H), 0.58-0.60(m, 2H), 0.78-0.92(m, 1H), 1.82(q, 2H), 4.25(t, 2H), 6.98-7.04(m, 3H), 7.38-7.45(m, 3H), 8.72(s, 1H), 11.81(s, 1H) |
| 266 | 5.25(s, 2H), 6.96(d, 1H), 7.10(d, 1H), 7.30-7.47(m, 9H), 8.75(s, 1H), 11.82(s, 1H) |
| 267 | 2.92(t, 2H), 3.43-3.49(m, 2H), 4.10(bs, 1H), 6.84-7.50(m, 11H), 11.61(s, 1H) |
| 283 | 0.83(d, 3H), 1.10(d, 3H), 2.05-2.03(m, 1H), 2.94(m, 1H), 4.31(t, 1H), 4.52-4.56(m, 1H), 6.98-7.44(m, 9H), 8.22(s, 1H), 8.66(s, 1H), 11.77(s, 1H) |

TABLE 2-continued

| Example # | $^1$H NMR(CDCl$_3$) δ |
|---|---|
| 295 | 1.24(t, 3H), 3.67(q, 2H), 3.85(t, 2H), 4.32(t, 2H), 6.98-7.06(m, 2H), 7.19-7.53(m, 3H), 8.73(s, 1H), 8.96(s, 1H), 12.01(bs, 1H) |
| 297 | 4.41(t, 2H), 4.55(t, 2H), 6.92-7.41(m, 10H), 8.74(s, 1H), 8.81(s, 1H), 11.71(s, 1H) |
| 305 | 3.12(t, 2H), 3.45(s, 2H), 3.65(s, 3H), 4.34(t, 2H), 6.60-7.36(m, 10H), 8.26(s, 1H), 8.38(s, 1H), 12.98(bs, 1H) |
| 309 | 2.35(s, 3H), 4.40-2.43(bs, 4H), 2.98-3.01(bs, 4H), 7.01(d, 1H), 7.32-7.43(m, 4H), 7.59(s, 1H), 8.74(s, 1H), 9.45(bs, 1H) |
| 310 | (d$_6$-DMSO) 3.14(t, 2H), 3.49(s, 2H), 4.24(t, 2H), 7.02-7.60(m, 9H), 7.99(s, 1H), 8.33(s, 1H), 10.85(s, 1H), 11.90(s, 1H), 12.20(s, 1H) |

TABLE 3

| Example # | $^1$H NMR(CDCl$_3$) δ |
|---|---|
| 9 | 3.10(t, 2H), 4.20(t, 2H), 6.80-7.10(m, 3H), 7.20-7-60(m, 8H), 8.10(s, 1H), 8.20(s, 1H) |
| 15 | 5.12(s, 2H), 6.65-8.10(m, 13H), 11.85(s, 1H) |
| 21 | 7.01(d, 1H), 7.50(d, 1H), 7.53-7.65(m, 6H), 7.84(d, 2H), 7.93-8.01(m, 3H), 11.75(s, 1H). |
| 23 | 6.98(d, 1H), 7.35-7.39(m, 1H), 7.55(t, 1H), 8.00(d, 1H), 8.16(d, 1H), 8.23(d, 1H), 8.67(s, 1H), 10.56(bs, 1H), 11.91(s, 1H). |
| 24 | 3.88(bs, 2H), 6.50(dd, 1H), 6.94(d, 2H), 7.12(t, 1H), 7.22(bs, 1H), 7.29-7.31(m, 1H), 8.05(d, 1H), 9.81(bs, 1H), 12.01(bs, 1H). |
| 25 | 6.98(d, 1H), 7.50(t, 1H), 7.47-7.90(m, 9H), 8.14(d, 1H), 10.36(s, 1H), 11.86(s, 1H). |
| 30 | 1.02-1.57(m, 6H), 2.95-3.63(m 6H), 4.30(t, 2H), 4.36(s, 2H), 6.27-6.55(m, 1H), 6.66-7.67(m, 10H), 8.08(s, 1H), 10.01(s, 1H) |
| 39 | 2.30(s, 3H), 3.10(t, 2H), 4.20(t, 2H), 6.7-7.5(m, 11H), 7.80(s, 1H), 8.10(s, 1H) |
| 56 | 6.98(d, 1H), 7.30-7.40(m, 2H), 7.50(t, 1H), 7.95-8.14(m, 3H), 10.50(bs, 1H), 11.93(s, 1H). |
| 58 | 7.00(d, 1H), 7.39(t, 1H), 7.62-7.73(m, 3H), 8.14-8.19(m, 3H), 11.65(bs, 1H). |
| 60 | 6.98(d, 1H), 7.20(t, 1H), 7.40-7.81(m, 9H), 8.60(d, 1H), 12.15(s, 1H). |
| 61 | 6.98(d, 1H), 7.36(dd, 1H), 7.61(d, 2H), 7.90(d, 2H), 8.13(d, 1H), 10.51(bs, 1H). |
| 85 | (CDCl$_3$+d$_6$-DMSO) 1.26(d, 6H), 2.85-3.01(m, 1H), 5.05(s, 2H), 6.74-6.83(m, 1H), 6.94(d, 1H), 7.18-7.54(m, 8H), 8.09(d, 1H), 9.99(bs, 1H), 12.00(s, 1H) |
| 93 | 6.97(d, 1H), 7.30-7.36(m, 3H), 7.69(d, 2H), 8.10(d, 1H), 10.32(bs, 1H), 12.00(bs, 1H). |
| 94 | 6.93(d, 1H), 7.07(d, 1H), 7.23-7.31(m, 2H), 7.54(d, 1H), 7.80(d, 1H), 8.05(d, 1H), 10.32(bs, 1H), 11.90(bs, 1H). |
| 100 | 1.14(s, 6H), 2.80(m, 1H), 3.14(t, 2H), 4.32(t, 2H), 6.70-7.43(m, 10H), 8.45(s, 1H), 11.98(s, 1H) |
| 114 | 2.34(s, 3H), 6.93(d, 1H), 7.17-7.56(m, 5H), 8.10(d, 1H), 10.04(s, 1H), 12.13(s, 1H). |
| 123 | 3.11(t, 2H), 4.21(t, 2H), 6.73(d, 1H), 7.11-7.42(m, 8H), 8.30(d, 1H), 8.59(d, 1H), 9.57(s, 1H), 12.20(s, 1H) |
| 138 | 3.24(t, 2H), 4.53(t, 2H), 6.98-7.55(m, 10H), 8.45(s, 1H), 8.60(bs, 1H), 11.34(s, 1H) |
| 156 | 3.11(t, 2H), 4.20(t, 2H), 6.95-7.40(m, 10H), 7.82(d, 1H), 7.92(s, 1H), 11.68(s, 1H) |
| 168 | (CDCl$_3$+d$_6$-DMSO) 6.94-7.68(m, 7H), 8.12(s, 1H), 10.16(s, 1H), 12.04(s, 1H) |
| 169 | (CDCl$_3$+d$_6$-DMSO) 6.97(d, 1H), 7.36-7.42(m, 3H), 8.12(d, 1H), 8.37(s, 1H), 10.88(s, 1H), 11.80(s, 1H) |
| 229 | 3.13(t, 2H), 3.85(s, 3H), 4.18(t, 2H), 6.76-7.36(m, 10H), 7.60(d, 1H), 8.1 1(d, 1H) |
| 230 | 3.11(t, 2H), 4.21(t, 2H), 7.01-7.34(m, 11H), 7.59(d, 1H), 8.12(d, 1H) |
| 245 | 3.25(t, 2H), 4.43(t, 2H), 6.97-7.42(m, 8H), 8.44(s, 1H), 8.69(s, 1H), 11.79(s, 1H) |

TABLE 3-continued

| Example # | $^1$H NMR(CDCl$_3$) δ |
|---|---|
| 254 | 3.32(t, 2H), 4.32(t, 2H), 6.75-7.37(m, 6H), 7.82(d, 1H), 8.85(s, 1H), 10.83(s, 1H), 11.10(bs, 1H) |
| 266 | 5.25(s, 2H), 6.97(d, 1H), 7.09(d, 1H), 7.11-7.47(m 9H), 8.75(s, 1H), 11.82(s, 1H) |
| 278 | 4.55(q, 2H), 6.98-7.03(m, 2H), 7.40-7.44(m, 3H), 8.65(s, 1H), 8.78(s, 1H), 11.55(s, 1H) |
| 285 | 3.24(t, 2H), 4.44(t, 2H), 6.98-7.43(m, 9H), 8.42(bs, 1H), 8.68(s 1H), 11.73(s, 1H) |
| 294 | 3.18(t, 2H), 4.39(t, 2H), 6.86-7.31(m, 7H), 8.27(s, 1H), 8.52(d, 1H), 8.59(d, 1H), 10.05(s, 1H), 11.60(bs, 1H) |
| 296 | 1.04(d, 3H), 1.21(d, 3H), 3.73(m, 1H), 3.75(t, 2H), 4.31(t, 2H), 6.98-7.05(m, 2H), 7.38-7.51(m, 3H), 8.73(s, 1H), 8.86(s, 1H), 11.93(s, 1H) |

WST-1 Cell Proliferation and Viability Assay

Cell proliferation and cell viability was assessed using the tetrazolium salt WST-1 (Roche Applied Science, Indianapolis Ind.). The assay is based on the cleavage of WST-1 (light red) by mitochondrial dehydrogenase causing the formation of formazan (dark red), which can be measured on an optical density (O.D.) reader. LNCaP cell lines were plated in 96 well tissue culture plates (Corning Costar, N.Y.) at a density of 5000 cells/well in 150 µl complete media phenol-red free (RPMI-1640 [Invitrogen, Carlsbad Calif.] and 10% fetal calf serum). This plate is termed the assay plate. After the cells are plated, they are then incubated overnight at 37 degrees Celsius in a humidified chamber containing 5% $CO_2$ (incubator).

Compounds are added to the assay plate in 50 µl of complete media and 0.4% DMSO (v:v) making the final DMSO concentration 0.1%. The assay plate is then returned to the incubator for 18-72 hours. WST-1 reagent is then added (20 µl/well) and the plate is placed on an ELISA plate shaker for 30 minutes at room temperature. Plates are then transferred back to the incubator for an additional 3 hours. Plates are then read on a 96 well plate O.D. reader at $A_{490}$-$A_{650}$.

Propidium Iodide and Annexin V Flow Cytometer-Based Assay

Necrotic versus apoptotic killing of human cell lines by compounds was determined using dual annexin V-FITC and propidium iodide (PI) staining. Flipping of phosphatidylserine to the outer leaflet of the plasma membrane is a characteristic of all apoptotic cells. AnnexinV is a serum protein that binds to phosphatidylserine in the presence of the divalent cations (calcium). PI is a DNA stain that is excluded from live cells and is used to discriminate between cells with intact or damaged plasma membranes.

Cells were plated at varying densities in 6 well plates and treated with varying concentrations of compounds for 18-72 hours. Cells were grown in RPMI-1640 media supplemented with 10% FCS. DMSO concentrations did not exceed 0.1% v:v in any assay. All cells in the wells were harvested and rinsed 1× with cold Hanks buffered saline solution (HBSS) containing calcium and magnesium (Invitrogen, Carlsbad Calif.). Carefully aspirate supernatant after the wash and resuspend in 100 µl Annexin V-FITC (Annexin V/PI Apoptosis Detection Kit; R & D Systems TA4638; Minneapolis, Minn.) in binding buffer (10 mM HEPES pH 7.4, 150 mM NaCl, 5 mM KCl, 1 mM $MgCl_2$, 1.8 mM $CaCl_2$ and 2% bovine serum albumin w:v). Incubate in dark for 15 minutes on ice. Prior to analyzing samples, the volume was adjusted to 500 µl with 1× Binding Buffer and 25 µl PI was added per sample. Staining was quantified on a flow cytometer (Becton-Dickenson, Franklin Lake, N.J.).

The following results were found. In the following, "Estimated" data is based on actual data at different concentrations. Although not specifically tabulated, in most instances of active compounds below, positive indications of apoptotic cell death were observed based on one or both of the relevant tests, above.

TABLE 4

| Compound | WST-1 $EC_{50}$ | Estimated |
|---|---|---|
| 1 | 500.00 | |
| 2 | 23.00 | |
| 3 | 500.00 | |
| 4 | 500.00 | |
| 5 | 5.00 | |
| 6 | 500.00 | |
| 7 | 30.00 | Estimated |
| 8 | 500.00 | |
| 9 | 500.00 | |
| 10 | 14.00 | |
| 11 | 40.00 | |
| 12 | 13.00 | |
| 13 | 18.00 | |
| 14 | 18.00 | |
| 15 | 12.00 | |
| 16 | 8.00 | |
| 17 | 2.00 | |
| 18 | 10.00 | |
| 19 | 7.00 | |
| 20 | 24.00 | |
| 21 | 9.00 | |
| 22 | 2.00 | |
| 23 | 4.00 | |
| 24 | 500.00 | |
| 25 | 20.00 | Estimated |
| 26 | 24.00 | |
| 27 | 4.00 | |
| 28 | 31.00 | |
| 29 | 30.00 | Estimated |
| 30 | 50.00 | |
| 31 | 2.00 | |
| 32 | 6.00 | |
| 33 | 3.00 | |
| 34 | 10.00 | |
| 35 | 10.00 | |
| 36 | 21.00 | |
| 37 | 3.00 | |
| 38 | | |
| 39 | 500.00 | |
| 40 | 500.00 | |
| 41 | 500.00 | |
| 42 | 3.00 | |
| 43 | 3.00 | |
| 44 | 5.00 | |
| 45 | 4.00 | |
| 46 | 5.00 | |
| 47 | 4.00 | |
| 48 | 7.00 | |
| 49 | 500.00 | |
| 50 | 500.00 | |
| 51 | 500.00 | |
| 52 | 500.00 | |
| 53 | 23.00 | |
| 54 | 13.00 | |
| 55 | 15.00 | |
| 56 | 1.00 | |
| 57 | 15.00 | |
| 58 | 10.00 | |
| 59 | 10.00 | |
| 60 | 500.00 | |
| 61 | 1.00 | |
| 62 | 4.00 | |
| 63 | 20.00 | |
| 64 | 500.00 | |
| 65 | 17.00 | |
| 66 | 50.00 | |
| 67 | 50.00 | |
| 68 | 500.00 | |
| 69 | 14.00 | |

TABLE 4-continued

| Compound | WST-1 $EC_{50}$ | Estimated |
|---|---|---|
| 70 | 500.00 | |
| 71 | 500.00 | |
| 72 | 500.00 | |
| 73 | 500.00 | |
| 74 | 9.00 | |
| 75 | 1.00 | |
| 76 | 1.00 | |
| 77 | 1.00 | |
| 78 | 2.00 | |
| 79 | 2.00 | |
| 80 | 4.00 | |
| 81 | 1.00 | |
| 82 | 0.70 | |
| 83 | 0.80 | |
| 84 | 14.00 | |
| 85 | 6.00 | |
| 86 | 30.00 | Estimated |
| 87 | 0.90 | |
| 88 | 500.00 | |
| 89 | 500.00 | |
| 90 | 18.00 | |
| 91 | 500.00 | |
| 92 | 2.00 | |
| 93 | 4.00 | |
| 94 | 3.00 | |
| 95 | 6.00 | |
| 96 | 10.00 | |
| 97 | 3.00 | |
| 98 | 4.00 | |
| 99 | 1.00 | |
| 100 | 1.00 | |
| 101 | 4.00 | |
| 102 | 2.00 | |
| 103 | 2.00 | |
| 104 | 0.80 | |
| 105 | 8.00 | |
| 106 | 1.00 | |
| 107 | 2.00 | |
| 108 | 3.00 | |
| 109 | 1.00 | |
| 110 | 1.00 | |
| 111 | 1.00 | |
| 112 | 2.00 | |
| 113 | 8.00 | |
| 114 | 10.00 | |
| 115 | 500.00 | |
| 116 | 30.00 | Estimated |
| 117 | 2.00 | |
| 118 | 30.00 | Estimated |
| 119 | 20.00 | Estimated |
| 120 | 18.00 | Estimated |
| 121 | 30.00 | Estimated |
| 122 | 9.00 | |
| 123 | 30.00 | Estimated |
| 124 | 8.00 | |
| 125 | 6.00 | |
| 126 | 6.00 | |
| 127 | 2.00 | |
| 128 | 2.00 | |
| 129 | 0.80 | |
| 130 | 2.00 | |
| 131 | 2.00 | |
| 132 | 5.00 | |
| 133 | 3.00 | |
| 134 | 0.90 | |
| 135 | 0.80 | |
| 136 | 1.00 | |
| 137 | 5.00 | |
| 138 | 6.00 | |
| 138 | 1.00 | |
| 140 | 3.00 | |
| 141 | 1.00 | |
| 142 | 3.00 | |
| 143 | 14.00 | |
| 144 | 30.00 | Estimated |
| 145 | 17.00 | |
| 146 | 30.00 | Estimated |

TABLE 4-continued

| Compound | WST-1 EC$_{50}$ | Estimated |
|---|---|---|
| 147 | 6.00 | |
| 148 | 500.00 | |
| 149 | 4.00 | |
| 150 | 6.00 | |
| 151 | 30.00 | Estimated |
| 152 | 7.00 | |
| 153 | 1.00 | |
| 154 | 4.00 | |
| 155 | 0.40 | |
| 156 | 16.00 | |
| 157 | 2.00 | |
| 158 | 2.00 | |
| 159 | 2.00 | |
| 160 | 0.70 | |
| 161 | 1.00 | |
| 162 | 0.90 | |
| 163 | 2.00 | |
| 164 | 1.00 | |
| 165 | 500.00 | |
| 166 | 10.00 | |
| 167 | 6.00 | |
| 168 | 17.00 | |
| 169 | 2.00 | |
| 170 | 4.00 | |
| 171 | 5.00 | |
| 172 | 3.00 | |
| 173 | 11.00 | |
| 174 | 11.00 | |
| 175 | 14.00 | |
| 176 | 500.00 | |
| 177 | 500.00 | |
| 178 | 500.00 | |
| 179 | 500.00 | |
| 180 | 12.00 | |
| 181 | 500.00 | |
| 182 | 23.00 | |
| 183 | 19.00 | |
| 184 | 15.00 | |
| 185 | 32.00 | |
| 186 | 22.00 | |
| 187 | 30.00 | |
| 188 | 500.00 | |
| 189 | 30.00 | |
| 190 | 35.00 | |
| 191 | 15.00 | |
| 192 | 30.00 | |
| 193 | 7.00 | |
| 194 | 9.00 | |
| 195 | 500.00 | |
| 196 | 500.00 | |
| 197 | 26.00 | |
| 198 | 21.00 | |
| 199 | 47.00 | Estimated |
| 200 | 37.00 | |
| 201 | 33.00 | |
| 202 | 500.00 | |
| 203 | 33.00 | |
| 204 | 500.00 | |
| 205 | 43.00 | |
| 206 | 34.00 | |
| 207 | 33.00 | |
| 208 | 21.00 | |
| 209 | 17.00 | |
| 210 | 22.00 | |
| 211 | 22.00 | |
| 212 | 20.00 | |
| 213 | 500.00 | |
| 214 | 500.00 | |
| 215 | 45.00 | Estimated |
| 216 | 32.00 | Estimated |
| 217 | 500.00 | |
| 218 | 32.00 | Estimated |
| 219 | 32.00 | |
| 220 | 20.00 | Estimated |
| 221 | 17.00 | |
| 222 | 500.00 | |
| 223 | 8.00 | |

TABLE 4-continued

| Compound | WST-1 EC$_{50}$ | Estimated |
|---|---|---|
| 224 | 22.00 | |
| 225 | 500.00 | |
| 226 | 7.00 | |
| 227 | 22.00 | Estimated |
| 228 | 30.00 | Estimated |
| 229 | 30.00 | Estimated |
| 230 | 500.00 | |
| 231 | 500.00 | |
| 232 | 500.00 | |
| 233 | 10.00 | |
| 234 | 10.00 | |
| 235 | 6.00 | |
| 236 | 11.00 | |
| 237 | 30.00 | Estimated |
| 238 | 30.00 | Estimated |
| 239 | 500.00 | |
| 240 | 10.00 | |
| 241 | 3.00 | |
| 242 | 2.00 | |
| 243 | 1.00 | |
| 244 | 0.90 | |
| 245 | 0.90 | |
| 246 | 2.00 | |
| 247 | 0.90 | |
| 248 | 0.50 | |
| 249 | 0.90 | |
| 250 | 2.00 | |
| 251 | 2.00 | |
| 252 | 1.00 | |
| 253 | 1.00 | |
| 254 | 1.00 | |
| 255 | 30.00 | Estimated |
| 256 | 26.00 | |
| 257 | 500.00 | |
| 258 | 500.00 | |
| 259 | 1.00 | |
| 260 | 1.00 | |
| 261 | 6.00 | |
| 262 | 0.90 | |
| 263 | 2.00 | |
| 264 | 1.00 | |
| 265 | 0.90 | |
| 266 | 0.90 | |
| 267 | | |
| 268 | 500.00 | |
| 269 | 8.00 | |
| 270 | 500.00 | |
| 271 | 0.90 | |
| 272 | 0.90 | |
| 273 | 500.00 | |
| 274 | 4.00 | |
| 275 | 3.00 | |
| 276 | 4.00 | |
| 277 | 3.00 | |
| 278 | 2.00 | Estimated |
| 279 | 6.00 | |
| 280 | 1.00 | |
| 281 | 3.00 | |
| 282 | 4.00 | |
| 283 | 0.90 | |
| 284 | 2.00 | |
| 285 | 0.90 | |
| 286 | 10.00 | |
| 287 | 3.10 | |
| 288 | 3.30 | |
| 289 | 3.30 | |
| 290 | 30.00 | Estimated |
| 291 | 30.00 | Estimated |
| 292 | 30.00 | Estimated |
| 293 | 30.00 | Estimated |
| 294 | 19.00 | |
| 295 | 1.00 | |
| 296 | 0.80 | |
| 297 | 0.90 | |
| 298 | 3.00 | |
| 299 | 1.00 | |
| 300 | 1.00 | |

TABLE 4-continued

| Compound | WST-1 EC$_{50}$ | Estimated |
|---|---|---|
| 301 | 0.67 | |
| 302 | 3.00 | |
| 303 | 3.30 | |
| 304 | 18.00 | |
| 305 | | |
| 306 | 2.00 | |
| 307 | 1.80 | |
| 308 | 0.83 | |
| 309 | 17.40 | |
| 310 | 500.00 | |
| 311 | 3.00 | |
| 312 | 0.85 | |
| 313 | 3.00 | |
| 314 | 500.00 | |
| 315 | 1.20 | |
| 316 | 40.00 | Estimated |
| 317 | 30.00 | Estimated |
| 318 | 40.00 | Estimated |
| 319 | 17.70 | |
| 320 | 17.50 | |
| 321 | 500.00 | |
| 322 | 500.00 | |
| 323 | 30.00 | Estimated |
| 324 | 500.00 | |
| 325 | 3.30 | |
| 326 | 6.20 | |
| 327 | 2.10 | |
| 328 | 1.60 | |
| 329 | 2.20 | |
| 330 | 19.70 | |
| 331 | 12.40 | |
| 332 | 0.74 | |
| 333 | 2.60 | |
| 334 | 9.00 | |
| 335 | 13.00 | |
| 336 | 28.00 | |
| 337 | 19.00 | |
| 338 | 7.00 | |
| 339 | 8.00 | |
| 340 | 16.00 | |
| 341 | 9.00 | |
| 342 | 10.00 | |
| 343 | 17.00 | |
| 344 | 16.00 | |
| 345 | 9.00 | |
| 346 | 28.00 | |
| 347 | 6.00 | |
| 348 | 17.00 | |
| 349 | 10.00 | |
| 350 | 10.00 | |
| 351 | 11.00 | |
| 352 | 7.00 | |
| 353 | 25.00 | Estimated |
| 354 | 7.30 | |
| 355 | 15.00 | |
| 356 | 16.00 | |
| 357 | 500.00 | |
| 358 | 16.3 | |
| 359 | 3.1 | |
| 360 | 2.4 | |
| 361 | 8.0 | |
| 362 | | |
| 363 | 4.0 | |
| 364 | 7.0 | |
| 365 | 2.0 | |
| 366 | | |
| 367 | | |
| 368 | | |
| 369 | 4.0 | |
| 370 | | |
| 371 | | |
| 372 | 2.0 | |
| 373 | 2.9 | |
| 374 | | |
| 375 | 19.0 | |
| 376 | 7.3 | |
| 377 | 4 | |

The invention has been described in considerable detail with reference to various preferred embodiments. However, numerous variations and modifications can be made without departing from the spirit and scope of the invention as described in the foregoing specification and defined in the following claims.

What is claimed is:

1. A method for promoting apoptosis in a cell of a mammal, comprising identifying a mammal in need of the promoting of apoptosis, and treating the mammal with a therapeutically effective amount of a compound having a structure according to Formula 2L:

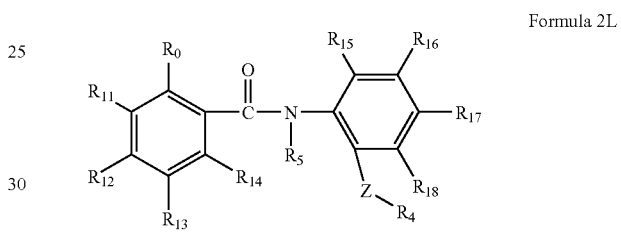

Formula 2L or pharmaceutically acceptable salts thereof, wherein,
$R_0$ is hydroxyl;
Z is O, $N(R^z)$ ($R^z$ is H or $C_{1-6}$ alkyl), or S;
$R_5$ is H or $C_{1-6}$alkyl;
$R_{11}$-$R_{18}$ are independently selected from
  (a) H, halo, $N_3$, nitro, hydroxy, thiol, sulfone, and CN,
  (b) $C_{1-6}$ alkyl, $C_{2-6}$ alkenyl, $C_{2-6}$ alkynyl, $C_{1-6}$ alkoxy, $C_{1-6}$ alkylthiol, $C_{2-6}$ alkenyloxy, $C_{2-6}$ alkynyloxy, $C_{1-6}$ haloalkyl, $C_{1-6}$ hydroxyalkyl, —$C_{1-6}$ alkyl-O—$C_{1-6}$ alkyl, $C_{1-6}$ alkylsulfonyl, $C_{1-6}$ alkylsulfonamide, each of which being optionally substituted with 1-3 substituents wherein each substituent is independently halo, $N_3$, nitro, hydroxy, thiol, —CN, $C_{1-6}$ alkyl, $C_{1-6}$ haloalkyl, $C_{1-6}$ alkoxy, —$N(R^{50})(R^{51})$, —$N(R^{50})C(=O)R_{40}$, —$N(R^{50})C(=O)N(R^{54})(R^{51})$, —$C(=O)N(R^{50})(R^{51})$, —$OC(=O)N(R^{50})(R^{51})$, —$C(=O)R_{40}$, —$OC(=O)R_{40}$, —$C(=G^1)R_{40}$, —$G^2C(=G^1R_{40}$, —$(R^{50})G^2C(=G^1)R_{40}$, —$C(=G^1)G^2R_{41}$ or —$G^3C(=G^1)G^2R_{41}$,
  (c) carbocycle, heterocycle, aryl, and heteroaryl, each of which being optionally substituted with 1-3 substituents wherein each substituent is independently halo, $N_3$, nitro, hydroxy, thiol, sulfone, CN, $C_{1-6}$ alkyl, $C_{1-6}$ haloalkyl, $C_{1-6}$ alkoxy, $C_{1-6}$ hydroxyalkyl, $C_{1-6}$ alkylsulfonyl, $C_{1-6}$ alkylsulfonamide, —$N(R^{52})(R^{53})$, —$N(R^{52})C(=O)R_{42}$, —$N(R^{52})C(=O)N(R^{55})(R^{53})$, —$C(=O)N(R^{52})(R^{53})$, —$OC(=O)N(R^{52})(R^{53})$, —$C(=O)R_{42}$, —$OC(=O)R_{42}$, —$C(=G^1)R_{42}$, —$G^2C(=G^1R_{42}$, —$(R^{52})G^2C(=G^1)R_{42}$, —$C(=G^1)G^2R_{43}$, or —$G^4C(=G^1)G^2R_{43}$,
  (d) —$N(R^{50})(R^{51})$, —$N(R^{50})C(=O)R_{40}$, —$N(R^{50})C(=O)N(R^{54})(R^{51})$, —$C(=O)N(R^{50})(R^{51})$, —$OC(=O)N(R^{50})(R^{51})$, —$C(=O)R_{40}$, —$OC(=O)R_{40}$, —C(=G¹)R$_{40}$, —G²C(=G¹)R$_{40}$, —(R$^{50}$)G²C(=G¹)R$_{40}$, —C(=G¹)G²R$_{41}$, or —G³C(=G¹)G²R$_{41}$;

R$_4$ represents (1) haloalkyl; (2) (C$_{2-6}$ alkoxy)C$_{2-6}$ alkyl; (3) -Ak-O—R$_8$, -Ak-R$_8$ or -Ak(R$_8$R$_9$), wherein Ak is C$_{1-6}$ alkylene, R$_8$ and R$_9$ are independently selected from cycloalkyl, aryl, heterocycle or heteroaryl; each being optionally substituted by one or more substituents independently selected from
  (a) H, halo, N$_3$, nitro, hydroxy, thiol, sulfone, and CN,
  (b) C$_{1-6}$ alkyl, C$_{2-6}$ alkenyl, C$_{2-6}$ alkynyl, C$_{1-6}$ alkoxy, C$_{1-6}$ alkylthiol, C$_{2-6}$ alkenyloxy, C$_{2-6}$ alkynyloxy, C$_{1-6}$ haloalkyl, C$_{1-6}$ hydroxyalkyl, C$_{1-6}$ alkyl-O—C$_{1-6}$ alkyl-, C$_{1-6}$ alkylsulfonyl, C$_{1-6}$ alkylsulfonamide, each of which being optionally substituted with 1-3 substituents wherein each substituent is independently halo, N$_3$, nitro, hydroxy, thiol, —CN, C$_{1-6}$ alkyl, C$_{1-6}$ haloalkyl, C$_{1-6}$ alkoxy, carbocycle, heterocycle, aryl, heteroaryl, —N(R$^{50}$)(R$^{51}$), —N(R$^{50}$)C(=O)R$_{40}$, —N(R$^{50}$)C(=O)N(R$^{54}$)(R$^{51}$), —C(=O)N(R$^{50}$)(R$^{51}$), —OC(=O)N(R$^{50}$)(R$^{51}$), —C(=O)R$_{40}$, —OC(=O)R$_{40}$, —C(=G¹)R$_{40}$, —G²C(=G¹)R$_{40}$, —(R$^{50}$)G²C(=G¹)R$_{40}$, —C(=G¹)G²R$_{41}$ or —G³C(=G¹)G²R$_{41}$,
  (c) carbocycle, heterocycle, aryl, heteroaryl, carbocycloxy, heterocycloxy, aryloxy, heteroaryloxy, each of which being optionally substituted with 1-3 substituents wherein each substituent is independently halo, N$_3$, nitro, hydroxy, thiol, sulfone, CN, C$_{1-6}$ alkyl, C$_{1-6}$ haloalkyl, C$_{1-6}$ alkoxy, C$_{1-6}$ hydroxyalkyl, C$_{1-6}$ alkylsulfonyl, C$_{1-6}$ alkylsulfonamide, carbocycle, heterocycle, aryl, heteroaryl, —N(R$^{52}$)(R$^{53}$), —N(R$^{52}$)C(=O)R$_{42}$, —N(R$^{52}$)C(=O)N(R$^{55}$)(R$^{53}$), —C(=O)N(R$^{52}$)(R$^{53}$), —OC(=O)N(R$^{52}$)(R$^{53}$), —C(=O)R$_{42}$, —OC(=O)R$_{42}$, —C(=G¹)R$_{42}$, —G²C(=G¹)R$_{42}$, —(R$^{52}$)G²C(=G¹)R$_{42}$, —C(=G¹)G²R$_{43}$, or —G⁴C(=G¹)G²R$_{43}$,
  (d) —N(R$^{50}$)(R$^{51}$), —N(R$^{50}$)C(=O)R$_{40}$, —N(R$^{50}$)C(=O)N(R$^{54}$)(R$^{51}$), —C(=O)N(R$^{50}$)(R$^{51}$), —OC(=O)N(R$^{50}$)(R$^{51}$), —C(=O)R$_{40}$, —OC(=O)R$_{40}$, —C(=G¹)R$_{40}$, —G²C(=G¹)R$_{40}$, —(R$^{50}$)G²C(=G¹)R$_{40}$, —C(=G¹)G²R$_{41}$ or —G³C(=G¹)G²R$_{41}$;

G¹ is S or N; G² and G³ are independently S or —N(R$^{50}$)—; G⁴ is —N(R$^{52}$)—;

R$_{40}$ is selected from: H, OH, C$_{1-6}$ alkyl, C$_{2-6}$ alkenyl, C$_{2-6}$ alkynyl, C$_{1-6}$ alkoxy, C$_{2-6}$ alkenyloxy, C$_{2-6}$ alkynyloxy and C$_{1-6}$ alkylthiol, wherein R$_{40}$ is optionally substituted with from one to three substituents independently selected from halo, N$_3$, nitro, hydroxy, thiol, CN, C$_{1-6}$ alkyl;

R$_{41}$ is H, C$_{1-6}$ alkyl, C$_{2-6}$ alkenyl or C$_{2-6}$ alkynyl, wherein R$_{41}$ is optionally substituted with from one to three substituents independently selected from halo, N$_3$, nitro, hydroxy, thiol, CN, C$_{1-6}$ alkyl;

R$_{42}$ is selected from: H, —OH, C$_{1-6}$ alkyl, C$_{2-6}$ alkenyl, C$_{2-6}$ alkynyl, C$_{1-6}$ alkoxy, C$_{2-6}$ alkenyloxy, C$_{2-6}$ alkynyloxy, and C$_{1-6}$ alkylthiol, wherein R$_{42}$ is optionally substituted with from one to three substituents independently selected from halo, N$_3$, nitro, hydroxy, thiol, CN and C$_{1-6}$ alkyl;

R$_{43}$ is H, C$_{1-6}$ alkyl, C$_{2-6}$ alkenyl or C$_{2-6}$ alkynyl, wherein R$_{43}$ is optionally substituted with from one to three substituents independently selected from halo, N$_3$, nitro, hydroxy, thiol, CN and C$_{1-6}$ alkyl;

R$^{50}$, R$^{51}$ and R$^{54}$ are independently H, OH (R$^{50}$ and R$^{51}$ are not both OH), C$_{1-10}$ alkyl, C$_{2-10}$ alkenyl, C$_{2-10}$ alkynyl, C$_{1-10}$ alkoxy, C$_{1-10}$ alkylthiol, C$_{2-10}$ alkenyloxy, C$_{2-10}$ alkynyloxy, C$_{1-10}$ haloalkyl, C$_{2-6}$ hydroxyalkyl, C$_{1-6}$ alkyl-O—C$_{1-6}$ alkyl-, wherein R$^{50}$ and R$^{51}$ each is optionally substituted with 1-3 substituents wherein each substituent is independently halo, N$_3$, nitro, hydroxy, thiol, CN, C$_{1-6}$ alkyl, C$_{1-6}$ haloalkyl, C$_{1-6}$ alkoxy, —C(=O)N(R$^{54}$)(R$^{55}$), R$_{44}$C(=O)— or —N(R$^{54}$)(R$^{55}$), wherein R$^{54}$ and R$^{55}$ are independently H, OH or C$_{1-4}$ alkyl, and wherein R$_{44}$ is H or C$_{1-4}$ alkyl; and R$^{52}$, R$^{53}$ and R$^{55}$ are independently H, OH (R$^{52}$ and R$^{53}$ are not both OH), C$_{1-10}$ alkyl, C$_{2-10}$ alkenyl, C$_{2-10}$ alkynyl, C$_{1-10}$ alkoxy, C$_{1-10}$ alkylthiol, C$_{2-10}$ alkenyloxy, C$_{2-10}$ alkynyloxy, C$_{1-10}$ haloalkyl, C$_{2-6}$ hydroxyalkyl, C$_{1-6}$ alkyl-O—C$_{1-6}$ alkyl-, or R$^{52}$ and R$^{53}$ together with the nitrogen atom to which they are both linked form a 3, 4, 5 or 6-membered heterocycle, wherein R$^{52}$ and R$^{53}$ each is optionally substituted with 1-3 substituents wherein each substituent is independently halo, N$_3$, nitro, hydroxy, thiol, CN, C$_{1-6}$ alkyl, C$_{1-6}$ haloalkyl, C$_{1-6}$ alkoxy, —C(=O)N(R$^{54}$)(R$^{55}$), R$_{44}$C(=O)— or —N(R$^{54}$)(R$^{55}$), wherein R$^{54}$ and R$^{55}$ are independently H, OH or C$_{1-4}$ alkyl, and wherein R$_{44}$ is H or C$_{1-4}$ alkyl.

2. A method for promoting apoptosis in a cell of a mammal comprising identifying a mammal in need of the promoting of apoptosis, and treating the mammal with a therapeutically effective amount of a compound having a structure according to Formula 2n:

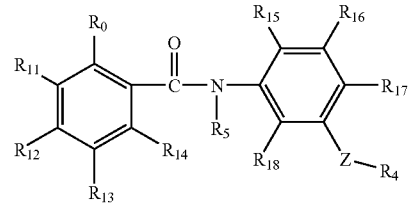

Formula 2n or pharmaceutically acceptable salts thereof, wherein,
  R$_0$ is hydroxyl;
  Z is O, N(R$^z$) (R$^z$ is H or C$_{1-6}$ alkyl), or S;
  R$_5$ is H or C$_{1-6}$ alkyl;
  R$_{11}$-R$_{18}$ are independently selected from
  (a) H, halo, N$_3$, nitro, hydroxy, thiol, sulfone, and CN,
  (b) C$_{1-6}$ alkyl, C$_{2-6}$ alkenyl, C$_{2-6}$ alkynyl, C$_{1-6}$ alkoxy, C$_{1-6}$ alkylthiol, C$_{2-6}$ alkenyloxy, C$_{2-6}$ alkynyloxy, C$_{1-6}$ haloalkyl, C$_{1-6}$ hydroxyalkyl, —C$_{1-6}$ alkyl-O—C$_{1-6}$ alkyl, C$_{1-6}$ alkylsulfonyl (i.e., —SO$_2$—C$_{1-6}$ alkyl), C$_{1-6}$ alkylsulfonamide, each of which being optionally substituted with 1-3 substituents wherein each substituent is independently halo, N$_3$, nitro, hydroxy, thiol, CN, C$_{1-6}$ alkyl, C$_{1-6}$ haloalkyl, C$_{1-6}$ alkoxy, —N(R$^{50}$)(R$^{51}$), —N(R$^{50}$)C(=O)R$_{40}$, —N(R$^{50}$)C(=O)N(R$^{54}$)(R$^{51}$), —C(=O)N(R$^{50}$)(R$^{51}$), —OC(=O)N(R$^{50}$)(R$^{51}$), —C(=O)R$_{40}$, —OC(=O)R$_{40}$, —C(=G¹)R$_{40}$, —G²C(=G¹)R$_{40}$, —(R$^{50}$)G²C(=G¹)R$_{40}$, —C(=G¹)G²R$_{41}$ or —G³C(=G¹)G²R$_{41}$,
  (c) carbocycle, heterocycle, aryl, and heteroaryl, each of which being optionally substituted with 1-3 substituents wherein each substituent is independently halo, N$_3$, nitro, hydroxy, thiol, sulfone, CN, C$_{1-6}$ alkyl, C$_{1-6}$ haloalkyl, C$_{1-6}$ alkoxy, C$_{1-6}$ hydroxyalkyl, C$_{1-6}$ alkylsulfonyl (i.e., —SO$_2$—C$_{1-6}$ alkyl), C$_{1-6}$ alkylsulfonamide, —N(R$^{52}$)(R$^{53}$), —N(R$^{52}$)C(=O)R$_{42}$, —N(R$^{52}$)C(=O)N(R$^{55}$)(R$^{53}$), —C(=O)N(R$^{52}$)(R$^{53}$), —OC(=O)N(R$^{52}$)(R$^{53}$), —C(=O)R$_{42}$, —OC(=O)R$_{42}$, —C(=G$^{1}$)R$_{42}$, —G$^{2}$C(=G$^{1}$)R$_{42}$, —(R$^{52}$)G$^{2}$C(=G$^{1}$)R$_{42}$, —C(=G$^{1}$)G$^{2}$R$_{43}$, or —G$^{4}$C(=G$^{1}$)G$^{2}$R$_{43}$, (d) —N(R$^{50}$)(R$^{51}$), —N(R$^{50}$)C(=O)R$_{40}$, —N(R$^{50}$)C(=O)N(R$^{54}$)(R$^{51}$), —C(=O)N(R$^{50}$)(R$^{51}$), —OC(=O)N(R$^{50}$)(R$^{51}$), —C(=O)R$_{40}$, —OC(=O)R$_{40}$, —C(=G$^{1}$)R$_{40}$, —G$^{2}$C(=G$^{1}$)R$_{40}$, —(R$^{50}$)G$^{2}$C(=G$^{1}$)R$_{40}$, —C(=G$^{1}$)G$^{2}$R$_{41}$ or —G$^{3}$C(=G$^{1}$)G$^{2}$R$_{41}$;

R$_{4}$ represents (1) haloalkyl; (2) (C$_{2-6}$ alkoxy)C$_{2-6}$ alkyl; (3) -Ak-O—R$_{8}$, -Ak-R$_{8}$ or -Ak(R$_{8}$R$_{9}$), wherein Ak is C$_{2-6}$ alkylene, R$_{8}$ and R$_{9}$ are independently selected from cycloalkyl, aryl, heterocycle or heteroaryl; each being optionally substituted by one or more substituents independently selected from (a) halo, N$_{3}$, nitro, hydroxy, thiol, sulfone, and CN, (b) C$_{1-6}$ alkyl, C$_{2-6}$ alkenyl, C$_{2-6}$ alkynyl, C$_{1-6}$ alkoxy, C$_{1-6}$ alkylthiol, C$_{2-6}$ alkenyloxy, C$_{2-6}$ alkynyloxy, C$_{1-6}$ haloalkyl, C$_{1-6}$ hydroxyalkyl, C$_{1-6}$ alkyl-O—C$_{1-6}$ alkyl-, C$_{1-6}$ alkylsulfonyl, C$_{1-6}$ alkylsulfonamide, each of which being optionally substituted with 1-3 substituents wherein each substituent is independently halo, N$_{3}$, nitro, hydroxy, thiol, CN, C$_{1-6}$ alkyl, C$_{1-6}$ haloalkyl, C$_{1-6}$ alkoxy, carbocycle, heterocycle, aryl, heteroaryl, —N(R$^{50}$)(R$^{51}$), —N(R$^{50}$)C(=O)R$_{40}$, —N(R$^{50}$)C(=O)N(R$^{54}$)(R$^{51}$), —C(=O)N(R$^{50}$)(R$^{51}$), —OC(=O)N(R$^{50}$)(R$^{51}$), —C(=O)$_{40}$, —OC(=O)R$_{40}$, —C(=G$^{1}$)R$_{40}$, —G$^{2}$C(=G$^{1}$)R$_{40}$, —(R$^{50}$)G$^{2}$C(=G$^{1}$)R$_{40}$, —C(=G$^{1}$)G$^{2}$R$_{42}$ or —G$^{3}$C(=G$^{1}$)G$^{2}$R$_{41}$, (c) carbocycle, heterocycle, aryl, heteroaryl, carbocycloxy, heterocycloxy, aryloxy, heteroaryloxy, each of which being optionally substituted with 1-3 substituents wherein each substituent is independently halo, N$_{3}$, nitro, hydroxy, thiol, sulfone, CN, C$_{1-6}$ alkyl, C$_{1-6}$ haloalkyl, C$_{1-6}$ alkoxy, C$_{1-6}$ hydroxyalkyl, C$_{1-6}$ alkylsulfonyl, C$_{1-6}$ alkylsulfonamide, carbocycle, heterocycle, aryl, heteroaryl, —N(R$^{52}$)(R$^{53}$), —N(R$^{52}$)C(=O)R$_{42}$, —N(R$^{52}$)C(=O)N(R$^{55}$)(R$^{53}$), —C(=O)N(R$^{52}$)(R$^{53}$), —OC(=O)N(R$^{52}$)(R$^{53}$), —C(=O)R$_{42}$, —OC(=O)R$_{42}$, —C(=G$^{1}$)R$_{42}$, —G$^{2}$C(=G$^{1}$)R$_{42}$, —(R$^{52}$)G$^{2}$C(=G$^{1}$)R$_{42}$, —C(=G$^{1}$)G$^{2}$R$_{43}$, or —G$^{4}$C(=G$^{1}$)G$^{2}$R$_{43}$, (d) —N(R$^{50}$)(R$^{51}$), —N(R$^{50}$)C(=O)R$_{40}$, —N(R$^{50}$)C(=O)N(R$^{54}$)(R$^{51}$), —C(=O)N(R$^{50}$)(R$^{51}$), —OC(=O)N(R$^{50}$)(R$^{51}$), —C(=O)R$_{40}$, —OC(=O)R$_{40}$, —C(=G$^{1}$)R$_{40}$, —G$^{2}$C(=G$^{1}$)R$_{40}$, —(R$^{50}$)G$^{2}$C(=G$^{1}$)R$_{40}$, —C(=G$^{1}$)G$^{2}$R$_{41}$ or —G$^{3}$C(=G$^{1}$)G$^{2}$R$_{41}$;

G$^{1}$ is S or N; G$^{2}$ and G$^{3}$ are independently S or N(R$^{50}$); G$^{4}$ is N(R$^{52}$);

R$_{40}$ is selected from: H, OH, C$_{1-6}$ alkyl, C$_{2-6}$ alkenyl, C$_{2-6}$ alkynyl, C$_{1-6}$ alkoxy, C$_{2-6}$ alkenyloxy, C$_{2-6}$ alkynyloxy and C$_{1-6}$ alkylthiol, wherein R$_{40}$ is optionally substituted with from one to three substituents independently selected from halo, N$_{3}$, nitro, hydroxy, thiol, CN, C$_{1-6}$ alkyl;

R$_{41}$ is H, C$_{1-6}$ alkyl, C$_{2-6}$ alkenyl or C$_{2-6}$ alkynyl, wherein R$_{41}$ is optionally substituted with from one to three substituents independently selected from halo, N$_{3}$, nitro, hydroxy, thiol, CN, C$_{1-6}$ alkyl;

R$_{42}$ is selected from: H, OH, C$_{1-6}$ alkyl, C$_{2-6}$ alkenyl, C$_{2-6}$ alkynyl, C$_{1-6}$ alkoxy, C$_{2-6}$ alkenyloxy, C$_{2-6}$ alkynyloxy, and C$_{1-6}$ alkylthiol, wherein R$_{42}$ is optionally substituted with from one to three substituents independently selected from halo, N$_{3}$, nitro, hydroxy, thiol, CN and C$_{1-6}$ alkyl;

R$_{43}$ is H, C$_{1-6}$ alkyl, C$_{2-6}$ alkenyl or C$_{2-6}$ alkynyl, wherein R$_{43}$ is optionally substituted with from one to three substituents independently selected from halo, N$_{3}$, nitro, hydroxy, thiol, CN and C$_{1-6}$ alkyl;

R$^{50}$, R$^{51}$ and R$^{54}$ are independently H, OH (R$^{50}$ and R$^{51}$ are not both OH), C$_{1-10}$ alkyl, C$_{2-10}$ alkenyl, C$_{2-10}$ alkynyl, C$_{1-10}$ alkoxy, C$_{1-10}$ alkylthiol, C$_{2-10}$ alkenyloxy, C$_{2-10}$ alkynyloxy, C$_{1-10}$ haloalkyl, C$_{2-6}$ hydroxyalkyl, C$_{1-6}$ alkyl-O—C$_{1-6}$ alkyl-, wherein R$^{50}$ and R$^{51}$ each is optionally substituted with 1-3 substituents wherein each substituent is independently halo, N$_{3}$, nitro, hydroxy, thiol, CN, C$_{1-6}$ alkyl, C$_{1-6}$ haloalkyl, C$_{1-6}$ alkoxy, —C(=O)N(R$^{54}$)(R$^{55}$), R$_{44}$C(=O)— or —N(R$^{54}$)(R$^{55}$), wherein R$^{54}$ and R$^{55}$ are independently H, OH or C$_{1-4}$ alkyl, and wherein R$_{44}$ is H or C$_{1-4}$ alkyl; and R$^{52}$, R$^{53}$ and R$^{55}$ are independently H, OH (R$^{52}$ and R$^{53}$ are not both OH), C$_{1-10}$ alkyl, C$_{2-10}$ alkenyl, C$_{2-10}$ alkynyl, C$_{1-10}$ alkoxy, C$_{1-10}$ alkylthiol, C$_{2-10}$ alkenyloxy, C$_{2-10}$ alkynyloxy, C$_{1-10}$ haloalkyl, C$_{2-6}$ hydroxyalkyl, C$_{1-6}$ alkyl-O—C$_{1-6}$ alkyl-, or R$_{52}$ and R$^{53}$ together with the nitrogen atom to which they are both linked form a 3, 4, 5 or 6-membered heterocycle, wherein R$^{52}$ and R$^{53}$ each is optionally substituted with 1-3 substituents wherein each substituent is independently halo, N$_{3}$, nitro, hydroxy, thiol, CN, C$_{1-6}$ alkyl, C$_{1-6}$ haloalkyl, C$_{1-6}$ alkoxy, —C(=O)N(R$^{54}$)(R$^{55}$), R$_{44}$C(=O)— or —N(R$^{54}$)(R$^{55}$), wherein R$^{54}$ and R$^{55}$ are independently H, OH or C$_{1-4}$ alkyl, and wherein R$_{44}$ is H or C$_{1-4}$ alkyl.

3. The method of claim 2, wherein Ak is is C$_{2-6}$ alkylene, and R$_{8}$ or R$_{9}$ or both are substituted with one or more said substituents defined for R$_{8}$ and R$_{9}$.

4. A method for promoting apoptosis in a cell of a mammal, comprising identifying a mammal in need of the promoting of apoptosis, and treating the mammal with a therapeutically effective amount of a compound having a structure according to Formula 2p:

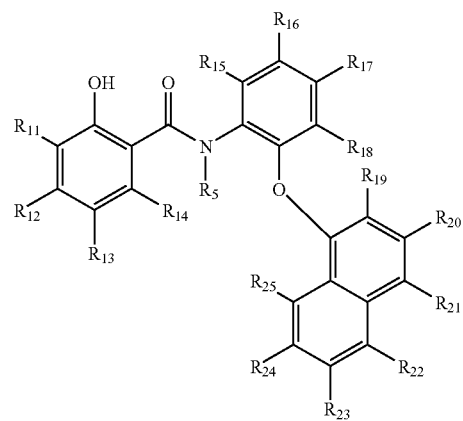

Formula 2p or pharmaceutically acceptable salt thereof, wherein

R$_{5}$ is H or C$_{1-6}$ alkyl;

R$_{11}$-R$_{25}$ are independently selected from (a) H, halo, N$_{3}$, nitro, hydroxy, thiol, sulfone, and CN, (b) C$_{1-6}$ alkyl, C$_{2-6}$ alkenyl, C$_{2-6}$ alkynyl, C$_{1-6}$ alkoxy, C$_{1-6}$ alkylthiol, C$_{2-6}$ alkenyloxy, C$_{2-6}$ alkynyloxy, C$_{1-6}$

213 haloalkyl, C$_{1-6}$ hydroxyalkyl, —C$_{1-6}$ alkyl-O—C$_{1-6}$ alkyl, C$_{1-6}$ alkylsulfonyl, C$_{1-6}$ alkylsulfonamide, each of which being optionally substituted with 1-3 substituents wherein each substituent is independently halo, N$_3$, nitro, hydroxy, thiol, —CN, C$_{1-6}$ alkyl, C$_{1-6}$ haloalkyl, C$_{1-6}$ alkoxy, —N(R$^{50}$)(R$^{51}$), —N(R$^{50}$)C(=O)R$_{40}$, —N(R$^{50}$)C(=O)N(R$^{54}$)(R$^{51}$), —C(=O)N(R$^{50}$)(R$^{51}$), —OC(=O)N(R$^{50}$)(R$^{51}$), —C(=O)R$_{40}$, —OC(=O)R$_{40}$, —C(=G$^1$)R$_{40}$, —G$^2$C(=G$^1$)R$_{40}$, —(R$^{50}$)G$^2$C(=G$^1$)R$_{40}$), —C(=G$^1$)G$^2$R$_{41}$ or —G$^3$C(=G$^1$)G$^2$R$_{41}$, (c) carbocycle, heterocycle, aryl, and heteroaryl, each of which being optionally substituted with 1-3 substituents wherein each substituent is independently halo, N$_3$, nitro, hydroxy, thiol, sulfone, CN, C$_{1-6}$ alkyl, C$_{1-6}$ haloalkyl, C$_{1-6}$ alkoxy, C$_{1-6}$ hydroxyalkyl, C$_{1-6}$ alkylsulfonyl, C$_{1-6}$ alkylsulfonamide, —N(R$^{52}$)(R$^{53}$), —N(R$^{52}$)C(=O)R$_{42}$, —N(R$^{52}$)C(=O)N(R$^{55}$)(R$^{53}$), —C(=O)N(R$^{52}$)(R$^{53}$), —OC(=O)N(R$^{52}$)(R$^{53}$), —C(=O)R$_{42}$, —OC(=O)R$_{42}$, —C(=G$^1$)R$_{42}$, —G$^2$C(=G$^1$)R$_{42}$, —(R$^{52}$)G$^2$C(=G$^1$)R$_{42}$, —C(=G$^1$)G$^2$R$_{43}$, or —G$^4$C(=G$^1$)G$^2$R$_{43}$, (d) —N(R$^{50}$)(R$^{51}$), —N(R$^{50}$)C(=O)R$_{40}$, —N(R$^{50}$)C(=O)N(R$^{54}$)(R$_{51}$), —C(=O)N(R$^{50}$)(R$^{51}$), —OC(=O)N(R$^{50}$)(R$^{51}$), —C(=O)R$_{40}$, —OC(=O)R$_{40}$, —C(=G$^1$)R$_{40}$, —G$^2$C(=G$^1$)R$_{40}$, —(R$^{50}$)G$^2$C(=G$^1$)R$_{40}$, —C(=G$^1$)G$^2$R$_{41}$ or —G$^3$C(=G$^1$)G$^2$R$_{41}$;

G$^1$ is S or N; G$^2$ and G$^3$ are independently S or N(R$^{50}$); G$^4$ is N(R$^{52}$);

R$_{40}$ is selected from: H, —OH, C$_{1-6}$ alkyl, C$_{2-6}$ alkenyl, C$_{2-6}$ alkynyl, C$_{1-6}$ alkoxy, C$_{2-6}$ alkenyloxy, C$_{2-6}$ alkynyloxy and C$_{1-6}$ alkylthiol, wherein R$_{40}$ is optionally substituted with from one to three substituents independently selected from halo, N$_3$, nitro, hydroxy, thiol, CN, C$_{1-6}$ alkyl;

R$_{41}$ is H, C$_{1-6}$ alkyl, C$_{2-6}$ alkenyl or C$_{2-6}$ alkynyl, wherein R$_{41}$ is optionally substituted with from one to three substituents independently selected from halo, N$_3$, nitro, hydroxy, thiol, CN, C$_{1-6}$ alkyl;

R$_{42}$ is selected from: H, —OH, C$_{1-6}$ alkyl, C$_{2-6}$ alkenyl, C$_{2-6}$ alkynyl, C$_{1-6}$ alkoxy, C$_{2-6}$ alkenyloxy, C$_{2-6}$ alkynyloxy, and C$_{1-6}$ alkylthiol, wherein R$_{42}$ is optionally substituted with from one to three substituents independently selected from halo, N$_3$, nitro, hydroxy, thiol, CN and C$_{1-6}$ alkyl;

R$_{43}$ is H, C$_{1-6}$ alkyl, C$_{2-6}$ alkenyl or C$_{2-6}$ alkynyl, wherein R$_{43}$ is optionally substituted with from one to three substituents independently selected from halo, N$_3$, nitro, hydroxy, thiol, CN and C$_{1-6}$ alkyl;

R$^{50}$, R$^{51}$ and R$^{54}$ are independently H, OH (R$^{50}$ and R$^{51}$ are not both OH), C$_{1-10}$ alkyl, C$_{2-10}$ alkenyl, C$_{2-10}$ alkynyl, C$_{1-10}$ alkoxy, C$_{1-10}$ alkylthiol, C$_{2-10}$ alkenyloxy, C$_{2-10}$ alkynyloxy, C$_{1-10}$ haloalkyl, C$_{2-6}$ hydroxyalkyl, C$_{1-6}$ alkyl-O—C$_{1-6}$ alkyl-, wherein R$^{50}$ and R$^{51}$ each is optionally substituted with 1-3 substituents wherein each substituent is independently halo, N$_3$, nitro, hydroxy, thiol, CN, C$_{1-6}$ alkyl, C$_{1-6}$ halo alkyl, C$_{1-6}$ alkoxy, —C(=O)N(R$^{54}$)(R$^{55}$), R$_{44}$C(=O)— or —N(R$^{54}$)(R$^{55}$), wherein R$^{54}$ and R$^{55}$ are independently H, OH or C$_{1-4}$ alkyl, and wherein R$_{44}$ is H or C$_{1-4}$ alkyl; and R$^{52}$, R$^{53}$ and R$^{55}$ are independently H, OH (R$^{52}$ and R$^{53}$ are not both OH), C$_{1-10}$ alkyl, C$_{2-10}$ alkenyl, C$_{2-10}$ alkynyl, C$_{1-10}$ alkoxy, C$_{1-10}$ alkylthiol, C$_{2-10}$ alkenyloxy, C$_{2-10}$ alkynyloxy, C$_{1-10}$ haloalkyl, C$_{2-6}$ hydroxyalkyl, C$_{1-6}$ alkyl-O—C$_{1-6}$ alkyl-, or R$^{52}$ and R$^{53}$ together with the

214 nitrogen atom to which they are both linked form a 3, 4, 5 or 6-membered heterocycle, wherein R$^{52}$ and R$^{53}$ each is optionally substituted with 1-3 substituents wherein each substituent is independently halo, N$_3$, nitro, hydroxy, thiol, CN, C$_{1-6}$ alkyl, C$_{1-6}$ haloalkyl, C$_{1-6}$ alkoxy, —C(=O)N(R$^{54}$)(R$^{55}$), R$_{44}$C(=O)— or —N(R$^{54}$)(R$^{55}$), wherein R$^{54}$ and R$^{55}$ are independently H, OH or C$_{1-4}$ alkyl, and wherein R$_{44}$ is H or C$_{1-4}$ alkyl.

5. The method of claim 4, wherein at least one of R$_{19}$-R$_{25}$ is selected from Cl, Br, I, or C$_{1-6}$ haloalkyl.

6. The method of claim 5, wherein R$_{21}$ is Cl, Br, I, or C$_{1-6}$ haloalkyl.

7. A compound having a structure according to Formula 2p:

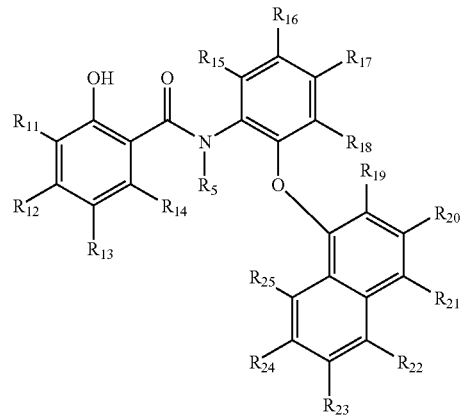

Formula 2p and pharmaceutically acceptable salts thereof, wherein

R$_5$ is H or C$_{1-6}$ alkyl;

R$_{15}$-R$_{20}$, and R$_{22}$-R$_{25}$ are independently selected from (a) H, halo, N$_3$, nitro, hydroxy, thiol, sulfone, and CN, (b) C$_{1-6}$ alkyl, C$_{2-6}$ alkenyl, C$_{2-6}$ alkynyl, C$_{1-6}$ alkoxy, C$_{1-6}$ alkylthiol, C2-6 alkenyloxy, C$_{2-6}$ alkynyloxy, C$_{1-6}$ haloalkyl, C$_{1-6}$ hydroxyalkyl, C$_{1-6}$ alkyl-O—C$_{1-6}$ alkyl, C$_{1-6}$ alkylsulfonyl, C$_{1-6}$ alkylsulfonamide, each of which being optionally substituted with 1-3 substituents wherein each substituent is independently halo, N$_3$, nitro, hydroxy, thiol, —CN, C$_{1-6}$ alkyl, C$_{1-6}$ haloalkyl, C$_{1-6}$ alkoxy, —N(R$^{50}$)(R$^{51}$), —N(R$^{50}$)C(=O)R$_{40}$, —N(R$^{50}$)C(=O)N(R$^{54}$)(R$^{51}$), —C(=O)N(R$^{50}$)(R$^{51}$), —OC(=O)N(R$^{50}$)(R$^{51}$), —C(=O)R$_{40}$, —OC(=O)R$_{40}$, —C(=G$^1$)R$_{40}$, —G$^2$C(=G$^1$)R$_{40}$, —(R$^{50}$)G$^2$C(=G$^1$)R$_{40}$, —C(=G$^1$)G$^2$R$_{41}$ or —G$^3$C(=G$^1$)G$^2$R$_{41}$, (c) carbocycle, heterocycle, aryl, and heteroaryl, each of which being optionally substituted with 1-3 substituents wherein each substituent is independently halo, N$_3$, nitro, hydroxy, thiol, sulfone, CN, C$_{1-6}$ alkyl, C$_{1-6}$ haloalkyl, C$_{1-6}$ alkoxy, C$_{1-6}$ hydroxyalkyl, C$_{1-6}$ alkylsulfonyl, C$_{1-6}$ alkylsulfonamide, —N(R$^{52}$)(R$^{53}$), —N(R$^{52}$)C(=O)R$_{42}$, —N(R$^{52}$)C(=O)N(R$^{55}$)(R$^{53}$), —C(=O)N(R$^{52}$)(R$^{53}$), —OC(=O)N(R$^{52}$)(R$^{53}$), —C(=O)R$_{42}$, —OC(=O)R$_{42}$, —C(=G$^1$)R$_{42}$, —G$^2$C(=G$^1$)R$_{42}$, —(R$^{52}$)G$^2$C(=G$^1$)R$_{42}$, —C(=G$^1$)G$^2$R$_{43}$, or —G$^4$C(=G$^1$)G$^2$R$_{43}$, (d) —N(R$^{50}$)(R$^{51}$), —N(R$^{50}$)C(=O)R$_{40}$, —N(R$^{50}$)C(=O)N(R$^{54}$)(R$_{51}$), —C(=O)N(R$^{50}$)(R$^{51}$), —OC(=O)N(R$^{50}$)(R$^{51}$), —C(=O)R$_{40}$, —OC(=O)R$_{40}$, —C(=G$^1$)R$_{40}$, —G$^2$C(=G$^1$)R$_{40}$, —(R$^{50}$)G$^2$C(=G$^1$)R$_{40}$, —C(=G$^1$)G$^2$R$_{41}$ or —G$^3$C(=G$^1$)G$^2$R$_{41}$;

G$^1$ is S or N; G$^2$ and G$^3$ are independently S or N(R$^{50}$); G$^4$ is N(R$^{52}$);

R$_{40}$ is selected from: H, —OH, C$_{1-6}$ alkyl, C$_{2-6}$ alkenyl, C$_{2-6}$ alkynyl, C$_{1-6}$ alkoxy, C$_{2-6}$ alkenyloxy, C$_{2-6}$ alkynyloxy and C$_{1-6}$ alkylthiol, wherein R$_{40}$ is optionally substituted with from one to three substituents independently selected from halo, N$_3$, nitro, hydroxy, thiol, CN, C$_{1-6}$ alkyl;

R$_{41}$ is H, C$_{1-6}$ alkyl, C$_{2-6}$ alkenyl or C$_{2-6}$ alkynyl, wherein R$_{41}$ is optionally substituted with from one to three substituents independently selected from halo, N$_3$, nitro, hydroxy, thiol, CN, C$_{1-6}$ alkyl;

R$_{42}$ is selected from: H, —OH, C$_{1-6}$ alkyl, C$_{2-6}$ alkenyl, C$_{2-6}$ alkynyl, C$_{1-6}$ alkoxy, C$_{2-6}$ alkenyloxy, C$_{2-6}$ alkynyloxy, and C$_{1-6}$ alkylthiol, wherein R$_{42}$ is optionally substituted with from one to three substituents independently selected from halo, N$_3$, nitro, hydroxy, thiol, CN and C$_{1-6}$ alkyl;

R$_{43}$ is H, C$_{1-6}$ alkyl, C$_{2-6}$ alkenyl or C$_{2-6}$ alkynyl, wherein R$_{43}$ is optionally substituted with from one to three substituents independently selected from halo, N$_3$, nitro, hydroxy, thiol, CN and C$_{1-6}$ alkyl;

R$^{50}$, R$^{51}$ and R$^{54}$ are independently H, OH (R$^{50}$ and R$^{51}$ are not both OH), C$_{1-10}$ alkyl, C$_{2-10}$ alkenyl, C$_{2-10}$ alkynyl, C$_{1-10}$ alkoxy, C$_{1-10}$ alkylthiol, C$_{2-10}$ alkenyloxy, C$_{2-10}$ alkynyloxy, C$_{1-10}$ haloalkyl, C$_{2-6}$ hydroxyalkyl, C$_{1-6}$ alkyl-O—C$_{1-6}$ alkyl-, wherein R$^{50}$ and R$^{51}$ each is optionally substituted with 1-3 substituents wherein each substituent is independently halo, N$_3$, nitro, hydroxy, thiol, CN, C$_{1-6}$ alkyl, C$_{1-6}$ haloalkyl, C$_{1-6}$ alkoxy, —C(=O)N(R$^{54}$)(R$^{55}$), R$_{44}$C(=O)— or —N(R$^{54}$)(R$^{55}$), wherein R$^{54}$ and R$^{55}$ are independently H, OH or C$_{1-4}$ alkyl, and wherein R$_{44}$ is H or C$_{1-4}$ alkyl; and R$^{52}$, R$^{53}$ and R$^{55}$ are independently H, OH (R$^{52}$ and R$^{53}$ are not both OH), C$_{1-10}$ alkyl, C$_{2-10}$ alkenyl, C$_{2-10}$ alkynyl, C$_{1-10}$ alkoxy, C$_{1-10}$ alkylthiol, C$_{2-10}$ alkenyloxy, C$_{2-10}$ alkynyloxy, C$_{1-10}$ haloalkyl, C$_{2-6}$ hydroxyalkyl, C$_{1-6}$ alkyl-O—C$_{1-6}$ alkyl-, or R$^{52}$ and R$^{53}$ together with the nitrogen atom to which they are both linked form a 3, 4, 5 or 6-membered heterocycle, wherein R$^{52}$ and R$^{53}$ each is optionally substituted with 1-3 substituents wherein each substituent is independently halo, N$_3$, nitro, hydroxy, thiol, CN, C$_{1-6}$ alkyl, C$_{1-6}$ haloalkyl, C$_{1-6}$ alkoxy, —C(=O)N(R$^{54}$)(R$^{55}$), R$_{44}$C(=O)— or —N(R$^{54}$)(R$^{55}$), wherein R$^{54}$ and R$^{55}$ are independently H, OH or C$_{1-4}$ alkyl, and wherein R$_{44}$ is H or C$_{1-4}$ alkyl; and wherein R$_{11}$, R$_{12}$ and R$_{14}$ are H; R$_{13}$ is halo; and R$_{21}$ is halo or C$_{1-6}$ haloalkyl.

8. The compound of claim 7, wherein R$_{11}$, R$_{12}$ and R$_{14}$ are H; R$_{13}$ is halo; R$_{15}$-R$_{18}$ are independently H, F, Cl, Br, I, or C$_{1-3}$ haloalkyl; R$_{21}$ is Cl, Br, I, or C$_{1-3}$ haloalkyl; and R$_{19}$, R$_{20}$, R$_{22}$-R$_{25}$ are independently H, F, Cl, Br, I, C$_{1-6}$ alkyl, or C$_{1-3}$ haloalkyl.

9. A method for promoting apoptosis in a cell of a mammal, comprising identifying a mammal in need of the promoting of apoptosis, and treating a mammal with a therapeutically effective amount of a compound having a structure according to Formula 2q:

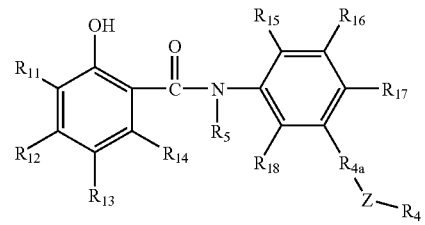

Formula 2q or pharmaceutically acceptable salts thereof, wherein
Z is O, N(R$^z$) (R$^z$ is H or C$_{1-6}$ alkyl), or S;
R$_{4a}$ is C$_{1-6}$ alkylene;
R$_5$ is H or C$_{1-6}$ alkyl;
R$_{11}$-R$_{18}$ are independently selected from
(a) H, halo, N$_3$, nitro, hydroxy, thiol, sulfone, and CN,
(b) C$_{1-6}$ alkyl, C$_{2-6}$ alkenyl, C$_{2-6}$ alkynyl, C$_{1-6}$ alkoxy, C$_{1-6}$ alkylthiol, C$_{2-6}$ alkenyloxy, C$_{2-6}$ alkynyloxy, C$_{1-6}$ haloalkyl, C$_{1-6}$ hydroxyalkyl, —C$_{1-6}$ alkyl-O—C$_{1-6}$ alkyl, C$_{1-6}$ alkylsulfonyl (i.e., —SO$_2$—C$_{1-6}$ alkyl), C$_{1-6}$ alkylsulfonamide, each of which being optionally substituted with 1-3 substituents wherein each substituent is independently halo, N$_3$, nitro, hydroxy, thiol, —CN, C$_{1-6}$ alkyl, C$_{1-6}$ haloalkyl, C$_{1-6}$ alkoxy, —N(R$^{50}$)(R$^{51}$), —N(R$^{50}$)C(=O)R$_{40}$, —N(R$^{50}$)C(=O)N(R$^{54}$)(R$^{51}$), —C(=O)N(R$^{50}$)(R$^{51}$), —OC(=O)N(R$^{50}$)(R$^{51}$), —C(=O)R$_{40}$, —OC(=O)R$_{40}$, —C(=G$^1$)R$_{40}$, —G$^2$C(=G$^1$)R$_{40}$, —(R$^{50}$)G$^2$C(=G$^1$)R$_{40}$, —C(=G$^1$)G$^2$R$_{41}$ or —G$^3$C(=G$^1$)G$^2$R$_{41}$, (c) carbocycle, heterocycle, aryl, and heteroaryl, each of which being optionally substituted with 1-3 substituents wherein each substituent is independently halo, N$_3$, nitro, hydroxy, thiol, sulfone, CN, C$_{1-6}$ alkyl, C$_{1-6}$ haloalkyl, C$_{1-6}$ alkoxy, C$_{1-6}$ hydroxyalkyl, C$_{1-6}$ alkylsulfonyl (i.e., —SO$_2$—C$_{1-6}$ alkyl), C$_{1-6}$ alkylsulfonamide, —N(R$^{52}$)(R$^{53}$), —N(R$^{52}$)C(=O)R$_{42}$, —N(R$^{52}$)C(=O)N(R$^{55}$)(R$^{53}$), —C(=O)N(R$^{52}$)(R$^{53}$), —OC(=O)N(R$^{52}$)(R$^{53}$), —C(=O)R$_{42}$, —OC(=O)R$_{42}$, —C(=G$^1$)R$_{42}$, —G$^2$C(=G$^1$)R$_{42}$, —(R$^{52}$)G$^2$C(=G$^1$)R$_{42}$, —C(=G$^1$)G$^2$R$_{43}$, or —G$^4$C(=G$^1$)G$^2$R$_{43}$, (d) —N(R$^{50}$)(R$^{51}$), —N(R$^{50}$)C(=O)R$_{40}$, —N(R$^{50}$)C(=O)N(R$^{54}$)(R$^{51}$), —C(=O)N(R$^{50}$)(R$^{51}$), —OC(=O)N(R$^{50}$)(R$^{51}$), —C(=O)R$^{40}$, —OC(=O)R$_{40}$, —C(=G$^1$)R$_{40}$, —G$^2$C(=G$^1$)R$_{40}$, —(R$^{50}$)G$^2$C(=G$^1$)R$_{40}$, —C(=G$^1$)G$^2$R$_{41}$ or —G$^3$C(=G$^1$)G$^2$R$_{41}$;

R$_4$ represents C$_{1-6}$ haloalkyl; (C$_{2-6}$ alkoxy)C$_{2-6}$ alkyl; R$_8$; -Ak-O—R$_8$; -Ak-R$_8$ or -Ak(R$_8$R$_9$), wherein Ak is lower alkyl, R$_8$ and R$_9$ are independently selected from (1) cycloalkyl, (2) aryl, (3) heterocycle, or (4) heteroaryl; each being optionally substituted by one or more substituents independently selected from (a) H, halo, N$_3$, nitro, hydroxy, thiol, sulfone, and CN,
(b) C$_{1-6}$ alkyl, C$_{2-6}$ alkenyl, C$_{2-6}$ alkynyl, C$_{1-6}$ alkoxy, C$_{1-6}$ alkylthiol, C$_{2-6}$ alkenyloxy, C$_{2-6}$ alkynyloxy, C$_{1-6}$ haloalkyl, C$_{1-6}$ hydroxyalkyl, C$_{1-6}$ alkyl-O—C$_{1-6}$ alkyl-, C$_{1-6}$ alkylsulfonyl, C$_{1-6}$ alkylsulfonamide, each of which being optionally substituted with 1-3 substituents wherein each substituent is independently halo, N$_3$, nitro, hydroxy, thiol, —CN, C$_{1-6}$ alkyl, C$_{1-6}$ haloalkyl, C$_{1-6}$ alkoxy, carbocycle, heterocycle, aryl, heteroaryl, —N(R$^{50}$)(R$^{51}$), —N(R$^{50}$)C (=O)R$_{40}$, —N(R$^{50}$)C(=O)N(R$^{54}$)(R$^{51}$), —C(=O)N(R$^{50}$)(R$^{51}$), —OC(=O)N(R$^{50}$)(R$^{51}$), —C(=O)R$_{40}$, —OC(=O)R$_{40}$, —C(=G$^1$)R$_{40}$, —G$^2$C(=G$^1$)R$_{40}$, —(R$^{50}$)G$^2$C(=G$^1$)R$_{40}$, —C(=G$^1$)G$^2$R$_{41}$ or —G$^3$C(=G$^1$)G$^2$R$_{41}$, (c) carbocycle, heterocycle, aryl, heteroaryl, carbocycloxy, heterocycloxy, aryloxy, heteroaryloxy, each of which being optionally substituted with 1-3 substituents wherein each substituent is independently halo, N$_3$, nitro, hydroxy, thiol, sulfone, CN, C$_{1-6}$ alkyl, C$_{1-6}$ haloalkyl, C$_{1-6}$ alkoxy, C$_{1-6}$ hydroxyalkyl, C$_{1-6}$ alkylsulfonyl, C$_{1-6}$ alkylsulfonamide, carbocycle, heterocycle, aryl, heteroaryl, —N(R$^{52}$)(R$^{53}$), —N(R$^{52}$)C(=O)R$_{42}$, —N(R$^{52}$)C(=O)N(R$^{55}$)(R$^{53}$), —C(=O)N(R$^{52}$)(R$^{53}$), —OC(=O)N(R$^{52}$)(R$^{53}$), —C(=O)R$_{42}$, —OC(=O)R$_{42}$, —C(=G$^1$)R$_{42}$, —G$^2$C(=G$^1$)R$_{42}$, —(R$^{52}$)G$^2$C(=G$^1$)R$_{42}$, —C(=G$^1$)G$^2$R$_{43}$, or —G$^4$C(=G$^1$)G$^2$R$_{43}$, (d) —N(R$^{50}$)(R$^{51}$), —N(R$^{50}$)C(=O)R$_{40}$, —N(R$^{50}$)C(=O)N(R$^{54}$)(R$^{51}$), —C(=O)N(R$^{50}$)(R$^{51}$), —OC(=O)N(R$^{50}$)(R$^{51}$), —C(=O)R$_{40}$, —OC(=O)R$_{40}$, —C(=G$^1$)R$_{40}$, —G$^2$C(=G$^1$)R$_{40}$, —(R$^{50}$)G$^2$C(=G$^1$)R$_{40}$, —C(=G$^1$)G$^2$R$_{41}$ or —G$^3$C(=G$^1$)G$^2$R$_{41}$;

G$^1$ is S or N; G$^2$ and G$^3$ are independently S or N(R$^{50}$); G$^4$ is N(R$^{52}$);

R$_{40}$ is selected from: H, —OH, C$_{1-6}$ alkyl, C$_{2-6}$ alkenyl, C$_{2-6}$ alkynyl, C$_{1-6}$ alkoxy, C$_{2-6}$ alkenyloxy, C$_{2-6}$ alkynyloxy and C$_{1-6}$ alkylthiol, wherein R$_{40}$ is optionally substituted with from one to three substituents independently selected from halo, N$_3$, nitro, hydroxy, thiol, CN, C$_{1-6}$ alkyl;

R$_{41}$ is H, C$_{1-6}$ alkyl, C$_{2-6}$ alkenyl or C$_{2-6}$ alkynyl, wherein R$_{41}$ is optionally substituted with from one to three substituents independently selected from halo, N$_3$, nitro, hydroxy, thiol, CN, C$_{1-6}$ alkyl;

R$_{42}$ is selected from: H, —OH, C$_{1-6}$ alkyl, C$_{2-6}$ alkenyl, C$_{2-6}$ alkynyl, C$_{1-6}$ alkoxy, C$_{2-6}$ alkenyloxy, C$_{2-6}$ alkynyloxy, and C$_{1-6}$ alkylthiol, wherein R$_{42}$ is optionally substituted with from one to three substituents independently selected from halo, N$_3$, nitro, hydroxy, thiol, CN and C$_{1-6}$ alkyl;

R$_{43}$ is H, C$_{1-6}$ alkyl, C$_{2-6}$ alkenyl or C$_{2-6}$ alkynyl, wherein R$_{43}$ is optionally substituted with from one to three substituents independently selected from halo, N$_3$, nitro, hydroxy, thiol, CN and C$_{1-6}$ alkyl;

R$^{50}$, R$^{51}$ and R$^{54}$ are independently H, OH (R$^{50}$ and R$^{51}$ are not both OH), C$_{1-10}$ alkyl, C$_{2-10}$ alkenyl, C$_{2-10}$ alkynyl, C$_{1-40}$ alkoxy, C$_{1-10}$ alkylthiol, C$_{2-10}$ alkenyloxy, C$_{2-10}$ alkynyloxy, C$_{1-10}$ haloalkyl, C$_{2-6}$ hydroxyalkyl, C$_{1-6}$ alkyl-O—C$_{1-6}$ alkyl-, wherein R$^{50}$ and R$^{51}$ each is optionally substituted with 1-3 substituents wherein each substituent is independently halo, N$_3$, nitro, hydroxy, thiol, CN, C$_{1-6}$ alkyl, C$_{1-6}$ haloalkyl, C$_{1-6}$ alkoxy, —C(=O)N(R$^{54}$)(R$^{55}$), R$_{44}$C(=O)— or —N(R$^{54}$)(R$^{55}$), wherein R$^{54}$ and R$^{55}$ are independently H, OH or C$_{1-4}$ alkyl, and wherein R$_{44}$ is H or C$_{1-4}$ alkyl; and R$^{52}$, R$^{53}$ and R$^{55}$ are independently H, OH (R$^{52}$ and R$^{53}$ are not both OH), C$_{1-10}$ alkyl, C$_{2-10}$ alkenyl, C$_{2-10}$ alkynyl, C$_{1-10}$ alkoxy, C$_{1-10}$ alkylthiol, C$_{2-10}$ alkenyloxy, C$_{2-10}$ alkynyloxy, C$_{1-10}$ haloalkyl, C$_{2-6}$ hydroxyalkyl, C$_{1-6}$ alkyl-O—C$_{1-6}$ alkyl-, or R$^{52}$ and R$^{53}$ together with the nitrogen atom to which they are both linked form a 3, 4, 5 or 6-membered heterocycle, wherein R$^{52}$ and R$^{53}$ each is optionally substituted with 1-3 substituents wherein each substituent is independently halo, N$_3$, nitro, hydroxy, thiol, CN, C$_{1-6}$ alkyl, C$_{1-6}$ haloalkyl, C$_{1-6}$ alkoxy, —C(=O)N(R$^{54}$)(R$^{55}$), R$_{44}$C(=O)— or —N(R$^{54}$)(R$^{55}$), wherein R$^{54}$ and R$^{55}$ are independently H, OH or C$_{1-4}$ alkyl, and wherein R$_{44}$ is H or C$_{1-4}$ alkyl; with the proviso that when Z is S, R$_4$ is not bicyclic heteroaryl.

10. The method of claim 9, wherein R$_{13}$ is not H or nitro.
11. The method of claim 9, wherein R$_{13}$ is halo.
12. The method of claim 9, wherein
Z is NH or O;
R$_{4a}$ is —CH$_2$— or —CH$_2$CH$_2$—;
R$_4$ is aryl, aralkyl or heteroaralkyl, each being optionally substituted with one to three substituents selected from F, Cl, Br, I, C$_{1-6}$ alkyl, and C$_{1-6}$ lower alkoxy;
R$_{11}$, R$_{12}$, and R$_{14}$-R$_{18}$ are H; and
R$_{13}$ is halo.

13. A method for promoting apoptosis in a cell of a mammal, comprising identifying a mammal in need of the promoting of apoptosis, and treating a mammal with a therapeutically effective amount of a compound having a structure according to Formula 2r:

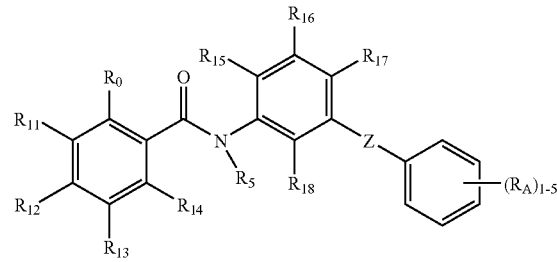

Formula 2r or pharmaceutically acceptable salts thereof, wherein

R$_0$ is hydroxyl;
Z is O, N(R$^z$) (R$^z$ is H or C$_{1-6}$ alkyl), or S;
R$_5$ is H or C$_{1-6}$ alkyl;
R$_{11}$-R$_{18}$ are independently selected from
 (a) H, halo, N$_3$, nitro, hydroxy, thiol, sulfone, and CN,
 (b) C$_{1-6}$ alkyl, C$_{2-6}$ alkenyl, C$_{2-6}$ alkynyl, C$_{1-6}$ alkoxy, C$_{1-6}$ alkylthiol, C$_{2-6}$ alkenyloxy, C$_{2-6}$ alkynyloxy, C$_{1-6}$ haloalkyl, C$_{1-6}$ hydroxyalkyl, —C$_{1-6}$ alkyl-O—C$_{1-6}$ alkyl, C$_{1-6}$ alkylsulfonyl (i.e., —SO$_2$—C$_{1-6}$ alkyl), C$_{1-6}$ alkylsulfonamide, each of which being optionally substituted with 1-3 substituents wherein each substituent is independently halo, N$_3$, nitro, hydroxy, thiol, —CN, C$_{1-6}$ alkyl, C$_{1-6}$ haloalkyl, C$_{1-6}$ alkoxy, —N(R$^{50}$)(R$^{51}$), —N(R$^{50}$)C(=O)R$_{40}$, —N(R$^{50}$)C(=O)N(R$^{54}$)(R$^{51}$), —C(=O)N(R$^{50}$)(R$^{51}$), —OC(=O)N(R$^{50}$)(R$^{51}$), —C(=O)R$_{40}$, —OC(=O)R$_{40}$, —C(=G$^1$)R$_{40}$, —G$^2$C(=G$^1$)R$_{40}$, —(R$^{50}$)G$^2$C(=G$^1$)R$_{40}$, —C(=G$^1$)G$^2$R$_{41}$ or —G$^3$C(=G$^1$)G$^2$R$_{41}$,
 (c) carbocycle, heterocycle, aryl, and heteroaryl, each of which being optionally substituted with 1-3 substituents wherein each substituent is independently halo, N$_3$, nitro, hydroxy, thiol, sulfone, CN, C$_{1-6}$ alkyl, C$_{1-6}$ haloalkyl, C$_{1-6}$ alkoxy, C$_{1-6}$ hydroxyalkyl, C$_{1-6}$ alkylsulfonyl (i.e., —SO$_2$—C$_{1-6}$ alkyl), C$_{1-6}$ alkylsulfonamide, —N(R$^{52}$)(R$^{53}$), —N(R$^{52}$)C(=O)R$_{42}$, —N(R$^{52}$)C(=O)N(R$^{55}$)(R$^{53}$), —C(=O)N(R$^{52}$)(R$^{53}$), —OC(=O)N(R$^{52}$)(R$^{53}$), —C(=O)R$_{42}$, —OC(=O)R$_{42}$, —C(=G$^1$)R$_{42}$, —G$^2$C(=G$^1$)R$_{42}$, —(R$^{52}$)G$^2$C(=G$^1$)R$_{42}$, —C(=G$^1$)G$^2$R$_{43}$, or —G$^4$C(=G$^1$)G$^2$R$_{43}$, (d) —N($R^{50}$)($R^{51}$), —N($R^{50}$)C(=O)$R_{40}$, —N($R^{50}$)C(=O)N($R^{54}$)($R^{51}$), —C(=O)N($R^{50}$)($R^{51}$), —OC(=O)N($R^{50}$)($R^{51}$), —C(=O)$R_{40}$, —OC(=O)$R_{40}$, —C(=$G^1$)$R_{40}$, —$G^2$C(=$G^1$)$R_{40}$, —($R^{50}$)$G^2$C(=$G^1$)$R_{40}$, —C(=$G^1$)$G^2R_{41}$ or —$G^3$C(=$G^1$)$G^2R_{41}$;

each $R_A$ when present is selected from the group consisting of (a) halo, $N_3$, nitro, hydroxy, thiol, sulfone, and CN, (b) $C_{1-6}$ alkyl, $C_{2-6}$ alkenyl, $C_{2-6}$ alkynyl, $C_{1-6}$ alkoxy, $C_{1-6}$ alkylthiol, $C_{2-6}$ alkenyloxy, $C_{2-6}$ alkynyloxy, $C_{1-6}$ haloalkyl, $C_{1-6}$ hydroxyalkyl, $C_{1-6}$ alkyl-O—$C_{1-6}$ alkyl-, $C_{1-6}$ alkylsulfonyl (i.e., $C_{1-6}$ alkyl-$SO_2$—), $C_{1-6}$ alkylsulfonamide, each of which being optionally substituted with 1-3 substituents wherein each substituent is independently halo, $N_3$, nitro, hydroxy, thiol, —CN, $C_{1-6}$ alkyl, $C_{1-6}$ haloalkyl, $C_{1-6}$ alkoxy, carbocycle, heterocycle, aryl, heteroaryl, —N($R^{50}$)($R^{51}$), —N($R^{50}$)C(=O)$R_{40}$, —N($R^{50}$)C(=O)N($R^{54}$)($R^{51}$), —C(=O)N($R^{50}$)($R^{51}$), —OC(=O)N($R^{50}$)($R^{51}$), —C(=O)$R_{40}$, —OC(=O)$R_{40}$, —C(=$G^1$)$R_{40}$, —$G^2$C(=$G^1$)$R_{40}$, —($R^{50}$)$G^2$C(=$G^1$)$R_{40}$, —C(=$G^1$)$G^2R_{41}$ or —$G^3$C(=$G^1$)$G^2R_{41}$, (c) carbocycle, heterocycle, aryl, heteroaryl, carbocycloxy, heterocycloxy, aryloxy, heteroaryloxy, each of which being optionally substituted with 1-3 substituents wherein each substituent is independently halo, $N_3$, nitro, hydroxy, thiol, sulfone, CN, $C_{1-6}$ alkyl, $C_{1-6}$ haloalkyl, $C_{1-6}$ alkoxy, $C_{1-6}$ hydroxyalkyl, $C_{1-6}$ alkylsulfonyl (i.e., $C_{1-6}$ alkyl-$SO_2$—), $C_{1-6}$ alkylsulfonamide, carbocycle, heterocycle, aryl, heteroaryl, —N($R^{52}$)($R^{53}$), —N($R^{52}$)C(=O)$R_{42}$, —N($R^{52}$)C(=O)N($R^{55}$)($R^{53}$), —C(=O)N($R^{52}$)($R^{53}$), —OC(=O)N($R^{52}$)($R^{53}$), —C(=O)$R_{42}$, —OC(=O)$R_{42}$, —C(=$G^1$)$R_{42}$, —$G^2$C(=$G^1$)$R_{42}$, —($R^{52}$)$G^2$C(=$G^1$)$R_{42}$, —C(=$G^1$)$G^2R_{43}$, or —$G^4$C(=$G^1$)$G^2R_{43}$, (d) —N($R^{50}$)($R^{51}$), —N($R^{50}$)C(=O)$R_{40}$, —N($R^{50}$)C(=O)N($R^{54}$)($R^{51}$), —C(=O)N($R^{50}$)($R^{51}$), —OC(=O)N($R^{50}$)($R^{51}$), —C(=O)$R_{40}$, —OC(=O)$R_{40}$, —C(=$G^1$)$R_{40}$, —$G^2$C(=$G^1$)$R_{40}$, —($R^{50}$)$G^2$C(=$G^1$)$R_{40}$, —C(=$G^1$)$G^2R_{41}$ or —$G^3$C(=$G^1$)$G^2R_{41}$;

(e) two adjacent $R_A$ can be taken together to form a carbocyclic, heterocyclic, aryl, or heteroaryl ring fused to the phenyl ring where the resultant bicyclic ring system is substituted with 1-3 substituents selected from the group consisting of halo, $N_3$, nitro, hydroxy, thiol, sulfone, CN, $C_{1-6}$ alkyl, $C_{1-6}$ haloalkyl, $C_{1-6}$ alkoxy, $C_{1-6}$ hydroxyalkyl, $C_{1-6}$ alkylsulfonyl (i.e., $C_{1-6}$ alkyl-$SO_2$—), $C_{1-10}$ alkylsulfonamide, carbocycle, heterocycle, aryl, heteroaryl, —N($R^{52}$)($R^{53}$), —N($R^{52}$)C(=O)$R_{42}$, —N($R^{52}$)C(=O)N($R^{55}$)($R^{53}$), —C(=O)N($R^{52}$)($R^{53}$), —OC(=O)N($R^{52}$)($R^{53}$), —C(=O)$R_{42}$, —OC(=O)$R_{42}$, —C(=$G^1$)$R_{42}$, —$G^2$C(=$G^1$)$R_{42}$, —($R^{52}$)$G^2$C(=$G^1$)$R_{42}$, —C(=$G^1$)$G^2R_{43}$, or —$G^4$C(=$G^1$)$G^2R_{43}$, —N($R^{50}$)($R^{51}$), —N($R^{50}$)C(=O)$R_{40}$, —N($R^{50}$)C(=O)N($R^{54}$)($R^{51}$), —C(=O)N($R^{50}$)($R^{51}$), —OC(=O)N($R^{50}$)($R^{51}$), —C(=O)$R_{40}$, —OC(=O)$R_{40}$, —C(=$G^1$)$R_{40}$, —$G^2$C(=$G^1$)$R_{40}$, —($R^{50}$)$G^2$C(=$G^1$)$R_{40}$, —C(=$G^1$)$G^2R_{41}$ or —$G^3$C(=$G^1$)$G^2R_{41}$;

wherein $G^1$ is S or N; $G^2$ and $G^3$ are independently S or N($R^{50}$); $G^4$ is N($R^{52}$);

$R_{40}$ is selected from: H, —OH, $C_{1-6}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy and $C_{1-6}$ alkylthiol, wherein $R_{40}$ is optionally substituted with from one to three substituents independently selected from halo, $N_3$, nitro, hydroxy, thiol, CN, $C_{1-6}$ alkyl;

$R_{41}$ is H, $C_{1-6}$ alkyl, $C_{2-6}$ alkenyl or $C_{2-6}$ alkynyl, wherein $R_{41}$ is optionally substituted with from one to three substituents independently selected from halo, $N_3$, nitro, hydroxy, thiol, CN, $C_{1-6}$ alkyl;

$R_{42}$ is selected from: H, —OH, $C_{1-6}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy, and $C_{1-6}$ alkylthiol, wherein $R_{42}$ is optionally substituted with from one to three substituents independently selected from halo, $N_3$, nitro, hydroxy, thiol, CN and $C_{1-6}$ alkyl;

$R_{43}$ is H, $C_{1-6}$ alkyl, $C_{2-6}$ alkenyl or $C_{2-6}$ alkynyl, wherein $R_{43}$ is optionally substituted with from one to three substituents independently selected from halo, $N_3$, nitro, hydroxy, thiol, CN and $C_{1-6}$ alkyl;

$R^{50}$, $R^{51}$ and $R^{54}$ are independently H, OH ($R^{50}$ and $R^{51}$ are not both OH), $C_{1-10}$ alkyl, $C_{2-10}$ alkenyl, $C_{2-10}$ alkynyl, $C_{1-10}$ alkoxy, $C_{1-10}$ alkylthiol, $C_{2-10}$ alkenyloxy, $C_{2-10}$ alkynyloxy, $C_{1-10}$ haloalkyl, $C_{2-6}$ hydroxyalkyl, $C_{1-6}$ alkyl-O—$C_{1-6}$ alkyl-, wherein $R^{50}$ and $R^{51}$ each is optionally substituted with 1-3 substituents wherein each substituent is independently halo, $N_3$, nitro, hydroxy, thiol, CN, $C_{1-6}$ alkyl, $C_{1-6}$ haloalkyl, $C_{1-6}$ alkoxy, —C(=O)N($R^{54}$)($R^{55}$), $R_{44}$C(=O)— or –N($R^{54}$)($R^{55}$), wherein $R^{54}$ and $R^{55}$ are independently H, OH or $C_{1-4}$ alkyl, and wherein $R_{44}$ is H or $C_{1-4}$ alkyl; and $R^{52}$, $R^{53}$ and $R^{55}$ are independently H, OH ($R^{52}$ and $R^{53}$ are not both OH), $C_{1-10}$ alkyl, $C_{2-10}$ alkenyl, $C_{2-10}$ alkynyl, $C_{1-10}$ alkoxy, $C_{1-10}$ alkylthiol, $C_{2-10}$ alkenyloxy, $C_{2-10}$ alkynyloxy, $C_{1-10}$ haloalkyl, $C_{2-6}$ hydroxyalkyl, $C_{1-6}$ alkyl-O—$C_{1-6}$ alkyl-, or $R^{52}$ and $R^{53}$ together with the nitrogen atom to which they are both linked form a 3, 4, 5 or 6-membered heterocycle (e.g., piperidinyl, pyrrolidinyl, and morpholinyl), wherein $R^{52}$ and $R^{53}$ each is optionally substituted with 1-3 substituents wherein each substituent is independently halo, $N_3$, nitro, hydroxy, thiol, CN, $C_{1-6}$ alkyl, $C_{1-6}$ haloalkyl, $C_{1-6}$ alkoxy, —C(=O)N($R^{54}$)($R^{55}$), $R_{44}$C(=O)— or —N($R^{54}$)($R^{55}$), wherein $R^{54}$ and $R^{55}$ are independently H, OH or $C_{1-4}$ alkyl, and wherein $R_{44}$ is H or $C_{1-4}$ alkyl, with the provision that the compound is not 5-chloro-N-[3-(2,4-dichlorophenoxy)-5-(trifluoromethyl)phenyl]-2-hydroxy-benzamide or 5-chloro-2-hydroxy-N-[3-(2-naphthalenyloxy)-5-(trifluoromethyl)phenyl]-benzamide.

14. A compound having a structure

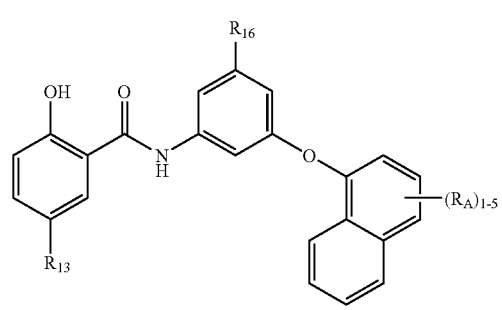

Formula 2r$^b$ and pharmaceutically acceptable salts thereof, wherein $R_{13}$ is a halo;

$R_{16}$ is selected from the group consisting of hydrogen, halo, $C_{1-6}$ alkyl, $C_{1-6}$ haloalkyl, and $C_{1-6}$ alkoxy; and each $R_4$ is independently selected from the group consisting of halo, $N_3$, nitro, hydroxy, thiol, sulfone, CN, $C_{1-6}$ alkyl, $C_{1-6}$ haloalkyl, $C_{1-6}$ alkoxy, $C_{1-6}$ hydroxyalkyl, $C_{1-6}$ alkylsulfonyl, $C_{1-6}$ alkylsulfonamide, carbocycle, heterocycle, aryl, heteroaryl, —N($R^{52}$)($R^{53}$), —N($R^{52}$)C(=O)$R_{42}$, —N($R^{52}$)C(=O)N($R^{55}$)($R^{53}$), —C(=O)N($R^{52}$)($R^{53}$), —OC(=O)N($R^{52}$)($R^{53}$), —C(=O)$R_{42}$, —OC(=O)$R_{42}$, —C(=$G^1$)$R_{42}$, —$G^2$C(=$G^1$)$R_{42}$, —($R^{52}$)$G^2$C(=$G^1$)$R_{42}$—C(=$G^1$)$G^2R_{43}$, or —$G^4$C(=$G^1$)$G^2R_{43}$, —N($R^{50}$)($R^{51}$), —N($R^{50}$)C(=O)$R_{40}$, —N($R^{50}$)C(=O)N($R^{54}$)($R^{51}$), —C(=O)N($R^{50}$)($R^{51}$), —OC(=O)N($R^{50}$)($R^{51}$), —C(=O)$R_{40}$, —OC(=O)$R_{40}$, —C(=$G^1$)$R_{40}$, —$G^2$C(=$G^1$)$R_{40}$, —($R^{50}$)$G^2$C(=$G^1$)$R_{40}$, —C(=$G^1$)$G^2R_{41}$ and —$G^3$C(=$G^1$)$G^2R_{41}$, wherein $G^1$ is S or N; $G^2$ and $G^3$ are independently S or N($R^{50}$); $G^4$ is N($R^{52}$);

$R_{40}$ is selected from: H, —OH, $C_{1-6}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy and $C_{1-6}$ alkylthiol, wherein $R_{40}$ is optionally substituted with from one to three substituents independently selected from halo, $N_3$, nitro, hydroxy, thiol, CN, $C_{1-6}$ alkyl;

$R_{41}$ is H, $C_{1-6}$ alkyl, $C_{2-6}$ alkenyl or $C_{2-6}$ alkynyl, wherein $R_{41}$ is optionally substituted with from one to three substituents independently selected from halo, $N_3$, nitro, hydroxy, thiol, CN, $C_{1-6}$ alkyl;

$R_{42}$ is selected from: H, —OH, $C_{1-6}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy, and $C_{1-6}$ alkylthiol, wherein $R_{42}$ is optionally substituted with from one to three substituents independently selected from halo, $N_3$, nitro, hydroxy, thiol, CN and $C_{1-6}$ alkyl;

$R_{43}$ is H, $C_{1-6}$ alkyl, $C_{2-6}$ alkenyl or $C_{2-6}$ alkynyl, wherein $R_{43}$ is optionally substituted with from one to three substituents independently selected from halo, $N_3$, nitro, hydroxy, thiol, CN and $C_{1-6}$ alkyl;

$R^{50}$, $R^{51}$ and $R^{54}$ are independently H, OH ($R^{50}$ and $R^{51}$ are not both OH), $C_{1-10}$ alkyl, $C_{2-10}$ alkenyl, $C_{2-10}$ alkynyl, $C_{1-10}$ alkoxy, $C_{1-10}$ alkylthiol, $C_{2-10}$ alkenyloxy, $C_{2-10}$ alkynyloxy, $C_{1-10}$ haloalkyl, $C_{2-6}$ hydroxyalkyl, $C_{1-6}$ alkyl-O—$C_{1-6}$ alkyl-, wherein $R^{50}$ and $R^{51}$ each is optionally substituted with 1-3 substituents wherein each substituent is independently halo, $N_3$, nitro, hydroxy, thiol, CN, $C_{1-6}$ alkyl, $C_{1-6}$ haloalkyl, $C_{1-6}$ alkoxy, —C(=O)N($R^{54}$)($R^{55}$), $R_{44}$C(=O)— or —N($R^{54}$)($R^{55}$), wherein $R^{54}$ and $R^{55}$ are independently H, OH or $C_{1-4}$ alkyl, and wherein $R_{44}$ is H or $C_{1-4}$ alkyl; and $R^{52}$, $R^{53}$ and $R^{55}$ are independently H, OH ($R^{52}$ and $R^{53}$ are not both OH), $C_{1-10}$ alkyl, $C_{2-10}$ alkenyl, $C_{2-10}$ alkynyl, $C_{1-10}$ alkoxy, $C_{1-10}$ alkylthiol, $C_{2-10}$ alkenyloxy, $C_{2-10}$ alkynyloxy, $C_{1-10}$ haloalkyl, $C_{2-6}$ hydroxyalkyl, $C_{1-6}$ alkyl-O—$C_{1-6}$ alkyl-, or $R^{52}$ and $R^{53}$ together with the nitrogen atom to which they are both linked form a 3, 4, 5 or 6-membered heterocycle (e.g., piperidinyl, pyrrolidinyl, and morpholinyl), wherein $R^{52}$ and $R^{53}$ each is optionally substituted with 1-3 substituents wherein each substituent is independently halo, $N_3$, nitro, hydroxy, thiol, CN, $C_{1-6}$ alkyl, $C_{1-6}$ haloalkyl, $C_{1-6}$ alkoxy, —C(=O)N($R^{54}$)($R^{55}$), $R_{44}$C(=O)— or —N($R^{54}$)($R^{55}$), wherein $R^{54}$ and $R^{55}$ are independently H, OH or $C_{1-4}$ alkyl, and wherein $R_{44}$ is H or $C_{1-4}$ alkyl.

15. A method for promoting apoptosis in a cell of a mammal, comprising identifying a mammal in need of the promoting of apoptosis, and treating a mammal with a therapeutically effective amount of a compound having a structure according to Formula 2s:

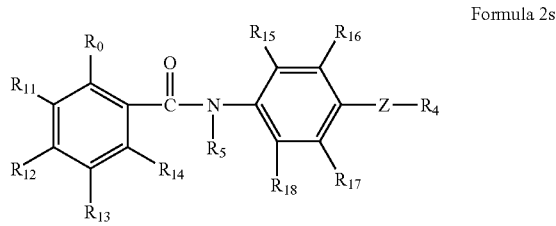

Formula 2s or pharmaceutically acceptable salts thereof, wherein $R_0$ is hydroxyl;

Z is O, N($R^z$) ($R^z$ is H or $C_{1-6}$ alkyl), or S;

$R_5$ is H or $C_{1-6}$ alkyl;

$R_{11}$-$R_{18}$ are independently selected from (a) H, halo, $N_3$, nitro, hydroxy, thiol, sulfone, and CN, (b) $C_{1-6}$ alkyl, $C_{2-6}$ alkenyl, $C_{2-6}$ alkynyl, $C_{1-6}$ alkoxy, $C_{1-6}$ alkylthiol, $C_{2-6}$ alkenyloxy, $C_{2-6}$ alkynyloxy, $C_{1-6}$ haloalkyl, $C_{1-6}$ hydroxyalkyl, —$C_{1-6}$ alkyl-O—$C_{1-6}$ alkyl, $C_{1-6}$ alkylsulfonyl (i.e., —$SO_2$—$C_{1-6}$ alkyl), $C_{1-6}$ alkylsulfonamide, each of which being optionally substituted with 1-3 substituents wherein each substituent is independently halo, $N_3$, nitro, hydroxy, thiol, CN, $C_{1-6}$ alkyl, $C_{1-6}$ haloalkyl, $C_{1-6}$ alkoxy, —N($R^{50}$)($R^{51}$), —N($R^{50}$)C(=O)$R_{40}$, —N($R^{50}$)C(=O)N($R^{54}$)($R^{51}$), —C(=O)N($R^{50}$)($R_{51}$), —OC(=O)N($R^{50}$)($R^{51}$), —C(=O)$R_{40}$, —OC(=O)$R_{40}$, —C(=$G^1$)$R_{40}$, —$G^2$C(=$G^1$)$R_{40}$, —($R^{50}$)$G^2$C(=$G^1$)$R_{40}$, —C(=$G^1$)$G^2R_{41}$ or —$G^3$C(=$G^1$)$G^2R_{41}$, (c) carbocycle, heterocycle, aryl, and heteroaryl, each of which being optionally substituted with 1-3 substituents wherein each substituent is independently halo, $N_3$, nitro, hydroxy, thiol, sulfone, CN, $C_{1-6}$ alkyl, $C_{1-6}$ haloalkyl, $C_{1-6}$ alkoxy, $C_{1-6}$ hydroxyalkyl, $C_{1-6}$ alkylsulfonyl (i.e., —$SO_2$—$C_{1-6}$ alkyl), $C_{1-6}$ alkylsulfonamide, —N($R^{52}$)($R^{53}$), —N($R^{52}$)C(=O)$R_{42}$, —N($R^{52}$)C(=O)N($R^{55}$)($R^{53}$), —C(=O)N($R^{52}$)($R^{53}$), —OC(=O)N($R^{52}$)($R^{53}$), —C(=O)$R_{42}$, —OC(=O)$R_{42}$, —C(=$G^1$)$R_{42}$, —$G^2$C(=$G^1$)$R_{42}$, —($R^{52}$)$G^2$C(=$G^1$)$R_{42}$, —C(=$G^1$)$G^2R_{43}$, or —$G^4$C(=$G^1$)$G^2R_{43}$, (d) —N($R^{50}$)($R^{51}$), —N($R^{50}$)C(=O)$R_{40}$, —N($R^{50}$)C(=O)N($R^{54}$)($R_{51}$), —C(=O)N($R^{50}$)($R^{51}$), —OC(=O)N($R^{50}$)($R^{51}$), —C(=O)$R_{40}$, —OC(=O)$R_{40}$, —C(=$G^1$)$R_{40}$, —$G^2$C(=$G^1$)$R_{40}$, —($R^{50}$)$G^2$C(=$G^1$)$R_{40}$, —C(=$G^1$)$G^2R_{41}$ or —$G^3$C(=$G^1$)$G^2R_{41}$;

$R_4$ represents (1) haloalkyl; (2) ($C_{2-6}$ alkoxy)$C_{2-6}$ alkyl; (3) -Ak-O—$R_8$, -Ak-$R_8$ or -Ak($R_8R_9$), wherein Ak is $C_{2-6}$ alkylene, $R_8$ and $R_9$ are independently selected from cycloalkyl, aryl, heterocycle or heteroaryl; each being optionally substituted by one or more substituents independently selected from (a) halo, $N_3$, nitro, hydroxy, thiol, sulfone, and CN, (b) $C_{1-6}$ alkyl, $C_{2-6}$ alkenyl, $C_{2-6}$ alkynyl, $C_{1-6}$ alkoxy, $C_{1-6}$ alkylthiol, $C_{2-6}$ alkenyloxy, $C_{2-6}$ alkynyloxy, $C_{1-6}$ haloalkyl, $C_{1-6}$ hydroxyalkyl, $C_{1-6}$ alkyl-O—$C_{1-6}$ alkyl-, $C_{1-6}$ alkylsulfonyl, $C_{1-6}$ alkylsulfonamide, each of which being optionally substituted with 1-3 substituents wherein each substituent is independently halo, $N_3$, nitro, hydroxy, thiol, CN, $C_{1-6}$ alkyl, $C_{1-6}$ haloalkyl, $C_{1-6}$ alkoxy, carbocycle, heterocycle, aryl, heteroaryl, —N($R^{50}$)($R^{51}$), —N($R^{50}$)C(=O) $R_{40}$, —N($R^{50}$)C(=O)N($R^{54}$)($R^{51}$), —C(=O)N($R^{50}$) ($R^{51}$), —OC(=O)N($R^{50}$)($R^{51}$), —C(=O)$R_{40}$, —OC (=O)$R_{40}$, —C(=$G^1$)$R_{40}$, —$G^2$C(=$G^1$)$R_{40}$, —($R^{50}$)$G^2$C(=$G^1$)$R_{40}$, —C(=$G^1$)$G^2R_{41}$ or —$G^3$C (=$G^1$)$G^2R_{41}$, (c) carbocycle, heterocycle, aryl, heteroaryl, carbocycloxy, heterocycloxy, aryloxy, heteroaryloxy, each of which being optionally substituted with 1-3 substituents wherein each substituent is independently halo, $N_3$, nitro, hydroxy, thiol, sulfone, CN, $C_{1-6}$ alkyl, $C_{1-6}$ haloalkyl, $C_{1-6}$ alkoxy, $C_{1-6}$ hydroxyalkyl, $C_{1-6}$ alkylsulfonyl, $C_{1-6}$ alkylsulfonamide, carbocycle, heterocycle, aryl, heteroaryl, —N($R^{52}$)($R^{53}$), —N($R^{52}$)C (=O)$R_{42}$, —N($R^{52}$)C(=O)N($R^{55}$)($R^{53}$), —C(=O) N($R^{52}$)($R^{53}$), —OC(=O)N($R^{52}$)($R^{53}$), —C(=O) $R_{42}$, —OC(=O)$R_{42}$, —C(=$G^1$)$R_{42}$, —$G^2$C(=$G^1$) $R_{42}$, —($R^{52}$)$G^2$C(=$G^1$)$R_{42}$, —C(=$G^1$)$G^2R_{43}$, or —$G^4$C(=$G^1$)$G^2R_{43}$, (d) —N($R^{50}$)($R^{51}$), —N($R^{51}$)C(=O)$R_{40}$, —N($R^{50}$)C (=O)N($R^{54}$)($R^{51}$), —C(=O)N($R^{50}$)($R^{51}$), —OC (=O)N($R^{50}$)($R^{51}$), —C(=O)$R_{40}$, —OC(=O)$R_{40}$, —C(=$G^1$)$R_{40}$, —$G^2$C(=$G^1$)$R_{40}$, —($R^{50}$)$G^2$C (=$G^1$)$R_{40}$, —C(=$G^1$)$G^2R_{41}$ or —$G^3$C(=$G^1$) $G^2R_{41}$;

$G^1$ is S or N; $G^2$ and $G^3$ are independently S or N($R^{50}$); $G^4$ is N($R^{52}$);

$R_{40}$ is selected from: H, OH, $C_{1-6}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy and $C_{1-6}$ alkylthiol, wherein $R_{40}$ is optionally substituted with from one to three substituents independently selected from halo, $N_3$, nitro, hydroxy, thiol, CN, $C_{1-6}$ alkyl;

$R_{41}$ is H, $C_{1-6}$ alkyl, $C_{2-6}$ alkenyl or $C_{2-6}$ alkynyl, wherein $R_4$ is optionally substituted with from one to three substituents independently selected from halo, $N_3$, nitro, hydroxy, thiol, CN, $C_{1-6}$ alkyl;

$R_{42}$ is selected from: H, OH, $C_{1-6}$ alkyl, $C_{2-6}$ alkenyl, $C_{2-6}$ alkynyl, $C_{1-6}$ alkoxy, $C_{2-6}$ alkenyloxy, $C_{2-6}$ alkynyloxy, and $C_{1-6}$ alkylthiol, wherein $R_{42}$ is optionally substituted with from one to three substituents independently selected from halo, $N_3$, nitro, hydroxy, thiol, CN and $C_{1-6}$ alkyl;

$R_{43}$ is H, $C_{1-6}$ alkyl, $C_{2-6}$ alkenyl or $C_{2-6}$ alkynyl, wherein $R_{43}$ is optionally substituted with from one to three substituents independently selected from halo, $N_3$, nitro, hydroxy, thiol, CN and $C_{1-6}$ alkyl;

$R^{50}$, $R^{51}$ and $R^{54}$ are independently H, OH($R^{50}$ and $R^{51}$ are not both OH), $C_{1-10}$ alkyl, $C_{2-10}$ alkenyl, $C_{2-10}$ alkynyl, $C_{1-10}$ alkoxy, $C_{1-10}$ alkylthiol, $C_{2-10}$ alkenyloxy, $C_{2-10}$ alkynyloxy, $C_{1-10}$ haloalkyl, $C_{2-6}$ hydroxyalkyl, $C_{1-6}$ alkyl-O—$C_{1-6}$ alkyl-, wherein $R^{50}$ and $R^{51}$ each is optionally substituted with 1-3 substituents wherein each substituent is independently halo, $N_3$, nitro, hydroxy, thiol, CN, $C_{1-6}$ alkyl, $C_{1-6}$ haloalkyl, $C_{1-6}$ alkoxy, —C(=O)N($R^{54}$)($R^{55}$), $R_{44}$C(=O)— or —N($R^{54}$)($R^{55}$), wherein $R^{54}$ and $R^{55}$ are independently H, OH or $C_{1-4}$ alkyl, and wherein $R_{44}$ is H or $C_{1-4}$ alkyl; and $R^{52}$, $R^{53}$ and $R^{55}$ are independently H, OH($R^{52}$ and $R^{53}$ are not both OH), $C_{1-10}$ alkyl, $C_{2-10}$ alkenyl, $C_{2-10}$ alkynyl, $C_{1-10}$ alkoxy, $C_{1-10}$ alkylthiol, $C_{2-10}$ alkenyloxy, $C_{2-10}$ alkynyloxy, $C_{1-40}$ haloalkyl, $C_{2-6}$ hydroxyalkyl, $C_{1-6}$ alkyl-O—$C_{1-6}$ alkyl-, or $R^{52}$ and $R^{53}$ together with the nitrogen atom to which they are both linked form a 3, 4, 5 or 6-membered heterocycle, wherein $R^{52}$ and $R^{53}$ each is optionally substituted with 1-3 substituents wherein each substituent is independently halo, $N_3$, nitro, hydroxy, thiol, CN, $C_{1-6}$ alkyl, $C_{1-6}$ haloalkyl, $C_{1-6}$ alkoxy, —C(=O)N($R^{54}$)($R^{55}$), $R_{44}$C(=O)— or —N($R^{54}$)($R^{55}$), wherein $R^{54}$ and $R^{55}$ are independently H, OH or $C_{1-4}$ alkyl, and wherein $R_{44}$ is H or $C_{1-4}$ alkyl.

16. The method of claim 15, wherein $R_8$ or $R_9$ or both are substituted with one or more said substituents defined for $R_8$ and $R_9$.

17. The method of claim 1, wherein said mammal is identified as having head or neck squamous cell carcinoma, and said promoting apoptosis comprises promoting apoptosis in a head or neck squamous cell carcinoma cell, and wherein said compound has the structure:

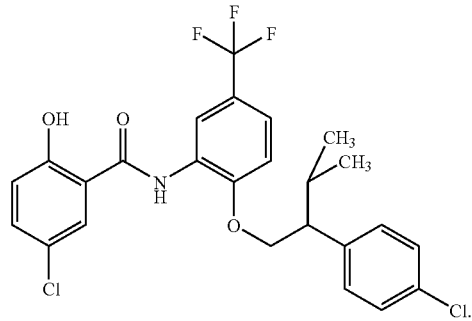

18. The method of claim 17, wherein the treating step comprises administering to the mammal said therapeutically effective amount of said compound or the pharmaceutically acceptable salt thereof.

19. A method for promoting apoptosis in a cell of a mammal comprising identifying a mammal in need of promoting apoptosis, and treating the mammal with a therapeutically effective amount of the compound of claim 7 or the pharmaceutically acceptable salt thereof.

20. The method of claim 4, wherein said compound has the structure:

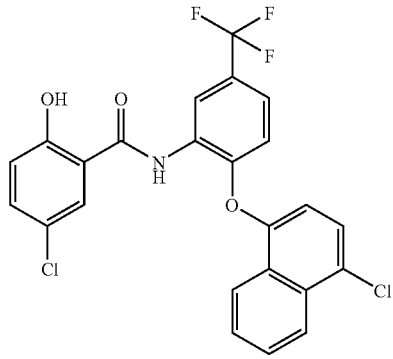

and wherein said mammal is diagnosed as having cancer selected from leukemia, lymphoma, prostate or ovarian cancer, and said promoting apoptosis comprises promoting apoptosis in a leukemia, lymphoma, prostate or ovarian cancer cell.

21. The method of claim 20, wherein the treating step comprises administering to the mammal said therapeutically effective amount of said compound or the pharmaceutically acceptable salt thereof.

22. The method of claim 4, wherein said compound has the structure:

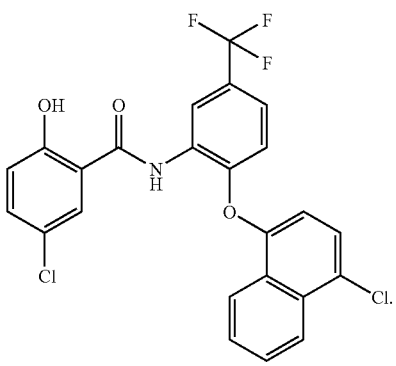

23. The compound of claim 8, wherein said compound has the structure:

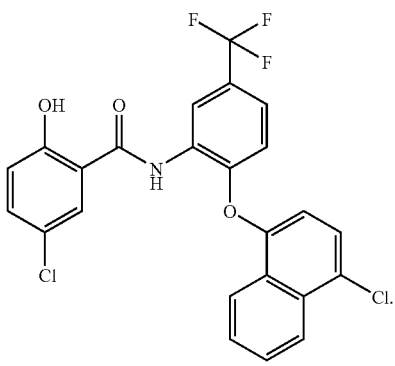

24. A pharmaceutical composition comprising a therapeutically effective amount of the compound of claim 7, and a pharmaceutically acceptable carrier.

25. A pharmaceutical composition comprising a therapeutically effective amount of the compound of claim 23, and a pharmaceutically acceptable carrier.

26. A pharmaceutical composition comprising a therapeutically effective amount of the compound of claim 14, and a pharmaceutically acceptable carrier.

* * * * *